(12) United States Patent
Fukatsu et al.

(10) Patent No.: US 7,795,267 B2
(45) Date of Patent: Sep. 14, 2010

(54) BICYCLIC PIPERAZINE COMPOUND HAVING TGR23 ANTAGONISTIC ACTIVITY

(75) Inventors: Kohji Fukatsu, Osaka (JP); Yutaka Nakayama, Kodaira (JP); Naoki Tarui, Osaka (JP); Masaaki Mori, Tsukuba (JP); Hirokazu Matsumoto, Tsukuba (JP); Osamu Kurasawa, Osaka (JP); Hiroshi Banno, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 743 days.

(21) Appl. No.: 10/570,270

(22) PCT Filed: Aug. 26, 2004

(86) PCT No.: PCT/JP2004/012683

§ 371 (c)(1),
(2), (4) Date: May 11, 2006

(87) PCT Pub. No.: WO2005/021555

PCT Pub. Date: Mar. 10, 2005

(65) Prior Publication Data

US 2007/0072865 A1 Mar. 29, 2007

(30) Foreign Application Priority Data

Aug. 29, 2003 (JP) .............................. 2003-306054
Mar. 26, 2004 (JP) .............................. 2004-093606

(51) Int. Cl.
*A61K 31/4965* (2006.01)
(52) U.S. Cl. .................. 514/255.05; 544/350; 546/187; 546/281.7; 549/60
(58) Field of Classification Search ............ 514/255.05; 544/350; 546/187, 281.7; 549/60
See application file for complete search history.

(56) References Cited

U.S. PATENT DOCUMENTS 6,657,063 B1  12/2003  Dow

FOREIGN PATENT DOCUMENTS

| JP | 2000-72771 | 3/2000 |
| JP | 2000-516639 | 12/2000 |
| WO | WO 97/19089 | * 5/1997 |
| WO | WO 98/58947 | 12/1998 |
| WO | WO 01/89570 | 11/2001 |
| WO | WO 02/00631 | 1/2002 |
| WO | WO 02/00654 | 1/2002 |
| WO | WO 02/18327 | 3/2002 |
| WO | WO 02/18372 | 3/2002 |
| WO | WO 03/011824 | 2/2003 |
| WO | WO 03/020699 | 3/2003 |
| WO | WO 03/030907 | 4/2003 |
| WO | WO 03/053354 | 7/2003 |

OTHER PUBLICATIONS

Patani, et al. Chem. Rev., 96, 1996, pp. 3147-3176.*
Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
S. Herrero, et al., "2-Oxopiperazine-Based Gamma-Turn Conformationally Constrained Peptides: Synthesis of CCK-4 Analogues", J. Org. Chem., (2002), 67: 3866-3873.
V. Schanin, et al., "Asymmetric Synthesis; XXXVII: Synthesis of 2,6-Disubstituted Piperazines from Chiral Non-Racemic Lactams", Synthesis, (1996), No. 7, pp. 833-837.
Supplementary European Search Report dated Mar. 13, 2009.
Database CA Chemical Abstracts Service, Columbus, Ohio, US; Falorni, Massimo et al: "General and versatile approach to the synthesis of optically active 5-alkylpiperazine-2-carboxylic acids" XP002517977 retrieved from STN Database accession No. 1994:701238 *abstract* & Synthesis, (4), 391-5 CODEN: SYNTBF; ISSN: 0039-7881, 1994.

* cited by examiner

*Primary Examiner*—James O Wilson
*Assistant Examiner*—Douglas M Willis
(74) *Attorney, Agent, or Firm*—Sughrue Mion, PLLC

(57) ABSTRACT

The present invention provides a compound represented by the formula:

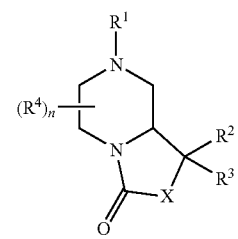

wherein $R^1$ is —(C=O)—$NR^7R^8$ or —(C=O)—$OR^6$, $R^2$ is a hydrocarbon group which may be substituted or the like, $R^3$ is a hydrocarbon group which may be substituted or the like, $R^4$ is a hydrocarbon group which may be substituted or the like, n is from 0 to 4, and X is an oxygen atom, or a salt thereof. The invention also provides a compound which has a TGR23 antagonist activity and thus is useful for prevention and treatment of cancer.

18 Claims, No Drawings

BICYCLIC PIPERAZINE COMPOUND HAVING TGR23 ANTAGONISTIC ACTIVITY

This application is the National Phase filing of International Patent Application No. PCT/JP2004/012683, filed Aug. 26, 2004.

TECHNICAL FIELD

The present invention relates to a novel compound which is useful in prevention and treatment of cancer, and more particularly, to a compound which has a prophylactic and therapeutic action on cancer by regulating, particularly inhibiting, the function of a TGR23 receptor.

BACKGROUND ART

TGR23, a G protein-coupled receptor, is characterized in having an amino acid sequence represented by SEQ ID NO: 1 or SEQ ID NO: 2 of the sequence listing. The TGR23 and its ligand (TGR23 ligand) are reported in WO 02/31145 (Patent Document 1) and WO 03/025179 (Patent Document 2), and when TGR23 responds to the ligand, the dietary behavior is suppressed, and tumors proliferate (WO 03/025179). In this regard, an antagonist of TGR23 is useful as a low toxic and safe medicine, such as a prophylactic and/or therapeutic agent for cancers (e.g., large intestine cancer, colon cancer, rectal cancer, breast cancer, lung cancer, non-small cell lung cancer, prostate cancer, esophageal cancer, stomach cancer, liver cancer, bile duct cancer, spleen cancer, renal cancer, urinary bladder cancer, uterine cancer, ovarian cancer, cervical cancer, testicular cancer, thyroid cancer, pancreatic cancer, brain tumor, blood tumor and the like), a feeding (appetite) promoting agent, a prophylactic and/or therapeutic agent for anorexia, an apoptosis inducing agent, and the like.

Meanwhile, the following bicyclic piperazine compounds are known.

(1) The following compounds are described in Synthesis, p. 833 (1996) (Non-Patent Document 1) as 2,6-disubstituted piperazine derivatives synthesized by an asymmetrical synthesis method, but no description is given on the action and use of the compounds.

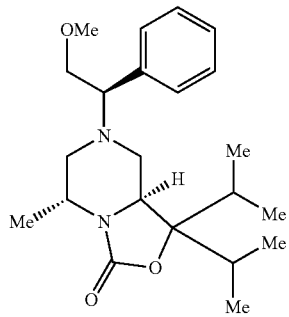

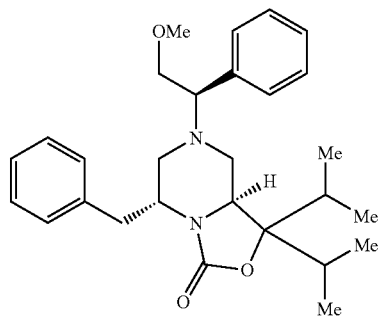

(2) The following compound is described in WO 97/19089 (Patent Document 3) as an intermediate of an oxazolidinone derivative having antibacterial action.

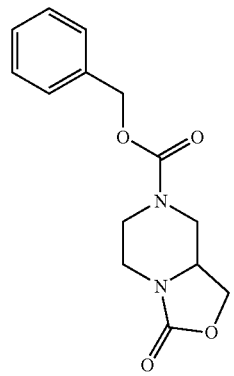

(3) The following compound is described in WO 98/58947 (Patent Document 4) as an intermediate of a dipeptide derivative having a growth hormone secretagogue action.

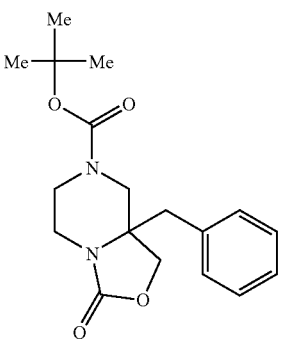

(4) The following compound is described in J. Org. Chem., Vol. 67, p. 3866 (2002) (Non-Patent Document 2) as a compound relevant to a monocyclic oxopiperazine derivative having affinity to a CCK receptor.

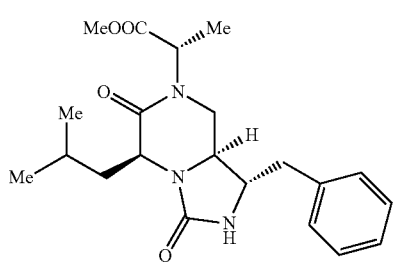

(5) The following compound is described in WO 03/30907 (Patent Document 5) as an exemplary compound useful as a prophylactic and/or therapeutic agent for inflammation, cell adhesion-mediated diseases and central nervous diseases.

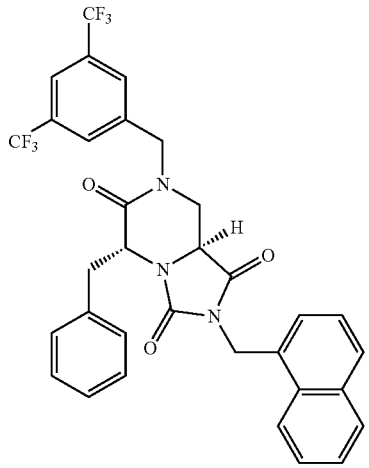

[Patent Document 1] WO 02/31145
[Patent Document 2] WO 03/025179
[Patent Document 3] WO 97/19089
[Patent Document 4] WO 98/58947
[Patent Document 5] WO 03/30907
[Non-Patent Document 1] Synthesis, p. 833 (1996)
[Non-Patent Document 2] J. Org. Chem., Vol. 67, p. 3866 (2002)

DISCLOSURE OF THE INVENTION

Since the conventionally used anticancer agents do not provide sufficient effects, anticancer agents that are excellent in safety are desirable.

The inventors of the present invention have diligently conducted research to address the above-described problem. As a result, they have synthesized for the first time a compound represented by the following formula, which has a chemical structure of a bicyclic piperazine compound having an acyl group on the 7-position and also having a substituent on the 1-position:

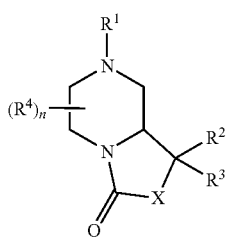

(I)

wherein $R^1$ is an acyl group;
$R^2$ is a hydrogen atom, a hydrocarbon group which may be substituted, or a heterocyclic group which may be substituted;
$R^3$ is a hydrocarbon group which may be substituted, or a heterocyclic group which may be substituted;
$R^4$ is a hydrocarbon group which may be substituted, or a heterocyclic group which may be substituted;
n is an integer from 0 to 4 (when n is an integer from 2 to 4, $R^4$ may be identical or different); and
X is an oxygen atom, a sulfur atom, or a group represented by the formula: $NR^5$ (wherein $R^5$ is a hydrogen atom, a hydrocarbon group which may be substituted, or a heterocyclic group which may be substituted),
or a salt thereof [hereinafter, may be simply referred to as Compound (I)]. Further, they have unexpectedly found that Compound (I) has an excellent TGR23 antagonist activity based on its specific chemical structure, and is useful as a safe prophylactic and/or therapeutic medicine against cancer, thus completing the invention.

Thus, the invention provides the following:

[1] A compound represented by the formula:

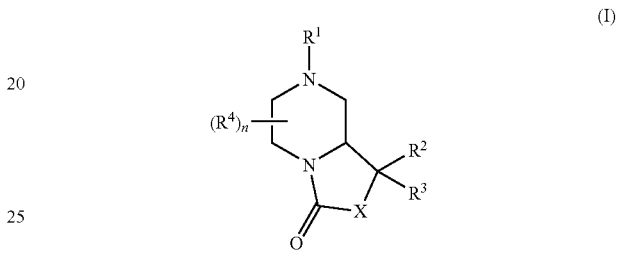

(I)

wherein $R^1$ is an acyl group;
$R^2$ is a hydrogen atom, a hydrocarbon group which may be substituted, or a heterocyclic group which may be substituted;
$R^3$ is a hydrocarbon group which may be substituted, or a heterocyclic group which may be substituted;
$R^4$ is a hydrocarbon group which may be substituted, or a heterocyclic group which may be substituted;
n is an integer from 0 to 4 (when n is an integer from 2 to 4, $R^4$ may be identical or different); and
X is an oxygen atom, a sulfur atom, or a group represented by the formula: $NR^5$ (wherein $R^5$ is a hydrogen atom, a hydrocarbon group which may be substituted, or a heterocyclic group which may be substituted),
or a salt thereof;

[2] The compound according to [1], wherein the acyl group represented by $R^1$ is a group represented by the formula: —(C=O)—$R^6$, —(C=O)—$OR^6$, —(C=O)—$NR^7R^8$, —(C=S)—$NR^7R^8$, —SO—$R^6$, —$SO_2$—$R^6$ or —$SO_2$—$NR^7R^8$ (wherein $R^6$ is a hydrocarbon group which may be substituted, or a heterocyclic group which may be substituted;
$R^7$ is a hydrogen atom, a hydrocarbon group which may be substituted, a heterocyclic group which may be substituted, a $C_{6-12}$ aryl-carbonyl group, a $C_{1-6}$ alkoxy-carbonyl group, or a 5- or 6-membered aromatic heterocyclic carbonyl group; and
$R^8$ is a hydrogen atom, a $C_{1-6}$ alkyl group, or an amino group which may be substituted; or
$R^7$ and $R^8$ may form, together with the adjacent nitrogen atom, a ring which may be substituted;

[3] The compound according to [2], wherein the acyl group represented by $R^1$ is a group represented by the formula: —(C=O)—$R^6$, —(C=O)—$OR^6$ or —(C=O)—$NR^7R^8$ (wherein each symbol is as defined in [2]);

[4] The compound according to [2], wherein $R^6$ is an aromatic group, a heterocyclic group, or a chain hydrocarbon group, each of which may be substituted;

[5] The compound according to [2], wherein $R^6$ is a $C_{6-12}$ aryl group which may be substituted, or a $C_{1-6}$ alkyl group having a 5- to 7-membered cyclic amino group which may be substituted;

[6] The compound according to [2], wherein $R^7$ is a hydrogen atom, a hydrocarbon group which may be substituted, a heterocyclic group which may be substituted, a $C_{6-12}$ arylcarbonyl group, or a $C_{1-6}$ alkoxy-carbonyl group;

[7] The compound according to [2], wherein $R^7$ is:
  (a) a $C_{1-6}$ alkyl group which may have (i) a 5- to 7-membered cyclic amino group which may be substituted, and/or (ii) a 5- to 10-membered aromatic heterocyclic group which may be substituted,
  (b) a $C_{6-12}$ aryl group which may be substituted, or
  (c) a $C_{7-13}$ aralkyl group which may be substituted;

[8] The compound according to [2], wherein $R^7$ is a group having an aromatic group which may be substituted;

[9] The compound according to [2], wherein $R^7$ and $R^8$ form, together with the adjacent nitrogen atom, a 5- to 10-membered heterocyclic ring which may be substituted;

[10] The compound according to [2], wherein $R^8$ is a hydrogen atom, or an amino group which may be substituted;

[11] The compound according to [1], wherein $R^1$ is a group represented by the formula: —(C=O)—$NR^7R^8$ (wherein each symbol is as defined in [2]);

[12] The compound according to [1], wherein $R^1$ is a group represented by the formula: —(C=O)—$R^6$ (wherein each symbol is as defined in [2]);

[13] The compound according to [1], wherein $R^2$ is an aryl group which may be substituted;

[14] The compound according to [1], wherein $R^3$ is an aryl group which may be substituted;

[15] The compound according to [1], wherein n is 0;

[16] The compound according to [1], wherein X is an oxygen atom;

[17] The compound according to [1], wherein $R^1$ is a group represented by the formula: —(C=O)—$R^{6b}$ or —(C=O)—$NR^{7b}R^{8b}$ (wherein $R^{6b}$ is
  (a) a $C_{1-6}$ alkyl group which may have a 5- to 7-membered cyclic amino group, or
  (b) a $C_{6-12}$ aryl group which may have a $C_{1-6}$ alkyl group which may have an amino group which may have one or two $C_{1-6}$ alkyl groups;
$R^{7b}$ is
  (a) a hydrogen atom,
  (b) a $C_{6-12}$ aryl group which may have a halogen atom,
  (c) a $C_{7-13}$ aralkyl group which may have a halogen atom,
  (d) a 5- or 6-membered aromatic heterocyclic group,
  (e) a $C_{1-6}$ alkyl group which may have a 5- to 7-membered cyclic amino group, or
  (f) a 5- or 6-membered non-aromatic heterocyclic group which may have a $C_{1-6}$ alkyl group; and
$R^{8b}$ is a hydrogen atom or a $C_{6-12}$ arylamino group; or
$R^{7b}$ and $R^{8b}$ may form, together with the adjacent nitrogen atom, a 5- to 10-membered heterocyclic ring which may have a 5- to 7-membered cyclic amino group);
$R^2$ and $R^3$ are respectively a $C_{6-12}$ aryl group;
n is 0; and
X is an oxygen atom;

[18] The compound according to [1], wherein $R^1$ is a group represented by the formula: —(C=O)—$R^{6a}$, —(C=O)—$OR^{6a}$, —(C=O)—$NR^{7a}R^{8a}$ or —$SO_2$—$R^{6a}$ (wherein $R^{6a}$ is
  (a) a $C_{7-13}$ aralkyl group,
  (b) a $C_{2-6}$ alkenyl group which may have a $C_{6-12}$ aryl group which may be halogenated,
  (c) a $C_{6-12}$ aryl group which may have a substituent selected from a halogen atom, a $C_{1-6}$ alkoxy group, a nitro group, and a $C_{1-6}$ alkyl group which may be halogenated,
  (d) a 5- or 6-membered aromatic heterocyclic group, or
  (e) a $C_{1-6}$ alkyl group which may have a substituent selected from a $C_{6-12}$ aryl group, a $C_{6-12}$ aryloxy group, and a $C_{3-8}$ cycloalkyl group which may be condensed;
$R^{7a}$ is
  (a) a hydrogen atom,
  (b) a $C_{6-12}$ aryl group which may have a substituent selected from a $C_{1-6}$ alkoxy-carbonyl group, a halogen atom and a $C_{1-6}$ alkoxy group,
  (c) a $C_{7-13}$ aralkyl group which may have a substituent selected from a halogen atom, a $C_{1-6}$ alkyl group which may be halogenated, a $C_{1-6}$ alkylsulfonyl group and a mono- or di-$C_{1-6}$ alkylamino group,
  (d) a $C_{1-6}$ alkyl group which may have a 5- or 6-membered aromatic heterocyclic group, or
  (e) a $C_{3-8}$ cycloalkyl group which may be condensed; and
$R^{8a}$ is a hydrogen atom, a $C_{1-6}$ alkyl group or a $C_{6-12}$ arylamino group; or
$R^{7a}$ and $R^{8a}$ may form, together with the adjacent nitrogen atom, a 5- to 10-membered non-aromatic heterocyclic ring);
$R^2$ and $R^3$ are respectively a $C_{1-6}$ alkyl group, a $C_{3-6}$ cycloalkyl group or a $C_{6-12}$ aryl group;
n is 0; and
X is an oxygen atom;

[19] The compound according to [1], wherein $R^1$ is a group represented by the formula: —(C=O)—$R^{6a}$, —(C=O)—$OR^{6a}$, —(C=O)—$NR^{7a}R^{8a}$ or —$SO_2$—$R^{6a}$ (wherein $R^{6a}$ is
  (a) a $C_{7-13}$ aralkyl group,
  (b) a $C_{2-6}$ alkenyl group which may have a $C_{6-12}$ aryl group which may be halogenated,
  (c) a $C_{6-12}$ aryl group which may have a substituent selected from
    (i) a halogen atom,
    (ii) a $C_{1-6}$ alkoxy group,
    (iii) a nitro group, and
    (iv) a $C_{1-6}$ alkyl group which may have a substituent selected from (1) a halogen atom, and (2) an amino group which may have one or two substituents selected from a $C_{1-6}$ alkoxy-carbonyl group and a $C_{1-6}$ alkyl group,
  (d) a 5- or 6-membered aromatic heterocyclic group,
  (e) a $C_{1-6}$ alkyl group which may have a substituent selected from
    (i) a $C_{6-12}$ aryloxy group,
    (ii) a $C_{3-8}$ cycloalkyl group which may be condensed with one or two benzene rings,
    (iii) a $C_{6-12}$ arylamino group which may be halogenated,
    (iv) a carboxy group,
    (v) a 5- to 7-membered cyclic amino group,
    (vi) a $C_{6-12}$ aryl group, and
    (vii) a halogen atom,
  (f) a 6-membered non-aromatic heterocyclic group which may have a $C_{1-6}$ alkoxy-carbonyl group, or
  (g) a 5- to 10-membered (preferably, 9-membered) aromatic heterocyclic group which may have an oxo group;
$R^{7a}$ is
  (a) a hydrogen atom,
  (b) a $C_{6-12}$ aryl group which may have a substituent selected from a $C_{1-6}$ alkoxy-carbonyl group, a halogen atom and a $C_{1-6}$ alkoxy group,
  (c) a $C_{7-13}$ aralkyl group which may have a substituent selected from (i) a halogen atom
(ii) a $C_{1-6}$ alkyl group which may have a substituent selected from an amino group which may be substituted with a $C_{1-6}$ alkoxy-carbonyl group, and a halogen atom,
(iii) a $C_{1-6}$ alkylsulfonyl group, and
(iv) a mono- or di-$C_{1-6}$ alkylamino group,
(d) a $C_{1-6}$ alkyl group which may have a substituent selected from
  (i) a 5- or 6-membered aromatic heterocyclic group which may be oxidized and may have a cyano group,
  (ii) a 5- to 7-membered cyclic amino group which may have a $C_{1-6}$ alkyl group and may be condensed with a benzene ring,
  (iii) a $C_{1-6}$ alkoxy-carbonyl group,
  (iv) a carboxy group,
  (v) a 5- to 7-membered saturated cyclic aminocarbonyl group,
  (vi) a $C_{6-12}$ aryl group,
  (vii) a $C_{6-12}$ aryl-carbonyl group,
  (viii) a hydroxy group, and
  (ix) an amino group which may have one or two substituents selected from a $C_{1-6}$ alkyl group, a $C_{1-6}$ alkoxy-$C_{1-6}$ alkyl group, an azidocarbonyl group, an aminocarbonyl group and a $C_{7-13}$ aralkyl group,
(e) a $C_{3-8}$ cycloalkyl group which may be condensed with one or two benzene rings,
(f) a 5- or 10-membered aromatic heterocyclic group which may have a substituent selected from an oxo group and a $C_{1-6}$ alkoxy-carbonyl group,
(g) a $C_{6-12}$ aryl-carbonyl group,
(h) a $C_{1-6}$ alkoxy-carbonyl group, or
(i) a 5- to 7-membered non-aromatic heterocyclic group which may have a substituent selected from a $C_{1-6}$ alkyl group, a $C_{1-6}$ alkoxy-carbonyl group and an oxo group, and may be condensed with a benzene ring; and
$R^{8a}$ is a hydrogen atom, a $C_{1-6}$ alkyl group or a $C_{6-12}$ aryl amino group; or
$R^{7a}$ and $R^{8a}$ may form, together with the adjacent nitrogen atom, a 5- to 10-membered non-aromatic heterocyclic ring which may have a 5- to 7-membered saturated cyclic amino group);
$R^2$ is a hydrogen atom, a $C_{1-6}$ alkyl group, a $C_{3-6}$ cycloalkyl group, a $C_{6-12}$ aryl group which may be halogenated, or a $C_{7-13}$ aralkyl group;
$R^3$ is a $C_{1-6}$ alkyl group, a $C_{3-6}$ cycloalkyl group, a $C_{6-12}$ aryl group which may be halogenated, or a $C_{7-13}$ aralkyl group;
n is 0; and
X is an oxygen atom;

[20] The compound according to [1], wherein $R^1$ is a group represented by the formula: —(C═O)—$R^{6a}$, —(C═O)—O$R^{6a}$, —(C═O)—N$R^{7a}R^{8a}$ or —SO$_2$—$R^{6a}$ (wherein $R^{6a}$ is
(a) a $C_{7-13}$ aralkyl group,
(b) a $C_{2-6}$ alkenyl group which may have a $C_{6-12}$ aryl group which may be halogenated,
(c) a $C_{6-12}$ aryl group which may have a substituent selected from:
  (i) a halogen atom,
  (ii) a $C_{1-6}$ alkoxy group,
  (iii) a nitro group,
  (iv) a formyl group, and
  (v) a $C_{1-6}$ alkyl group which may have a substituent selected from (1) a halogen atom, (2) an amino group which may have one or two substituents selected from a $C_{1-6}$ alkoxy-carbonyl group and a $C_{1-6}$ alkyl group, and (3) a 5- to 7-membered cyclic amino group which may be substituted,
(d) a 5- or 6-membered aromatic heterocyclic group,
(e) a $C_{1-6}$ alkyl group which may have a substituent selected from:
  (i) a $C_{6-12}$ aryloxy group,
  (ii) a $C_{3-8}$ cycloalkyl group which may be condensed with one or two benzene rings,
  (iii) a $C_{6-12}$ arylamino group which may be halogenated,
  (iv) a carboxy group,
  (v) a 5- to 7-membered cyclic amino group,
  (vi) a 5- to 7-membered non-aromatic heterocyclic group,
  (vii) a $C_{6-12}$ aryl group, and
  (viii) a halogen atom,
(f) a 5- to 7-membered non-aromatic heterocyclic group which may have a $C_{1-6}$ alkoxy-carbonyl group, a formyl group, or a $C_{1-6}$ alkyl group which may have a substituent selected from:
  (i) a $C_{1-6}$ alkoxy-carbonyl group,
  (ii) a carbamoyl group,
  (iii) a hydroxy group,
  (iv) a 5- to 7-membered cyclic amino-carbonyl group,
  (v) a $C_{3-8}$ cycloalkyl group, and
  (vi) a $C_{2-8}$ alkenyl group,
(g) a 5- to 10-membered (preferably, 9-membered) aromatic heterocyclic group which may have an oxo group, or
(h) a 5- to 10-membered cyclic amino group which may have an oxo group and may be condensed with a benzene ring;
$R^{7a}$ is
(a) a hydrogen atom,
(b) a $C_{6-12}$ aryl group which may have a substituent selected from:
  (i) a $C_{1-6}$ alkoxy-carbonyl group,
  (ii) a halogen atom, and
  (iii) a $C_{1-6}$ alkoxy group,
(c) a $C_{7-13}$ aralkyl group which may have a substituent selected from:
  (i) a halogen atom,
  (ii) a $C_{1-6}$ alkyl group which may have a substituent selected from an amino group which may be substituted with a $C_{1-6}$ alkoxy-carbonyl group, and a halogen atom,
  (iii) a $C_{1-6}$ alkylsulfonyl group, and
  (iv) a mono- or di-$C_{1-6}$ alkylamino group,
(d) a $C_{1-6}$ alkyl group which may have one or two substituents selected from:
  (i) a 5- or 6-membered aromatic heterocyclic group which may be oxidized and may be substituted with a cyano group, a hydroxy group or a $C_{1-6}$ alkyl group,
  (ii) a 5- to 7-membered cyclic amino group which may have a $C_{1-6}$ alkyl group, a hydroxy group, an oxo group or a $C_{1-6}$ alkoxy-carbonyl group, and may be condensed with a benzene ring,
  (iii) a $C_{1-6}$ alkoxy-carbonyl group,
  (iv) a carboxy group,
  (v) a 5- to 7-membered cyclic aminocarbonyl group,
  (vi) a $C_{6-12}$ aryl group which may be halogenated,
  (vii) a $C_{6-12}$ aryl-carbonyl group,
  (viii) a hydroxy group,
  (ix) an amino group which may have one or two substituents selected from (1) a $C_{1-6}$ alkyl group which may be substituted with a $C_{3-8}$ cycloalkyl group, (2) a $C_{1-6}$ alkoxy-$C_{1-6}$ alkyl group, (3) an azidocarbonyl group, (4) an aminocarbonyl group, (5) a $C_{7-13}$ aralkyl group, (6) a $C_{3-8}$ cycloalkyl group, (7) a sulfonyl group which may be substituted with a benzene ring which may be substituted with a nitro group, (8) a $C_{2-8}$ alkenyl group, (9) a $C_{1-6}$ alkylsulfonyl group, and (10) a $C_{1-6}$ alkyl-carbonyl group, (x) a $C_{3-8}$ cycloalkyl group, and (xi) a 5- to 7-membered non-aromatic heterocyclic group, (e) a $C_{3-8}$ cycloalkyl group which may be condensed with one or two benzene rings, (f) a 5- to 10-membered aromatic heterocyclic group which may have a substituent selected from an oxo group, a $C_{1-6}$ alkoxy-carbonyl group and a $C_{1-6}$ alkyl group, (g) a $C_{6-12}$ aryl-carbonyl group, (h) a $C_{1-6}$ alkoxy-carbonyl group, (i) a 5- to 7-membered non-aromatic heterocyclic group which may have a substituent selected from a $C_{1-6}$ alkyl group, a $C_{1-6}$ alkoxy-carbonyl group and an oxo group, and may be condensed with a benzene ring, (j) a 5- to 7-membered cyclic amino-$C_{1-6}$ alkyl-carbonyl group, (k) a $C_{3-8}$ cycloalkyl group which may be substituted with a $C_{1-6}$ alkyl group which may have a 5- to 7-membered cyclic amino group, or (l) a $C_{6-12}$ arylamino group; and $R^{8a}$ is a hydrogen atom or a $C_{1-6}$ alkyl group; or $R^{7a}$ and $R^{8a}$ may form, together with the adjacent nitrogen atom, a 5- to 10-membered non-aromatic heterocyclic ring which may have a substituent selected from a 5- to 7-membered saturated cyclic amino group and a $C_{1-6}$ alkyl group);

$R^2$ is (i) a hydrogen atom (ii) a $C_{1-6}$ alkyl group, (iii) a $C_{3-6}$ cycloalkyl group, (iv) a $C_{6-12}$ aryl group which may have a substituent selected from a halogen atom and a $C_{1-6}$ alkyl group, or (v) a $C_{7-13}$ aralkyl group;

$R^3$ is (i) a $C_{1-6}$ alkyl group, (ii) a $C_{3-6}$ cycloalkyl group, (iii) a $C_{6-12}$ aryl group which may have a substituent selected from a halogen atom and a $C_{1-6}$ alkyl group, or (iv) a $C_{7-13}$ aralkyl group;

n is 0; and

X is an oxygen atom;

[21] Phenyl tetrahydro-3-oxo-1,1-diphenyl-3H-oxazolo[3,4-a]pyrazine-7(1H)-carboxylate, hexahydro-7-(1-oxo-3-phenyl-2-propenyl)-1,1-diphenyl-3H-oxazolo[3,4-a]pyrazin-3-one, (+)-N-[(4-fluorophenyl)methyl]-tetrahydro-3-oxo-1,1-diphenyl-3H-oxazolo[3,4-a]pyrazine-7(1H)-carboxamide, (−)-N-[(4-fluorophenyl)methyl]-tetrahydro-3-oxo-1,1-diphenyl-3H-oxazolo[3,4-a]pyrazine-7(1H)-carboxamide, (+)-N-[2-(3,6-dihydropyridin-1(2H)-yl)ethyl]-tetrahydro-3-oxo-1,1-diphenyl-3H-oxazolo[3,4-a]pyrazine-7(1H)-carboxamide, (−)-N-[2-(3,6-dihydropyridin-1(2H)-yl)ethyl]-tetrahydro-3-oxo-1,1'-diphenyl-3H-oxazolo[3,4-a]pyrazine-7(1H)-carboxamide, 1,1-bis(3-fluorophenyl)-N-[2-(3,6-dihydropyridin-1(2H)-yl)ethyl]-tetrahydro-3-oxo-3H-oxazolo[3,4-a]pyrazine-7(1H)-carboxamide, N-[2-(3,6-dihydropyridin-1(2H)-yl)ethyl]-tetrahydro-3-oxo-1,1-diphenyl-3H-oxazolo[3,4-a]pyrazine-7(1H)-carboxamide, 1,1-bis(3-fluorophenyl)-N-[2-(cyclopropylamino)ethyl]-tetrahydro-3-oxo-3H-oxazolo[3,4-a]pyrazine-7(1H)-carboxamide hydrochloride, tetrahydro-3-oxo-1,1-diphenyl-N-[(3-thienyl)methyl]-3H-oxazolo[3,4-a]pyrazine-7(1H)-carboxamide, 7-[4-(3,6-dihydropyridin-1(2H)-yl)-1-oxobutyl]-hexahydro-1,1-diphenyl-3H-oxazolo[3,4-a]pyrazin-7(1H)-3-one, N-[2-[(cyclopropylmethyl)amino]ethyl]-tetrahydro-3-oxo-1,1-diphenyl-3H-oxazolo[3,4-a]pyrazine-7(1H)-carboxamide hydrochloride, N-[(4-fluorophenyl)methyl]-tetrahydro-3-oxo-1,1-diphenyl-3H-oxazolo[3,4-a]pyrazine-7(1H)-carboxamide, or 1,1-bis(3-fluorophenyl)-tetrahydro-3-oxo-N-[2-(1-piperidinyl)ethyl]-3H-oxazolo[3,4-a]pyrazine-7(1H)-carboxamide, or a salt thereof;

[22] A medicine comprising the compound according to [1], or a salt or a prodrug thereof;

[23] A TGR23 function regulator comprising a compound represented by the formula:

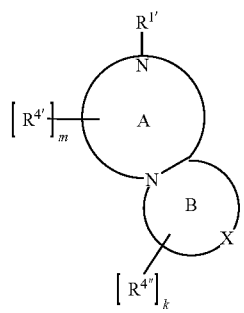

(II)

wherein ring A is a 5- to 10-membered ring;

ring B is a 5- to 9-membered ring;

$R^{1'}$ is a hydrogen atom, an acyl group, a hydrocarbon group which may be substituted, or a heterocyclic group which may be substituted;

$R^{4'}$ is a hydrocarbon group which may be substituted, or a heterocyclic group which may be substituted;

$R^{4''}$ is an oxo group, a hydrocarbon group which may be substituted, or a heterocyclic group which may be substituted;

m is an integer from 0 to 8 (when m is an integer from 2 to 8, $R^{4'}$ may be identical or different)

k is an integer from 0 to 8 (when k is an integer from 2 to 8, $R^{4''}$ may be identical or different); and X is an oxygen atom, a sulfur atom, or a group represented by the formula: $NR^5$ (wherein $R^5$ is a hydrogen atom, a hydrocarbon group which may be substituted, or a heterocyclic group which may be substituted), or a salt thereof;

[24] The medicine according to [22] or [23], which is a prophylactic and/or therapeutic agent for cancer, Alzheimer's disease, dementia, dietary disorder, hypertension, gonadal dysfunction, thyroid dysfunction, pituitary dysfunction, diabetes mellitus, lipidosis, hyperlipidemia or anorexia nervosa;

[25] The medicine according to [22] or [23], which is a prophylactic and/or therapeutic agent for a disease attributable to TGR23;

[26] A method for preventing and/or treating cancer, Alzheimer's disease, dementia, dietary disorder, hypertension, gonadal dysfunction, thyroid dysfunction, pituitary dysfunction, diabetes mellitus, lipidosis, hyperlipidemia or anorexia nervosa, which comprises administering an effective amount of the compound according to [1] or a salt thereof to a mammal;

[27] A method for preventing and/or treating a disease attributable to TGR23 in a mammal, which comprises administering an effective amount of the compound according to [1] or a salt thereof to said mammal;

[28] Use of the compound according to [1] for the manufacture of a prophylactic and/or therapeutic agent for cancer, Alzheimer's disease, dementia, dietary disorder, hypertension, gonadal dysfunction, thyroid dysfunction, pituitary dysfunction, diabetes mellitus, lipidosis, hyperlipidemia or anorexia nervosa;

[29] Use of the compound according to [1] for the manufacture of a prophylactic and/or therapeutic agent for a disease attributable to TGR23;

[30] A method for preventing and/or treating cancer, Alzheimer's disease, dementia, dietary disorder, hypertension, gonadal dysfunction, thyroid dysfunction, pituitary dysfunction, diabetes mellitus, lipidosis, hyperlipidemia or anorexia nervosa, which comprises administering an effective amount of the compound represented by formula (II) in [23] or a salt thereof to a mammal;

[31] A method for preventing and/or treating a disease attributable to TGR23 in a mammal, which comprises administering an effective amount of the compound represented by formula (II) in [23] or a salt thereof to said mammal;

[32] Use of the compound represented by formula (II) in [23] for the manufacture of a prophylactic and/or therapeutic agent for cancer, Alzheimer's disease, dementia, dietary disorder, hypertension, gonadal dysfunction, thyroid dysfunction, pituitary dysfunction, diabetes mellitus, lipidosis, hyperlipidemia or anorexia nervosa; and

[33] Use of the compound represented by formula (II) in [23] for the manufacture of a prophylactic and/or therapeutic agent for a disease attributable to TGR23.

Compound (II), which includes Compound (I), has an excellent TGR23 antagonist activity based on its specific chemical structure, and thus the Compound (II) including Compound (I) is useful as a prophylactic and/or therapeutic medicine for preventing and/or treating cancer, Alzheimer's disease, dementia, dietary disorder, hypertension, gonadal dysfunction, thyroid dysfunction, pituitary dysfunction, diabetes mellitus, lipidosis, hyperlipidemia and anorexia nervosa.

BEST MODE FOR CARRYING OUT THE INVENTION

Hereinafter, each reference symbol in the formulas will be described.

1) Regarding $R^1$ ($R^{1'}$)

The "acyl group" represented by $R^1$ or $R^{1'}$ in formula (I) and (II) may be exemplified by a group represented by the formula: —(C=O)—$R^6$, —(C=O)—$OR^6$, —(C=O)—$NR^7R^8$, —(C=S)—$NR^7R^8$, —SO—$R^6$, —$SO_2$—$R^6$ or —$SO_2$—$NR^7R^8$

[wherein $R^6$ is a hydrocarbon group which may be substituted, or a heterocyclic group which may be substituted, $R^7$ is a hydrogen atom, a hydrocarbon group which may be substituted, a heterocyclic group which may be substituted, a $C_{6-12}$ aryl-carbonyl group, a $C_{1-6}$ alkoxy-carbonyl group, or a 5- to 6-membered aromatic heterocyclic carbonyl group, and $R^8$ is a hydrogen atom, a $C_{1-6}$ alkyl group, or an amino group which may be substituted, or $R^7$ and $R^8$ may form, together with the adjacent nitrogen atom, a ring which may be substituted.

In the formulas, the "hydrocarbon group" of the "hydrocarbon group which may be substituted" represented by $R^6$ may be exemplified by a straight-chained or cyclic hydrocarbon group (e.g., an alkyl group, an alkenyl group, an alkynyl group, a cycloalkyl group, an aryl group, an aralkyl group, etc.) or the like. Among these, straight-chained or cyclic hydrocarbon groups having 1 to 16 carbon atoms are preferred.

Examples of the "alkyl group" preferably include a $C_{1-6}$ alkyl group (e.g., a methyl group, an ethyl group, a propyl group, an isopropyl group, a butyl group, an isobutyl group, a sec-butyl group, a tert-butyl group, a pentyl group, a hexyl group, etc.) and the like.

Examples of the "alkenyl group" preferably include a $C_{2-6}$ alkenyl group (e.g., a vinyl group, an allyl group, an isopropenyl group, a 1-butenyl group, a 2-butenyl group, a 3-butenyl group, a 2-methyl-2-propenyl group, a 1-methyl-2-propenyl group, a 2-methyl-1-propenyl group, etc.) and the like.

Examples of the "alkynyl group" preferably include a $C_{2-6}$ alkynyl group (e.g., an ethynyl group, a propargyl group, a 1-butynyl group, a 2-butynyl group, a 3-butynyl group, a 1-hexynyl group, etc.) and the like.

Examples of the "cycloalkyl group" preferably include a $C_{3-6}$ cycloalkyl group (e.g., a cyclopropyl group, a cyclobutyl group, a cyclopentyl group, a cyclohexyl group, etc.) and the like. The "cycloalkyl group" may be condensed with one or two $C_{6-14}$ aromatic carbon rings (e.g., a benzene ring, etc.) (e.g., a 1-indanyl group, a 1,2,3,4-tetrahydro-1-naphthyl group, etc.).

Examples of the "aryl group" preferably include a $C_{6-14}$ aryl group (e.g., a phenyl group, a 1-naphthyl group, a 2-naphthyl group, a 2-biphenylyl group, a 3-biphenylyl group, a 4-biphenylyl group, a 2-anthryl group, etc.) and the like.

Examples of the "aralkyl group" preferably include a $C_{7-16}$ aralkyl group (e.g., a benzyl group, a phenethyl group, a diphenylmethyl group, a 1-naphthylmethyl group, a 2-naphthylmethyl group, a 2,2-diphenylethyl group, a 3-phenylpropyl group, a 4-phenylbutyl group, a 5-phenylpentyl group, etc.) and the like.

The "substituent" for the "hydrocarbon group which may be substituted" represented by $R^6$ may be exemplified by a halogen atom (e.g., fluorine, chlorine, bromine, iodine, etc.), a $C_{1-3}$ alkylenedioxy group (e.g., a methylenedioxy group, an ethylenedioxy group, etc.), a nitro group, a cyano group, a $C_{1-6}$ alkyl group which may be substituted, a $C_{2-6}$ alkenyl group which may be halogenated, a carboxy-$C_{2-6}$ alkenyl group (e.g., a 2-carboxyethenyl group, a 2-carboxy-2-methylethenyl group, etc.), a $C_{2-6}$ alkynyl group which may be halogenated, a $C_{3-8}$ cycloalkyl group which may be halogenated and may be condensed, a $C_{6-14}$ aryl group which may be halogenated, a $C_{1-8}$ alkoxy group which may be halogenated, a $C_{1-6}$ alkoxy-carbonyl-$C_{1-6}$ alkoxy group (e.g., an ethoxycarbonylmethyloxy group, etc.), a hydroxy group, a $C_{6-14}$ aryloxy group (e.g., a phenyloxy group, a 1-naphthyloxy group, a 2-naphthyloxy group, etc.), a $C_{7-16}$ aralkyloxy group (e.g., a benzyloxy group, a phenethyloxy group, etc.), a mercapto group, a $C_{1-6}$ alkylthio group which may be halogenated, a $C_{6-14}$ arylthio group (e.g., a phenylthio group, a 1-naphthylthio group, a 2-naphthylthio group, etc.), a $C_{7-16}$ aralkylthio group (e.g., a benzylthio group, a phenethylthio group, etc.), an amino group, a mono-$C_{1-6}$ alkylamino group (e.g., a methylamino group, an ethylamino group, etc.), a di-$C_{1-6}$ alkylamino group (e.g., a dimethylamino group, a diethylamino group, an ethylmethylamino group, etc.), a mono- or di-$C_{6-14}$ arylamino group which may be halogenated, a sulfonyl-amino group which may be substituted with a benzene ring which may be substituted with a nitro group (e.g., a nitrobenzylsulfonylamino group), a $C_{3-7}$ cycloalkylamino group (e.g., a cyclopropylamino group), a $C_{1-6}$ alkylsulfonyl-amino group (e.g., a methylsulfonylamino group), a $C_{3-8}$ cycloalkyl-$C_{1-6}$ alkyl-amino group (e.g., a cycloalkylmethylamino group), a $C_{1-6}$ alkyl-carbonyl-amino group (e.g., a methylcarbonylamino group), a $C_{2-8}$ alkenyl-amino group (e.g., an allylamino group), $C_{1-6}$ alkoxy-$C_{1-6}$ alkylamino group (e.g., a methoxyethylamino group), an azidocarbonylamino group, an aminocarbonylamino group, a $C_{7-13}$ aralkylamino group (e.g., a benzylamino group), a formyl group, a carboxy group, a $C_{1-6}$ alkyl-carbonyl group (e.g., an acetyl group, a propionyl group, etc.), a $C_{3-6}$ a cycloalkyl-carbonyl group (e.g., a cyclopropylcarbonyl group, a cyclopentylcarbonyl group, a cyclohexylcarbonyl group, etc.), a $C_{1-6}$ alkoxy-carbonyl group (e.g., a methoxycarbonyl group, an ethoxycarbonyl group a propoxycarbonyl group, a tert-butoxycarbonyl group, etc.), a 5- to 7-membered cyclic aminocarbonyl group (e.g., a morpholinocarbonyl group), a $C_{6-14}$ aryl-carbonyl group (e.g., a benzoyl group, a 1-naphthoyl group, a 2-naphthoyl group, etc.), a $C_{7-16}$ aralkyl-carbonyl group (e.g., a phenylacetyl group, a 3-phenylpropionyl group, etc.), a $C_{6-14}$ an aryloxy-carbonyl group (e.g., a phenoxycarbonyl group, etc.), a $C_{7-16}$ aralkyloxy-carbonyl group (e.g., a benzyloxycarbonyl group, a phenethyloxycarbonyl group, etc.), a 5- to 6-membered heterocyclic carbonyl group (e.g., a nicotinoyl group, an isonicotinoyl group, a thenoyl group, a furoyl group, a morpholinocarbonyl group, a thiomorpholinocarbonyl group, a piperazin-1-ylcarbonyl group, a pyrrolidin-1-ylcarbonyl group, etc.), a carbamoyl group, a mono-$C_{1-6}$ alkyl-carbamoyl group (e.g., a methylcarbamoyl group, an ethylcarbamoyl group, etc.), a di-$C_{1-6}$ alkyl-carbamoyl group (e.g., a dimethylcarbamoyl group, a diethylcarbamoyl group, an ethylmethylcarbamoyl group, etc.), a $C_{6-14}$ arylcarbamoyl group (e.g., a phenylcarbamoyl group, a 1-naphthylcarbamoyl group, a 2-naphthylcarbamoyl group, etc.), a 5- to 6-membered heterocyclic carbamoyl group, (e.g., a 2-pyridylcarbamoyl group, a 3-pyridylcarbamoyl group, a 4-pyridylcarbamoyl group, a 2-thienylcarbamoyl group, a 3-thienylcarbamoyl group, etc.), a $C_{1-6}$ alkylsulfonyl group (e.g., a methylsulfonyl group, an ethylsulfonyl group, etc.), a $C_{6-14}$ arylsulfonyl group (e.g., a phenylsulfonyl group, a 1-naphthylsulfonyl group, a 2-naphthylsulfonyl group, etc.), a formylamino group, a $C_{1-6}$ alkyl-carbonylamino group (e.g., an acetylamino group, etc.), a $C_{6-14}$ aryl-carbonylamino group (e.g., a benzoylamino group, a naphthoylamino group, etc.), a $C_{1-6}$ alkoxy-carbonylamino group (e.g., a methoxycarbonylamino group, an ethoxycarbonylamino group, a propoxycarbonylamino group, a butoxycarbonylamino group, etc.), a $C_{1-6}$ alkylsulfonylamino group (e.g., a methylsulfonylamino group, an ethylsulfonylamino group, etc.), a $C_{6-14}$ arylsulfonylamino group (e.g., a phenylsulfonylamino group, a 2-naphthylsulfonylamino group, a 1-naphthylsulfonylamino group, etc.), a $C_{1-6}$ alkyl-carbonyloxy group (e.g., an acetoxy group, a propionyloxy group, etc.), a $C_{6-14}$ arylcarbonyloxy group (e.g., a benzoyloxy group, a naphthylcarbonyloxy group, etc.), a $C_{1-6}$ alkoxy-carbonyloxy group, (e.g., a methoxycarbonyloxy group, an ethoxycarbonyloxy group, a propoxycarbonyloxy group, a butoxycarbonyloxy group, etc.), a mono-$C_{1-6}$ alkyl-carbamoyloxy group (e.g., a methylcarbamoyloxy group, an ethylcarbamoyloxy group, etc.), a di-$C_{1-6}$ alkyl-carbamoyloxy group (e.g., a dimethylcarbamoyloxy group, a diethylcarbamoyloxy group, etc.), a $C_{6-14}$ aryl-carbamoyloxy group (e.g., a phenylcarbamoyloxy group, a naphthylcarbamoyloxy group, etc.), a 5- to 6-membered heterocyclic carbonyloxy group (e.g., a nicotinoyloxy group, an isonicotinoyloxy group, etc.), a 5- to 10-membered (preferably, 5- to 7-membered) cyclic amino group which may be substituted with a substituent (e.g., an oxo group, etc.) and may be condensed with a benzene ring, a 5- or 7-membered non-aromatic heterocyclic group which may be substituted, a 5- to 10-membered aromatic heterocyclic group which may be substituted (e.g., a 2-thienyl group, a 3-thienyl group, a 2-furyl group, a 3-furyl group, a 2-pyridyl group, a 3-pyridyl group, a 4-pyridyl group, a 2-quinolyl group, a 3-quinolyl group, a 4-quinolyl group, a 5-quinolyl group, a 8-quinolyl group, a 1-isoquinolyl group, a 3-isoquinolyl group, a 4-isoquinolyl group, a 5-isoquinolyl group, a 1-indolyl group, a 2-indolyl group, a 3-indolyl group, a 2-benzothiazolyl group, a 2-benzo[b]thienyl group, a 3-benzo[b]thienyl group, a 2-benzo[b]furanyl group, a 3-benzo[b]furanyl group, etc., preferably a 5- to 6-membered aromatic heterocyclic group), a sulfo group, an oxo group, or the like.

The "hydrocarbon group" may have, for example, 1 to 5, preferably 1 to 3, of the above-described substituents at substitutable positions, and when there are two or more substituents, the substituents may be identical or different.

The "$C_{1-6}$ alkyl group" of the "$C_{1-6}$ alkyl group which may be substituted" may be exemplified by a $C_{1-6}$ alkyl group such as a methyl group, an ethyl group, a propyl group, an isopropyl group, a butyl group, an isobutyl group, a sec-butyl group, a tert-butyl group, a pentyl group or a hexyl group.

The "substituent" for the "$C_{1-6}$ alkyl group which may be substituted" may be exemplified by (i) a halogen atom (e.g., fluorine, chlorine, bromine, iodine, etc.), (ii) an amino group which may have one or two substituents selected from a halogen atom, a $C_{1-6}$ alkoxy-carbonyl group, a $C_{1-6}$ alkyl group, a $C_{1-6}$ alkoxy-$C_{1-6}$ alkyl group, an azidocarbonyl group, an aminocarbonyl group and a $C_{7-13}$ aralkyl group (e.g., an amino group, a methylamino group, an ethylamino group, a propylamino group, an isopropylamino group, a sec-butylamino group, a dimethylamino group, a diethylamino group, a dipropylamino group, a diisopropylamino group, a methoxycarbonylamino group, an ethoxycarbonylamino group, a tert-butoxycarbonylamino group, a [(methoxycarbonyl)methyl]amino group, a (methoxymethyl)amino group, an azidocarbonylamino group, an aminocarbonylamino group, a benzylamino group, a dibenzylamino group, etc.), (iii) a 5- to 10-membered aromatic heterocyclic group which may be oxidized and may have a cyano group (e.g., a 2-thienyl group, a 3-thienyl group, a 2-furyl group, a 3-furyl group, a 2-pyridyl group, a 3-pyridyl group, a 4-pyridyl group, a 2-quinolyl group, a 3-quinolyl group, a 4-quinolyl group, a 5-quinolyl group, an 8-quinolyl group, a 1-isoquinolyl group, a 3-isoquinolyl group, a 4-isoquinolyl group, a 5-isoquinolyl group, a 1-indolyl group, a 2-indolyl group, a 3-indolyl group, a 2-benzothiazolyl group, a 2-benzo[b]thienyl group, a 3-benzo[b]thienyl group, a 2-benzo[b]furanyl group, a 3-benzo[b]furanyl group, etc.), (iv) a 5- to 7-membered cyclic amino group which may be substituted with substituents (e.g., one to five $C_{1-6}$ alkyl groups, etc.) and may be condensed with one or two benzene rings (e.g., a pyrrolidino group, a piperidino group, a piperazino group, a morpholino group, a thiomorpholino group, a hexahydroazepin-1-yl group, etc.), a (v) a $C_{1-6}$ alkoxy-carbonyl group, (vi) a carboxy group, a (vii) a 5- to 7-membered saturated cyclic amino-carbonyl group (e.g., a pyrrolidinocarbonyl group, a piperidinocarbonyl group, a morpholinocarbonyl group, etc.), a (viii) a $C_{6-12}$ aryl group (e.g., a phenyl group, a 1-naphthyl group, a 2-naphthyl group, etc.), a (ix) a $C_{6-12}$ arylcarbonyl group (e.g., a benzoyl group, a 1-naphthoyl group, a 2-naphthoyl group, etc.), (x) a hydroxy group, (xi) a $C_{3-8}$ cycloalkyl group, (xii) a $C_{2-8}$ alkenyl group, (xiii) a carbamoyl group, or the like. The "$C_{1-6}$ alkyl group" may have, for example, 1 to 5, preferably 1 to 3, of the above-described substituents at substitutable positions, and when there are two or more substituents, the substituents may be identical or different.

Specific examples of the "$C_{1-6}$ alkyl group which may be substituted" include a methyl group, a trifluoromethyl group, a (2-thienyl)methyl group, an ethyl group, a 2-piperidinoethyl group, a propyl group, a 3-(1-oxido-3-pyridyl)propyl group, a 2-(4-chlorophenyl)butyl group, and the like.

The "$C_{2-6}$ alkenyl group which may be halogenated" may be exemplified by a $C_{2-6}$ alkenyl group which may have 1 to 5, preferably 1 to 3, halogen atoms (e.g., fluorine, chlorine, bromine, iodine, etc.) (e.g., a vinyl group, a propenyl group, an isopropenyl group, a 2-buten-1-yl group, a 4-penten-1-yl group, a 5-hexen-1-yl group, etc.), or the like.

The "$C_{2-6}$ alkynyl group which may be halogenated" may be exemplified by a $C_{2-6}$ alkynyl group which may have 1 to 5, preferably 1 to 3, halogen atoms (e.g., fluorine, chlorine, bromine, iodine, etc.) (e.g., a 2-butyn-1-yl group, a 4-pentyn-1-yl group, a 5-hexyn-1-yl group, etc.), or the like.

The "$C_{3-8}$ cycloalkyl group which may be halogenated" of the "$C_{3-8}$ cycloalkyl group which may be halogenated and may be condensed" may be exemplified by a $C_{3-6}$ cycloalkyl group which may have 1 to 5, preferably 1 to 3, halogen atoms (e.g., fluorine, chlorine, bromine, iodine, etc.) (e.g., a cyclopropyl group, a cyclobutyl group, a cyclopentyl group, a cyclohexyl group, etc.), or the like. Specific examples include a cyclopropyl group, a cyclobutyl group, a cyclopentyl group, a cyclohexyl group, a 4,4-dichlorocyclohexyl group, a 2,2,3,3-tetrafluorocyclopentyl group, a 4-chlorocyclohexyl group and the like.

The "$C_{3-8}$ cycloalkyl group which may be condensed" of the "$C_{3-8}$ cycloalkyl group which may be halogenated and may be condensed" may be exemplified by a 3 to 8-membered bicyclic or tricyclic cycloalkyl group (e.g., a 9-fluorenyl group, a 1-indanyl group, a 1,2,3,4-tetrahydro-1-naphthyl group, etc.), preferably a $C_{3-8}$ cycloalkyl group condensed with 1 or 2 benzene rings. Further, the "condensed $C_{3-8}$ cycloalkyl group" may be halogenated.

The "$C_{6-14}$ aryl group which may be halogenated" may be exemplified by a $C_{6-14}$ aryl group which may have 1 to 5, preferably 1 to 3, halogen atoms (e.g., fluorine, chlorine, bromine, iodine, etc.) (e.g., a phenyl group, a 1-naphthyl group, a 2-naphthyl group, a 2-biphenylyl group, a 3-biphenylyl group, a 4-biphenylyl group, a 2-anthryl group, etc.), or the like. Specific examples include a 3,4-dichlorophenyl group, a 4-bromophenyl group, a 6-fluoro-1-naphthyl group, a 2'-chloro-4-biphenylyl group and the like.

The "$C_{1-8}$ alkoxy group which may be halogenated" may be exemplified by a $C_{1-8}$ alkoxy group which may have 1 to 5, preferably 1 to 3, halogen atoms (e.g., fluorine, chlorine, bromine, iodine, etc.) (e.g., a methoxy group, an ethoxy group, a propoxy group, an isopropoxy group, a butoxy group, an isobutoxy group, a sec-butoxy group, a pentyloxy group, a hexyloxy group, etc.), or the like. Specific examples thereof include a methoxy group, a difluoromethoxy group, a trifluoromethoxy group, an ethoxy group, a 2,2,2-trifluoroethoxy group, a propoxy group, an isopropoxy group, a butoxy group, a 4,4,4'-trifluorobutoxy group, an isobutoxy group, a sec-butoxy group, a pentyloxy group, a hexyloxy group and the like.

The "mono- or di-$C_{6-14}$ arylamino group which may be halogenated" may be exemplified by a mono-$C_{6-14}$ arylamino group which may have 1 to 5, preferably 1 to 3, halogen atoms (e.g., fluorine, chlorine, bromine, iodine, etc.) (e.g., a phenylamino group, a 1-naphthylamino group, a 2-naphthylamino group, etc.), or a di-$C_{6-14}$ arylamino group which may have 1 to 5, preferably 1 to 3, halogen atoms (e.g., fluorine, chlorine, bromine, iodine, etc.) (e.g., a diphenylamino group, etc.), or the like. Specific examples thereof include a 2,4-difluorophenylamino group, a 3-chlorophenylamino group, a bis(4-chlorophenyl)amino group, and the like.

The "$C_{1-6}$ alkylthio group which may be halogenated" may be exemplified by a $C_{1-6}$ alkylthio group which may have, for example, 1 to 5, preferably 1 to 3, halogen atoms (e.g., fluorine, chlorine, bromine, iodine, etc.) (e.g., a methylthio group, an ethylthio group, a propylthio group, an isopropylthio group, a butylthio group, a sec-butylthio group, a tert-butylthio group, etc.), or the like. Specific examples thereof include a methylthio group, a difluoromethylthio group, a trifluoromethylthio group, an ethylthio group, a propylthio group, an isopropylthio group, a butylthio group, a 4,4,4-trifluorobutylthio group, a pentylthio group, a hexylthio group, and the like.

The "5- to 10-membered (preferably 5- to 7-membered) cyclic amino group" of the "5- to 10-membered (preferably 5- to 7-membered) cyclic amino group which may be substituted and may be condensed with a benzene ring" may be exemplified by a 5- to 10-membered (preferably 5- to 7-membered) cyclic amino saturated or unsaturated cyclic amino group which may have, in addition to one nitrogen atom and carbon atoms, 1 to 4 heteroatoms of one or two species selected from a nitrogen atom, a sulfur atom and an oxygen atom. Specific examples of the 5- to 10-membered (preferably 5- to 7-membered) saturated cyclic amino group include a pyrrolidino group, a piperidino group, a piperazino group, a morpholino group, a thiomorpholino group, a hexahydroazepin-1-yl group and the like. Specific examples of the 5- to 10-membered (preferably 5- to 7-membered) unsaturated cyclic amino group include a 3,6-dihydropyridin-1(2H)-yl group, a 1,2,5,6-tetrahydro-1H-azepin-1-yl group and the like.

The "substituent" of the "5- to 10-membered (preferably 5- to 7-membered) cyclic amino group which may be substituted and may be condensed with a benzene ring" may be exemplified by, for example, a $C_{1-6}$ alkyl group (e.g., a methyl group, an ethyl group, a propyl group, an isopropyl group, a butyl group, an isobutyl group, a sec-butyl group, a tert-butyl group, a pentyl group, a hexyl group, etc.), a hydroxy group, a $C_{1-6}$ alkoxy-carbonyl group (e.g., a methoxycarbonyl group, an ethoxycarbonyl group, a propoxycarbonyl group, a butoxycarbonyl group, a t-butoxycarbonyl group), a $C_{6-14}$ aryl group (e.g., a phenyl group, a 1-naphthyl group, a 2-naphthyl group, a 2-biphenylyl group, a 3-biphenylyl group, a 4-biphenylyl group, a 2-anthryl group, etc.), a $C_{1-6}$ alkyl-carbonyl group (e.g., an acetyl group, a propionyl group, etc.), a 5- to 10-membered aromatic heterocyclic group (e.g., a 2-thienyl group, a 3-thienyl group, a 2-pyridyl group, a 3-pyridyl group, a 4-pyridyl group, a 2-quinolyl group, a 3-quinolyl group, a 4-quinolyl group, a 5-quinolyl group, a 8-quinolyl group, a 1-isoquinolyl group, a 3-isoquinolyl group, a 4-isoquinolyl group, a 5-isoquinolyl group, a 1-indolyl group, a 2-indolyl group, a 3-indolyl group, a 2-benzothiazolyl group, a 2-benzo[b]thienyl group, a 3-benzo[b]thienyl group, a 2-benzo[b]furanyl group, a 3-benzo[b]furanyl group, etc.), an oxo group, or the like. The "5- to 7-membered cyclic amino group" may have, for example, 1 to 5, preferably 1 to 3, of the above-described substituents at substitutable positions, and when there are two or more substituents, the substituents may be identical or different.

The "5- or 7-membered non-aromatic heterocyclic group" of the "5- or 7-membered non-aromatic heterocyclic group which may be substituted" may be exemplified by a 2-morpholinyl group, a 3-morpholinyl group, a 2-piperidyl group, a 4-piperidinyl group, a 2-piperazinyl group, or the like.

The "substituent" of the "5- or 7-membered non-aromatic heterocyclic group which may be substituted" or the "5- to 10-membered (preferably 5- or 6-membered) aromatic heterocyclic group which may be substituted" may be exemplified by a $C_{1-6}$ alkyl group (e.g., a methyl group, an ethyl group, a propyl group, an isopropyl group, a butyl group, an isobutyl group, a sec-butyl group, a tert-butyl group, a pentyl group, a hexyl group, etc.), a hydroxy group, a cyano group, a $C_{6-14}$ aryl group (e.g., a phenyl group, a 1-naphthyl group, a 2-naphthyl group, a 2-biphenylyl group, a 3-biphenylyl group, a 4-biphenylyl group, a 2-anthryl group, etc.), a $C_{1-6}$ alkyl-carbonyl group (e.g., an acetyl group, a propionyl group, etc.), a 5- to 10-membered aromatic heterocyclic group (e.g., a 2-thienyl group, a 3-thienyl group, a 2-pyridyl group, a 3-pyridyl group, a 4-pyridyl group, a 2-quinolyl group, a 3-quinolyl group, a 4-quinolyl group, a 5-quinolyl group, an 8-quinolyl group, a 1-isoquinolyl group, a 3-isoquinolyl group, a 4-isoquinolyl group, a 5-isoquinolyl group, a 1-indolyl group, a 2-indolyl group, a 3-indolyl group, a 2-benzothiazolyl group, a 2-benzo[b]thienyl group, a 3-benzo[b]thienyl group, a 2-benzo[b]furanyl group, a 3-benzo[b]furanyl group, etc.), an oxo group or the like. The "5- or 7-membered non-aromatic heterocyclic group" and "5- to 10-membered (preferably 5- or 6-membered) aromatic heterocyclic group" may have, for example, 1 to 5, preferably 1 to 3, of the above-described substituents at substitutable positions, and when there are two or more substituents, the substituents may be identical or different.

The "heterocyclic group" of the "heterocyclic group which may be substituted" represented by $R^6$ may be exemplified by a 5- to 14-membered (monocyclic, bicyclic or tricyclic) heterocyclic ring containing, in addition to carbon atoms, 1 to 4 heteroatoms of one or two species selected from a nitrogen atom, a sulfur atom and an oxygen atom, preferably (i) a 5- to 14-membered (preferably 5 to 10-membered, more preferably 5- or 6-membered) aromatic heterocyclic ring, (ii) a 5- to 10-membered (preferably 5- or 6-membered) non-aromatic heterocyclic ring, or (iii) a monovalent group formed by excluding any one hydrogen atom from a 7- to 10-membered heterocyclic bridged ring, or the like.

The "5- to 14-membered (preferably 5- to 10-membered) aromatic heterocyclic ring" may be exemplified by an aromatic heterocyclic ring such as thiophene, benzo[b]thiopene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazane or phenoxadine, or a ring formed from any of these rings (preferably monocyclic) condensed with one or more (preferably one or two) aromatic rings (e.g., a benzene ring, etc.), or the like.

Examples of the "5- to 10-membered (preferably 5- or 6-membered) non-aromatic heterocyclic ring" include pyrrolidine, imidazoline, pyrazolidine, pyrazoline, piperidine, piperazine, morpholine, thiomorpholine, dioxazole, oxadiazoline, thiadiazoline, triazoline, thiadiazole, dithiazole, and the like.

The "7- to 10-membered heterocyclic bridged ring" may be exemplified by quinuclidine, 7-azabicyclo[2.2.1]heptane or the like.

The "heterocyclic group" is preferably a 5- to 14-membered (preferably 5- to 10-membered, more preferably 5- or 6-membered) (monocyclic or bicyclic) heterocyclic group containing, in addition to carbon atoms, preferably 1 to 4 heteroatoms of one or two species selected from a nitrogen atom, a sulfur atom and an oxygen atom. Specific examples thereof include aromatic heterocyclic groups such as a 2-thienyl group, a 3-thienyl group, a 2-furyl group, a 3-furyl group, a 2-pyridyl group, a 3-pyridyl group, a 4-pyridyl group, a 2-quinolyl group, a 3-quinolyl group, a 4-quinolyl group, a 5-quinolyl group, an 8-quinolyl group, a 1-isoquinolyl group, a 3-isoquinolyl group, a 4-isoquinolyl group, a 5-isoquinolyl group, a pyrazinyl group, a 2-pyrimidinyl group, a 4-pyrimidinyl group, 3-pyrrolyl group, a 2-imidazolyl group, a 3-pyridazinyl group, a 3-isothiazolyl group, a 3-isoxazolyl group, a 1-indolyl group, a 2-indolyl group, a 3-indolyl group, a 2-benzothiazolyl group, a 2-benzo[b]thienyl group, a 3-benzo[b]thienyl group, a 2-benzo[b]furanyl group, and a 3-benzo[b]furanyl group; a non-aromatic heterocyclic group such as a 1-pyrrolidinyl group, a 2-pyrrolidinyl group, 3-pyrrolidinyl group, a 2-imidazolinyl group, a 4-imidazolinyl group, a 2-pyrazolidinyl group, a 3-pyrazolidinyl group, a 4-pyrazolidinyl group, a piperidino group, a 2-piperidyl group, a 3-piperidiyl group, a 4-piperidyl group, a 1-piperazinyl group, a 2-piperazinyl group, a morpholino group, and a thiomorpholino group; and the like.

Among these, a 5- to 6-membered non-aromatic or aromatic heterocyclic group containing, in addition to carbon atoms, for example, 1 to 3 heteroatoms selected from a nitrogen atom, a sulfur atom and an oxygen atom, or the like is even more preferred. Specific examples thereof include a 2-thienyl group, a 3-thienyl group, a 2-pyridyl group, a 3-pyridyl group, a 4-pyridyl group, a 2-furyl group, a 3-furyl group, a pyrazinyl group, a 2-pyrimidinyl group, a 3-pyrrolyl group, a 3-pyridazinyl group, a 3-isothiazolyl group, a 3-isoxazolyl group, a 1-pyrrolidinyl group, a 2-pyrrolidinyl group, a 3-pyrrolidinyl group, a 2-imidazolinyl group, a 4-imidazolinyl group, a 2-pyrazolidinyl group, a 3-pyrazolidinyl group, a 4-pyrazolidinyl group, a piperidino group, a 2-piperidyl group, a 3-piperidyl group, a 4-piperidyl group, a 1-piperazinyl group, a 2-piperazinyl group, a morpholino group, a thiomorpholino group and the like.

The "substituent" for the "heterocyclic group which may be substituted" may be exemplified by the same one as the "substituent" for the above-described "hydrocarbon group which may be substituted" represented by $R^6$, or an oxo group or the like.

The "heterocyclic group" may have, for example, 1 to 5, preferably 1 to 3, of the above-described substituents at substitutable positions, and when there are two or more substituents, the substituents may be identical or different.

The "hydrocarbon group which may be substituted" and the "heterocyclic group which may be substituted" represented by $R^7$ may be exemplified by the same ones as the "hydrocarbon group which may be substituted" and the "heterocyclic group which may be substituted" represented by $R^6$, and (a) a 5- to 7-membered cyclic amino group which may be substituted with a substituent (a hydroxy group, a $C_{1-6}$ alkoxy-carbonyl group, etc.) and may be condensed with a benzene ring, (b) a 5- to 6-membered aromatic heterocyclic-$C_{1-6}$ alkyl group which may be substituted with a substituent (a hydroxy group, a $C_{1-6}$ alkyl group, a cyano group, etc.) and may be an oxide, (c) a 5- to 10-membered (preferably 5- or 6-membered) aromatic heterocyclic group which may be substituted with a substituent (an oxo group, a $C_{1-6}$ alkoxy-carbonyl group, a $C_{1-6}$ alkyl group, etc.), (d) a 5- to 7-membered non-aromatic heterocyclic group which may be substituted with a substituent (a $C_{1-6}$ alkyl group, a $C_{1-6}$ alkoxy-carbonyl group, an oxo group, etc.), (e) a 5- to 7-membered cyclic amino-$C_{1-6}$ alkyl-carbonyl group, (f) a $C_{3-8}$ cycloalkyl group which may be substituted with a $C_{1-6}$ alkyl group which may be have a cyclic amino group, (g) a $C_{1-6}$ alkyl group which may be substituted with a substituent (a $C_{3-8}$ cycloalkyl-amino group, a $C_{1-6}$ alkyl-amino group which may be substituted with a $C_{3-8}$ cycloalkyl, a sulfonylamino group which may be substituted with a benzene ring which may be substituted with a nitro group, a $C_{2-8}$ alkenyl-amino group, etc.), or the like.

Examples of the "$C_{6-12}$ aryl-carbonyl group" represented by $R^7$ include a benzoyl group, a 1-naphthoyl group, a 2-naphthoyl group and the like.

Examples of the "$C_{1-6}$ alkoxy-carbonyl group" represented by $R^7$ include a methoxy group, a carbonyl group, an ethoxycarbonyl group, a propoxycarbonyl group, a tert-butoxycarbonyl group and the like.

Examples of the "5- or 6-membered aromatic heterocyclic carbonyl group" represented by $R^7$ include a 3-furoyl group, a 2-thenoyl group, a nicotinoyl group, an isonicotinoyl group and the like.

Examples of the "$C_{1-6}$ alkyl group" represented by $R^8$ include a methyl group, an ethyl group, a propyl group, an isopropyl group, a butyl group, an isobutyl group, a sec-butyl group, a tert-butyl group, a pentyl group, a hexyl group and the like.

The "substituent" for the "amino group which may be substituted" represented by $R^8$ may be exemplified by one or two of the "substituent" for the above-described "hydrocarbon group which may be substituted" represented by $R^6$. When there are two substituents, the substituents may be identical or different.

The "ring" of the "ring which may be substituted" formed by $R^7$ and $R^8$ together with the adjacent nitrogen atom may be exemplified by a monocyclic or polycyclic (preferably monocyclic, bicyclic or tricyclic) 5- to 14-membered ring (preferably 5- to 10-membered ring) which may contain, in addition to one nitrogen atom and carbon atoms, 1 to 4 heteroatoms of one or two species selected from a nitrogen atom, a sulfur atom and an oxygen atom (e.g., pyrrolidine, piperidine, piperazine, morpholine, thiomorpholine, 1,2,3,4-tetrahydroquinoline, 1,2,3,4-tetrahydroisoquinoline, etc.). The "substituent" for the "ring which may be substituted" may be exemplified by one or two of the "substituent" for the above-described "hydrocarbon group which may be substituted" represented by $R^6$. For example, a 5- to 7-membered saturated cyclic amino group, a $C_{1-6}$ alkyl group or the like is used. When there are two substituents, the substituents may be identical or different.

With regard to the compound represented by formula (II), $R^{1'}$ is a hydrogen atom, a hydrocarbon group which may be substituted, or a heterocyclic group which may be substituted, in addition to the above-mentioned acyl group. In formula (II), the "hydrocarbon group which may be substituted" and the "heterocyclic group which may be substituted" represented by $R^{1'}$ may be exemplified by the above-described "hydrocarbon group which may be substituted" and the "heterocyclic group which may be substituted" represented by $R^6$, respectively.

2) Regarding $R^2$ and $R^3$

The "hydrocarbon group which may be substituted" and the "heterocyclic group which may be substituted" represented by $R^2$ may be exemplified by the above-described "hydrocarbon group which may be substituted" and the "heterocyclic group which may be substituted" represented by $R^6$, respectively.

The "hydrocarbon group which may be substituted" and the "heterocyclic group which may be substituted" represented by $R^3$ may be exemplified by the above-described "hydrocarbon group which may be substituted" and the "heterocyclic group which may be substituted" represented by $R^6$, respectively.

3) Regarding $R^4$, $R^{4'}$, $R^{4''}$ and $R^5$

The "hydrocarbon group which may be substituted" and the "heterocyclic group which may be substituted" represented by $R^4$, $R^{4'}$, $R^{4''}$ and $R^5$ may be exemplified by the above-described "hydrocarbon group which may be substituted" and the "heterocyclic group which may be substituted" represented by $R^6$, respectively. $R^{4''}$ may be also an oxo group, and $R^5$ may be a hydrogen atom.

4) Regarding n, m and k n, m and k are an integer from 0 to 4, an integer from 0 to 8, and an integer from 0 to 8, respectively, and when n is 2 to 4, m is 2 to 8, and k is 2 to 8, $R^4$, $R^{4'}$ and $R^{4''}$ may be identical or different.

5) Regarding X

X is an oxygen atom, a sulfur atom, or a group represented by the formula $NR^5$ (wherein $R^5$ is a hydrogen atom, a hydrocarbon group which may be substituted, or a heterocyclic group which may be substituted). $R^5$ has the same meaning as defined above.

6) Regarding Ring A and Ring B

Ring A is a 5- to 10-membered ring, that is, a 5- to 10-membered ring containing the nitrogen atom to which $R^{1'}$ is bonded, preferably a 5- to 7-membered ring containing the nitrogen atom.

Ring B is a 5- to 9-membered ring, that is, a 5- to 9-membered ring containing X, preferably a 5- to 6-membered ring containing X.

$R^1$ and $R^{1'}$ are each preferably a group represented by the formula: —(C=O)—$R^6$, —(C=O)—$OR^6$ or —(C=O)—$NR^7R^8$ [wherein each symbol is as defined above]. More preferably, mention may be made of a group represented by the formula: —(C=O)—$R^6$ or —(C=O)—$NR^7R^8$ [wherein each symbol is as defined above]. Even more preferably, mention may be made of a group represented by the formula: —(C=O)—$NR^7R^8$ [wherein each symbol is as defined above].

$R^6$ is preferably (i) an aromatic group which may be substituted, (ii) a heterocyclic group which may be substituted, (iii) a chain hydrocarbon group which may be substituted (e.g., (a) an alkyl group which may have a 5- to 7-membered cyclic amino group which may be substituted, (b) an alkyl group which may have an aryl group which may be substituted, etc.), or the like. More preferably, mention may be made of a $C_{7-13}$ aralkyl group which may be substituted, a $C_{6-12}$ aryl group which may be substituted, a $C_{1-6}$ alkyl group which may have a 5- to 7-membered cyclic amino group which may be substituted, or the like. Even more preferably, mention may be made of a $C_{6-12}$ aryl group which may be substituted, a $C_{1-6}$ alkyl group having a 5- to 7-membered cyclic amino group which may be substituted, or the like.

$R^7$ is preferably a hydrogen atom, a hydrocarbon group which may be substituted [e.g., (a) an alkyl group which may have (i) a 5- to 7-membered cyclic amino group which may be substituted, and/or (ii) a 5- to 10-membered heterocyclic group which may be substituted, (b) an aryl group which may be substituted, (c) an aralkyl group which may be substituted, etc.], a heterocyclic group which may be substituted (e.g., a 5- or 6-membered non-aromatic heterocyclic group which may have an alkyl group, etc.), an aryl-carbonyl group (e.g., a $C_{6-12}$ aryl-carbonyl group), an alkoxy-carbonyl group (e.g., a $C_{1-6}$ alkoxy-carbonyl group), or the like. More preferably, mention may be made of (a) a $C_{1-6}$ alkyl group which may have (i) a 5- to 7-membered cyclic amino group which may be substituted, and/or (ii) a 5- to 10-membered aromatic heterocyclic group which may be substituted, (b) a $C_{6-12}$ aryl group which may be substituted, (c) a $C_{7-13}$ aralkyl group which may be substituted, or the like. $R^7$ is also preferably a group having an aromatic group which may be substituted.

$R^8$ is preferably a hydrogen atom, or an amino group which may be substituted.

When $R^8$ is an amino group which may be substituted, $R^7$ is preferably a hydrogen atom.

Further, the "ring" of the "ring which may be substituted" formed by $R^7$ and $R^5$ together with the adjacent nitrogen atom, is preferably a 5- to 10-membered (non-aromatic) heterocyclic ring (e.g., pyrrolidine, piperidine, piperazine, morpholine, thiomorpholine, 1,2,3,4-tetrahydroquinoline, 1,2,3,4-tetrahydroisoquinoline, etc.) or the like.

$R^2$ is preferably an aryl which may be substituted. It is more preferably a $C_{6-12}$ aryl group.

$R^3$ is preferably an aryl group which may be substituted. It is more preferably a $C_{6-12}$ aryl group.

Furthermore, $R^6$ is preferably
(a) a $C_{7-13}$ aralkyl group,
(b) a $C_{2-6}$ alkenyl group which may have a $C_{6-12}$ aryl group which may be halogenated,
(c) a $C_{6-12}$ aryl group which may have a substituent selected from:
  (i) a halogen atom,
  (ii) a $C_{1-6}$ alkoxy group,
  (iii) a nitro group,
  (iv) a formyl group, and
  (v) a $C_{1-6}$ alkyl group which may have a substituent selected from (1) a halogen atom, (2) an amino group which may have one or two substituents selected from a $C_{1-6}$ alkoxy-carbonyl group and a $C_{1-6}$ alkyl group, and (3) a 5- to 7-membered cyclic amino group which may be substituted,
(d) a 5- or 6-membered aromatic heterocyclic group,
(e) a $C_{1-6}$ alkyl group which may have a substituent selected from:
  (i) a $C_{6-12}$ aryloxy group,
  (ii) a $C_{3-8}$ cycloalkyl group which may be condensed with one or two benzene rings,
  (iii) a $C_{6-12}$ arylamino group which may be halogenated,
  (iv) a carboxy group,
  (v) a 5- to 7-membered cyclic amino group,
  (vi) a 5- to 7-membered non-aromatic heterocyclic group,
  (vii) a $C_{6-12}$ aryl group, and
  (viii) a halogen atom,
(f) a 5- to 7-membered non-aromatic heterocyclic group which may have a $C_{1-6}$ alkoxy-carbonyl group, a formyl group, or a $C_{1-6}$ alkyl group which may have a substituent selected from:
  (i) a $C_{1-6}$ alkoxy-carbonyl group,
  (ii) a carbamoyl group,
  (iii) a hydroxy group,
  (iv) a 5- to 7-membered cyclic amino-carbonyl group,
  (v) a $C_{3-8}$ cycloalkyl group, and
  (vi) a $C_{2-8}$ alkenyl group,
(g) a 5- to 10-membered (preferably 9-membered) aromatic heterocyclic group which may have an oxo group, or
(h) a 5- to 10-membered cyclic amino group which may have an oxo group and may be condensed with a benzene ring.

Furthermore, $R^7$ is preferably
(a) a hydrogen atom,
(b) a $C_{6-12}$ aryl group which may have a substituent selected from:
  (i) a $C_{1-6}$ alkoxy-carbonyl group,
  (ii) a halogen atom, and
  (iii) a $C_{1-6}$ alkoxy group,
(c) a $C_{7-13}$ aralkyl group which may have a substituent selected from:
  (i) a halogen atom,
  (ii) a $C_{1-6}$ alkyl group which may have a substituent selected from an amino group which may be substituted with a $C_{1-6}$ alkoxy-carbonyl group, and a halogen atom,
  (iii) a $C_{1-6}$ alkylsulfonyl group, and
  (iv) a mono- or di-$C_{1-6}$ alkylamino group,
(d) a $C_{1-6}$ alkyl group which may have one or two substituents selected from:
  (i) a 5- or 6-membered aromatic heterocyclic group which may be oxidized and may be substituted with a cyano group, a hydroxy group or a $C_{1-6}$ alkyl group,
  (ii) a 5- to 7-membered cyclic amino group which may have a $C_{1-6}$ alkyl group, a hydroxy group, an oxo group or a $C_{1-6}$ alkoxy-carbonyl group, and may be condensed with a benzene ring,
  (iii) a $C_{1-6}$ alkoxy-carbonyl group,
  (iv) a carboxy group,
  (v) a 5- to 7-membered cyclic aminocarbonyl group,
  (vi) a $C_{6-12}$ aryl group which may be halogenated,
  (vii) a $C_{6-12}$ aryl-carbonyl group,
  (viii) a hydroxy group,
  (ix) an amino group which may have one or two substituents selected from (1) a $C_{1-6}$ alkyl group which may be substituted with a $C_{3-8}$ cycloalkyl group, (2) a $C_{1-6}$ alkoxy-$C_{1-6}$ alkyl group, (3) an azidocarbonyl group, (4) an aminocarbonyl group, (5) a $C_{7-13}$ aralkyl group, (6) a $C_{3-8}$ cycloalkyl group, (7) a sulfonyl group which may be substituted with a benzene ring which may be substituted with a nitro group, (8) a $C_{2-8}$ alkenyl group, (9) a $C_{1-6}$ alkylsulfonyl group, and (10) a $C_{1-6}$ alkyl-carbonyl group,
  (x) a $C_{3-8}$ cycloalkyl group, and
  (xi) a 5- to 7-membered non-aromatic heterocyclic group,
(e) a $C_{3-8}$ cycloalkyl group which may be condensed with one or two benzene rings,
(f) a 5- to 10-membered aromatic heterocyclic group which may have a substituent selected from an oxo group, a $C_{1-6}$ alkoxy-carbonyl group and a $C_{1-6}$ alkyl group,
(g) a $C_{6-12}$ aryl-carbonyl group,
(h) a $C_{1-6}$ alkoxy-carbonyl group,
(i) a 5- to 7-membered non-aromatic heterocyclic group which may have a substituent selected from a $C_{1-6}$ alkyl group, a $C_{1-6}$ alkoxy-carbonyl group and an oxo group, and may be condensed with a benzene ring,
(j) a 5- to 7-membered cyclic amino-$C_{1-6}$ alkyl-carbonyl group,
(k) a $C_{3-8}$ cycloalkyl group which may be substituted with a $C_{1-6}$ alkyl group which may have a 5- to 7-membered cyclic amino group, or
(l) a $C_{6-12}$ arylamino group.

$R^8$ is preferably a hydrogen atom or a $C_{1-6}$ alkyl group. Alternatively, $R^7$ and $R^8$ may form, together with the adjacent nitrogen atom, a 5- to 10-membered non-aromatic heterocyclic ring which may have a substituent selected from a 5- to 7-membered saturated cyclic amino group and a $C_{1-6}$ alkyl group.

$R^2$ is preferably
(i) a hydrogen atom,
(ii) a $C_{1-6}$ alkyl group,
(iii) a $C_{3-6}$ cycloalkyl group, (iv) a $C_{6-12}$ aryl group which may have a substituent selected from a halogen atom and a $C_{1-6}$ alkyl group, or (v) a $C_{7-13}$ aralkyl group.

$R^3$ is a preferably (i) a $C_{1-6}$ alkyl group, (ii) a $C_{3-6}$ cycloalkyl group, (iii) a $C_{6-12}$ aryl group which may have a substituent selected from a halogen atom and a $C_{1-6}$ alkyl group, or (iv) a $C_{7-13}$ aralkyl group.

n is preferably 0.

X is preferably an oxygen atom.

A suitable example of Compound (I) may be a compound in which:

$R^1$ is a group represented by the formula: —(C=O)—$R^{6a}$, —(C=O)—$OR^{6a}$, —(C=O)—$NR^{7a}R^{8a}$ or —$SO_2$—$R^{6a}$

[wherein $R^{6a}$ is (a) a $C_{7-13}$ aralkyl group, (b) a $C_{2-6}$ alkenyl group which may have a $C_{6-12}$ aryl group which may be halogenated, (c) a $C_{6-12}$ aryl group which may have a substituent selected from:

(i) a halogen atom, (ii) a $C_{1-6}$ alkoxy group, (iii) a nitro group, (iv) a formyl group, and (v) a $C_{1-6}$ alkyl group which may have a substituent selected from (1) a halogen atom, (2) an amino group which may have one or two substituents selected from a $C_{1-6}$ alkoxy-carbonyl group and a $C_{1-6}$ alkyl group, and (3) a 5- to 7-membered cyclic amino group which may be substituted, (d) a 5- or 6-membered aromatic heterocyclic group, (e) a $C_{1-6}$ alkyl group which may have a substituent selected from:

(i) a $C_{6-12}$ aryloxy group, (ii) a $C_{3-8}$ cycloalkyl group which may be condensed with one or two benzene rings, (iii) a $C_{6-12}$ arylamino group which may be halogenated, (iv) a carboxy group, (v) a 5- to 7-membered cyclic amino group, (vi) a 5- to 7-membered non-aromatic heterocyclic group, (vii) a $C_{6-12}$ aryl group, and (viii) a halogen atom, (f) a 5- to 7-membered non-aromatic heterocyclic group which may have a $C_{1-6}$ alkoxy-carbonyl group, a formyl group, or a $C_{1-6}$ alkyl group which may have a substituent selected from:

(i) a $C_{1-6}$ alkoxy-carbonyl group, (ii) a carbamoyl group, (iii) a hydroxy group, (iv) a 5- to 7-membered cyclic amino-carbonyl group, (v) a $C_{3-8}$ cycloalkyl group, and (vi) a $C_{2-8}$ alkenyl group, (g) a 5- to 10-membered (preferably 9-membered) aromatic heterocyclic group which may have an oxo group, or (h) a 5- to 10-membered cyclic amino group which may have an oxo group and may be condensed with a benzene ring;

$R^{7a}$ is (a) a hydrogen atom, (b) a $C_{6-12}$ aryl group which may have a substituent selected from:

(i) a $C_{1-6}$ alkoxy-carbonyl group, (ii) a halogen atom, and (iii) a $C_{1-6}$ alkoxy group, (c) a $C_{7-13}$ aralkyl group which may have a substituent selected from:

(i) a halogen atom, (ii) a $C_{1-6}$ alkyl group which may have a substituent selected from an amino group which may be substituted with a $C_{1-6}$ alkoxy-carbonyl group, and a halogen atom, (iii) a $C_{1-6}$ alkylsulfonyl group, and (iv) a mono- or di-$C_{1-6}$ alkylamino group, (d) a $C_{1-6}$ alkyl group which may have one or two substituents selected from:

(i) a 5- or 6-membered aromatic heterocyclic group which may be oxidized and may be substituted with a cyano group, a hydroxy group or a $C_{1-6}$ alkyl group, (ii) a 5- to 7-membered cyclic amino group which may have a $C_{1-6}$ alkyl group, a hydroxy group, an oxo group or a $C_{1-6}$ alkoxy-carbonyl group, and may be condensed with a benzene ring, (iii) a $C_{1-6}$ alkoxy-carbonyl group, (iv) a carboxy group, (v) a 5- to 7-membered cyclic aminocarbonyl group, (vi) a $C_{6-12}$ aryl group which may be halogenated, (vii) a $C_{6-12}$ aryl-carbonyl group, (viii) a hydroxy group, (ix) an amino group which may have one or two substituents selected from (1) a $C_{1-6}$ alkyl group which may be substituted with a $C_{3-8}$ cycloalkyl group, (2) a $C_{1-6}$ alkoxy-$C_{1-6}$ alkyl group, (3) an azidocarbonyl group, (4) an aminocarbonyl group, (5) a $C_{7-13}$ aralkyl group, (6) a $C_{3-8}$ cycloalkyl group, (7) a sulfonyl group which may be substituted with a benzene ring which may be substituted with a nitro group, (8) a $C_{2-8}$ alkenyl group, (9) a $C_{1-6}$ alkylsulfonyl group, and (10) a $C_{1-6}$ alkyl-carbonyl group, (x) a $C_{3-8}$ cycloalkyl group, and (xi) a 5- to 7-membered non-aromatic heterocyclic group, (e) a $C_{3-8}$ cycloalkyl group which may be condensed with one or two benzene rings, (f) a 5- to 10-membered aromatic heterocyclic group which may have a substituent selected from an oxo group, a $C_{1-6}$ alkoxy-carbonyl group and a $C_{1-6}$ alkyl group, (g) a $C_{6-12}$ aryl-carbonyl group, (h) a $C_{1-6}$ alkoxy-carbonyl group, (i) a 5- to 7-membered non-aromatic heterocyclic group which may have a substituent selected from a $C_{1-6}$ alkyl group, a $C_{1-6}$ alkoxy-carbonyl group and an oxo group, and may be condensed with a benzene ring, (j) a 5- to 7-membered cyclic amino-$C_{1-6}$ alkyl-carbonyl group, (k) a $C_{3-8}$ cycloalkyl group which may be substituted with a $C_{1-6}$ alkyl group which may have a 5- to 7-membered cyclic amino group, or (l) a $C_{6-12}$ arylamino group; and $R^{8a}$ is a hydrogen atom or a $C_{1-6}$ alkyl group; or $R^{7a}$ and $R^{8a}$ may form, together with the adjacent nitrogen atom, a 5- to 10-membered non-aromatic heterocyclic ring which may have a substituent selected from a 5- to 7-membered saturated cyclic amino group and a $C_{1-6}$ alkyl group];

$R^2$ is (i) a hydrogen atom, (ii) a $C_{1-6}$ alkyl group, (iii) a $C_{3-6}$ cycloalkyl group, (iv) a $C_{6-12}$ aryl group which may be have a substituent selected from a halogen atom and a $C_{1-6}$ alkyl group, or (v) a $C_{7-13}$ aralkyl group;

$R^3$ is (i) a $C_{1-6}$ alkyl group, (ii) a $C_{3-6}$ cycloalkyl group, (iii) a $C_{6-12}$ aryl group which may have a substituent selected from a halogen atom and a $C_{1-6}$ alkyl group, or
(iv) a $C_{7-13}$ aralkyl group;
n is 0; and
X is an oxygen atom.

Another suitable example of Compound (I) may be a compound in which:
$R^1$ is a group represented by the formula: —(C=O)—$R^{6a}$, —(C=O)—$OR^{6a}$, —(C=O)—$NR^{7a}R^{8a}$ or —$SO_2$—$R^{6a}$
[wherein $R^{6a}$ is
  (a) a $C_{7-13}$ aralkyl group,
  (b) a $C_{2-6}$ alkenyl group which may have a $C_{6-12}$ aryl group which may be halogenated,
  (c) a $C_{6-12}$ aryl group which may have a substituent selected from:
    (i) a halogen atom,
    (ii) a $C_{1-6}$ alkoxy group,
    (iii) a nitro group, and
    (iv) a $C_{1-6}$ alkyl group which may have a substituent selected from (1) a halogen atom, and (2) an amino group which may have one or two substituents selected from a $C_{1-6}$ alkoxy-carbonyl group and a $C_{1-6}$ alkyl group,
  (d) a 5- or 6-membered aromatic heterocyclic group,
  (e) a $C_{1-6}$ alkyl group which may have a substituent selected from:
    (i) a $C_{6-12}$ aryloxy group,
    (ii) a $C_{3-8}$ cycloalkyl group which may be condensed with one or two benzene rings,
    (iii) a $C_{6-12}$ arylamino group which may be halogenated,
    (iv) a carboxy group,
    (v) a 5- to 7-membered cyclic amino group,
    (vi) a $C_{6-12}$ aryl group, and
    (vii) a halogen atom,
  (f) a 6-membered non-aromatic heterocyclic group which may have a $C_{1-6}$ alkoxy-carbonyl group, or
  (g) a 5- to 10-membered (preferably 9-membered) aromatic heterocyclic group which may have an oxo group;
$R^{7a}$ is
  (a) a hydrogen atom,
  (b) a $C_{6-12}$ aryl group which may have a substituent selected from a $C_{1-6}$ alkoxy-carbonyl group, a halogen atom and a $C_{1-6}$ alkoxy group,
  (c) a $C_{7-13}$ aralkyl group which may have a substituent selected from:
    (i) a halogen atom,
    (ii) a $C_{1-6}$ alkyl group which may have a substituent selected from an amino group which may be substituted with a $C_{1-6}$ alkoxy-carbonyl group, and a halogen atom,
    (iii) a $C_{1-6}$ alkylsulfonyl group, and
    (iv) a mono- or di-$C_{1-6}$ alkylamino group,
  (d) a $C_{1-6}$ alkyl group which may have a substituent selected from:
    (i) a 5- or 6-membered aromatic heterocyclic group which may be oxidized and may have a cyano group,
    (ii) a 5- to 7-membered cyclic amino group which may have a $C_{1-6}$ alkyl group and may be condensed with a benzene ring,
    (iii) a $C_{1-6}$ alkoxy-carbonyl group,
    (iv) a carboxy group,
    (v) a 5- to 7-membered saturated cyclic amino-carbonyl group,
    (vi) a $C_{6-12}$ aryl group,
    (vii) a $C_{6-12}$ aryl-carbonyl group,
    (viii) a hydroxy group, and
    (ix) an amino group which may have one or two substituents selected from a $C_{1-6}$ alkyl group, a $C_{1-6}$ alkoxy-$C_{1-6}$ alkyl group, an azidocarbonyl group, an aminocarbonyl group and a $C_{7-13}$ aralkyl group,
  (e) a $C_{3-8}$ cycloalkyl group which may be condensed with one or two benzene rings,
  (f) a 5- to 10-membered aromatic heterocyclic group which may have a substituent selected from an oxo group and a $C_{1-6}$ alkoxy-carbonyl group,
  (g) a $C_{6-12}$ aryl-carbonyl group,
  (h) a $C_{1-6}$ alkoxy-carbonyl group, or
  (i) a 5- to 7-membered non-aromatic heterocyclic group which may have a substituent selected from a $C_{1-6}$ alkyl group, a $C_{1-6}$ alkoxy-carbonyl group and an oxo group, and may be condensed with a benzene ring; and
$R^{8a}$ is a hydrogen atom, a $C_{1-6}$ alkyl group or a $C_{6-12}$ arylamino group; or
$R^{7a}$ and $R^{8a}$ may form, together with the adjacent nitrogen atom, a 5- to 10-membered non-aromatic heterocyclic ring which may have a 5- to 7-membered saturated cyclic amino group];
$R^2$ is a hydrogen atom, a $C_{1-6}$ alkyl group, a $C_{3-6}$ cycloalkyl group, a $C_{6-12}$ aryl group which may be halogenated, or a $C_{7-13}$ aralkyl group;
$R^3$ is a $C_{1-6}$ alkyl group, a $C_{3-6}$ cycloalkyl group, a $C_{6-12}$ aryl group which may be halogenated, or a $C_{7-13}$ aralkyl group;
n is 0; and
X is an oxygen atom.

Another suitable example of Compound (I) may be a compound in which:
$R^1$ is a group represented by the formula: —(C=O)—$R^{6a}$, —(C=O)—$OR^{6a}$, —(C=O)—$NR^{7a}R^{8a}$ or —$SO_2$—$R^{6a}$
[wherein $R^{6a}$ is
  (a) a $C_{7-13}$ aralkyl group,
  (b) a $C_{2-6}$ alkenyl group which may have a $C_{6-12}$ aryl group which may be halogenated,
  (c) a $C_{6-12}$ aryl group which may have a substituent selected from a halogen atom, a $C_{1-6}$ alkoxy group, a nitro group, and a $C_{1-6}$ alkyl group which may be halogenated,
  (d) a 5- or 6-membered aromatic heterocyclic group, or
  (e) a $C_{1-6}$ alkyl group which may have a substituent selected from a $C_{6-12}$ aryl group, a $C_{6-12}$ aryloxy group, and a $C_{3-8}$ cycloalkyl group which may be condensed;
$R^{7a}$ is
  (a) a hydrogen atom,
  (b) a $C_{6-12}$ aryl group which may have a substituent selected from a $C_{1-6}$ alkoxy-carbonyl group, a halogen atom and a $C_{1-6}$ alkoxy group,
  (c) a $C_{7-13}$ aralkyl group which may have a substituent selected from a halogen atom, a $C_{1-6}$ alkyl group which may be halogenated, a $C_{1-6}$ alkylsulfonyl group and a mono- or di-$C_{1-6}$ alkylamino group,
  (d) a $C_{1-6}$ alkyl group which may have a 5- or 6-membered aromatic heterocyclic group, or
  (e) a $C_{3-8}$ cycloalkyl group which may be condensed; and
$R^{8a}$ is a hydrogen atom, a $C_{1-6}$ alkyl group or a $C_{6-12}$ arylamino group; or
$R^{7a}$ and $R^{8a}$ may form, together with the adjacent nitrogen atom, a 5- to 10-membered non-aromatic heterocyclic ring];
$R^2$ and $R^3$ are each a $C_{1-6}$ alkyl group, a $C_{3-6}$ cycloalkyl group or a $C_{6-12}$ aryl group;
n is 0; and
X is an oxygen atom.

Another suitable example of Compound (I) may be a compound in which:

$R^1$ is a group represented by the formula: —(C=O)—$R^{6b}$ or —(C=O)—$NR^{7b}R^{8b}$

[wherein $R^{6b}$ is
(a) a $C_{1-6}$ alkyl group which may have a 5- to 7-membered cyclic amino group, or
(b) a $C_{6-12}$ aryl group which may have a $C_{1-6}$ alkyl group which may have an amino group which may have one or two $C_{1-6}$ alkyl groups;
$R^{7b}$ is
(a) a hydrogen atom,
(b) a $C_{6-12}$ aryl group which may have a halogen atom,
(c) a $C_{7-13}$ aralkyl group which may have a halogen atom,
(d) a 5- or 6-membered aromatic heterocyclic group,
(e) a $C_{1-6}$ alkyl group which may have a 5- to 7-membered cyclic amino group, or
(f) a 5- or 6-membered non-aromatic heterocyclic group which may have a $C_{1-6}$ alkyl group; and
$R^{8b}$ is a hydrogen atom or a $C_{6-12}$ arylamino group; or
$R^{7b}$ and $R^{8b}$ may form, together with the adjacent nitrogen atom, a 5- to 10-membered heterocyclic ring which may have a 5- to 7-membered cyclic amino group];
$R^2$ and $R^3$ and each a $C_{6-12}$ aryl group;
n is 0; and
X is an oxygen atom.

More specifically, mention may be made of:
phenyl tetrahydro-3-oxo-1,1-diphenyl-3H-oxazolo[3,4-a]pyrazine-7(1H)-carboxylate,
hexahydro-7-(1-oxo-3-phenyl-2-propenyl)-1,1-diphenyl-3H-oxazolo[3,4-a]pyrazin-3-one,
(+)-N-[(4-fluorophenyl)methyl]-tetrahydro-3-oxo-1,1-diphenyl-3H-oxazolo[3,4-a]pyrazine-7(1H)-carboxamide,
(−)-N-[(4-fluorophenyl)methyl]-tetrahydro-3-oxo-1,1-diphenyl-3H-oxazolo[3,4-a]pyrazine-7(1H)-carboxamide,
(+)-N-[2-(3,6-dihydropyridin-1(2H)-yl)ethyl]-tetrahydro-3-oxo-1,1-diphenyl-3H-oxazolo[3,4-a]pyrazine-7(1H)-carboxamide,
(−)-N-[2-(3,6-dihydropyridin-1(2H)-yl)ethyl]-tetrahydro-3-oxo-1,1-diphenyl-3H-oxazolo[3,4-a]pyrazine-7(1H)-carboxamide,
1,1-Bis(3-fluorophenyl)-N-[2-(3,6-dihydropyridin-1(2H)-yl)ethyl]-tetrahydro-3-oxo-3H-oxazolo[3,4-a]pyrazine-7(1H)-carboxamide,
N-[2-(3,6-dihydropyridin-1(2H)-yl)ethyl]-tetrahydro-3-oxo-1,1-diphenyl-3H-oxazolo[3,4-a]pyrazine-7(1H)-carboxamide,
1,1-Bis(3-fluorophenyl)-N-[2-(cyclopropylamino)ethyl]-tetrahydro-3-oxo-3H-oxazolo[3,4-a]pyrazine-7(1H)-carboxamide hydrochloride,
tetrahydro-3-oxo-1,1-diphenyl-N-[(3-thienyl)methyl]-3H-oxazolo[3,4-a]pyrazine-7(1H)-carboxamide,
7-[4-(3,6-Dihydropyridin-1(2H)-yl)-1-oxobutyl]-hexahydro-1,1-diphenyl-3H-oxazolo[3,4-a]pyrazin-7(1H)-3-one,
N-[2-[(cyclopropylmethyl)amino]ethyl]-tetrahydro-3-oxo-1,1-diphenyl-3H-oxazolo[3,4-a]pyrazine-7(1H)-carboxamide hydrochloride,
N-[(4-fluorophenyl)methyl]-tetrahydro-3-oxo-1,1-diphenyl-3H-oxazolo[3,4-a]pyrazine-7(1H)-carboxamide, and
1,1-Bis(3-fluorophenyl)-tetrahydro-3-oxo-N-[2-(1-piperidinyl)ethyl]-3H-oxazolo[3,4-a]pyrazine-7(1H)-carboxamide, and salts thereof.

With regard to Compound (II), ring A that can be used may be exemplified by:

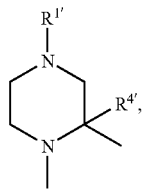
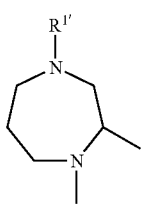

or the like.

$R^{1'}$ is, in addition to the above-described acyl group represented by $R^1$, preferably (i) a hydrogen atom, (ii) a $C_{1-6}$ alkyl group (e.g., a methyl group) which may be substituted with a substituent selected from a $C_{6-14}$ aryl-carbonyl group (e.g., a benzoyl group), a $C_{6-14}$ aryl group (e.g., a phenyl group), a $C_{6-14}$ aryloxy-carbonyl group (e.g., a phenyloxycarbonyl group) and the like, (iii) a 5- to 10-membered heterocyclic group (e.g., a benzoxazol-2-yl group) containing one to three of a nitrogen atom, an oxygen atom or a sulfur atom, or the like.

Ring B that can be used may be exemplified by:

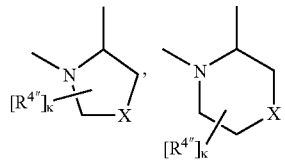

or the like.

X is preferably an oxygen atom or NH, and particularly preferred is an oxygen atom.

More specifically, ring B is preferably:

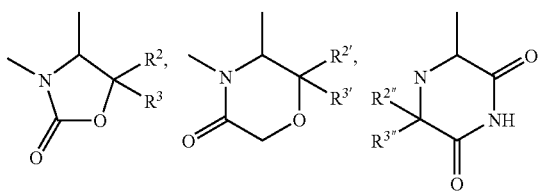

or the like.

A combination of ring A and ring B is preferably:

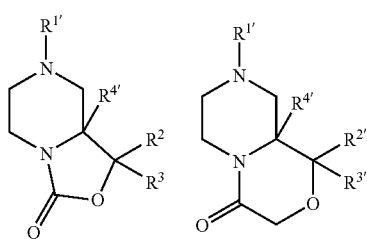

-continued

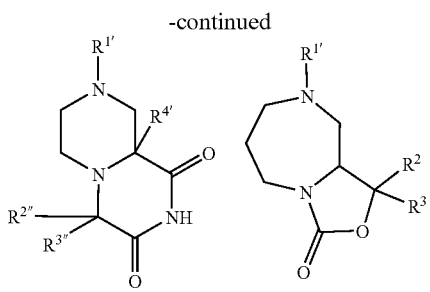

or the like.

Here, $R^{2'}$ and $R^{2''}$ are each preferably a hydrogen atom, a hydrocarbon group which may be substituted, or a heterocyclic group which may be substituted, and the same substituents as those for $R^2$ are used. Among those, a $C_{6-14}$ aryl group (e.g., a phenyl group) is preferred.

$R^{3'}$ and $R^{3''}$ are each preferably a hydrocarbon group which may be substituted, or a heterocyclic group which may be substituted, and the same substituents as those for $R^3$ are used. Among those, a $C_{6-14}$ aryl group (e.g., a phenyl group) is preferred. For $R^2$ and $R^3$, the same substituents as described above are preferably used.

The salts of Compounds (I) and (II) and intermediates thereof may be exemplified by metal salts, ammonium salts, salts with organic bases, salts with inorganic acids, salts with organic acids, salts with basic or acidic amino acids, or the like. Suitable examples of the metal salt include alkali metal salts such as sodium salts and potassium salts; alkaline earth metal salts such as calcium salts, magnesium salts and barium salts; aluminum salts; and the like. Suitable examples of the salt with an organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Suitable examples of the salt with an inorganic acid include salts with hydrochloric acid, hydrobromic acid, nitric acid, sulfuric acid, phosphoric acid and the like. Suitable examples of the salt with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Suitable examples of the salt with a basic amino acid include salts with arginine, lysine, ornithine and the like, and suitable examples of the salt with an acidic amino acid include salts with aspartic acid, glutamic acid and the like.

Among these, pharmaceutically acceptable salts are preferred. For example, when the compound has an acidic functional group, mention may be made of inorganic salts such as alkali metal salts (e.g., sodium salts, potassium salts, etc.), alkaline earth metal salts (e.g., calcium salts, magnesium salts, barium salts, etc.) and the like, ammonium salts, and the like; when the compound has a basic functional group, mention may be made of salts with inorganic acids such as hydrobromic acid, nitric acid, sulfuric acid, phosphoric acid and the like, or salts with organic acids such as acetic acid, phthalic acid, fumaric acid, oxalic acid, tartaric acid, maleic acid, citric acid, succinic acid, methanesulfonic acid, p-toluenesulfonic acid and the like.

Compounds (I) and (II) (hereinafter, may be simply referred to as Compound (I)) may be either hydrates or non-hydrates. The hydrate may be exemplified by a 0.5-hydrate, a 1-hydrate, a 1.5-hydrate, a 2-hydrate or the like.

If necessary, Compound (I) can be obtained as a desired R-isomer or S-isomer, by using a method known per se, such as asymmetric synthesis, optical resolution or the like.

A prodrug of Compound (I) refers to a compound which is converted to Compound (I) by an in vivo reaction of enzyme, gastric acid or the like under the physiological conditions, that is, a compound which changes to Compound (I) upon enzymatic oxidation, reduction, hydrolysis or the like, or a compound which changes to Compound (I) upon hydrolysis by gastric acid or the like. The prodrug of Compound (I) may be exemplified by a compound resulting from acylation, alkylation or phosphorylation of the amino group of Compound (I) [e.g., a compound in which the amino group of Compound (I) is in the form of eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl or the like]; a compound resulting from acylation, alkylation, phosphorylation or boration of the hydroxy group of Compound (I) [e.g., a compound in which the hydroxy group of Compound (I) is in the form of acetyl, palmitoyl, propanoyl, pivaloyl, succinyl, fumaryl, alanyl, dimethylaminomethylcarbonyl or the like); a compound resulting from esterification or amidation of the carboxy group of Compound (I) [e.g., a compound in which the carboxy group of Compound (I) is in the form of ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methylamide or the like); or the like. These compounds can be produced from Compound (I) by methods known per se in the art.

The prodrug of Compound (I) may also be a compound which changes to Compound (I) under the physiological conditions, as described in "Development of Pharmaceutical Products", Vol. 7, Design of Molecules, Hirokawa Publisher, pp. 163-198 (1990).

The method for preparation of Compound (I) will be described in the following.

Compound (I) can be obtained by the methods represented by the following Reaction Schemes 1 to 4 or methods equivalent thereto.

Each reference symbol in the compounds shown in the following Reaction Schemes 1 to 4 has the same meaning as defined above. The compounds shown in the reaction schemes include salts formed from the compounds, and examples of the salts include the same ones as the salts of Compound (I), and the like.

A product can be used in the subsequent reaction in the form of a reaction liquid or a crude preparation product, but the product can be isolated from the reaction mixture by a conventional method, or can be easily purified by a conventional separation means (e.g., recrystallization, distillation, chromatography, etc.).

The solvents used in the following reactions, indicated in their generic names, will be described below.

An "alcohol" that can be used may be exemplified by methanol, ethanol, 1-propanol, 2-propanol, tert-butyl alcohol or the like.

An "ether" that can be used may be exemplified by diethyl ether, diisopropyl ether, diphenyl ether, tetrahydrofuran, 1,4-dioxane, 1,2-dimethoxyethane or the like.

A "hydrocarbon" that can be used may be exemplified by benzene, toluene, cyclohexane, hexane or the like.

An "amide" that can be used may be exemplified by N,N-dimethylformamide, N,N-dimethylacetamide, hexamethylphosphoric triamide or the like.

A "halogenated hydrocarbon" that can be used may be exemplified by dichloromethane, chloroform, carbon tetrachloride, 1,2-dichloroethane or the like.

A "nitrile" that can be used may be exemplified by acetonitrile, propionitrile or the like.

A "ketone" that can be used may be exemplified by acetone, ethyl methyl ketone or the like.

An "organic acid" that can be used may be exemplified by formic acid, acetic acid, propionic acid, trifluoroacetic acid, methanesulfonic acid or the like.

An "aromatic amine" that can be used may be exemplified by pyridine, 2,6-lutidine, quinoline or the like.

A "sulfoxide" that can be used may be exemplified by dimethylsulfoxide or the like.

The bases used in the following reactions, indicated in their generic names, will be described below.

An "inorganic base" that can be used may be exemplified by sodium hydroxide, potassium hydroxide, lithium hydroxide, barium hydroxide or the like.

A "basic salt" that can be used may be exemplified by sodium carbonate, potassium carbonate, cesium carbonate, sodium hydrogen carbonate, sodium acetate, ammonium acetate or the like.

An "aromatic amine" that can be used may be exemplified by pyridine, lutidine or the like.

A "tertiary amine" that can be used may be exemplified by triethylamine, tripropylamine, tributylamine, diisopropylethylamine, cyclohexyldimethylamine, 4-dimethylaminopyridine, N,N-dimethylaniline, N-methylpiperidine, N-methylpyrrolidine, N-methylmorpholine or the like.

An "alkali metal hydride" that can be used may be exemplified by sodium hydride, potassium hydride or the like.

A "metal amide" that can be used may be exemplified by sodium amide, lithium diisopropyl amide, lithium hexamethyl disilazide or the like.

An "alkyl metal" that can be used may be exemplified by butyllithium, sec-butyllithium, tert-butyllithium or the like.

An "aryl metal" that can be used may be exemplified by phenyllithium or the like.

A "metal alkoxide" that can be used may be exemplified by sodium methoxide, sodium ethoxide, sodium tert-butoxide, potassium tert-butoxide or the like.

[Reaction Scheme 1]

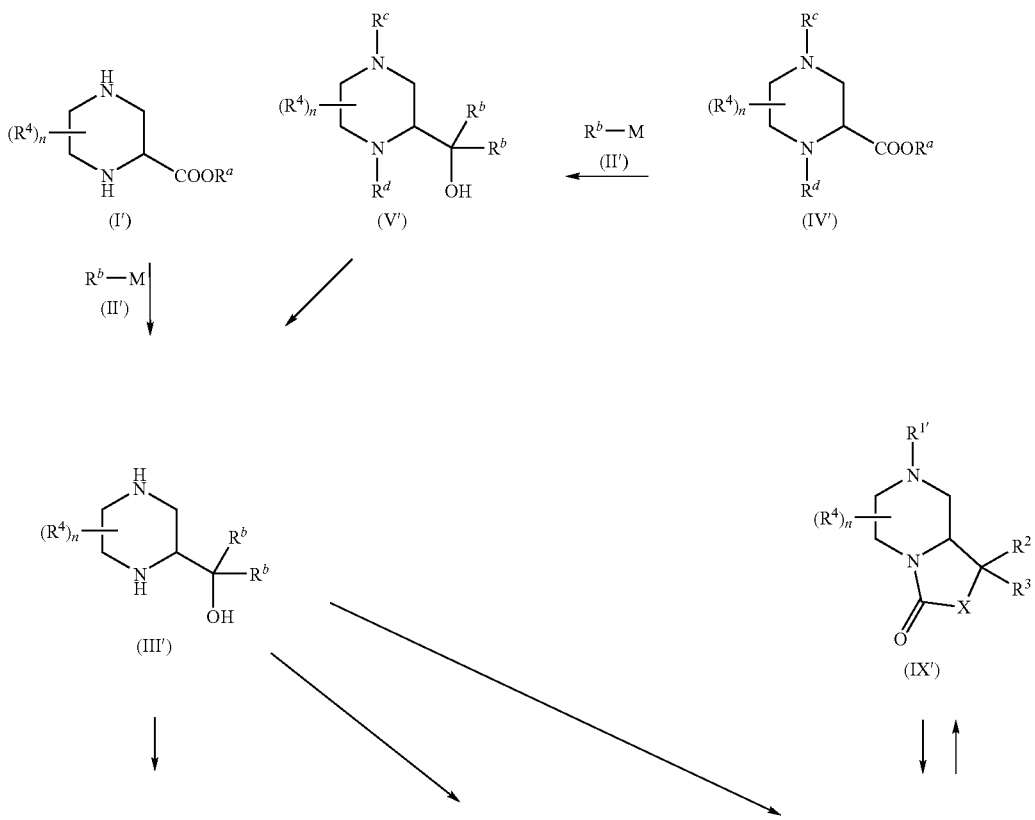

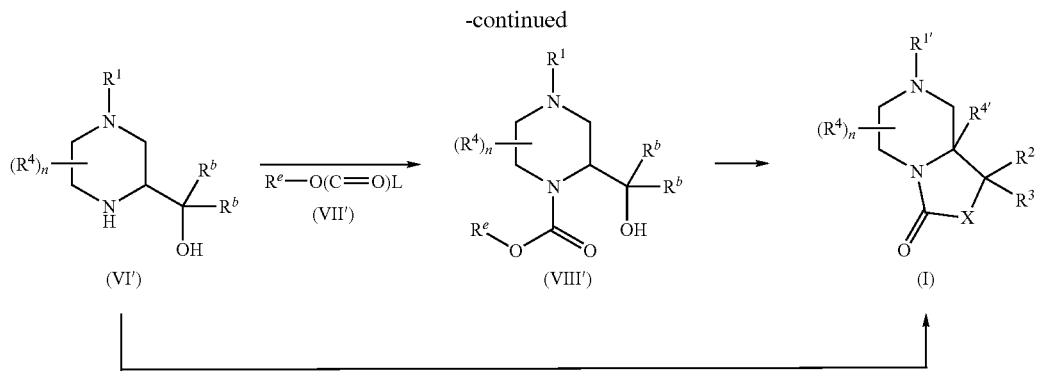

In the above formulas, $R^a$ is a hydrocarbon group which may be substituted.

The "hydrocarbon group which may be substituted" represented by $R^a$ may be exemplified by the above-described "hydrocarbon group which may be substituted" represented by $R^6$.

$R^b$ is a hydrocarbon group which may be substituted, or a heterocyclic group which may be substituted.

The "hydrocarbon group which may be substituted" and the "heterocyclic group which may be substituted" represented by $R^b$ may be exemplified by the above-described "hydrocarbon group which may be substituted" and the "heterocyclic group which may be substituted" represented by $R^6$, respectively.

$R^c$ and $R^d$ are each a protective group.

The "protective group" represented by $R^c$ or $R^d$ may be exemplified by a $C_{7-19}$ aralkyl group (e.g., a benzyl group, a trityl group, etc.) or the like.

$R^e$ is a hydrocarbon group which may be substituted.

The "hydrocarbon group which may be substituted" represented by $R^e$ may be exemplified by the above-described "hydrocarbon group which may be substituted" represented by $R^6$, or the like.

M is a metal. When M is polyvalent, the salts are also included.

The "metal" represented by M may be exemplified by magnesium halide (e.g., magnesium bromide, magnesium chloride, etc.), lithium or the like.

L is a leaving group.

The "leaving group" represented by L may be exemplified by a halogen atom (e.g., chlorine, bromine, etc.), a group represented by the formula: —O(C=O)—O—$R^f$ (wherein $R^f$ is a hydrocarbon group which may be substituted), or the like.

The "hydrocarbon group which may be substituted" represented by $R^f$ may be exemplified by the above-described "hydrocarbon group which may be substituted" represented by $R^6$, or the like.

Compound (III') can be produced by reacting Compound (I') with Compound (II').

Compound (I') can be a commercially available compound, and also can be produced by a method known per se or a method equivalent thereto.

Compound (II') can be a commercially available compound, and also can be produced by a method known per se or a method equivalent thereto.

The amount of Compound (II') to be used is about 2 to about 12 moles, preferably about 2 to about 7 moles, relative to 1 mole of Compound (I').

Additives may be used, if desired, in this reaction. The "additive" may be exemplified by cerium (III) chloride, copper (I) iodide, or the like. The amount of the additive to be used is about 0.1 to about 12 moles, preferably about 0.1 to about 7 moles, relative to 1 mole of Compound (I').

This reaction is advantageously carried out in a solvent that is inert to the reaction. The solvent is not particularly limited as long as it allows the reaction to proceed, and examples thereof include solvents such as ethers and hydrocarbons, or mixtures of two or more of these solvents.

The reaction time is usually about 10 minutes to about 48 hours, preferably about 30 minutes to about 24 hours. The reaction temperature is usually about −100° C. to about 150° C., preferably about −80° C. to about 100° C.

Compound (V') can be produced by reacting Compound (IV') with Compound (II').

Compound (IV') can be a commercially available compound, and also can be produced by a method known per se or a method equivalent thereto.

The amount of Compound (II') to be used is about 2 to about 10 moles, preferably about 2 to about 5 moles, relative to 1 mole of Compound (IV').

Additives may be used, if desired, in this reaction. The "additive" may be exemplified by cerium (III) chloride, copper (I) iodide, or the like. The amount of the additive to be used is about 0.1 to about 1 mole, preferably about 0.1 to about 5 moles, relative to 1 mole of Compound (IV').

This reaction is advantageously carried out in a solvent that is inert to the reaction. The solvent is not particularly limited as long as it allows the reaction to proceed, and examples thereof include solvents such as ethers and hydrocarbons, or mixtures of two or more of these solvents.

The reaction time is usually about 10 minutes to about 48 hours, preferably about 30 minutes to about 24 hours. The reaction temperature is usually about −100° C. to about 150° C., preferably about −80° C. to about 100° C.

Compound (III') can be produced by subjecting Compound (V') to a deprotection reaction.

This reaction can be carried out according to a method known per se, for example, a method described in "Protection for the Amino Group", Protective Groups in Organic Synthesis, Vol. 3 (1999), or the like.

When the "protective group" represented by $R^c$ or $R^d$ is the "benzyl group which may be substituted", the deprotection reaction is facilitated by addition of hydrogen. In this case, for example, a catalyst (e.g., palladium carbon, Raney nickel, Raney cobalt, etc.) may be used. The amount of the catalyst to be used is about 1 to about 1000% by weight, preferably about 5 to about 300% by weight, based on Compound (V').

This reaction is advantageously carried out in a solvent that is inert to the reaction. The solvent is not particularly limited as long as it allows the reaction to proceed, and examples thereof preferably include solvents such as alcohols, ethers, hydrocarbons, halogenated hydrocarbons, amides, organic acids and water, or mixtures of two or more of these solvents.

The reaction time varies depending on the activity or amount of the catalyst, but is usually about 1 hour to about 100 hours, preferably about 1 hour to about 50 hours. The reaction temperature is usually about −20° C. to about 120° C., preferably about 0° C. to about 80° C. The hydrogen pressure is usually about 1 to about 100 atmospheres. Instead of gaseous hydrogen, various hydrogen sources also can be used. The "hydrogen source" that can be used is formic acid, ammonium formate, triethylammonium formate, sodium phosphinate, hydrazine or the like. The amounts of the hydrogen sources to be used are about 1 to about 10 moles, preferably about 1 to about 5 moles, respectively, relative to 1 mole of Compound (V').

Compound (VI') can be produced by reacting Compound (III') with an acylating agent, if desired, in the presence of a base.

The "acylating agent" may be exemplified by an acid represented by the formula: $R^1$—OH, or its reactive derivatives (e.g., acid halide, acid anhydride, carboxylic acid ester, isocyanic acid ester, dicarboxylic acid diester, etc.), or the like. The amount of the acylating agent to be used is about 1 to about 5 moles, preferably about 1 to about 2 moles, relative to 1 mole of Compound (III').

The "base" that is used as desired may be exemplified by inorganic bases, basic salts, aromatic amines, tertiary amines or the like. The amount of the base to be used is about 1 to about 5 moles, preferably about 1 to about 3 moles, relative to 1 mole of Compound (III').

This reaction is advantageously carried out without solvent or in a solvent that is inert to the reaction. The solvent is not particularly limited as long as it allows the reaction to proceed, and examples thereof include solvents such as ethers, hydrocarbons, amides, halogenated hydrocarbons, nitrites, ketones, sulfoxides, aromatic amines and water, or mixtures of two or more of these solvents.

The reaction temperature is about −20° C. to about 200° C., preferably about 0° C. to about 150° C. The reaction time is usually about 5 minutes to about 48 hours, preferably about 10 minutes to about 24 hours.

Among Compounds (VI'), the compound in which $R^1$ is represented by the formula: —(C=O)—$NR^7R^8$ can be produced by condensing Compound (III') with an amine represented by the formula: $R^7R^8NH$ and an active carbonyl compound [e.g., phosgene, bis(trichloromethyl)carbonate, N,N'-carbonyldiimidazole, isobutyl chlorocarbonate, etc.].

The amount of the amine represented by the formula: $R^7R^8NH$ to be used is about 1 to about 3 moles, preferably about 1 to about 2 moles, relative to 1 mole of Compound (III').

The amount of the active carbonyl compound to be used is about 1 to about 10 moles, preferably about 1 to about 5 moles, relative to 1 mole of Compound (III').

This reaction can be carried out in the presence of base, if desired. The "base" that is used as desired may be exemplified by inorganic bases, basic salts, aromatic amines, tertiary amines and the like. The amount of the base to be used is about 1 to about 10 moles, preferably about 1 to about 5 moles, relative to 1 mole of Compound (III').

This reaction is advantageously carried out without solvent or in a solvent that is inert to the reaction. This solvent is not particularly limited as long as it allows the reaction to proceed, and preferred examples thereof include solvents such as ethers, hydrocarbons, amides, halogenated hydrocarbons, nitrites, ketones, sulfoxides and aromatic amines, or mixtures of two or more of these solvents.

The reaction temperature is about −20° C. to about 200° C., preferably about −10° C. to about 100° C. The reaction time is typically about 5 minutes to about 48 hours, preferably about 10 minutes to about 24 hours.

Compound (VIII') can be produced by reacting Compound (VI') with Compound (VII'), if desired, in the presence of base.

The amount of Compound (VII') to be used is about 1 to about 10 moles, preferably about 1 to about 4 moles, relative to 1 mole of Compound (VI').

The "base" that is used as desired may be exemplified by inorganic bases, basic salts, aromatic amines, tertiary amines and the like. The amount of the base to be used is about 1 to about 10 moles, preferably about 1 to about 4 moles, relative to 1 moles of Compound (VI').

This reaction is advantageously carried out without solvent or in a solvent that is inert to the reaction. This solvent is not particularly limited as long as it allows the reaction to proceed, and preferred examples thereof include solvents such as ethers, hydrocarbons, amides, halogenated hydrocarbons, nitrites, ketones, sulfoxides, aromatic amines and water, or mixtures of two or more of these solvents.

The reaction temperature is about −20° C. to about 200° C., preferably about 0° C. to about 150° C. The reaction time is usually about 5 minutes to about 48 hours, preferably about 10 minutes to about 24 hours.

Among Compounds (VIII'), the compound in which $R^1$ is represented by the formula: —(C=O)—$OR^e$ can be produced by reacting Compound (III') with an acylating agent, if desired, in the presence of base.

Examples of the "acylating agent" include halogenocarboxylic acid esters (e.g., ethyl chlorocarbonate, benzyl chlorocarbonate, etc.), dicarboxylic acid diesters (e.g., di-tert-butyl dicarbonate, etc.), and the like. The amount of the acylating agent to be used is about 2 to about 10 moles, preferably about 2 to about 7 moles, relative to 1 mole of Compound (III').

The "base" that is used as desired may be exemplified by inorganic bases, basic salts, aromatic amines, tertiary amines, or the like. The amount of the base to be used is about 2 to about 10 moles, preferably about 1 to about 7 moles, relative to 1 mole of Compound (III').

This reaction is advantageously carried out without solvent or in a solvent that is inert to the reaction. The solvent is not particularly limited as long as it allows the reaction to proceed, but preferred examples thereof include solvents such as ethers, hydrocarbons, amides, halogenated hydrocarbons, nitrites, ketones, sulfoxides, aromatic amines and water, or mixtures of two or more of these solvents.

The reaction temperature is about −20° C. to about 200° C., preferably about 0° C. to about 150° C. The reaction time is usually about 5 minutes to about 48 hours, preferably about 10 minutes to about 24 hours.

Compound (I) can be produced by subjecting Compound (VIII') to a ring closure reaction in the presence of base.

The ring closure reaction is carried out according to a known method.

The "base" may be exemplified by inorganic bases, basic salts, aromatic amines, tertiary amines, alkali metal hydrides, metal amides, metal alkoxides, or the like. The amount of the base to be used is about 0.1 to about 10 moles, preferably about 0.1 to about 5 moles, relative to 1 mole of Compound (VIII').

This reaction is advantageously carried out in a solvent that is inert to the reaction. The solvent is not particularly limited as long as it allows the reaction to proceed, but preferred examples thereof include solvents such as alcohols, ethers, hydrocarbons and water, or mixtures of two or more of these solvents.

The reaction time is usually about 10 minutes to about 48 hours, preferably about 30 minutes to about 24 hours. The reaction temperature is usually about −20° C. to about 150° C., preferably about −10° C. to about 120° C.

Compound (I) can be produced by reacting Compound (VI′) with an acylating agent, if desired, in the presence of base.

Examples of the "acylating agent" include halogenocarboxylic acid esters (e.g., ethyl chlorocarbonate, benzyl chlorocarbonate, etc.), dicarboxylic acid diesters (e.g., di-tert-butyl dicarbonate, etc.), and the like. The amount of the acylating agent to be used is about 1 to about 10 moles, preferably about 1 to about 4 moles, relative to 1 mole of Compound (VI′).

The "base" that is used as desired may be exemplified by inorganic bases, basic salts, aromatic amines, tertiary amines, or the like. The amount of the base to be used is about 1 to about 10 moles, preferably about 1 to about 5 moles, relative to 1 mole of Compound (VI′).

This reaction is advantageously carried out without solvent or in a solvent that is inert to the reaction. The solvent is not particularly limited as long as it allows the reaction to proceed, but preferred examples thereof include solvents such as ethers, hydrocarbons, amides, halogenated hydrocarbons, nitrites, ketones, sulfoxides, aromatic amines and water, or mixtures of two or more of these solvents.

The reaction temperature is about −20° C. to about 200° C., preferably about 0° C. to about 150° C. The reaction time is usually about 5 minutes to about 48 hours, preferably about 10 minutes to about 36 hours.

Compound (I) can be produced from Compound (III′) by using the same method as in the preparation of Compound (I) from Compound (VI′).

Compound (IX′) can be produced by removing "R¹" from Compound (I).

This reaction can be carried out according to a method known per se, for example, the method described in "Protection for the Amino Group", Protective Groups in Organic Synthesis, Vol. 3 (1999), or the like.

Compound (I) can be produced from Compound (IX′) by using the same method as in the preparation of Compound (VI′) from Compound (III′).

[Reaction Scheme 2]

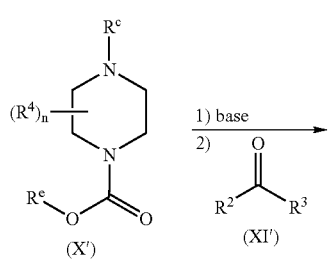

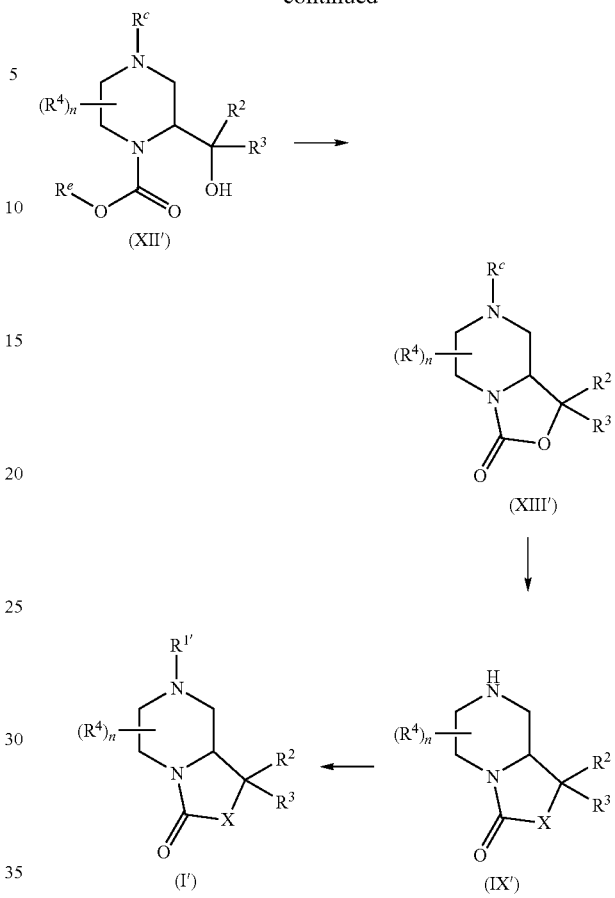

wherein $R^c$ and $R^e$ have the same meanings as defined above.

Compound (XII′) can be obtained by reacting Compound (X′) with a base and then condensing the product with Compound (XI′).

Compound (X′) can be a commercially available compound, or can be produced according to a method known per se or a method equivalent thereto.

The base to be used in this reaction may be exemplified by alkyl metals (e.g., sec-butyllithium, etc.), tertiary amines (e.g., tetramethylethylene diamine, etc.), and the like, and these bases are used in combination. The amount of the alkyl metal to be used is about 1 to about 10 moles, preferably about 2 to about 5 moles, relative to 1 mole of Compound (X′). The amount of the tertiary amine to be used is about 1 to about 10 moles, preferably about 2 to about 5 moles, relative to 1 mole of Compound (X′).

Compound (XI′) can be a commercially available compound, or can be produced according to a method known per se or a method equivalent thereto. The amount of Compound (XI′) to be used is about 1 to about 10 moles, preferably about 1.5 to about 5 moles, relative to 1 mole of Compound (X′).

This reaction is advantageously carried out in a solvent that is inert to the reaction. The solvent is not particularly limited as long as it allows the reaction to proceed, but preferred examples thereof include solvents such as ethers and hydrocarbons, or mixtures of two or more of these solvents.

The reaction temperature is usually about −100° C. to about 80° C., preferably about −80° C. to about 50° C. The reaction time is usually about 30 minutes to about 48 hours, preferably about 1 hour to about 24 hours.

Compound (XIII') can be produced from Compound (XII') by using the same method as in the preparation of Compound (I) from Compound (VIII').

Among Compounds (IX'), the compound in which X is an oxygen atom can be produced from Compound (XIII') by using the same method as in the preparation of Compound (IX') from Compound (I).

Compound (I) can be produced from Compound (IX') obtained according to Reaction Scheme 2, by using the same method as in the preparation of Compound (I) from Compound (IX') obtained according to Reaction Scheme 1.

The "hydrocarbon group which may be substituted" represented by $R^g$, $R^h$ and $R^i$ may be exemplified by the above-described "hydrocarbon group which may be substituted" represented by $R^6$.

The Compound (XV') in which Y is a halogen atom can be produced by reacting Compound (XIV') with a halogenating agent.

Compound (XIV') can be a commercially available compound, or can be produced according to a method known per se or a method equivalent thereto.

The halogenating agent used in this reaction may be exemplified by a phosphorus halide such as phosphorus trichloride, phosphorus oxychloride, phosphorus pentachloride or phos-

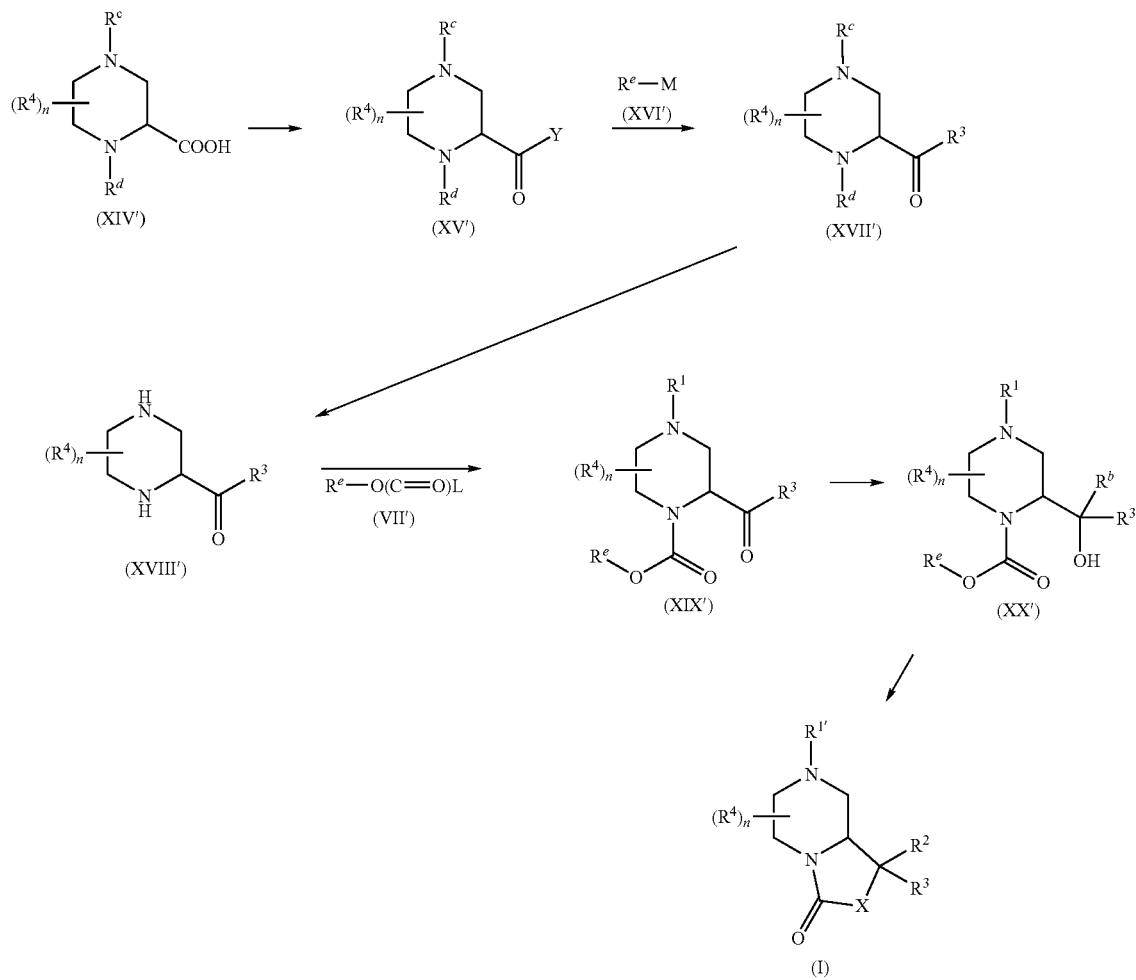

[Reaction Scheme 3]

wherein $R^c$, $R^d$, $R^e$, L and M have the same meanings as defined above.

Y is a leaving group.

The "leaving group" represented by Y may be exemplified by a halogen atom (e.g., chlorine, bromine, etc.), a group represented by the formula: —O(C=O)—$R^g$ (where $R^g$ is a hydrocarbon group which may be substituted), a group represented by the formula: —N($R^h$)—O—$R^i$ (wherein $R^h$ and $R^i$ are each a hydrocarbon group which may be substituted), or the like.

phorus bromide, halogen, thionyl chloride, or the like. The amount of the halogenating agent to be used is about 1 to about 100 moles, preferably about 1 to about 10 moles, relative to 1 mole of Compound (XIV').

This reaction is advantageously carried out without solvent or in a solvent that is inert to the reaction. The solvent is not particularly limited as long as it allows the reaction to proceed, but examples thereof include solvents such as ethers, hydrocarbons, amides, halogenated hydrocarbons, nitrites and sulfoxides, or mixtures of two or more of these solvents.

The reaction temperature is usually about 0° C. to about 200° C., preferably about 10° C. to about 100° C. The reaction time is usually about 10 minutes to about 24 hours, preferably about 30 minutes to about 12 hours.

The Compound (XV') in which Y is a group represented by the formula: —O(C=O)—R$^g$ can be produced by reacting Compound (XIV') with an acylating agent, if desired, in the presence of base.

Compound (XIV') can be a commercially available compound, or can be produced according to method known per se or a method equivalent thereto.

Examples of the "acylating agent" include halogenocarboxylic acid esters (e.g., ethyl chlorocarbonate, benzyl chlorocarbonate, etc.), dicarboxylic acid diesters (e.g., di-tert-butyl bicarbonate, etc.), and the like. The amount of the acylating agent to be used is about 1 to about 10 moles, preferably about 1 to about 4 moles, relative to 1 mole of Compound (XIV').

The "base" used as desired may be exemplified by inorganic bases, basic salts, aromatic amines, tertiary amines or the like. The amount of the base to be used is about 1 to about 10 moles, preferably about 1 to about 5 moles, relative to Compound (XIV').

This reaction is advantageously carried out without solvent or in a solvent that is inert to the reaction. The solvent is not particularly limited as long as it allows the reaction to proceed, but preferred examples thereof include solvents such as ethers, hydrocarbons, amides, halogenated hydrocarbons, nitrites, ketones and aromatic amines, or mixtures of two or more of these solvents.

The reaction temperature is usually about −20° C. to about 100° C., preferably about −10° C. to about 60° C. The reaction time is usually about 5 minutes to about 48 hours, preferably about 10 minutes to about 36 hours.

The Compound (XV') in which Y is a group represented by the formula: —N(R$^h$)—O—R$^i$ can be produced by condensing Compound (XIV') with a hydroxylamine derivative represented by the formula: N(R$^h$)H—O—R$^i$ (wherein each symbol is as defined above).

Compound (XIV') can be a commercially available compound, and can be produced according to a method known per se or a method equivalent thereto.

The "hydroxylamine derivative" may be exemplified by N,O-dimethylhydroxylamine hydrochloride or the like. The amount of the hydroxylamine derivative to be used is about 1 to about 10 moles, preferably about 1 to about 3 moles, relative to 1 mole of Compound (XIV').

The condensing agent used in the reaction may be exemplified by N,N'-disubstituted carbodiimide [e.g., N,N'-dicyclohexylcarbodiimide, 1-ethyl-3-(3-dimethylaminopropyl) carbodiimide hydrochloride, etc.], an azolide (e.g., N,N'-carbonyldiimidazole, etc.), a dehydrating agent (e.g., N-ethoxycarbonyl-2-ethoxy-1,2-dihydroquinoline, phosphorus oxychloride, alkoxyacetylene, etc.), a 2-halogenopyridinium salt (e.g., 2-chloromethylpyridinium iodide, 2-fluoro-1-methylpyridinium iodide, etc.), or the like. The amount of the condensing agent to be used may vary with the condensation agent to be used, but the amount is about 1 to about 10 moles, preferably about 1 to about 5 moles, relative to 1 mole of Compound (XIV').

This reaction may be carried out in the presence of an additive (e.g., 1-hydroxybenzotriazole, N-hydroxysuccinimide, etc.). The amount of the additive to be used is about 1 to about 10 moles, preferably about 1 to about 5 moles, relative to 1 mole of Compound (XIV').

This reaction is advantageously carried out in a solvent that is inert to the reaction. The solvent is not particularly limited as long as it allows the reaction to proceed, and preferred examples thereof include solvents such as ethers, hydrocarbons, amides, halogenated hydrocarbons, nitrites, sulfoxides and water, or mixtures of these solvents.

The reaction temperature is usually about 0° C. to about 100° C., preferably about 0° C. to about 70° C. The reaction time is usually about 30 minutes to about 24 hours, preferably about 30 minutes to about 4 hours.

Compound (XVII') can be produced by reacting Compound (XV') with Compound (XVI').

Compound (XVI') can be a commercially available compound, and can be produced according to a method known per se or a method equivalent thereto. The amount of Compound (XVI') to be used is about 1 to about 10 moles, preferably about 1 to about 4 moles, relative to 1 mole of Compound (XV').

This reaction is advantageously carried out in a solvent that is inert to the reaction. The solvent is not particularly limited as long as it allows the reaction to proceed, but preferred examples thereof include solvents such as ethers and hydrocarbons, or mixture of these solvents.

The reaction temperature is usually about 0° C. to about 100° C., preferably about 0° C. to about 70° C. The reaction time is usually about 30 minutes to about 24 hours, preferably about 1 hour to about 15 hours.

Compound (XVIII') can be produced from Compound (XVII') by using the same method as in the preparation of Compound (III') from Compound (V').

Among Compounds (XIX'), the Compound (XIX') in which R$^1$ is represented by the formula: —(C=O)—OR$^e$ can be produced from Compound (XVIII') and Compound (VII') by using the same method as in the preparation of Compound (VIII') from Compound (VI') and Compound (VII').

Among Compounds (XX'), the compound in which R$^2$ is a hydrogen atom can be produced by reducing the carbonyl group of Compound (XIX').

Examples of the reducing agent to be used include metal hydrogen complex compounds (e.g., sodium borohydride, etc.) and the like. The amount of the reducing agent to be used is, for example, in the case of metal hydrogen complex compounds, about 1 to about 10 moles, preferably about 1 to about 3 moles, relative to 1 mole of Compound (XIX').

This reaction is advantageously carried out in a solvent that is inert to the reaction. The solvent is not particularly limited as long as it allows the reaction to proceed, but preferred examples thereof include solvents such as alcohols, ethers, hydrocarbons and amides, or mixtures of these solvents.

The reaction temperature is usually about −30° C. to about 80° C., preferably about −20° C. to about 50° C. The reaction time is usually about 10 minutes to about 48 hours, preferably about 30 minutes to about 24 hours.

Compound (I) can be produced from Compound (XX') by using the same method as in the preparation of Compound (I) from Compound (XIII').

In the above-described reactions, when the starting compound is substituted with amino, carboxyl or hydroxyl, the starting compound may have such substituent protected by a protective group such as those generally used in peptide chemistry or the like, and the target compound can be obtained, if necessary, by removing the protective group after the reaction.

The amino-protective group that can be used may be exemplified by a formyl group, or a $C_{1-6}$ alkyl-carbonyl group (e.g., an acetyl group, a propionyl group, etc.), a phenylcarbonyl group, a $C_{1-6}$ alkoxy-carbonyl group (e.g., methoxycarbonyl group, an ethoxycarbonyl group, etc.), a phenyloxycarbonyl group, a $C_{7-10}$ aralkyloxy-carbonyl group (e.g., a benzyloxy-carbonyl group, etc.), a trityl group or a phthaloyl group, each of which may be substituted, or the like. A substituent thereof may be exemplified by a halogen atom (e.g., fluorine, chlorine, bromine, iodine, etc.), a $C_{1-6}$ alkyl-carbonyl group (e.g., an acetyl group, a propionyl group, a valeryl group, etc.), a nitro group, or the like, and there may be 1 to 3 substituents.

The carboxyl-protective group that can be used may be exemplified by a $C_{1-6}$ alkyl group (e.g., a methyl group, an ethyl group, a propyl group, an isopropyl group, a butyl group, a tert-butyl group, a 2-trimethyl group, etc.), a phenyl group, a trityl group or a silyl group, each of which may be substituted, or the like. A substituent thereof may be exemplified by a halogen atom (e.g., fluorine, chlorine, bromine, iodine, etc.), a formyl group, a $C_{1-6}$ alkyl-carbonyl group (e.g., an acetyl group, a propionyl group, a butylcarbonyl group, etc.), a nitro group, a $C_{1-6}$ alkyl group (e.g., a methyl group, an ethyl group, a tert-butyl group, etc.), a $C_{6-10}$ aryl group (e.g., a phenyl group, a naphthyl group, etc.) or the like, and there may be 1 to 3 substituents.

The hydroxyl-protective group that can be used may be exemplified by a $C_{1-6}$ alkyl group (e.g., a methyl group, an ethyl group, a propyl group, an isopropyl group, a butyl group, a tert-butyl group, etc.), a phenyl group, a $C_{7-11}$ aralkyl group (e.g., a benzyl group, etc.), a formyl group, a $C_{1-6}$ alkyl-carbonyl group (e.g., an acetyl group, a propionyl group, etc.), a phenyloxycarbonyl group, a $C_{7-11}$ aralkyloxy-carbonyl group (e.g., a benzyloxycarbonyl group, etc.), a tetrahydropyranyl group, a tetrahydrofuranyl group or a silyl group, each of which may be substituted, or the like. A substituent thereof may be a halogen atom (e.g., fluorine, chlorine, bromine, iodine, etc.), a $C_{1-6}$ alkyl group (e.g., a methyl group, an ethyl group, a tert-butyl group, etc.), a $C_{7-11}$ aralkyl group (e.g., a benzyl group, etc.), a $C_{6-10}$ aryl group (e.g., a phenyl group, a naphthyl group, etc.), a nitro group, or the like, and there may be 1 to 4 substituents.

Removal of the protective group is carried out using a method known per se or a method equivalent thereto, and for example, a method treating with acid, base, ultraviolet light, hydrazine, phenylhydrazine, sodium N-methyldithiocarbamate, tetrabutylammonium fluoride, palladium acetate or the like, or a reduction reaction is used.

In any case, if further desired, Compound (I) can be synthesized by carrying out known deprotection, acylation, alkylation, hydrogenation, oxidation, reduction, carbon chain extension or substituent exchange, individually or in combination of two or more of these reactions. These reactions employ, for example, the methods described in New Experimental Chemistry Lecture 14, Vol. 15, Maruzen Co., Ltd. (1977) or the like.

Specifically, for example, as shown in Reaction Scheme 4, Compound (XXII') which is included in Compound (I) of the invention can be produced from Compound (XXI') which is included in Compound (I) of the invention, by using a substituent exchange reaction.

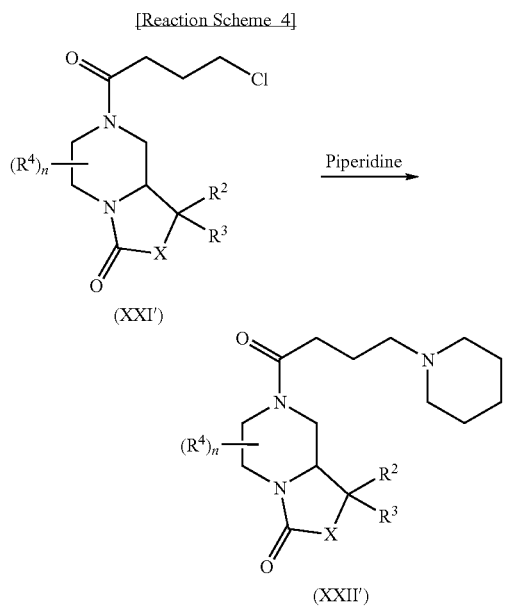

When the target product is obtained in its free form by the above-described reactions, the product may be converted to a salt according to a conventional method. When the product is obtained in a salt form, the product may be converted to a free product or to another salt according to a conventional method. Compound (I) thus obtained can be isolated or purified from the reaction solution by a known technique such as phase transfer, concentration, solvent extraction, fractional distillation, crystallization, recrystallization, or chromatography.

If Compound (I) exists as a mixture of configurational isomers, diastereomers, conformers or the like, each isomer can be isolated, if desired, by the above-described separation or purification techniques.

If Compound (I) exists as a mixture of stereoisomers, the invention includes the individual isomers as well as their mixtures.

Compound (I) or (II) of the invention, or a salt or prodrug thereof (hereinafter, simply referred to as Compound (I) of the invention) has an effect of altering the binding property of TGR23 (e.g., human TGR23 containing the amino acid sequence represented by SEQ ID NO:1 or SEQ ID NO:2, etc.) with a TGR23 ligand, especially a TGR23 function regulating effect (preferably, TGR23 antagonist activity), and has low toxicity and fewer side effects. Therefore, Compound (I) of the invention is useful as a safe pharmaceutical product and is useful as a less toxic, safe medicine as a TGR23 function regulator (preferably, TGR23 antagonist), a prophylactic and/or therapeutic agent for diseases attributable to TGR23, such as cancers (e.g., large intestine cancer, colon cancer, rectal cancer, breast cancer, lung cancer, non-small cell lung cancer, prostate cancer, esophageal cancer, stomach cancer, liver cancer, bile duct cancer, spleen cancer, kidney cancer, urinary bladder cancer, uterine cancer, ovarian cancer, cervical cancer, testicular cancer, thyroid cancer, pancreas cancer, brain tumor, blood tumor, etc.), an eating (appetite) promoter, a prophylactic and/or therapeutic agent for anorexia nervosa, an apoptosis inducing agent or the like. Further, the compound is useful as a medicine such as a safe and less toxic prophylactic and/or therapeutic agent for central nervous diseases (e.g., Alzheimer's disease, dementia, dietary disorder, etc.), endocrine diseases (e.g., hypertension, gonadal dysfunction, thyroid dysfunction, pituitary dysfunction, etc.), metabolic diseases (e.g., diabetes mellitus, lipidosis, hyperlipidemia, etc.), and the like. Preferably, the compound is useful as a prophylactic and/or therapeutic agent for cancer, an apoptosis inducing agent, an eating promoter or the like.

When Compound (I) of the invention is used as a prophylactic and/or therapeutic agent of the aforementioned diseases, an apoptosis inducing agent, an eating promoter or the like, the compound can be administered orally as well as parenterally according to a method known per se, and can be mixed with a pharmaceutically acceptable carrier and in general, either orally administered as a solid preparation such as tablet, capsule, granule or powder, or parenterally administered as an intravenous, subcutaneous or intramuscular injectable preparation, a suppository or a sublingual tablet. The compound may also be administered sublingually, subcutaneously and intramuscularly as a sustained release preparation such as sublingual tablet or microcapsule.

The dosage of Compound (I) of the invention may vary depending on the subject of administration, administration route or symptom and thus not particularly limited. However, when the compound is orally administered to an adult patient for the purpose of treating cancer for example, the dose is usually about 0.01 to about 20 mg/kg of body weight, preferably about 0.1 to about 10 mg/kg of body weight, and even more preferably about 0.1 to about 2 mg/kg of body weight, and such dose is preferably administered about 1 to 3 times a day in accordance with the symptoms.

The content of Compound (I) of the invention in the "preparation (pharmaceutical composition)" may vary depending on the form of preparation, but the content is usually about 0.01 to 100% by weight, preferably about 0.1 to 50% by weight, and even more preferably 0.5 to 20% by weight, of the total pharmaceutical composition.

The content of the pharmaceutically acceptable carrier in the "preparation (pharmaceutical composition)" may vary depending on the form of preparation, but the content is usually about 1 to 99.99% by weight, and preferably about 10 to 90% by weight, of the total pharmaceutical composition.

For the pharmaceutically acceptable carrier, use can be made of various organic or inorganic carrier materials that are conventionally used as materials for preparation, and the carrier materials are mixed as an excipient, a lubricant, a binding agent or a disintegrant in solid preparations; and as a solvent, a dissolution aid, a suspending agent, an isotonic agent, a buffer or a soothing agent in liquid preparations. If necessary, additives for preparation such as an antiseptic agent, an antioxidant, a colorant and a sweetener also can be used.

Suitable examples of the excipient include lactose, sucrose, D-mannitol, starch, crystalline cellulose, light silicic anhydride and the like. Suitable examples of the lubricant include magnesium stearate, calcium stearate, talc, colloidal silica and the like. Suitable examples of the binding agent include crystalline cellulose, sucrose, D-mannitol, dextrin, hydroxypropylcellulose, hydroxypropyl methylcellulose, polyvinylpyrrolidone and the like. Suitable examples of the disintegrant include starch, carboxymethylcellulose, calcium carboxymethylcellulose, sodium croscarmellose, sodium carboxymethyl starch and the like. Suitable examples of the solvent include water for injection, alcohol, propylene glycol, macrogol, sesame oil, corn oil and the like. Suitable examples of the dissolution aid include polyethylene glycol, propylene glycol, D-mannitol, benzyl benzoate, ethanol, trisaminomethane, cholesterol, triethanolamine, sodium carbonate, sodium citrate and the like. Suitable examples of the suspending agent include surfactants such as stearyl triethanolamine, sodium lauryl sulfate, lauryl aminopropionic acid, lecithin, benzalkonium chloride, benzethonium chloride, glycerin monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropyl cellulose and the like; and the like. Suitable examples of the isotonic agent include sodium chloride, glycerin, D-mannitol and the like. Suitable examples of the buffer include buffer solutions of phosphates, acetates, carbonates, citrates and the like. Suitable examples of the soothing agent include benzyl alcohol and the like. Suitable examples of the antiseptic agent include parahydroxybenzoic acid esters, chlorobutanol, benzyl alcohol, phenethyl alcohol, dehydroacetic acid, sorbic acid and the like. Suitable examples of the antioxidant include sulfites, ascorbic acid and the like.

Compound (I) of the invention can be mixed with suspending agents, dissolution aids, stabilizers, isotonic agents, preservatives and the like, and then formulated into intravenous, subcutaneous or intramuscular injectable preparations by methods known per se. Here, if necessary, the preparations can be also made into lyophilization products by methods known per se.

When Compound (I) of the invention is administered to human for example, the compound itself, or a pharmaceutical composition containing the compound mixed with appropriate pharmaceutically acceptable carriers, excipients or diluents, can be safely administered orally or parenterally.

The pharmaceutical composition may be exemplified by an oral preparation (e.g., powder, granule, capsule and tablet), an injectable preparation, an infusion fluid, an external preparation (e.g., intranasal preparation, topical preparation, etc.), a suppository (e.g., rectal suppository, vaginal suppository) or the like.

These preparations can be produced by known methods that are generally employed in formulating processes.

Compound (I) of the invention can be produced into an injectable preparation by formulating the compound into aqueous injectable preparations together with dispersants (e.g., Tween 80 (Atlas Powder Co., US), HCO60 (Nikko Chemicals Co., Ltd.), polyethylene glycol, carboxymethylcellulose, sodium alginate, etc.), preservatives (e.g., methylparaben, propylparaben, benzyl alcohol, etc.), isotonic agents (e.g., sodium chloride, mannitol, sorbitol, glucose, etc.) and the like, or into an oil-based injectable preparation by dissolving, suspending or emulsifying the compound in plant oils such as olive oil, sesame oil, cotton seed oil or corn oil, propylene glycol or the like.

Compound (I) of the invention can be produced into an oral preparation by mixing the compound with, for example, excipients (e.g., lactose, sucrose, starch, etc.), disintegrants (e.g., starch, calcium carbonate, etc.), binding agents (e.g., starch, gum arabic, carboxymethylcellulose, polyvinylpyrrolidone, hydroxypropylcellulose, etc.), lubricants (e.g., talc, magnesium stearate, polyethylene glycol 6000, etc.) or the like; molding the mixture by compression; and then coating the compression product by a method known per se, if necessary, for the purposes of masking of taste, or enteric or sustained release. Examples of the coating agent that can be used for the purpose include hydroxypropyl methylcellulose, ethylcellulose, hydroxymethylcellulose, hydroxypropylcellulose, polyoxyethylene glycol, Tween 80, Pluronic F68, cellulose acetate phthalate, hydroxypropyl methylcellulose phthalate, hydroxymethylcellulose acetate succinate, Eudragit (Röhm Pharma GmbH, Germany; copolymer of methacrylic acid and acrylic acid), colorants (e.g., red iron oxide, titanium dioxide, etc.) and the like. In order to use Compound (I) of the invention as enteric preparations, an intermediate phase can be provided in between an enteric phase and a drug-containing phase of the preparation by a method known per se, for the purpose of separation of the enteric phase and the drug-containing phase.

In order to use Compound (I) of the invention as external preparations, the compound or a salt thereof can be formulated into solid, semi-solid or liquid externally administered preparations by methods known per se. For the solid preparation for example, Compound (I) of the invention or a salt thereof is directly used or mixed with excipients (e.g., glycol, mannitol, starch, microcrystalline cellulose, etc.), thickening agents (e.g., natural gums, cellulose derivatives, acrylic acid polymers, etc.) and the like, to be produced into a pulverized composition. For the liquid preparation, an oil-based preparation or an aqueous suspension is produced, in the virtually same manner as in the preparation of injectable preparations. For the semi-solid preparation, aqueous or oil-based gel preparations, or ointments are preferable. All of these preparations may also have pH adjusting agents (e.g., carbonate, phosphate, citrate, hydrochloric acid, sodium hydroxide, etc.), antiseptic agents (e.g., parahydroxybenzoic acid esters, chlorobutanol, benzalkonium chloride, etc.) and the like added therein.

For example, in order to use Compound (I) of the invention as suppositories, the compound can be formulated into oil-based or aqueous, solid, semi-solid or liquid suppositories by methods known per se. The oil-based base that can be used in the compositions may be exemplified by glycerides of high fatty acids [e.g., cacao butter, Witepsols (Dynamit Nobel, Inc., Germany), etc.], intermediate fatty acids [e.g., migliols (Dynamit Nobel, Inc., Germany), etc.], plant oils (e.g., sesame oil, soybean oil, cotton seed oil, etc.) or the like. The aqueous base that can be used in the compositions may be exemplified by polyethylene glycols, propylene glycol or the like, and the aqueous gel base may be exemplified by natural gums, cellulose derivatives, vinyl polymers, acrylic acid polymers or the like.

A drug which can be used in combination with Compound (I) of the invention (hereinafter, may be simply referred to as combination drug) may be exemplified by other therapeutic agents for diabetes mellitus, therapeutic agents for diabetic complications, therapeutic agents for hyperlipidemia, hypotensor drugs, anti-obesity drugs, diuretics, chemotherapeutic drugs, immunotherapeutic drugs, immunoregulating drugs, anti-inflammation drugs, antithrombotic drugs, therapeutic agents for osteoporosis, antibacterial drugs, antifungal drugs, antiprotozoal drugs, antibiotics, antitussives and expectorants, sedatives, anesthetic drugs, antiulcerative drugs, tranquilizer drugs, antipsychotic drugs, antitumor drugs, muscle relaxing drugs, antiepileptic drugs, antidepressant drugs, antiallergic drugs, cardiac stimulants, antiarrhythmic drugs, vasodilatory drugs, vasoconstrictor drugs, antinarcotics drugs, vitamin drugs, vitamin derivatives, antiasthmatic drugs, antidementia drugs, therapeutic agents for frequent urination and urinary incontinence, therapeutic agents for dysuria, therapeutic agents for atopic dermatitis, therapeutic agents for allergic rhinitis, hypertensors, endotoxin antagonists or antibodies, signal transduction inhibitors, inflammatory mediator inhibitors, inflammatory mediator inhibiting antibodies, anti-inflammatory mediator inhibitors, anti-inflammatory mediator inhibiting antibodies, or the like. Specifically, mention may be made of the following.

Examples of the other therapeutic agents for diabetes mellitus include insulin preparations [e.g., preparations of animal insulin extracted from bovine or porcine pancreas; preparations of human insulin synthesized in a genetically engineered manner using E. coli or yeast; insulin zinc; protamine insulin zinc; fragments or derivatives of insulin (e.g., INS-1, etc.), oral insulin preparations, etc.], insulin sensitivity enhancers (e.g., pioglitazone or salts thereof (preferably hydrochloride salts), troglitazone, rosiglitazone or salts thereof (preferably maleic acid salts), reglixane (JTT-501), netoglitazone (MCC-555), YM-440, GI-262570, KRP-297, FK-614, CS-011, (γE)-γ-[[[4-[(5-methyl-2-phenyl-4-oxazolyl)methoxy]phenyl]methoxy]imino]benzene-butanoic acid or the like, compounds described in WO 99/58510 (e.g., (E)-4-[4-(5-methyl-2-phenyl-4-oxazolylmethoxy)benzyloxyimino]-4-phenylbutyric acid), compounds described in WO 01/38325, tesaglitazar (AZ-242), ragaglitazar (NN-622), BMS-298585, ONO-5816, BM-13-1258, LM-4156, MBX-102, LY-519818, MX-6054, LY-510929, balaglitazone (NN-2344), T-131 or salts thereof, THR-0921), α-glucosidase inhibitors (e.g., voglibose, acarbose, miglitol, emiglitate, etc.), biguanide agents (e.g., phenformin, metformin, buformin, etc.), insulin secretion promoters [sulfonylurea agents (e.g., tolbutamide, glibenclamide, gliclizide, chlorpropamide, tolazamide, acetohexamide, glyclopyramide, glimepiride, etc.), repaglinide, senaglinide, mitiglinide or calcium salt hydrates thereof, nateglinide, etc.], GLP-1 receptor agonist [e.g., GLP-1, GLP-1MR agent, NN-2211, AC-2993 (exendin-4), BIM-51077, Aib(8,35)hGLP-1(7,37)NH$_2$, CJC-1131, etc.], dipeptidylpeptidase IV inhibitors (e.g., NVP-DPP-278, PT-100, P32/98, P93/01, NVP-DPP-728, LAF237, TS-021, etc.), β3 agonists (e.g., CL-316243, SR-58611-A, UL-TG-307, AJ-9677, AZ40140, etc.), amylin agonists (e.g., pramlintide, etc.), phosphotyrosine phosphatase inhibitors (e.g., vanadic acid, etc.), glucogenesis inhibitors (e.g., glycogenphosphorylase inhibitors, glucose-6-phosphatase inhibitors, glucagon antagonists, etc.), SGLT (sodium-glucose cotransporter) inhibitors (e.g., T-1095, etc.), 11β-hydroxysteroid dehydrogenase inhibitors (e.g., BVT-3498, etc.), adiponectin or agonists thereof, IKK inhibitors (e.g., AS-2868, etc.), leptin resistance improving agents, somatostatin receptor agonists (compounds described in WO 01/25228, WO 03/42204, compounds described in WO 98/44921, WO 98/45285, WO 99/22735, etc.), glucokinase activators (e.g., Ro-28-1675) and the like.

Examples of the therapeutic agent for diabetic complications include aldose reductase inhibitors (e.g., tolrestat, epalrestat, zenarestat, zopolrestat, fidarestat (SNK-860), minalrestat (ARI-509), CT-112, etc.), neurotrophic factors and enhancers thereof (e.g., NGF, NT-3, BDNF, neurotrophin production/secretion promoting agents described in WO 01/14372 (e.g., 4-(4-chlorophenyl)-2-(2-methyl-1-imidazolyl)-5-[3-(2-methylphenoxy)propyl]oxazole, etc.), etc.), protein kinase C (PKC) inhibitors (e.g., LY-333531, etc.), AGE inhibitors (e.g., ALT-945, pimagedine, pyratoxathine, N-phenacylthiazolium bromide (ALT-766), EXO-226, ALT-711, pyridorin, pyridoxamine, etc.), active oxygen scavenger drugs (e.g., thioctic acid, etc.), cerebral vasodilators (e.g., thiapride, etc.), somatostatin receptor agonists (BIM23190), apoptosis signal regulating kinase 1 (ASK-1) inhibitors, and the like.

Examples of the therapeutic agent for hyperlipidemia include statin compounds as cholesterol synthesis inhibitors (e.g., pravastatin, simvastatin, lovastatin, atorvastatin, fluvastatin, cerivastatin or salts thereof (e.g., sodium salts, etc.) etc.), squalene synthetase inhibitors (e.g., compounds described in WO 97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl] acetyl]piperidine-4-acetic acid, etc.), fibrate compounds (e.g., bezafibrate, clofibrate, simfibrate, clinofibrate, etc.), antioxidants (e.g., lipoic acid, probucol, etc.), and the like.

Examples of the hypotensor drug include angiotensin-converting enzyme inhibitors (e.g., captopril, enalapril, delapril, etc.), angiotensin II antagonists (e.g., losartan, candesartan cilexetil, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid, calcium antagonists (e.g., manidipine, nifedipine, amlodipine, efonidipine, nicardipine, etc.), clonidine, and the like.

Examples of the anti-obesity drug include central nervous anti-obesity drugs (e.g., dexfenfluramine, fenfluramine, phentermine, sibutramine, anfepramone, dexamphetamine, mazindol, phenylpropanolamine, clobenzorex; MCH receptor antagonists (e.g., SB-568849; SNAP-7941; compounds included in WO 01/82925 and WO 01/87834, etc.); neuropeptide Y antagonists (e.g., CP-422935, etc.); cannabinoid receptor antagonists (e.g., SR-141716, SR-147778, etc.); ghrelin antagonists; 11β-hydroxysteroid dehydrogenase inhibitors (e.g., BVT-3498, etc.), etc.), pancreatic lipase inhibitors (e.g., orlistat, ATL-962, etc.), β3 agonists (e.g., CL-316243, SR-58611-A, UL-TG-307, AJ-9677, AZ40140, etc.), peptidic anorectic drugs (e.g., leptin, CNTF (ciliary neurotrophic factor), etc.), cholecystokinin agonists (e.g., lintitript, FPL-15849, etc.), dietary inhibitors (e.g., P-57, etc.), and the like.

Examples of the diuretic include xanthine derivatives (e.g., theobromine sodium salicylate, theobromine calcium salicylate, etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide, etc.), anti-aldosterone preparations (e.g., spironolactone, triamteren, etc.), carboxylic acid dehydrogenase inhibitors (e.g., acetazolamide, etc.), chlorbenzenesulfonamide preparations (e.g., chlorthalidone, mefruside, indapamide, etc.), azosemide, isosorbide, ethacrynic acid, piretanide, bumetanide, furosemide, and the like.

Examples of the chemotherapeutic agent include alkylating agents (e.g., cyclophosphamide, iphosphamide, etc.), metabolic antagonists (e.g., methotrexate, 5-fluorouracil, etc.), anticancerous antibiotics (e.g., mitomycin, adriamycin, etc.), plant-derived antitumor agents (e.g., vincristine, vindesine, taxol, etc.), cisplatin, carboplatin, etoposide and the like. Among these, furtulon or neofurtulon, both being 5-fluorouracil derivatives, and the like are preferred.

Examples of the immunotherapeutic agents include microorganic or bacterial components (e.g., muramyl dipeptide derivatives, picibanil, etc.), polysaccharides having immunopotentiating activity (e.g., lentinan, sizofuran, Krestin, etc.), cytokines obtained by genetically engineered means (e.g., interferon, interleukin (IL), etc.), colony-stimulating glycoproteins (e.g., granulocyte colony-stimulating glycoproteins, erythropoietin, etc.), and the like. Among these, interleukins such as IL-1, IL-2 and IL-12 are preferred.

Examples of the anti-inflammatory drug include non-steroid anti-inflammatory drugs such as aspirin, acetaminophen and indomethacin, and the like.

Examples of the antithrombotic agent include heparin (e.g., heparin sodium, heparin calcium, dalteparin sodium, etc.), warfarin (e.g., warfarin potassium, etc.), antithrombin drugs (e.g., aragatroban, etc.), antithrombotic drugs (e.g., urokinase, tisokinase, alteplase, nateplase, monteplase, pamiteplase, etc.), platelet aggregation inhibitors (e.g., ticlopidine hydrochloride, cilostazol, ethyl icosapentate, beraprost sodium, sarpogrelate hydrochloride, etc.) and the like.

Examples of the therapeutic agent for osteoporosis include alfacalcidol, calcitriol, elcatonin, calcitonin salmon, estriol, ipriflavone, disodium pamidronate, sodium alendronate hydrate, disodium incadronate, and the like.

Examples of the vitamin drug include vitamin $B_1$, vitamin $B_{12}$ and the like.

Examples of the antidementia drug include tacrine, donepezil, rivastigmine, galantamine and the like.

Examples of the therapeutic agent for frequent urination and urinary incontinence include flavoxate hydrochloride, oxybutynin hydrochloride, propiverine hydrochloride, and the like.

Examples of the therapeutic agent for dysuria include acetylcholinesterase inhibitors (e.g., distigmine) and the like.

Moreover, drugs that are acknowledged to have a cachexia-improving function in animal models or in clinical studies, namely, cyclooxygenase inhibitors (e.g., indomethacin, etc.) [Cancer Research, 49, 5935-5939 (1989)], progesterone derivatives (e.g., megestrol acetate) [Journal of Clinical Oncology, 12, 213-225 (1994)], glucosteroids (e.g., dexamethasone, etc.), methoclopramide drugs, tetrahydrocannabinol drugs (the same references as given above), lipid metabolism improving agents (e.g., eicosapentaenoic acid, etc.) [British Journal of Cancer, 68, 314-318 (1993)], growth hormones, IGF-1, or TNF-α, a cachexia-inducing factor, LIF, IL-6, oncostatin M antibody, and the like also can be used in combination with Compound (I) of the invention.

Furthermore, glycosylation inhibitors (e.g., ALT-711, etc.), neurogenesis promoting drugs (e.g., Y-128, VX853, prosaptide, etc.), antidepressants (e.g., desipramine, amitriptiline, imipramine), antiepileptic drugs (e.g., lamotrigine, trileptal, Keppra, Zonegran, Pregabalin, Harkoseride, carbamazepin), antiarrhythmic drugs (e.g., mexiletine), acetylcholine receptor ligands (e.g., ABT-594), endothelin receptor antagonists (e.g., ABT-627), monoamine uptake inhibitors (e.g., tramadol), narcotic analgesic drugs (e.g., morphine), GABA receptor agonists (e.g., gabapentine, gabapentine MR agent), α2 receptor agonists (e.g., clonidine), topical analgesic drugs (e.g., capsaicin), anxiolytic drugs (e.g., benzothiazepine), phosphodiesterase inhibitors (e.g., sildenafil), dopamine receptor agonists (e.g., apomorphine), and the like also can be used in combination with Compound (I) of the invention.

Combining Compound (I) of the invention with a combination drug can give excellent effects such as that:

(1) Compared with the case where Compound (I) of the invention or a combination drug is individually administered, the dosage can be reduced;

(2) The drug to be combined with Compound (I) of the invention can be selected in accordance with the patient's symptoms (mild, severe, etc.);

(3) The duration of treatment can be lengthened by selecting a combination drug whose mechanism is different from that of Compound (I) of the invention;

(4) It can be attempted to sustain the effect of treatment by selecting a combination drug having a mechanism different from that of Compound (I) of the invention (5) A synergistic effect can be obtained by using a combination drug in combination with Compound (I) of the invention.

Hereinafter, the combination of Compound (I) of the invention and a combination drug will be referred to as a "combination preparation of the invention."

In respect to the use of the combination preparation of the invention, the time for administration of Compound (I) of the invention and the combination drug is not limited, and Compound (I) of the invention and the combination drug may be administered simultaneously or with a time interval, to the subject of administration. Dosage of the combination drug may be determined according to the clinically used dosage, and can be appropriately selected in accordance with the subject of administration, route of administration, disease to be treated, combinations thereof and the like.

The administration mode for the combination preparation of the invention is not particularly limited, and it will be sufficient to combine Compound (I) of the invention and the combination drug upon administration. Examples of such administration mode include (1) administration of a single preparation obtained by simultaneously formulating Compound (I) of the invention and the combination drug; (2) simultaneous administration of two preparations obtained by separately formulating Compound (I) of the invention and the combination drug, via the same route of administration; (3) administration of two preparations obtained by separately formulating Compound (I) of the invention and the combination drug, with a time interval via the same route of administration; (4) simultaneous administration of two preparations obtained by separately formulating Compound (I) of the invention and the combination drug, via different routes of administration; (5) administration of two preparations obtained by separately formulating Compound (I) of the invention and the combination drug, with a time interval via different routes of administration (e.g., administration in order of Compound (I) of the invention and the combination drug, or administration in the inverse order); and the like.

The combination preparation of the invention is less toxic, and for example, Compound (I) of the invention or(and) the combination drug can be formulated by mixing with a pharmaceutically acceptable carrier into a pharmaceutical composition such as tablet (including sugar-coated tablet and film-coated tablet), powder, granule, capsule (including soft capsule), liquid, injectable preparation, suppository, sustained release preparation or the like, according to a method known per se, and then safely administered orally or parenterally (e.g., topical, rectal, intravenous administration, etc.). The injectable preparation can be administered intravenously, intramuscularly, subcutaneously or intraorganically, or directly into the lesion.

The pharmaceutically acceptable carrier which may be used in the production of the combination preparation of the invention, may be exemplified by the same carriers as the pharmaceutically acceptable carriers which may be used in the production of the above-described medicine of the invention. Furthermore, if necessary, the additives which may be used in the production of the medicine of the invention, such as antiseptic, antioxidant, colorant, sweetener, adsorbent, wetting agent and the like, can be appropriately used in appropriate amounts.

The mixing ratio of Compound (I) of the invention and the combination drug in the combination preparation of the invention can be appropriately selected in accordance with the subject of administration, route of administration, disease to be treated, or the like.

For example, the content of Compound (I) of the invention in the combination preparation of the invention may vary depending on the form of preparation, but the content is usually about 0.01 to 100% by weight, preferably about 0.1 to 50% by weight, and more preferably about 0.5 to 20% by weight, based on the total preparation.

The content of the combination drug in the combination preparation of the invention may vary depending on the form of preparation, but the content is usually about 0.01 to 90% by weight, preferably about 0.1 to 50% by weight, and more preferably about 0.5 to 20% by weight, based on the total preparation.

The content of the additives such as carrier in the combination preparation of the invention may vary depending on the form of preparation, but the content is usually about 1 to 99.98% by weight, and preferably about 10 to 90% by weight, based on the total preparation.

When compound (I) of the invention and the combination drug are separately formulated, Compound (I) of the invention and the combination drug may be contained in the same amounts, and the content of the additives such as carrier is usually about 1 to 99.99% by weight, and preferably about 10 to 90% by weight, based on the total preparation.

Such preparations can be produced by known methods that are generally employed in formulating processes.

For example, Compound (I) of the invention or the combination drug can be produced into injectable preparations by formulating the compound into an aqueous injectable preparation together with dispersants (e.g., Tween 80 (Atlas Powder Co., US), HCO60 (Nikko Chemicals Co., Ltd.), polyethylene glycol, carboxymethylcellulose, sodium alginate, hydroxypropyl methylcellulose, dextrin, etc.), stabilizers (e.g., ascorbic acid, sodium pyrosulfite, etc.), surfactants (e.g., Polysorbate 80, macrogol, etc.), solubilizing agents (e.g., glycerin, ethanol, etc.), buffers (e.g., phosphoric acid and alkali metal salts thereof, citric acid and alkali metal salts thereof, etc.), isotonic agents (e.g., sodium chloride, potassium chloride, mannitol, sorbitol, glucose, etc.), pH adjusting agents (e.g., hydrochloric acid, sodium hydroxide, etc.), preservatives (e.g., ethyl parahydroxybenzoate, benzoic acid, methylparaben, propylparaben, benzyl alcohol, etc.), dissolving agents (e.g., concentrated glycerin, meglumine, etc.), dissolving aids (e.g., propylene glycol, sucrose, etc.), soothing agents (e.g., glucose, benzyl alcohol, etc.) and the like, or into an oil-based injectable preparation by dissolving, suspending or emulsifying the compound in dissolving aids, such as plant oils such as olive oil, sesame oil, cotton seed oil or corn oil, propylene glycol or the like.

Furthermore, Compound (I) of the invention or the combination drug can be produced into an orally administrable preparation according to a method known per se, by mixing with, for example, excipients (e.g., lactose, sucrose, starch, etc.), disintegrants (e.g., starch, calcium carbonate, etc.), binding agents (e.g., starch, gum arabic, carboxymethylcellulose, polyvinylpyrrolidone, hydroxypropylcellulose, etc.), lubricants (e.g., talc, magnesium stearate, polyethylene glycol 6000, etc.) or the like; molding the mixture by compression; and then coating the compression product by a method known per se, if necessary, for the purposes of masking of taste, or enteric or sustained release. Examples of the coating agent that can be used for the purpose include hydroxypropyl methylcellulose, ethylcellulose, hydroxymethylcellulose, hydroxypropylcellulose, polyoxyethylene glycol, Tween 80, Pluronic F68, cellulose acetate phthalate, hydroxypropyl methylcellulose phthalate, hydroxymethylcellulose acetate succinate, Eudragit (Röhm Pharma GmbH, Germany; copolymer of methacrylic acid and acrylic acid), colorants (e.g., red iron oxide, titanium dioxide, etc.) and the like. The orally administrable preparation may be either an immediate release preparation or a sustained release preparation.

Moreover, Compound (I) of the invention or the combination drug can be produced into an oil-based or aqueous, solid, semi-solid or liquid suppository according to a method known per se, by mixing the compound with oil-based bases, aqueous bases or aqueous gel bases. Examples of the oil-based base include glycerides of high fatty acids (e.g., cacao butter, Witepsols (Dynamit Nobel, Inc., Germany), etc.], intermediate fatty acids [e.g., miglyols (Dynamit Nobel, Inc., Germany), etc.], plant oils (e.g., sesame oil, soybean oil, cotton seed oil, etc.) or the like. Examples of the aqueous base include polyethylene glycols, propylene glycol, or the like. Examples of the aqueous gel base include natural gums, cellulose derivatives, vinyl polymers, acrylic acid polymers, or the like.

The sustained release preparation may be exemplified by a sustained release microcapsule. The sustained release microcapsule is produced by a method known per se, for example a method as described in the following [2].

Compound (I) of the invention is preferably formulated into an orally administrable preparation such as solid preparation (e.g., powder, granule, tablet, capsule), or formulated into a rectally administrable preparation such as suppository. An orally administrable preparation is particularly preferred.

The combination drug can be formulated into the above-described forms in accordance with the type of the drug.

Hereinafter, specific explanations will be given on [1] an injectable preparation of Compound (I) of the invention or the combination drug, and production thereof; [2] a sustained release preparation or immediate release preparation of Compound (I) of the invention or the combination drug, and production thereof; and [3] a sublingual tablet, or buccal or intraoral disintegrant of Compound (I) of the invention or the combination drug, and production thereof.

[1] Injectable Preparation and Production Thereof

An injectable preparation produced by dissolving Compound (I) of the invention or the combination drug in water is preferred. The injectable preparation may contain benzoates or/and salicylates.

The injectable preparation can be obtained by dissolving Compound (I) of the invention or the combination drug and, if desired, either of benzoate or/and salicylate in water.

Examples of benzoate or salicylate include salts of alkali metals such as sodium and potassium, salts of alkaline earth metals such as calcium and magnesium, ammonium salts, meglumine salts, and in addition to those, salts of organic acids such as trometamol, and the like.

The concentration of Compound (I) of the invention or the combination drug in the injectable preparation is 0.5 to 50 w/v %, and preferably about 3 to 20 w/v %. The concentration of benzoate or/and salicylate is 0.5 to 50 w/v %, and preferably about 3 to 20 w/v %.

The injectable preparation can contain appropriate additives that are generally used in injectable preparations, such as stabilizers (e.g., ascorbic acid, sodium pyrosulfite, etc.), surfactants (e.g., Polysorbate 80, macrogol, etc.), solubilizing agents (e.g., glycerin, ethanol, etc.), buffers (e.g., phosphoric acid and alkali metal salts thereof, citric acid and alkali metal salts thereof, etc.), isotonic agents (e.g., sodium chloride, potassium chloride, etc.), dispersants (e.g., hydroxypropyl methylcellulose, dextrin), pH adjusting agents (e.g., hydrochloric acid, sodium hydroxide, etc.), preservatives (e.g., ethyl parahydroxybenzoate, benzoic acid, etc.), dissolving aids (e.g., concentrated glycerin, meglumine, etc.), dissolving aids (e.g., propylene glycol, sucrose, etc.), soothing agents (e.g., glucose, benzyl alcohol, etc.), or the like. These additives are incorporated in proportions that are generally used in injectable preparations.

The injectable preparation may be adjusted to pH 2 to 12, and preferably pH 2.5 to 8.0, by addition of a pH adjusting agent.

The injectable preparation can be obtained by dissolving Compound (I) of the invention or the combination drug and if desired, benzoate or/and salicylate, and if necessary, the above-mentioned additives in water. The dissolution may be done in any order and can be appropriately carried out in the same manner as in conventional methods for producing injectable preparations.

The aqueous solution for injection may be warmed, and the injectable preparation can be provided in the same manner as in conventional injectable preparations, for example, after sterilization, or sterilization by autoclaving.

The aqueous solution for injection is preferably sterilized by autoclaving, for example, at 100 to 121° C. for 5 to 30 minutes.

Moreover, in order to use the preparation as a preparation for multiple administrations, the preparation may be imparted with antibacterial properties in the solution.

[2] Sustained Release Preparation or Immediate Release Preparation and Production Thereof A sustained release preparation is preferred which is produced by coating a core containing Compound (I) of the invention or the combination drug with, if desired, a coating agent such as a water-insoluble material or a swellable polymer. For example, an orally administrable sustained release preparation for once-a-day administration is preferred.

Examples of the water-insoluble material used as the coating agent include cellulose ethers such as ethylcellulose and butylcellulose, cellulose esters such as cellulose acetate and cellulose propionate; polyvinyl esters such as polyvinyl acetate and polyvinyl butyrate; acrylic acid polymers such as acrylic acid/methacrylic acid copolymers, methyl methacrylate copolymers, ethoxyethyl methacrylate/cinnamoethyl methacrylate/aminoalkyl methacrylate copolymers, polyacrylic acid, polymethacrylic acid, methacrylic acid alkylamide copolymers, poly(methyl methacrylate), polymethacrylate, polymethacrylamide, aminoalkyl methacrylate copolymers, poly(methacryl anhydride), glycidyl methacrylate copolymers, and in particular, Eudragits (Röhm Pharma GmbH) such as Eudragit RS-100, RL-100, RS-30D, RL-30D, RL-PO, RS-PO (ethyl acrylate/methyl methacrylate/trimethylammoniumethyl ethacrylate chloride copolymers) and Eudragit NE-30D (methyl methacrylate/ethyl acrylate copolymers); hydrogenated oils such as hydrogenated castor oil (e.g., Lubri Wax (Freund Industrial Co., Ltd.); waxes such as carnauba wax, fatty acid glycerin esters and paraffins; polyglycerin fatty acid esters; and the like.

A swellable polymer is preferably a polymer having an acidic dissociable group and thus exhibiting pH-dependent swelling, and is preferably a polymer having an acidic dissociable group which swells less in acidic regions such as the inside of the stomach and swells more in neutral regions such as the small intestine or large intestine.

Examples of such polymer having an acidic dissociable group and thus exhibiting pH-dependent swelling include crosslinked polyacrylic acid polymers such as Carbomers 934P, 940, 941, 974P, 980, 1342 and the like, polycarbophil, calcium polycarbophil (all products by BF Goodrich Company), Highvis Wakos 103, 104, 105, 304 (all products by Wako Pure Chemicals Co., Ltd.) and the like.

The coating agent that is used in the sustained release preparation may further contain a hydrophilic material.

Examples of the hydrophilic material include polysaccharides which may have sulfuric acid group such as pullulan, dextrin and alginate salts of alkali metals; polysaccharides having hydroxyalkyl group or carboxyalkyl group such as hydroxypropylcellulose, hydroxypropyl methylcellulose, and sodium carboxymethylcellulose, methylcellulose, polyvinylpyrrolidone, polyvinyl alcohol, polyethylene glycol and the like.

The content of the water-insoluble material which can be used in the coating agent for the sustained release preparation is about 30 to about 90% (w/w), preferably about 35 to about 80% (w/w), and even more preferably about 40 to 75% (w/w), and the content of the swellable polymer is about 3 to about 30% (w/w), and preferably about 3 to about 15% (w/w). The coating agent may further contain a hydrophilic material, and in this case, the content of the hydrophilic material which can be used in the coating agent is about 50% (w/w) or less, preferably about 5 to about 40% (w/w), and more preferably about 5 to about 35% (w/w). Here, the term % (w/w) indicates the percentage by weight based on the coating agent composition, with the solvent (e.g., water, lower alcohol such as methanol or ethanol, etc.) excluded from the coating agent solution.

The sustained release preparation is produced, as described below, by providing a core containing the drug and then coating the obtained core with a coating agent solution in which a water-insoluble material, a swellable polymer or the like is melted by heating, or dissolved or dispersed in a solvent.

I. Production of Core Containing Drug

The form of the core containing a drug (hereinafter, may be simply referred to the core) that is to be coated with a coating agent is not particularly limited, but it is preferably formed into a particulate form such as granule or microparticle.

When the core is a granule or a microparticle, the average particle size is preferably about 150 to 2,000 μm, and more preferably about 500 to about 1,400 μm.

The core can be produced by a conventional production method. For example, the core is produced by wet extrusion particle production, fluidized bed particle production or the like, after mixing the drug with appropriate excipients, binding agents, disintegrants, lubricants, stabilizers and the like.

The content of the drug in the core is about 0.5 to about 95% (w/w), preferably about 5.0 to about 80% (w/w), and even more preferably about 30 to about 70% (w/w).

Examples of the excipients contained in the core include saccharides such as sucrose, lactose, mannitol and glucose, starch, crystalline cellulose, calcium phosphate, corn starch and the like. Among these, crystalline cellulose and corn starch are preferred.

Examples of the binding agent that can be used include polyvinyl alcohol, hydroxypropylcellulose, polyethylene glycol, polyvinylpyrrolidone, Pluronic F68, gum arabic, gelatin, starch and the like. Examples of the disintegrant that can be used include calcium carboxymethylcellulose (ECG505), croscarmellose sodium (Ac-Di-Sol), crosslinked polyvinylpyrrolidone (Crospovidone), low-substituted hydroxypropylcellulose (L-HPC) and the like. Among these, hydroxypropylcellulose, polyvinylpyrrolidone and low-substituted hydroxypropylcellulose are preferred. Examples of the lubricant and aggregation preventing agent include talc, magnesium stearate and inorganic salts thereof, and examples of the lubricant include polyethylene glycol and the like. Examples of the stabilizer include acids such as tartaric acid, citric acid, succinic acid, fumaric acid, maleic acid and the like.

In addition to the production methods described above, the core can be also produced by particle production by rolling, in which inert carrier particles to be the center of the core are subjected to spraying with a binding agent dissolved in a suitable solvent such as water or lower alcohol (e.g., methanol, ethanol, etc.), while adding thereto small amounts of the drug or its mixture with excipients, lubricants and the like, or by pan coating, fluidized bed coating or particle production by melting. Examples of the inert carrier particle that can be used include the particles made of sucrose, lactose, starch, crystalline cellulose or waxes, and the average particle size is preferably about 100 μm to about 1,500 μm.

In order to separate the drug contained in the core and the coating agent, the surface of the core may be coated with a protective agent. The protective agent that can be used may be the above-described hydrophilic materials or water-insoluble materials. The protective agent that can be used is preferably polyethylene glycol, or polysaccharides having hydroxyalkyl group or carboxyalkyl group, more preferably hydroxypropyl methylcellulose and hydroxypropylcellulose. The protective agent may contain an acid such as tartaric acid, citric acid, succinic acid, fumaric acid or maleic acid as a stabilizer, or a lubricant such as talc. When the protective agent is used, the amount of coating is about 1 to about 15% (w/w), preferably about 1 to about 10% (w/w), and even more preferably about 2 to about 8% (w/w), based on the core.

The protective agent can be coated by a conventional coating method, and specifically, the protective agent can be coated by spray coating the core by, for example, fluidized bed coating, pan coating or the like.

II. Coating of Core with Coating Agent

The sustained release preparation is produced by coating the core obtained in section I above with a coating agent solution in which the above-described water-insoluble material, the pH-dependent swellable polymer and the hydrophilic material are melted by heating, or are dissolved or dispersed in a solvent.

The method of coating the core with a coating agent solution may be exemplified by spray coating, or the like.

The composition ratio of the water-insoluble material, swellable polymer or hydrophilic material in the coating agent solution is appropriately selected such that the content of each component in the coating film corresponds to the above-described content.

The amount of the coating agent to be coated is about 1 to about 90% (w/w), preferably about 5 to about 50% (w/w), and more preferably about 5 to about 35% (w/w), based on the core (not including the amount of the protective agent to be coated).

The solvent of the coating agent solution that can be used is water or an organic solvent, individually or as a mixture of the two. The mixing ratio of water and the organic solvent when used as a mixture (water/organic solvent; weight ratio) may vary within the range of 1 to 100%, and is preferably 1 to about 30%. The organic solvent is not particularly limited as long as it dissolves the water-insoluble material, but examples thereof include lower alcohols such as methyl alcohol, ethyl alcohol, isopropyl alcohol and n-butyl alcohol, lower alkanones such as acetone, acetonitrile, chloroform, methylene chloride and the like. Among these, lower alcohols are preferred, and ethyl alcohol and isopropyl alcohol are particularly preferred. Water and a mixture of water and an organic solvent are preferably used as the solvent of the coating agent. Here, if necessary, the coating agent solution may further contain an acid such as tartaric acid, citric acid, succinic acid, fumaric acid or maleic acid, for the purpose of stabilizing the coating agent solution.

The operation of coating the core by spray coating can be carried out by a conventional coating method, and specifically, it can be carried out by spray coating the core with the coating agent solution by, for example, fluidized bed coating, pan coating or the like. Here, if necessary, the coating agent solution may further contain talc, titanium oxide, magnesium stearate, calcium stearate, light silicic anhydride or the like as the lubricant, and glycerin fatty acid esters, hydrogenated castor oil, triethyl citrate, cetyl alcohol, stearyl alcohol or the like as the plasticizer.

After coating with the coating agent, an antistatic agent such as talc may be also incorporated, if necessary.

The immediate release preparation may be liquid (solution, suspension, emulsion, etc.) or solid (particle, pill, tablet, etc.). Orally administrable preparations and parenterally administrable preparations such as injectable preparation are used as the immediate release preparation, but orally administrable preparations are preferred.

In general, the immediate release preparation may contain, in addition to the active ingredient drug, carriers, additives or excipients (hereinafter, may be simply referred to as excipients) that are conventionally used in the pharmaceutical field. The excipient that can be used is not particularly limited as long as it is an excipient conventionally used for pharmaceutical preparations. Examples of the excipient for oral solid preparations include lactose, starch, corn starch, crystalline cellulose (Asahi Kasei Corp., Avicel PH101, etc.), powdered sugar, granulated sugar, mannitol, light silicic anhydride, magnesium carbonate, calcium carbonate, L-cysteine and the like, and corn starch, mannitol and the like are preferred. These excipients can be used individually or in combination of two or more species. The content of the excipient is, for example, about 4.5 to about 99.4 w/w %, preferably about 20 to about 98.5 w/w %, and more preferably about 30 to about 97 w/w %, relative to the total amount of the immediate release preparation.

The content of the drug in the immediate release preparation can be appropriately selected from the range of about 0.5 to about 95%, and preferably in the range of about 1 to about 60%, relative to the total amount of the immediate release preparation.

When the immediate release preparation is an oral solid preparation, the preparation usually contains a disintegrant, in addition to the above-described components. Examples of the disintegrant include carboxymethylcellulose calcium (Gotoku Chemical Co., Ltd.; ECG-505), croscarmellose sodium (e.g., Asahi Kasei Corp., Ac-Di-sol), Crospovidone (e.g., BASF Corp., Kollidon CL), low-substituted hydroxypropylcellulose (Shin-Etsu Chemical Co., Ltd.), carboxymethyl starch (Matsutani Chemical Industry Co., Ltd.), carboxymethyl starch sodium (Kimura Sangyo Co., Ltd., Exprotab), partially pregelatinized starch (Asahi Kasei Corp., PCS) and the like, and for example, those disintegrating granules by absorbing water and swelling, or forming a channel between the active ingredient constituting the core and the excipient, upon contact with water, can be used. Such disintegrants can be used individually or in combination of two or more species. The mixing amount of the disintegrant may be appropriately selected in accordance with the type or mixing amount of the drug used, the design of the release preparation or the like, but the amount is, for example, about 0.05 to about 30 w/w %, and preferably about 0.5 to about 15 w/w %, relative to the total amount of the immediate release preparation.

When the immediate release preparation is an oral solid preparation, the oral solid preparation may further contain conventionally used additives, if desired, in addition to the above-described composition for solid preparation. Examples of the additives include binding agents (e.g., sucrose, gelatin, powdered gum arabic, methylcellulose, hydroxypropylcellulose, hydroxypropyl methylcellulose, carboxymethylcellulose, polyvinylpyrrolidone, pullulan, dextrin, etc.), lubricants (e.g., polyethylene glycol, magnesium stearate, talc, light silicic anhydride (e.g., Aerosil (Nippon Aerosil Co., Ltd.)), surfactants (e.g., anionic surfactants such as sodium alkylsulfate, nonionic surfactants such as polyoxyethylene fatty acid esters and polyoxyethylene sorbitan fatty acid esters, polyoxyethylene castor oil derivatives and the like), colorants (e.g., tar colorants, caramel, red iron oxide, titanium oxide, riboflavins), if necessary, flavoring agents (e.g., sweeteners, flavors, etc.), adsorbents, antiseptic agents, wetting agents, antistatic agents and the like. Also, organic acids such as tartaric acid, citric acid, succinic acid or fumaric acid may be added as a stabilizer.

For the binding agent, hydroxypropylcellulose, polyethylene glycol, polyvinylpyrrolidone and the like are preferably used.

Immediate release preparation can be produced by mixing the above-described ingredients and, if necessary, further kneading, and then molding the mixture, based on conventional formulating methods. The process of mixing is carried out by a generally used method, such as mixing or kneading. Specifically, in the case of forming the immediate release preparation into a particulate form for example, the preparation can be produced in the same method as in the production of the core of the sustained release preparation, by mixing the ingredients using a vertical granulator, an all-purpose kneader (Hata Iron Works Co., Ltd.), a fluidized bed granulator FD-5S (Powrex Corp.) or the like, and then granulating by wet extrusion granulation, fluidized bed granulation or the like.

The immediate release preparation and the sustained release preparation thus obtained may be formulated separately by a standard method, without any modification or together with appropriate excipients for preparation, and then administered in combination simultaneously or with an arbitrary time interval; alternatively, the preparations may be formulated into a single orally administrable preparation (e.g., granule, microparticle, tablet, capsule, etc.) without modification or together with appropriate excipients for preparation. The two preparations may be also produced into granules or microparticles and then filled in the same capsule to give an orally administrable preparation.

[3] Sublingual Tablet, Buccal or Intraoral Rapidly Disintegrating Preparation and Production Thereof The sublingual tablet, buccal preparation and intraoral rapidly disintegrating preparation may be solid preparations such as tablets, or may be oral mucosa plasters (films).

The sublingual tablet, or the buccal or intraoral rapidly disintegrating preparation is preferably a preparation containing Compound (I) of the invention or the combination drug and excipients. The preparation may also contain auxiliary agents such as lubricant, isotonic agent, hydrophilic carrier, water-dispersible polymer or stabilizer. Further, the preparation may also contain β-cyclodextrin, β-cyclodextrin derivatives (e.g., hydroxypropyl-β-cyclodextrin, etc.) or the like in order to facilitate absorption of the preparation and thus to increase the bioavailability thereof.

Examples of the excipient include lactose, sucrose, D-mannitol, starch, crystalline cellulose, light silicic anhydride and the like. Examples of the lubricant include magnesium stearate, calcium stearate, talc, colloidal silica and the like, and magnesium stearate or colloidal silica in particular is preferred. Examples of the isotonic agent include sodium chloride, glucose, fructose, mannitol, sorbitol, lactose, saccharose, glycerin, urea and the like, and mannitol in particular is preferred. Examples of the hydrophilic carrier include hydrophilic swellable carriers such as crystalline cellulose, ethylcellulose, crosslinkable polyvinylpyrrolidone, light silicic anhydride, silicic acid, dicalcium phosphate and calcium carbonate, and crystalline cellulose (e.g., microcrystalline cellulose, etc.) in particular is preferred. Examples of the water-dispersible polymer include gums (e.g., tragacanth gum, acacia gum, guar gum), alginic acid salts (e.g., sodium alginate), cellulose derivatives (e.g., methylcellulose, carboxymethylcellulose, hydroxymethylcellulose, hydroxypropylcellulose, hydroxypropyl methylcellulose), gelatin, water-soluble starch, polyacrylic acid (e.g., Carbomer), polymethacrylic acid, polyvinyl alcohol, polyethylene glycol, polyvinylpyrrolidone, polycarbophil, ascorbic acid, palmitic acid salts, and the like, and hydroxypropyl methylcellulose, polyacrylic acid, alginic acid salts, gelatin, carboxymethylcellulose, polyvinylpyrrolidone, polyethylene glycol and the like are preferred. In particular, hydroxypropyl methylcellulose is preferred. Examples of the stabilizer include cysteine, thiosorbitol, tartaric acid, citric acid, sodium carbonate, ascorbic acid, glycine, sodium sulfite and the like, and citric acid and ascorbic acid in particular are preferred.

The sublingual tablet and the buccal or intraoral rapidly disintegrating preparation can be produced by mixing Compound (I) of the invention or the combination drug with excipients by a method known per se. Furthermore, the above-described auxiliary agents such as lubricant, isotonic agent, hydrophilic carrier, water-dispersible polymer, stabilizer, colorant, sweetener and antiseptic agent may be also mixed therewith, if desired. The sublingual tablet, buccal tablet or intraoral rapidly disintegrating tablet can be obtained by mixing the above-described ingredients simultaneously or with a time interval, and then molding the mixture by tabletting under pressure. In order to obtain appropriate hardness, the tablets may be also produced by, before or after the process of tabletting, upon necessity, moisturizing and/or wetting the ingredients with a solvent such as water or alcohol, molding and then drying.

In the case of molding into the mucosa plaster (film), Compound (I) of the invention or the combination drug as well as the above-described water-dispersible polymer (preferably, hydroxypropylcellulose, hydroxypropyl methylcellulose), excipients and the like are dissolved in a solvent such as water, and the resulting solution is flow cast into a film. Furthermore, additives such as plasticizer, stabilizer, antioxidant, preservative, colorant, buffer and sweetener may be also added thereto. A glycol such as polyethylene glycol or propylene glycol may be added in order to impart the film with appropriate elasticity, or a bioadhesive polymer (e.g., polycarbophil, Carbopol) may be added in order to enhance the adhesion of the film to the oral mucosal lining. The flow casting is achieved by pouring a solution onto a non-adhesive surface, spreading the solution using a coater such as a doctor blade into a uniform thickness (preferably about 10 to 1000 microns), and then drying the solution to form a film. The film thus formed is dried at room temperature or with warming, and then cut into pieces having a desired surface area.

A preferred intraoral rapidly disintegrating preparation may be exemplified by a solid rapid diffusion formulation in the form of a network consisting of Compound (I) of the invention or the combination drug, and a water-soluble or water-diffusible carrier which is inert to Compound (I) of the invention or the combination drug. The network can be obtained by sublimating the solvent from a solid composition consisting of a solution of Compound (I) of the invention or the combination drug dissolved in an appropriate solvent.

The composition of the intraoral rapidly disintegrating preparation preferably contains, in addition to Compound (I) of the invention or the combination drug, a matrix-forming agent and a secondary component.

Examples of the matrix-forming agent include animal proteins or vegetable proteins such as gelatin, dextrin, and soybean, wheat and psyllium seed proteins; gummy materials such as gum arabic, guar gum, agar and xanthan gum; polysaccharides; alginic acid; carboxymethylcellulose; carrageenan; dextran; pectin; synthetic polymers such as polyvinylpyrrolidone; and materials derived from gelatin-gum arabic complexes. Also included are saccharides such as mannitol, dextrose, lactose, galactose and trehalose; cyclic saccharides such as cyclodextrin; inorganic salts such as sodium phosphate, sodium chloride and aluminum silicate; amino acids having 2 to 12 carbon atoms such as glycine, L-alanine, L-aspartic acid, L-glutamic acid, L-hydroxyproline, L-isoleucine, L-leucine and L-phenylalanine; and the like.

One or more matrix-forming agents may be introduced into the solution or suspension before solidification. Such a matrix-forming agent may be present in addition to surfactants, or may be present in the absence of surfactants. The matrix-forming agent serves not only to form a matrix itself, but also to aid in maintaining Compound (I) of the invention or the combination drug as being diffused in the solution or suspension.

A secondary agent such as preservative, antioxidant, surfactant, thickening agent, colorant, pH adjusting agent, flavor, sweetener or taste masking agent, may be contained in the composition. Suitable examples of the colorant include red, black and yellow iron oxides, and FD&C dyes available from Ellis and Everard, Ltd., such as FD&C Blue No. 2 and FD&C Red No. 40. Suitable examples of the flavor include mint, raspberry, licorice, orange, lemon, grape fruit, caramel, vanilla, cherry and grape flavor, as well as combinations thereof. Suitable examples of the pH adjusting agent include citric acid, tartaric acid, phosphoric acid, hydrochloric acid and maleic acid. Suitable examples of the sweetener include aspartame, acesulfame K, thaumatin and the like. Suitable examples of the taste masking agent may include sodium bicarbonate, ion exchange resin, cyclodextrin inclusion complex, adsorptive materials and microencapsulated apomorphine.

The preparation contains Compound (I) of the invention or the combination drug in an amount of usually about 0.1 to about 50% by weight, preferably about 0.1 to about 30% by weight, and is preferably a preparation (sublingual or buccal preparation described above) which allows 90% or more of Compound (I) of the invention or the combination drug to be dissolved (in water) within a time period of about 1 minute to about 60 minutes, preferably about 1 minute to about 15 minutes, and more preferably about 2 minutes to about 5 minutes, or an intraoral rapidly disintegrating preparation which disintegrates within 1 to 60 seconds, preferably 1 to 30 seconds, and more preferably 1 to 10 seconds, after being placed in the oral cavity.

The content of the above-described excipients based on the entire preparation is about 10 to about 99% by weight, and preferably about 30 to about 90% by weight. The content of β-cyclodextrin or β-cyclodextrin derivatives based on the entire preparation is 0 to about 30% by weight. The content of the lubricant based on the entire preparation is about 0.01 to about 10% by weight, and preferably about 1 to about 5% by weight. The content of the isotonic agent based on the entire preparation is about 0.1 to about 90% by weight, and preferably about 10 to about 70% by weight. The content of the hydrophilic carrier based on the entire preparation is about 0.1 to about 50% by weight, and preferably about 10 to about 30% by weight. The content of the water-dispersible polymer based on the entire preparation is about 0.1 to about 30% by weight, and preferably about 10 to about 25% by weight. The content of the stabilizer based on the entire preparation is about 0.1 to about 10% by weight, and preferably about 1 to about 5% by weight. The preparation may further contain, if necessary, additives such as colorant, sweetener and antiseptic agent.

The combination drug can be contained in any amount within the scope of not causing any side effects.

The dosage of the combination preparation of the invention may vary depending on the type of Compound (I) of the invention and the combination drug, the subject's age, body weight and symptom, the dosage form, administration mode and duration, and the like, but the daily dose for a cancer patient for example (adult, body weight of about 60 kg) is about 0.01 to about 20 mg/kg, preferably about 0.01 to about 10 mg/kg, and more preferably about 0.1 to about 2 mg/kg, as Compound (I) of the invention and the combination drug, which is administered intravenously once or in several portions a day. As a matter of fact, since the dosage may vary depending on various factors as described above, an amount less than the above-described dosage may sometimes be sufficient, or an excessive amount beyond the range may sometimes be necessary.

With regard to administration of the combination preparation of the invention, Compound (I) of the invention and the combination drug may be administered nearly simultaneously, but it is also possible to administer the combination drug first and then Compound (I) of the invention, or to administer Compound (I) of the invention first and then the combination drug. When the drugs are administered with a time interval, the time interval may vary depending on the active ingredient to be administered, the dosage form and the administration mode; but, when the combination drug is to be administered first for example, Compound (I) of the invention may be administered within 1 minute to 3 days, preferably within 10 minutes to 1 day, and more preferably within 15 minutes to 1 hour after the administration of the combination drug. When the Compound (I) of the invention is to be administered first, the combination drug may be administered within 1 minute to 1 day, preferably within 10 minutes to 6 hours, and more preferably within 15 minutes to 1 hour after the administration of Compound (I) of the invention.

The sequence identification numbers in the sequence listing of the present specification represent the following sequences:

[SEQ ID NO: 1]

Represents the amino acid sequence of the human-derived G protein-coupled receptor protein TGR23-1 (human TGR23-1).

[SEQ ID NO: 2]

Represents the amino acid sequence of the human-derived G protein-coupled receptor protein TGR23-2 (human TGR23-2).

EXAMPLES

Hereinafter, the invention will be described in more detail with reference to Reference Examples, Examples, Preparation Examples and Experimental Examples, but they are not to be construed to limit the scope thereof.

"%" in the following Reference Examples and Examples means percent by weight unless otherwise stated.

$^1$H-NMR spectra were measured with a BRUKER AVANCE DPX-300 spectrometer (300 MHz) using tetramethylsilane as an internal standard. All of the δ values are represented in ppm.

Abbreviations employed here are described below.

s: Singlet d: Doublet t: Triplet q: Quartet m: Multiplet br: Broad

J: Coupling constant

Hz: Hertz $CDCl_3$: deutero chloroform

DMSO-$d_6$: deutero dimethylsulfoxide

Room temperature usually represents a temperature of about 10° C. to 35° C., but is not particularly exactly limited.

Reference Example 1

(1,1-Dimethylethyl)3-(hydroxydiphenylmethyl)-1-piperazine carboxylate

Methyl 2-piperazine carboxylate dihydrochloride (20 g, 87 mmol) was suspended in tetrahydrofuran (300 mL), diisopropylethylamine (22 g, 0.17 mmol) was added thereto, and the mixture was stirred at room temperature for 1 hour. Next, a 2.0 M solution of phenylmagnesium bromide in tetrahydrofuran (260 mL, 0.52 mol) was added dropwise over 30 minutes, and the mixture was stirred at room temperature for 14 hours. The reaction solution was ice cooled, water (400 mL) was then added dropwise thereto, and the mixture was stirred for 30 minutes with ice cooling. Di-tert-butyl dicarbonate (13 g, 61 mmol) was added dropwise thereto, and the mixture was stirred at room temperature for 30 minutes. To the reaction solution was added an aqueous saturated ammonium chloride solution, and the resulting mixture was extracted with ethyl acetate. The extract was washed with water, and then concentrated under reduced pressure. The residue was purified with silica gel column chromatography (hexane:ethyl acetate=3:1) to obtain the title compound (9.7 g, yield 30%).

Amorphous.

$^1$H NMR (CDCl$_3$) δ 1.39 (9H, s), 2.71-2.93 (4H, m), 3.63 (1H, d, J=9.3 Hz), 3.75 (1H, d, J=12.6 Hz), 3.98 (1H, m), 4.11 (1H, m), 7.14-7.36 (6H, m), 7.50 (2H, d, J=7.4 Hz), 7.60 (2H, d, J=7.4 Hz).

Reference Example 2

Hexahydro-1,1-diphenyl-3H-oxazolo[3,4-a]pyrazin-3-one

To a solution of (1,1-dimethylethyl)tetrahydro-3-oxo-1,1-diphenyl-3H-oxazolo[3,4-a]pyrazine-7(1H)-carboxylate (2.3 g, 5.5 mmol) in dichloromethane (20 mL) was added trifluoroacetic acid (4 mL), and the mixture was stirred at room temperature for 2 hours. To the reaction solution was added an aqueous saturated sodium hydrogen carbonate solution (10 mL), and the resulting mixture was extracted with ethyl acetate. The extract was washed with water, and then concentrated under reduced pressure. The residue was crystallized from diisopropyl ether to obtain the title compound (1.6 g, yield 99%).

Melting point 188-191° C. (decomposed).

$^1$H NMR (DMSO-$d_6$) δ 2.09 (1H, t, J=12.0 Hz), 2.96 (1H, dt, J=12.3 Hz, 4.1 Hz), 3.12 (1H, dd, J=12.0 Hz, 3.1 Hz), 3.21-3.33 (2H, m), 3.81 (1H, dd, J=14.1 Hz, 3.7 Hz), 4.81 (1H, m), 7.31-7.55 (10H, m), 8.84 (1H, br s).

Reference Example 3

Ethyl 1,4-bis(phenylmethyl)-2-piperazine carboxylate

Ethyl 1,4-bis(phenylmethyl)-2-piperazine carboxylate dihydrochloride (21 g, 52 mmol) was neutralized with an aqueous sodium hydrogen carbonate solution, and then extracted with ethyl acetate. The extract was washed with water, dried over magnesium sulfate, and then concentrated under reduced pressure to obtain the title compound (18 g, quantitative). The obtained compound was used in the next process without further purification.

Oil.

Reference Example 4

Bis(phenylmethyl)2-(1-hydroxy-1-methylethyl)-1,4-piperazinedicarboxylate

To a solution of ethyl 1,4-bis(phenylmethyl)-2-piperazine carboxylate (2.0 g, 5.9 mmol) in tetrahydrofuran (30 mL) was added dropwise over 5 minutes a 1 M solution of methylmagnesium bromide in tetrahydrofuran (24 mL, 24 mmol) with ice cooling, and the mixture was stirred for 30 minutes with ice cooling. After stirring at room temperature overnight, to the reaction solution was added an aqueous saturated ammonium chloride solution (200 mL), and the resulting mixture was extracted with ethyl acetate. The extract was washed with water, dried over magnesium sulfate and concentrated under reduced pressure. The residue was dissolved in ethanol/water (30 mL/10 mL). 10% Palladium carbon (0.20 g) was added thereto, and the resulting mixture was stirred under hydrogen pressure (2.8 bar) at room temperature one whole day and night. The reaction solution was filtered through a Celite, the Celite was washed with ethanol, and then the filtrate was concentrated under reduced pressure. The residue was dissolved in tetrahydrofuran (50 mL). A 0.5 M aqueous sodium hydrogen carbonate solution (100 mL) and benzyl chlorocarbonate (3.4 mL, 24 mmol) were added thereto. The mixture was stirred at room temperature for 6 hours, and the reaction solution was extracted with ethyl acetate (200 mL). The extract was washed with water, dried over magnesium sulfate and concentrated under reduced pressure. Then, the residue was purified with silica gel column chromatography (hexane:ethyl acetate=3:1 to 1:1) to obtain the title compound (1.8 g, yield 73%).

Oil.

$^1$H NMR (CDCl$_3$) δ 1.10-1.29 (6H, m), 3.00-3.18 (1H, m), 3.40-3.52 (2H, m), 3.86-4.16 (4H, m), 5.08-5.20 (4H, m), 7.28-7.39 (10H, m).

Reference Example 5

Hexahydro-1,1-dimethyl-3H-oxazolo[3,4-a]pyrazin-3-one (Phenylmethyl)tetrahydro-3-oxo-1,1-dimethyl-3H-oxazolo[3,4-a]pyrazine-7(1H)-carboxylate (0.97 g, 3.2 mmol) was dissolved in ethanol (50 mL). 10% Palladium carbon (0.10 g) was added thereto, and the resulting mixture was stirred under hydrogen atmosphere at room temperature one whole day and night. The reaction solution was filtered through a Celite, and the Celite was washed with ethanol. The filtrate was concentrated under reduced pressure and left to stand at room temperature overnight. The resulting crystals were collected by filtration and washed with diethyl ether to obtain the title compound (0.39 g, yield 73%).

Melting point 92-93° C.

$^1$H NMR (DMSO-d$_6$) δ 1.22 (3H, s), 1.35 (3H, s), 2.31-2.41 (2H, m), 2.78-2.90 (3H, m), 3.18-3.60 (2H, m).

Reference Example 6

1,4-Bis(phenylmethyl)-α,α-dicyclopropyl-2-piperazinemethanol

To a solution of ethyl 1,4-bis(phenylmethyl)-2-piperazine carboxylate (5.0 g, 15 mmol) in tetrahydrofuran (70 mL) was added dropwise over 20 minutes a 0.5 M solution of cyclopropylmagnesium bromide in tetrahydrofuran (100 mL, 50 mmol) with ice cooling, and the mixture was stirred for 30 minutes with ice cooling. After further stirring at room temperature overnight, to the reaction solution was added an aqueous saturated ammonium chloride solution (300 mL), and the resulting mixture was extracted with ethyl acetate. The extract was washed with water, dried over magnesium sulfate and concentrated under reduced pressure. The residue was purified with silica gel column chromatography (hexane:ethyl acetate=15:1) to obtain the title compound (1.3 g, yield 24%).

Oil.

$^1$H NMR (CDCl$_3$) δ −0.11-0.00 (2H, m), 0.13-0.21 (1H, m), 0.29-0.41 (5H, m), 0.63-0.74 (1H, m), 1.12-1.20 (1H, m), 2.34-2.61 (5H, m), 3.34-3.41 (3H, m), 3.60-3.72 (1H, m), 3.99-4.12 (2H, m), 5.79 (1H, br s), 7.23-7.39 (10H, m).

Reference Example 7

Bis(phenylmethyl)2-(dicyclopropylhydroxymethyl)-1,4-piperazinedicarboxylate 1,4-Bis(phenylmethyl)-α,α-dicyclopropyl-2-piperazinemethanol (1.2 g, 3.1 mmol) was dissolved in ethanol/water (40 mL/4 mL). 10% Palladium carbon (0.12 g) was added thereto, and the mixture was stirred under hydrogen pressure (3.6 bar) at room temperature one whole day and night. The reaction solution was filtered through a Celite, the Celite was washed with ethanol, and then the filtrate was concentrated under reduced pressure. The residue was dissolved in tetrahydrofuran (50 ml). A 0.5 M aqueous sodium hydrogen carbonate solution (50 mL) and benzyl chlorocarbonate (1.8 mL, 12 mmol) were added thereto. The resulting mixture was stirred at room temperature for 4 hours and the reaction solution was extracted with ethyl acetate (100 mL). The extract was washed with water, dried over magnesium sulfate and concentrated under reduced pressure. Then, the residue was purified with silica gel column chromatography (hexane:ethyl acetate=21:1 to 4:1) to obtain the title compound (1.4 g, quantitative) as an oily matter.

Reference Example 8

Hexahydro-1,1-diphenyl-7-(phenylmethyl)-3H-oxazolo[3,4-a]pyrazin-3-one 1,1-Dimethylethyl 4-(phenylmethyl)-1-piperazine carboxylate (20 g, 72 mmol) and tetramethylethylenediamine (18 g, 0.16 mol) were dissolved in tetrahydrofuran (100 mL), and the solution was cooled to −78° C. A 1.0 M solution of sec-butyllithium in hexane and cyclohexane (150 mL, 0.15 mol) was added thereto, and the mixture was stirred for 2 hours and the temperature was elevated to −30° C. After cooling to −78° C. again, a solution of benzophenone (28 g, 0.15 mol) in tetrahydrofuran (70 mL) was added dropwise thereto, and the mixture was stirred for 18 hours while elevating the temperature to room temperature. To the reaction solution was added an aqueous saturated ammonium chloride solution, and the resulting mixture was extracted with ethyl acetate. The extract was washed with water and concentrated under reduced pressure. The residue was purified with silica gel column chromatography (hexane:ethyl acetate=3:1) to obtain the title compound (18 g, yield 64%) as crystals.

$^1$H NMR (CDCl$_3$) δ 1.58 (1H, m), 1.94 (1H, dt, J=11.7 Hz, 3.6 Hz), 2.55 (1H, dd, J=11.4 Hz, 2.4 Hz), 2.69 (1H, dd, J=11.7 Hz, 3.6 Hz), 3.10 (1H, dt, J=13.0 Hz, 3.6 Hz), 3.32, 3.50 (2H, ABq, J=13.1 Hz), 3.81 (1H, dd, J=13.2 Hz, 2.4 Hz), 4.54 (1H, dd, J=11.0 Hz, 3.6 Hz), 7.18-7.40 (13H, m), 7.50 (2H, d, J=7.2 Hz).

Reference Example 9

Hexahydro-1,1-diphenyl-3H-oxazolo[3,4-a]pyrazin-3-one

To a solution of hexahydro-1,1-diphenyl-7-(phenylmethyl)-3H-oxazolo[3,4-a]pyrazin-3-one (19 g, 48 mmol) in 1,2-dichloroethane (80 mL) was added 1-chloroethyl chloroformate (8.7 g, 61 mmol), and the mixture was stirred at 60° C. for 3 hours. 1-Chloroethyl chloroformate (1.7 g, 12 mmol) was further added thereto, and the resulting mixture was stirred at 60° C. for 2 hours. The reaction solution was concentrated under reduced pressure and methanol was added thereto, and the mixture was heated under reflux for 2.5 hours. The reaction solution was concentrated under reduced pressure, and crystallized by adding ethyl acetate and hexane. The precipitated crystals were collected by filtration. The crystals were dissolved by adding ethyl acetate and an aqueous saturated sodium hydrogen carbonate solution. Then, the organic layer was washed with water and concentrated under reduced pressure. To the residue was added diisopropyl ether, and the precipitated crystals were washed with diisopropyl ether and dried to obtain the title compound (13 g, yield 92%). $^1$H NMR of the above obtained compound corresponded with the compound obtained in Reference Example 2.

Reference Example 10

1,1-Dicyclohexyl-hexahydro-7-(triphenylmethyl)-3H-oxazolo[3,4-a]pyrazin-3-one 1,1-Dimethylethyl 4-(triphenylmethyl)-1-piperazine carboxylate (1.0 g, 2.3 mmol) and tetramethylethylenediamine (1.0 g, 8.6 mmol) were dissolved in tetrahydrofuran (10 mL), which was cooled to −78° C. A 1.0 M solution of sec-butyllithium in hexane and cyclohexane (7.2 mL, 7.2 mmol) was added thereto, and the mixture was stirred for 2 hours and the temperature was elevated to −50° C. After cooling to −78° C. again, a solution of dicyclohexyl ketone (1.1 g, 5.9 mmol) in tetrahydrofuran (10 mL) was added dropwise thereto, and the mixture was stirred for 15 hours while elevating the temperature to room temperature. To the reaction solution was added an aqueous saturated ammonium chloride solution, and the resulting mixture was extracted with ethyl acetate. The extract was washed with water and concentrated under reduced pressure. The residue was purified with silica gel column chromatography (hexane:ethyl acetate=7:3) to obtain the title compound (0.95 g, yield 74%).

$^1$H NMR (CDCl$_3$) δ 0.86 (3H, m), 1.00-1.29 (10H, m), 1.40-1.60 (4H, m), 1.65 (1H, m), 1.76 (3H, m), 1.88 (3H, m), 2.99 (1H, m), 3.10 (1H, m), 3.23 (1H, dt, J=12.3 Hz, 3.6 Hz), 3.67 (1H, dd, J=12.2 Hz, 3.1 Hz), 4.06 (1H, dd, J=11.1 Hz, 3.5 Hz), 7.16-7.20 (3H, m), 7.24-7.32 (6H, m), 7.49 (6H, m).

Reference Example 11

1,1-Dicyclohexyl-hexahydro-3H-oxazolo[3,4-a]pyrazin-3-one

To a solution of hexahydro-1,1-dicyclohexyl-7-(triphenylmethyl)-3H-oxazolo[3,4-a]pyrazin-3-one (0.92 g, 1.7 mmol) in tetrahydrofuran (5 mL) was added a 4 M hydrogen chloride/ethyl acetate solution (5 mL) with ice cooling, and the mixture was stirred at room temperature for 2.5 hours. The reaction solution was concentrated under reduced pressure, water was then added thereto and washed with diethyl ether. To the aqueous layer was added sodium hydrogen carbonate, and the mixture was adjusted to pH 7 and then extracted with ethyl acetate. The extract was washed with water and concentrated under reduced pressure. The precipitated crystals were washed with hexane and dried to obtain the title compound (0.41 g, yield 80%).

Melting point 151-152° C.

$^1$H NMR (CDCl$_3$) δ 0.81-1.40 (10H, m), 1.48 (2H, m), 1.69-1.83 (8H, m), 1.96 (2H, m), 2.66 (1H, dt, J=12.3 Hz, 2.4 Hz), 2.80-2.92 (3H, m), 3.01 (1H, m), 3.60 (1H, dd, J=9.2 Hz, 5.7 Hz), 3.74 (1H, dd, J=12.6 Hz, 3.0 Hz).

Reference Example 12

1,1-Bis(4-fluorophenyl)-hexahydro-7-(triphenylmethyl)-3H-oxazolo[3,4-a]pyrazin-3-one In the same manner as in Reference Example 10, the title compound was obtained using 4,4'-difluorobenzophenone instead of dicyclohexyl ketone. Yield 67%.

$^1$H NMR (CDCl$_3$) δ 0.72 (1H, t, J=11.3 Hz), 1.37 (1H, dt, J=11.9 Hz, 3.0 Hz), 2.77 (1H, m), 3.07 (1H, m), 3.37 (1H, dt, J=12.4 Hz, 3.5 Hz), 3.79 (1H, m), 4.65 (1H, dd, J=10.9 Hz, 3.3 Hz), 6.84 (2H, t, J=8.6 Hz), 6.94-7.45 (21H, m).

Reference Example 13

1,1-Bis(4-fluorophenyl)-hexahydro-3H-oxazolo[3,4-a]pyrazin-3-one

In the same manner as in Reference Example 11, the title compound was obtained from 1,1-bis(4-fluorophenyl)-hexahydro-7-(triphenylmethyl)-3H-oxazolo[3,4-a]pyrazin-3-one. Yield 72%.

$^1$H NMR (CDCl$_3$) δ 2.08 (1H, t, J=11.3 Hz), 2.61 (1H, dt, J=12.0 Hz, 3.6 Hz), 2.68 (1H, dd, J=12.0 Hz, 3.5 Hz), 2.92 (1H, dd, J=12.0 Hz, 3.6 Hz), 3.10 (1H, dt, J=12.2 Hz, 3.7 Hz), 3.84 (1H, dd, J=13.1 Hz, 3.2 Hz), 4.35 (1H, dd, J=11.0 Hz, 3.5 Hz), 6.99-7.22 (4H, m), 7.24 (2H, m), 7.47 (2H, m).

Reference Example 14

α,α,1,4-Tetrakis(phenylmethyl)-2-piperazinemethanol

Ethyl 1,4-bis(phenylmethyl)-2-piperazine carboxylate (8.2 g, 24 mmol) was dissolved in tetrahydrofuran (100 mL) under argon atmosphere. With ice cooling, a 1.0 M solution of benzyl magnesium bromide in tetrahydrofuran (100 mL, 0.10 mol) was added dropwise thereto over 30 minutes. After stirring at room temperature for 14 hours, an aqueous saturated ammonium chloride solution (300 mL) was added dropwise thereto with ice cooling, and the mixture was extracted with ethyl acetate. The extract was washed with saturated brine, dried over anhydrous magnesium sulfate and concentrated under reduced pressure. The residue was purified with silica gel column chromatography (hexane to hexane:ethyl acetate=5:1) to obtain the title compound (5.1 g, yield 44%).

Oil.

$^1$H NMR (CDCl$_3$) δ 2.35-2.48 (3H, m), 2.54-2.78 (6H, m), 3.23-3.37 (3H, m), 3.61-3.74 (2H, m), 3.92 (1H, d, J=13.4 Hz), 6.48 (1H, br s), 7.03-7.33 (20H, m).

Reference Example 15

α,α-Bis(phenylmethyl)-2-piperazinemethanol

α,α,1,4-Tetrakis(phenylmethyl)-2-piperazinemethanol (4.9 g, 10 mmol) was dissolved in ethanol/water (100 mL/5 mL). 10% Palladium carbon (0.49 g) was added thereto, and the mixture was stirred under hydrogen pressure (3.0 bar) at room temperature one whole day and night. The reaction system was filtered through a Celite, the Celite was washed with ethanol, and then the filtrate was concentrated under reduced pressure. The resulting crystals were washed with diethyl ether to obtain the title compound (2.8 g, yield 91%).

Melting point 144-145° C.

$^1$H NMR (CDCl$_3$) δ 2.55-2.89 (9H, m), 3.06 (1H, d, J=13.6 Hz), 3.20 (1H, d, J=12.5 Hz), 7.20-7.34 (10H, m).

Reference Example 16

Bis(1,1-dimethylethyl)2-[1-hydroxy-2-phenyl-1-(phenylmethyl)ethyl]-1,4-piperazinedicarboxylate α,α-Bis(phenylmethyl)-2-piperazinemethanol (2.7 g, 9.1 mmol) was dissolved in tetrahydrofuran (100 mL) and a 0.5 M aqueous sodium hydrogen carbonate solution (100 mL) was added thereto. Di-tert-butyl dicarbonate (5.9 g, 27 mmol) was added dropwise at room temperature and the mixture was stirred one whole day and night. The reaction mixture was extracted with ethyl acetate, washed with a 0.5 M aqueous sodium hydrogen carbonate solution, dried over anhydrous magnesium sulfate and concentrated under reduced pressure. To the residue was added diisopropyl ether, and the resulting crystals were collected by filtration and washed with diisopropyl ether to obtain the title compound (4.1 g, yield 90%).

Melting point 150° C.

$^1$H NMR (CDCl$_3$) δ 1.28-1.54 (18H, m), 2.75-2.79 (3H, m), 3.00-3.06 (2H, m), 3.25-3.35 (1H, m), 3.60-4.11 (5H, m), 7.21-7.33 (10H, m).

Reference Example 17

1,1-Bis(phenylmethyl)-hexahydro-3H-oxazolo[3,4-a]pyrazin-3-one

To a solution of 1,1-dimethylethyl 1,1-bis(phenylmethyl)-tetrahydro-3-oxo-3H-oxazolo[3,4-a]pyrazine-7(1H)-carboxylate (1.3 g, 3.2 mmol) in dichloromethane (15 mL) was added trifluoroacetic acid (4 mL), and the mixture was stirred at room temperature for 4 hours. The reaction solution was concentrated and extracted with ethyl acetate. The extract was washed with a 0.5 M aqueous sodium hydrogen carbonate solution, dried over anhydrous magnesium sulfate and concentrated under reduced pressure. To the residue was added diethyl ether, the resulting crystals were collected by filtration and washed with diethyl ether to obtain the title compound (0.86 g, yield 85%).

Melting point 132-133° C.

$^1$H NMR (CDCl$_3$) δ 2.58-2.97 (8H, m), 3.27 (1H, d, J=16.7 Hz), 3.35-3.60 (2H, m), 7.14-7.40 (10H, m).

Reference Example 18

1,4-Bis(phenylmethyl)-2-piperazine carboxylic acid

To ethyl 1,4-bis(phenylmethyl)-2-piperazine carboxylate dihydrochloride (21 g, 52 mmol) were added ethanol (300 mL) and a 1 M aqueous sodium hydroxide solution (300 mL, 0.30 mmol), and the mixture was stirred at 80° C. for 3 hours. The reaction solution was concentrated, and then 1 M hydrochloric acid was added thereto until the pH was adjusted to 5. The reaction solution was extracted with ethyl acetate, dried over anhydrous sodium sulfate and concentrated under reduced pressure. To the resulting crystals was added diethyl ether, collected by filtration, and washed with diethyl ether to obtain the title compound (12 g, yield 76%).

Melting point 184-185° C.

$^1$H NMR (CDCl$_3$) δ 2.50-2.56 (2H, m), 2.62-2.78 (3H, m), 2.82-3.08 (2H, m), 3.40-3.56 (2H, m), 3.65 (2H, s), 3.86-3.90 (1H, m), 7.26-7.37 (10H, m).

Reference Example 19

1,4-Bis(phenylmethyl)-N-methoxy-N-methyl-2-piperazine carboxamide 1,4-Bis(phenylmethyl)-2-piperazine carboxylic acid (5.0 g, 16 mmol) was dissolved in N,N-dimethylformamide (80 mL). 1-Ethyl-3-(3-dimethylaminopropyl)carbodiimide hydrochloride (3.1 g, 16 mmol), 1-hydroxybenzotriazole (2.2 g, 16 mmol), N,O-dimethylhydroxylamine hydrochloride (1.9 g, 19 mmol) and triethylamine (2.7 mL, 19 mmol) were added thereto, and the mixture was stirred at room temperature for 3 days. To the reaction solution was added ethyl acetate, and the resulting mixture was washed with a 0.5 M aqueous sodium hydrogen carbonate solution, dried over anhydrous magnesium sulfate and concentrated under reduced pressure. The residue was purified with silica gel column chromatography (hexane:ethyl acetate=2:1 to 1:1) to obtain the title compound (5.0 g, yield 87%).

Oil.

$^1$H NMR (CDCl$_3$) δ 2.32-2.79 (5H, m), 3.06-3.09 (1H, m), 3.18 (3H, s), 3.33-3.60 (7H, m), 3.87 (1H, d, J=12.9 Hz), 7.19-7.34 (10H, m).

Reference Example 20

2-Benzoyl-1,4-bis(phenylmethyl)piperazine dihydrochloride 1,4-Bis(phenylmethyl)-N-methoxy-N-methyl-2-piperazine carboxamide (2.9 g, 8.1 mmol) was dissolved in tetrahydrofuran (30 mL) under argon atmosphere. A 1.0 M solution of phenylmagnesium bromide in tetrahydrofuran (24 mL, 24 mmol) was added dropwise thereto over 30 minutes with ice cooling. After the mixture was stirred at room temperature for 14 hours, an aqueous saturated ammonium chloride solution (200 mL) was added dropwise thereto with ice cooling, and the resulting mixture was extracted with ethyl acetate (200 ml). The extract was washed with saturated brine, dried over anhydrous magnesium sulfate and concentrated under reduced pressure. The residue was purified with silica gel column chromatography (hexane to hexane:ethyl acetate=2:1). The fractions were collected and concentrated. The residue was dissolved in ethyl acetate, a 4 N hydrogen chloride/ethyl acetate solution (4 mL) was added thereto, and the resulting mixture was stirred at room temperature for 5 minutes. The resulting crystals were collected by filtration and washed with ethyl acetate to obtain the title compound (1.5 g, yield 51%).

Melting point 153-155° C.

$^1$H NMR (DMSO-d$_6$) δ 2.71-3.49 (7H, m), 4.20-4.44 (4H, m), 7.08-8.13 (15H, m).

Reference Example 21

Bis(1,1-dimethylethyl)2-benzoyl-1,4-piperazinedicarboxylate

2-Benzoyl-1,4-bis(phenylmethyl)piperazine dihydrochloride (7.1 g, 16 mmol) was suspended in ethanol/water (50 mL/10 mL). 10% Palladium carbon (0.50 g) were added thereto, and the mixture was stirred under hydrogen atmosphere at room temperature one whole day and night. The reaction system was filtered through a Celite, the Celite was washed with ethanol, and then the filtrate was concentrated under reduced pressure. To the residue was added ethanol-ethyl acetate and the obtained solid matter was collected by filtration. To the obtained solid matter (4.2 g) were added tetrahydrofuran (200 mL) and a 0.5 M aqueous sodium hydrogen carbonate solution (250 mL). Di-tert-butyl dicarbonate (10.4 g, 47.7 mmol) was added dropwise thereto at room temperature, and the mixture was stirred one whole day and night. To the reaction solution was added ethyl acetate, and the resulting mixture was washed with a 0.5 M aqueous sodium hydrogen carbonate solution, dried over anhydrous magnesium sulfate and concentrated under reduced pressure. The residue was purified with silica gel column chromatography (hexane:ethyl acetate=40:1 to 7:3) to obtain the title compound (1.2 g, yield 19%).

Amorphous.

$^1$H NMR (CDCl$_3$) δ 1.13-1.56 (18H, m), 2.96-3.13 (3H, m), 4.00-4.16 (2H, m), 4.40-4.70 (2H, m), 7.26-7.32 (3H, m), 7.47-7.88 (2H, m).

Reference Example 22

1,1-Dimethylethyl 4-nitro-1H-benzimidazole-1-carboxylate

To a solution of 4-nitrobenzimidazole (0.74 g, 4.5 mmol) in tetrahydrofuran (30 mL) were sequentially added diisopropylethylamine (1.2 mL, 6.8 mmol), di-tert-butyl dicarbonate (1.6 mL, 6.8 mmol) and 4-(dimethylamino)pyridine (5 mg), and then the mixture was stirred at room temperature overnight. To the reaction solution was added ethyl acetate, and the resulting mixture was washed with a 0.5 M aqueous sodium hydrogen carbonate solution, dried over anhydrous magnesium sulfate and concentrated under reduced pressure. To the residue was added diethyl ether, and the resulting crystals were collected by filtration and washed with diethyl ether to obtain the title compound (1.0 g, yield 85%).

Melting point 249° C.

$^1$H NMR (CDCl$_3$) δ 1.73 (9H, s), 7.53 (1H, t, J=8.2 Hz), 8.20 (1H, dd, J=0.81 Hz, 8.2 Hz), 8.39 (1H, dd, J=0.81 Hz, 8.2 Hz), 8.61 (1H, s).

Reference Example 23

1,1-Dimethylethyl 4-amino-1H-benzimidazole-1-carboxylate

To a solution of 1,1-dimethylethyl 4-nitro-1H-benzimidazole-1-carboxylate (0.95 g, 3.6 mmol) in ethanol (20 mL) was added 10% palladium carbon (0.10 g), and the mixture was stirred under hydrogen atmosphere at room temperature for 4 hours. The reaction solution was filtered through a Celite, the Celite was washed with ethanol, and then the filtrate was concentrated under reduced pressure to obtain the title compound (0.84 g, quantitative).

Melting point 117° C.

$^1$H NMR (CDCl$_3$) δ 1.69 (9H, s), 4.35 (2H, br s), 6.61 (1H, dd, J=0.69 Hz, 7.7 Hz), 7.16 (1H, t, J=7.9 Hz), 7.32 (1H, dd, J=0.63 Hz, 8.2 Hz), 8.29 (1H, s).

Reference Example 24

4-(Chloroacetyl)morpholine

To a solution of morpholine (3.6 mL, 41 mmol) and triethylamine (5.2 g, 51 mmol) in tetrahydrofuran (100 mL) was added chloroacetyl chloride (3.0 mL, 38 mmol) at 0° C., and the mixture was stirred at 0° C. for 20 minutes. The reaction solution was concentrated and ethyl acetate was added thereto. The resulting mixture was washed with water and saturated brine and dried over magnesium sulfate. The solid was filtered off, and the filtrate was concentrated to obtain the title compound (4.0 g, yield 64%) as an oily matter.

$^1$H NMR (CDCl$_3$) δ 3.52-3.55 (2H, m), 3.62-3.65 (2H, m), 3.69-3.75 (4H, m), 4.07 (2H, s).

Reference Example 25

2,2,2-Trichloro-N-(5-quinolinyl)acetamide

To a solution of 5-aminoquinoline (1.0 g, 6.9 mmol) and triethylamine (1.0 mL, 7.2 mmol) in dichloromethane (40 mL) was added trichloroacetyl chloride (1.4 g, 7.7 mmol) at 0° C., and the mixture was stirred at room temperature for 90 minutes. The reaction solution was concentrated, and to the residue was added ethyl acetate, and the resulting mixture was extracted three times with 1 N hydrochloric acid. The aqueous layers were combined and neutralized with an aqueous saturated sodium hydrogen carbonate solution and extracted with ethyl acetate. The organic layer was washed with water and saturated brine and dried over magnesium sulfate. The solid was filtered off, and the filtrate was concentrated. The residue was washed with diisopropyl ether and collected by filtration to obtain the title compound (1.9 g, yield 94%) as colorless crystals.

Melting point 145-147° C.

$^1$H NMR (CDCl$_3$) δ 7.49 (1H, dd, J=4.2 Hz, 8.6 Hz), 7.75 (1H, t, J=7.8 Hz), 7.85 (1H, d, J=7.3 Hz), 8.09 (1H, d, J=8.4 Hz), 8.18 (1H, d, J=8.5 Hz), 8.76 (1H, br s), 8.97 (1H, dd, J=1.5 Hz, 4.2 Hz).

Reference Example 26

2,2,2-Trichloro-N-(3-pyridinyl)acetamide

To a solution of 3-aminopyridine (1.0 g, 11 mmol) and triethylamine (1.3 g, 13 mmol) in tetrahydrofuran (30 mL)

was added at 0° C. trichloroacetyl chloride (1.4 mL, 13 mmol), and the mixture was stirred at 0° C. for 20 minutes. The reaction solution was concentrated, and ethyl acetate was added to the residue. The resulting mixture was washed with water and saturated brine and dried over magnesium sulfate. The solid was filtered off, and the filtrate was concentrated. The residue was washed with diisopropyl ether and collected by filtration to obtain the title compound (2.3 g, yield 89%) as colorless powder.

Melting point 149-151° C.

$^1$H NMR (CDCl$_3$) δ 7.38 (1H, dd, J=4.8 Hz, 8.3 Hz), 8.18 (1H, d, J=8.3 Hz), 8.48 (1H, d, J=4.8 Hz), 8.70 (1H, d, J=2.2 Hz), 8.74 (1H, br s).

Reference Example 27

2,2,2-Trichloro-N-(4-pyridinyl)acetamide

In the same manner as in Reference Example 26, the title compound was obtained using 4-aminopyridine instead of 3-aminopyridine. Yield 94%.

Melting point 151-153° C.

$^1$H NMR (CDCl$_3$) δ 7.58-7.60 (2H, m), 8.60-8.62 (2H, m), 8.91 (1H, br s).

Reference Example 28

2,2,2-Trichloro-N-(isoquinolin-6-yl)acetamide

In the same manner as in Reference Example 26, the title compound was obtained using 6-aminoisoquinoline instead of 3-aminopyridine. Yield 80%.

Amorphous.

$^1$H NMR (CDCl$_3$) δ 7.62-7.69 (2H, m), 8.03 (1H, d, J=8.8 Hz), 8.32 (1H, s), 8.56 (1H, d, J=5.7 Hz), 8.62 (1H, br s), 9.24 (1H, s).

Reference Example 29

2,2,2-Trichloro-N-(isoquinolin-5-yl)acetamide

In the same manner as in Reference Example 26, the title compound was obtained using 5-aminoisoquinoline instead of 3-aminopyridine. Yield 82%.

Amorphous.

$^1$H NMR (CDCl$_3$) δ 7.61-7.71 (2H, m), 7.95 (1H, d, J=8.2 Hz), 8.15 (1H, d, J=7.6 Hz), 8.62 (1H, d, J=6.0 Hz), 8.88 (1H, br s), 9.31 (1H, s).

Reference Example 30

1,1-Bis(4-methylphenyl)-hexahydro-7-[(4-methylphenyl)methyl]-3H-oxazolo[3,4-a]pyrazin-3-one In the same manner as in Reference Example 37, the title compound was obtained using 4,4'-dimethylbenzophenone instead of benzophenone. Yield 86%.

Amorphous.

$^1$H NMR (CDCl$_3$) δ 1.58 (1H, t, J=11.2 Hz), 1.84-1.93 (1H, m), 2.32 (3H, s), 2.326 (3H, s), 2.332 (3H, s), 2.55 (1H, dd, J=2.6 Hz, 11.3 Hz), 2.64-2.69 (1H, m), 3.01-3.11 (1H, m), 3.24 (1H, d, J=13.0 Hz), 3.49 (1H, d, J=13.0 Hz), 3.78 (1H, dd, J=2.6 Hz, 14.0 Hz), 4.49 (1H, dd, J=3.5 Hz, 10.9 Hz), 7.08-7.11 (6H, m), 7.16 (4H, d, J=8.1 Hz), 7.38 (2H, d, J=8.2 Hz).

Reference Example 31

1,1-Bis(4-methylphenyl)-hexahydro-3H-oxazolo[3,4-a]pyrazin-3-one

In the same manner as in Reference Example 38, the title compound was obtained using 1,1-bis(4-methylphenyl)-hexahydro-7-[(4-methylphenyl)methyl]-3H-oxazolo[3,4-a]pyrazin-3-one instead of hexahydro-7-[(4-methylphenyl)methyl]-1,1-diphenyl-3H-oxazolo[3,4-a]pyrazin-3-one. Yield 79%.

Amorphous.

$^1$H NMR (CDCl$_3$) δ 2.09 (1H, t, J=11.6 Hz), 2.30 (3H, s), 2.33 (3H, s), 2.55-2.65 (1H, m), 2.72 (1H, dd, J=3.5 Hz, 11.9 Hz), 2.90 (1H, dd, J=3.6 Hz, 12.0 Hz), 3.01-3.11 (1H, m), 3.82 (1H, d, J=10.0 Hz), 4.36 (1H, dd, J=3.6 Hz, 11.0 Hz), 7.09-7.19 (6H, m), 7.37-7.39 (2H, m).

Reference Example 32

N-Cyclopropyl-2-nitrobenzenesulfonamide

To a solution of cyclopropylamine (1.0 g, 18 mmol) and triethylamine (3.7 mL, 27 mmol) in tetrahydrofuran (20 mL) was added 2-nitrobenzenesulfonyl chloride (3.9 g, 18 mmol) at 0° C., and the mixture was stirred at 0° C. for 1 hour. The solvent was distilled off under reduced pressure, and the residue was diluted with ethyl acetate. The reaction solution was washed with water and saturated brine and dried over magnesium sulfate. The solid was filtered off, and the filtrate was concentrated. The residue was purified with silica gel column chromatography (hexane:ethyl acetate=1:1) and concentrated. The residue was washed with hexane and collected by filtration to obtain the title compound (3.7 g, 87%).

$^1$H NMR (CDCl$_3$) δ 0.65-0.76 (4H, m), 2.32-2.39 (1H, m), 5.59 (1H, br s), 7.75-7.80 (2H, m), 7.85-7.88 (1H, m), 8.20-8.23 (1H, m).

Reference Example 33

N-(2-Aminoethyl)-N-cyclopropyl-2-nitrobenzenesulfonamide

In the same manner as in Reference Example 52, the title compound was obtained using N-cyclopropyl-2-nitrobenzenesulfonamide instead of N-(cyclopropylmethyl)-2-nitrobenzenesulfonamide. Yield 73%.

Oil.

$^1$H NMR (CDCl$_3$) δ 0.63-0.72 (4H, m), 1.37 (2H, br s), 2.47-2.54 (1H, m), 2.96 (2H, t, J=6.4 Hz), 3.41 (2H, t, J=6.4 Hz), 7.61-7.73 (3H, m), 8.13-8.16 (1H, m).

Reference Example 34

N-Allyl-2-nitrobenzenesulfonamide

In the same manner as in Reference Example 32, the title compound was obtained as pale brown crystals using allylamine instead of cyclopropylamine. Yield 85%.

$^1$H NMR (CDCl$_3$) δ 3.75-3.80 (2H, m), 5.11 (1H, dd, J=1.2 Hz, 10.3 Hz), 5.18-5.24 (1H, m), 5.40 (1H, br s), 5.68-5.79 (1H, m), 7.72-7.78 (2H, m), 7.85-7.89 (1H, m), 8.12-8.15 (1H, m).

Reference Example 35

N-Allyl-N-(2-aminoethyl)-2-nitrobenzenesulfonamide

In the same manner as in Reference Example 52, the title compound was obtained using N-allyl-2-nitrobenzenesulfonamide instead of N-(cyclopropylmethyl)-2-nitrobenzenesulfonamide, and using 1,1'-(azodicarbonyl)dipiperidine instead of diethyl azodicarboxylate. Yield 41%.

Oil.

$^1$H NMR (CDCl$_3$) δ 2.85 (2H, t, J=6.5 Hz), 3.36 (2H, t, J=6.5 Hz), 3.96 (2H, d, J=6.4 Hz), 5.17-5.27 (2H, m), 5.66-5.75 (1H, m), 7.62-7.72 (3H, m), 8.05-8.08 (1H, m).

Reference Example 36

1,1-Dimethylethyl 4-[(4-methylphenyl)methyl]-1-piperazine carboxylate

Piperazine (170 g, 2.0 mol) was suspended in toluene (800 mL) and warmed to 85° C. The mixture was dissolved while stirring for 10 minutes. To the solution was added 4-methylbenzyl chloride (53 mL, 0.4 mol), and the mixture was stirred at 85° C. for 2 hours and then left to stand for cooling to 50° C. A 1 N aqueous sodium hydroxide solution (440 mL) and ethyl acetate (100 mL) were added thereto, and the process of phase separation was performed. The resulting organic layer was washed with a 1 N aqueous sodium hydroxide solution (400 mL) and dried over magnesium sulfate. The solvent was distilled off under reduced pressure, and the residue was dissolved in tetrahydrofuran (420 mL). Triethylamine (84 mL, 0.6 mol) was added thereto, and the resulting mixture was ice cooled. t-Butyl dicarbonate (97 mL, 0.42 mol) was added thereto, and the mixture was stirred overnight while elevating the temperature to room temperature. The solvent was distilled off under reduced pressure. A 4 N aqueous sodium hydroxide solution (200 mL) and ethyl acetate (300 mL) were added thereto, and the process of phase separation was performed. The resulting organic layer was washed with an aqueous saturated sodium hydrogen carbonate solution (400 mL) and dried over magnesium sulfate. The solvent was distilled off under reduced pressure. To the residue was added a small amount of hexane, and the mixture was ice cooled. The obtained crystals were collected by filtration and washed with ice-cooled hexane to obtain the title compound (70 g, yield 60%). The mother liquor was concentrated under reduced pressure, and then the residue was purified with silica gel column chromatography (hexane to hexane:ethyl acetate=3:1). The resulting oily matter was left to stand at room temperature. The obtained crystals were collected by filtration and washed with ice-cooled hexane to obtain the title compound (22 g, yield 19%).

Melting point 61-62° C.

$^1$H NMR (CDCl$_3$) δ 1.47 (9H, s), 2.34-2.38 (7H, m), 3.41-3.48 (6H, m), 7.12-7.27 (4H, m).

Reference Example 37

Hexahydro-7-[(4-methylphenyl)methyl]-1,1-diphenyl-3H-oxazolo[3,4-a]pyrazin-3-one 1,1-Dimethylethyl 4-[(4-methylphenyl)methyl]-1-piperazine carboxylate (58 g, 0.2 mol) and N,N,N',N'-tetramethylethylenediamine (35 g, 0.3 mol) were dissolved in tetrahydrofuran (400 mL), and the mixture was cooled to −78° C. under argon atmosphere. A 1.0 M solution of sec-butyllithium in hexane and cyclohexane (240 mL, 0.24 mol) was added dropwise over 1.5 hours, and the mixture was stirred at −78° C. for 3 hours. Then, the temperature was elevated to −30° C. for 2 hours. After cooling to −78° C. again, a solution of benzophenone (55 g, 0.3 mol) in tetrahydrofuran (200 mL) was added dropwise over 1 hour, and the resulting mixture was stirred overnight while elevating the temperature to room temperature. After ice cooling, an aqueous saturated ammonium chloride solution (300 mL) was added thereto, and the mixture was stirred for 30 minutes with ice cooling. Ethyl acetate (300 mL) was added thereto, and the process of phase separation was performed. The resulting organic layer was washed with water (500 mL) and dried over magnesium sulfate. The solvent was distilled off under reduced pressure, and to the residue was added diisopropyl ether-hexane (3:1, v/v, 300 mL). The obtained crystals were collected by filtration and washed with diisopropyl ether-hexane (3:1, v/v) to obtain the title compound (66 g, yield 82%).

Melting point 154-155° C.

$^1$H NMR (CDCl$_3$) δ 1.55-1.60 (1H, m), 1.85-1.95 (1H, m), 2.33 (3H, s), 2.52-2.58 (1H, m), 2.66-2.71 (1H, m), 3.05-3.13 (1H, m), 3.26 (1H, d, J=13.0 Hz), 3.47 (1H, d, J=13.0 Hz), 3.79 (1H, dd, J=2.5 Hz, 13.2 Hz), 4.53 (1H, dd, J=3.5 Hz, 11.0 Hz), 7.06-7.10 (4H, m), 7.26-7.37 (8H, m), 7.50-7.53 (2H, m).

Reference Example 38

Hexahydro-1,1-diphenyl-3H-oxazolo[3,4-a]pyrazin-3-one

Hexahydro-7-[(4-methylphenyl)methyl]-1,1-diphenyl-3H-oxazolo[3,4-a]pyrazin-3-one (65 g, 0.16 mol) was dissolved in 1,2-dichloroethane (300 mL). 1-Chloroethyl chloroformate (22 mL, 0.2 mol) was added thereto, and the mixture was warmed and refluxed for 3 hours. The solvent was distilled off under reduced pressure, and then methanol (300 mL) was added thereto. The mixture was warmed and refluxed for 3 hours. The solvent was distilled off under reduced pressure, and to the residue was added ethyl acetate (500 mL) to obtain powder. The obtained powder was collected by filtration, washed with ethyl acetate, and dried under reduced pressure. To the obtained powder (54 g) were added an aqueous saturated sodium hydrogen carbonate solution (500 mL) and ethyl acetate (500 mL), and the process of phase separation was performed. The resulting organic layer was washed with an aqueous saturated sodium hydrogen carbonate solution (400 mL) and dried over magnesium sulfate. The solvent was distilled off under reduced pressure. The residue was recrystallized from diethyl ether and the resulting crystals (42 g) were recrystallized from ethyl acetate again to obtain the title compound (38 g, yield 78%). $^1$H NMR of the above obtained compound corresponded with the compound obtained in Reference Example 2.

Reference Example 39

1,1-Dimethylethyl N-[2-(3,6-dihydropyridin-1(2H)-yl)ethyl]carbamate

To 1,1-dimethylethyl N-(2-oxoethyl)carbamate (2.0 g, 13 mmol) were added N,N-dimethylformamide (50 mL), tetrahydrofuran (50 mL), 1,2,3,6-tetrahydropyridine (1.2 mL, 13 mmol) and sodium triacetoxyborohydride (5.3 g, 25 mmol), and the mixture was stirred at room temperature for 14 hours. To the reaction solution was added ethyl acetate, and the resulting mixture was washed with a 0.5 M aqueous sodium hydrogen carbonate solution, dried over anhydrous magnesium sulfate and concentrated under reduced pressure. The residue was purified with silica gel column chromatography (ethyl acetate to ethyl acetate:methanol=8:2) and further purified with amino silica gel column chromatography (hexane:ethyl acetate=9:1 to ethyl acetate) to obtain the title compound (1.2 g, yield 41%).

Oil.

$^1$H NMR (CDCl$_3$) δ 1.45 (9H, s), 2.02-2.05 (2H, m), 2.50-2.58 (4H, m), 2.94-2.97 (2H, m), 3.23-3.27 (2H, m), 5.04 (1H, br), 5.64-5.74 (2H, m).

Reference Example 40

N-[2-(3,6-Dihydropyridin-1(2H)-yl)ethyl]-N-methylamine

80% Aluminum lithium hydride (0.36 g, 7.5 mmol) was suspended in tetrahydrofuran (10 mL). A solution of 1,1-dimethylethyl N-[2-(3,6-dihydropyridin-1(2H)-yl)ethyl]carbamate (0.68 g, 3.0 mmol) in tetrahydrofuran (10 mL) was added dropwise thereto at room temperature over 10 minutes, and the mixture was refluxed for 3 hours. The reaction solution was cooled to room temperature, and then a 1 N aqueous sodium hydroxide solution (20 mL) was added portionwise thereto. Insolubles were filtered off through a Celite, and the Celite was washed with tetrahydrofuran. The filtrate was concentrated under reduced pressure, and the residue was purified with amino silica gel column chromatography (hexane:ethyl acetate=19:1 to ethyl acetate) to obtain the title compound (0.18 g, yield 42%).

Oil.

$^1$H NMR (CDCl$_3$) δ 2.17 (2H, s), 2.44 (3H, s), 2.56 (4H, s), 2.69-2.73 (2H, m), 2.96-2.98 (2H, m), 5.67-5.73 (2H, m).

Reference Example 41

1,1-Dimethylethyl N-[2-(3,6-dihydropyridin-1(2H)-yl)-1,1-dimethylethyl]carbamate In the same manner as in Reference Example 39, the title compound was obtained using 1,1-dimethylethyl (1,1-dimethyl-2-oxoethyl)carbamate instead of 1,1-dimethylethyl(2-oxoethyl)carbamate. Yield 14%.

Oil.

$^1$H NMR (CDCl$_3$) δ 1.27 (6H, s), 1.43 (9H, s), 2.12-2.16 (2H, m), 2.50 (2H, s), 2.66 (2H, t, J=5.6 Hz), 3.07-3.10 (2H, m), 4.94 (1H, br), 5.65-5.77 (2H, m).

Reference Example 42

N-[2-(3,6-Dihydropyridin-1(2H)-yl)-1,1-dimethylethyl]amine dihydrochloride

In the same manner as in Example 125, the title compound was obtained using 1,1-dimethylethyl N-[2-(3,6-dihydropyridin-1(2H)-yl)-1,1-dimethylethyl]carbamate instead of 1,1-dimethylethyl 4-[[(tetrahydro-3-oxo-1,1-diphenyl-3H-oxazolo[3,4-a]pyrazin-7(1H)-yl)carbonyl]amino]-1H-benzimidazole-1-carboxylate. Yield 94%.

Melting point 228-229° C.

$^1$H NMR (DMSO-d$_6$) δ 1.46 (6H, s), 2.27-2.37 (1H, m), 2.50-2.72 (1H, m), 3.28-3.52 (4H, m), 3.70-3.97, (2H, m), 5.68-5.72 (1H, m), 5.89-5.92 (1H, m), 8.76 (3H, br).

Reference Example 43

1,1-Dimethylethyl N-[2-(3,6-dihydropyridin-1(2H)-yl)-2,2-dimethylethyl]carbamate A solution of acetone cyanohydrin (1.1 mL, 12 mmol) and 1,2,3,6-tetrahydropyridine (1.1 mL, 12 mmol) in toluene (60 mL) was dehydrated using a Dean-Stark apparatus while refluxing for 24 hours. The reaction solution was concentrated under reduced pressure, and the resulting residue (0.72 g) was dissolved in diethyl ether (20 mL). The mixture was added dropwise to an 80% suspension of aluminum lithium hydride (0.27 g, 7.2 mmol) in diethyl ether (20 mL) with ice cooling. The resulting mixture was stirred at room temperature for 14 hours. Water (10 mL) was added portionwise thereto, and then insolubles were filtered off through Celite, and the Celite was washed with tetrahydrofuran. The filtrate was concentrated under reduced pressure, and the residue was dissolved in tetrahydrofuran (50 mL). Triethylamine (0.84 mL, 6.0 mmol) and di-tert-butyl dicarbonate (1.0 g, 4.7 mmol) were added thereto, and the mixture was stirred at room temperature for 14 hours. To the reaction solution was added ethyl acetate, and the resulting mixture was washed with a 0.5 M aqueous sodium hydrogen carbonate solution, dried over anhydrous magnesium sulfate and concentrated under reduced pressure. The residue was purified with silica gel column chromatography (hexane:ethyl acetate=9:1 to ethyl acetate) to obtain the title compound (0.74 g, yield 24%).

Oil.

$^1$H NMR (CDCl$_3$) δ 1.04 (6H, s), 1.45 (9H, s), 2.08-2.12 (2H, m), 2.50-2.56 (2H, m), 3.05-3.10 (4H, m), 5.13 (1H, br), 5.68-5.76 (2H, m).

Reference Example 44

N-[2-(3,6-Dihydropyridin-1(2H)-yl)-2,2-dimethylethyl]amine dihydrochloride

In the same manner as in Example 125, the title compound was obtained using 1,1-dimethylethyl N-[2-(3,6-dihydropyridin-1(2H)-yl)-2,2-dimethylethyl]carbamate instead of 1,1-dimethylethyl 4-[[(tetrahydro-3-oxo-1,1-diphenyl-3H-oxazolo[3,4-a]pyrazin-7(1H)-yl)carbonyl]amino]-1H-benzimidazole-1-carboxylate. Yield 95%.

Melting point 246-247° C.

$^1$H NMR (DMSO-d$_6$) δ 1.43 (6H, s), 2.27-2.31 (1H, m), 2.58-2.73 (1H, m), 2.92-2.98 (1H, m), 3.28-3.31 (2H, m), 3.70-3.74 (3H, m), 5.70-5.74 (1H, m), 5.88-5.91 (1H, m), 8.47 (3H, br).

Reference Example 45

1,1-Dimethylethyl N-[1-[(3,6-dihydropyridin-1(2H)-yl)methyl]cyclopropyl]carbamate In the same manner as in Reference Example 39, the title compound was obtained using 1,1-dimethylethyl [(1-oxomethyl)cyclopropyl]carbamate instead of 1,1-dimethylethyl (2-oxoethyl)carbamate. Yield 92%.

Oil.

$^1$H NMR (CDCl$_3$) δ 0.60-0.64 (2H, m), 0.84-0.88 (2H, m), 1.43 (9H, s), 2.14-2.17 (2H, m), 2.51 (2H, s), 2.64 (2H, t, J=5.7 Hz), 3.01-3.05 (2H, m), 5.01 (1H, br), 5.63-5.68 (1H, m), 5.72-5.77 (1H, m).

Reference Example 46

N-[1-[(3,6-Dihydropyridin-1(2H)-yl)methyl]cyclopropyl]amine dihydrochloride

In the same manner as in Example 125, the title compound was obtained using 1,1-dimethylethyl N-[1-[(3,6-dihydropyridin-1(2H)-yl)methyl]-cyclopropyl]carbamate instead of 1,1-dimethylethyl 4-[[(tetrahydro-3-oxo-1,1-diphenyl-3H-oxazolo[3,4-a]pyrazin-7(1H)-yl)carbonyl]amino]-1H-benzimidazole-1-carboxylate. Yield 80%.

Melting point 204-205° C.

$^1$H NMR (DMSO-d$_6$) δ 1.05 (2H, s), 1.19 (2H, s), 2.27-4.02 (8H, m), 5.69-5.74 (1H, m), 5.90-5.94 (1H, m), 8.89 (3H, br).

Reference Example 47

1,1-Bis(3-fluorophenyl)-hexahydro-7-[(4-methylphenyl)methyl]-3H-oxazolo[3,4-a]pyrazin-3-one In the same manner as in Reference Example 37, the title compound was obtained using 3,3'-difluorobenzophenone instead of benzophenone. Yield 59%.

Melting point 144-145° C.

$^1$H NMR (CDCl$_3$) δ 1.53-1.61 (1H, m), 1.92 (1H, dt, J=3.7 Hz, 11.8 Hz), 2.34 (3H, s), 2.54 (1H, dd, J=3.4 Hz, 11.3 Hz), 2.69 (1H, dd, J=3.6 Hz, 11.6 Hz), 3.08 (1H, dt, J=3.7 Hz, 12.1 Hz), 3.29 (1H, d, J=13.0 Hz), 3.48 (1H, d, J=13.0 Hz), 3.78 (1H, dd, J=2.6 Hz, 13.0 Hz), 4.46 (1H, dd, J=3.5 Hz, 11.0 Hz), 7.01-7.10 (8H, m), 7.17-7.36 (4H, m).

Reference Example 48

1,1-Bis(3-fluorophenyl)-hexahydro-3H-oxazolo[3,4-a]pyrazin-3-one

In the same manner as in Reference Example 38, the title compound was obtained using 1,1-bis(3-fluorophenyl)-hexahydro-7-[(4-methylphenyl)methyl]-3H-oxazolo[3,4-a]pyrazin-3-one instead of hexahydro-7-[(4-methylphenyl)methyl]-1,1-diphenyl-3H-oxazolo[3,4-a]pyrazin-3-one. Yield 75%.

Amorphous.

$^1$H NMR (CDCl$_3$) δ 2.12 (1H, t, J=9.4 Hz), 2.59-2.67 (1H, m), 2.72-2.77 (1H, m), 2.90-2.95 (1H, m), 3.04-3.14 (1H, m), 3.81-3.86 (1H, m), 4.35 (1H, dd, J=3.4 Hz, 10.9 Hz), 6.96-7.07 (4H, m), 7.23-7.37 (4H, m).

Reference Example 49

(+)-Hexahydro-1,1-diphenyl-3H-oxazolo[3,4-a]pyrazin-3-one

Racemate (5.0 g) of hexahydro-1,1-diphenyl-3H-oxazolo[3,4-a]pyrazin-3-one was resolved with the following HPLC conditions.

Preparative HPLC Conditions:
Column; CHIRALPAK AD 50 mmID×500 mL (manufactured by Daicel Chemical Industries, Ltd.)
Mobile phase; hexane/ethanol=50/50
Flow rate; 60 mL/min
Temperature; 30° C.
Detection; UV 220 nm
Loading dose; 4.5 g Each fraction was concentrated under reduced pressure, and hexane/ethanol was added thereto. For an enantiomer having a long retention time, the title compound (2.3 g, yield 46%, 99.9% ee) was obtained as powder. $^1$H NMR of the above obtained compound corresponded with the compound obtained in Reference Example 2.

$[α]^{20}{}_D$ +272.9° (c 0.971, chloroform).

Reference Example 50

(−)-Hexahydro-1,1-diphenyl-3H-oxazolo[3,4-a]pyrazin-3-one

When the operation was carried out in Reference Example 49, for an enantiomer having a short retention time, the title compound (2.1 g, yield 43%, 99.9% ee) was obtained as powder. $^1$H NMR of the above obtained compound corresponded with the compound obtained in Reference Example 2.

$[α]^{20}{}_D$ −273.1° (c 0.998, chloroform).

Reference Example 51

N-(Cyclopropylmethyl)-2-nitrobenzenesulfonamide

To a solution of cyclopropylmethylamine (0.5 g, 7.0 mmol) and triethylamine (1.5 mL, 11 mmol) in tetrahydrofuran (30 mL) was added (2-nitrobenzene)sulfonyl chloride (1.7 g, 7.0 mmol) with ice cooling, and the mixture was stirred for 16 hours with ice cooling. To the reaction solution was added ethyl acetate. The resulting mixture was sequentially washed with water, 1 N hydrochloric acid and a 0.5 M aqueous sodium hydrogen carbonate solution, dried over anhydrous magnesium sulfate and concentrated under reduced pressure. The residue was purified with silica gel column chromatography (hexane:ethyl acetate=49:1 to hexane:ethyl acetate=1:1) to obtain the title compound (1.7 g, yield 92%).

Amorphous.

$^1$H NMR (CDCl$_3$) δ 0.14-0.15 (2H, m), 0.48 (2H, dd, J=6.0 Hz, 13.8 Hz), 0.88-0.94 (1H, m), 2.98 (2H, t, J=6.0 Hz), 5.39 (1H, br), 7.72-7.75 (2H, m), 7.86-7.89 (1H, m), 8.13-8.16 (1H, m).

Reference Example 52

N-(2-Aminoethyl)-N-(cyclopropylmethyl)-2-nitrobenzenesulfonamide

To a solution of N-(cyclopropylmethyl)-2-nitrobenzenesulfonamide (1.7 g, 6.4 mmol), t-butyl N-(2-hydroxyethyl)carbamate (1.3 g, 8.3 mmol) and triphenylphosphine (2.2 g, 8.3 mmol) in toluene (20 mL) was added a 40% solution of diethyl azodicarboxylate in toluene (3.6 g, 8.3 mmol) with ice cooling, and the mixture was stirred at room temperature for 16 hours. The reaction solution was concentrated under reduced pressure to a half its original volume, and diethyl ether (30 mL) was added thereto. The precipitates were filtered off, and the filtrate was concentrated under reduced pressure. The residue was purified with silica gel column chromatography (hexane:ethyl acetate=49:1 to hexane:ethyl acetate=1:1) to obtain a condensed compound as an oily matter. A 4 M hydrogen chloride/ethyl acetate solution (20 mL) was added thereto, and the mixture was stirred at room temperature for 30 minutes. To the reaction solution was added water (70 mL) and extracted. The aqueous layer was collected by separation and washed with ethyl acetate. The aqueous layer was basified with a 4 N aqueous sodium hydroxide solution (pH=12), and extracted with ethyl acetate. The extract was dried over anhydrous magnesium sulfate and concentrated under reduced pressure. The residue was purified with amino silica gel column chromatography (hexane: ethyl acetate=19:1 to ethyl acetate) to obtain the title compound (1.2 g, yield 62%).

Oil.

$^1$H NMR (CDCl$_3$) δ 0.18-0.23 (2H, m), 0.51-0.57 (2H, m), 0.88-1.02 (1H, m), 2.92 (2H, t, J=6.3 Hz), 3.18-3.20 (2H, m), 3.46 (2H, t, J=6.3 Hz), 7.61-7.70 (3H, m), 8.05-8.08 (1H, m).

Reference Example 53

1,1-Dimethylethyl 4-(chloroacetyl)-3-[hydroxy (diphenyl)methyl]piperazine-1-carboxylate To a solution of 1,1-dimethylethyl 3-[hydroxy(diphenyl) methyl]-1-piperazine carboxylate (0.50 g, 1.4 mmol) in tetrahydrofuran (5 mL) were sequentially added diisopropylethylamine (2 mL) and chloroacetyl chloride (0.46 g, 4.1 mmol) with ice cooling, and the mixture was stirred for 4 hours while elevating the temperature to room temperature. To the reaction solution was added ethyl acetate, and the resulting mixture was washed with water, dried over anhydrous magnesium sulfate and concentrated under reduced pressure. The residue was purified with silica gel column chromatography (hexane:ethyl acetate=4:1) to obtain the title compound (0.28 g, yield 46%).

Oil.

Amide rotamer ratio (α:β=1:3.2).

$^1$H NMR (CDCl$_3$) δ 1.34-1.38 (9H of α, 9H of β, m), 2.80-4.41 (8H of α, 8H of β, m), 4.52-4.55 (1H of β, m), 4.68-4.71 (1H of α, m), 7.15-7.60 (10H of α, 10H of β, m).

Reference Example 54

1,1-Dimethylethyl hexahydro-4-oxo-1,1-diphenylpyrazino[2,1-c][1,4]oxazine-8(1H)-carboxylate To a solution of 1,1-dimethylethyl 4-(chloroacetyl)-3-[hydroxy(diphenyl)methyl]piperazine-1-carboxylate (0.28 g, 0.63 mmol) in tetrahydrofuran (5 mL) was added 60% sodium hydride (40 mg, 1.0 mmol), and the mixture was stirred at room temperature for 3 hours. To the reaction solution was added ethyl acetate, and the resulting mixture was washed with water, dried over anhydrous magnesium sulfate and concentrated under reduced pressure to obtain the title compound (0.24 g, yield 93%).

Amorphous.

$^1$H NMR (CDCl$_3$) δ 1.44 (9H, s), 2.81-2.88 (3H, m), 3.42 (1H, br), 3.73 (1H, d, J=15.9 Hz), 4.08-4.16 (2H, m), 4.27 (2H, d, J=16.9 Hz), 4.70-4.73 (1H, m), 7.19-7.41 (10H, m).

Reference Example 55

1,4-Bis(1,1-dimethylethyl)2-ethyl piperazine-1,2,4-tricarboxylate

To ethyl 1,4-bis(phenylmethyl)-2-piperazine carboxylate dihydrochloride (10 g, 24 mmol) were added ethanol (150 mL), water (20 mL) and 10% palladium carbon (0.60 g), and the mixture was stirred under hydrogen atmosphere at room temperature for 7 hours. The reaction solution was filtered through Celite, the Celite was washed with ethanol-water (4:1), and then the filtrate was concentrated under reduced pressure. To the residue were added tetrahydrofuran (300 mL), a 0.5 M aqueous sodium hydrogen carbonate solution (300 mL) and di-tert-butyl dicarbonate (18 g, 81 mmol), and the mixture was stirred at room temperature for 16 hours. The mixture was extracted with ethyl acetate (500 mL), and the organic layer was dried over anhydrous magnesium sulfate and concentrated under reduced pressure. The residue was purified with silica gel column chromatography (hexane: ethyl acetate=9:1 to hexane:ethyl acetate=1:1) to obtain the title compound (8.8 g, quantitative).

Oil.

$^1$H NMR (CDCl$_3$) δ 1.25-1.30 (3H, m), 1.44 (18H, s), 2.72-3.26 (3H, m), 3.71-4.22 (4H, m), 4.42-4.72 (2H, m).

Reference Example 56

1,4-Bis(1,1-dimethylethyl)2-ethyl 2-(phenylmethyl)piperazine-1,2,4-tricarboxylate 2-Ethyl piperazine-1,2,4-tricarboxylate 1,4-bis(1,1-dimethylethyl)ester (4.4 g, 12 mmol) were dissolved in tetrahydrofuran (120 mL) and N,N-dimethylformamide (12 mL), and the mixture was cooled to −78° C. A 1 M solution of sodium bis(trimethylsilyl)amide in tetrahydrofuran (19 mL, 19 mmol) was added thereto, and the mixture was stirred at −78° C. for 1 hour. Then, benzyl bromide (3.2 g, 19 mmol) was added thereto, and the mixture was stirred at −78° C. for 30 minutes, warmed to room temperature, and further stirred for 70 hours. To the reaction solution was added a 0.5 M aqueous sodium hydrogen carbonate solution, and the resulting solution was extracted with ethyl acetate. The extract was dried over anhydrous magnesium sulfate and concentrated under reduced pressure. The residue was purified with silica gel column chromatography (hexane:ethyl acetate=9:1 to hexane:ethyl acetate=7:3) to obtain the title compound (4.9 g, yield 90%).

Oil.

$^1$H NMR (CDCl$_3$) δ 1.23-1.29 (3H, m), 1.41-1.43 (9H, s), 1.51 (9H, s), 2.40-2.52 (1H, m), 2.93-3.06 (2H, m), 3.28-3.52 (2H, m), 3.63-3.89 (2H, m), 4.02-4.18 (3H, m), 7.14-7.26 (5H, m).

Reference Example 57

Bis(1,1-dimethylethyl)2-(hydroxymethyl)-2-(phenylmethyl)piperazine-1,4-dicarboxylate 1,4-Bis(1,1-dimethylethyl)2-ethyl 2-(phenylmethyl)piperazine-1,2,4-tricarboxylate (4.8 g, 11 mmol) was dissolved in tetrahydrofuran (50 mL). With ice cooling, a 1 M solution of triethyl lithium borohydride in tetrahydrofuran (24 mL, 24 mmol) was added thereto, and the mixture was stirred at room temperature for 1 hour. To the reaction solution was added a 0.5 M aqueous sodium hydrogen carbonate solution, and the resulting mixture was extracted with ethyl acetate. The extract was dried over anhydrous magnesium sulfate and concentrated under reduced pressure. The residue was purified with silica gel column chromatography (hexane:ethyl acetate=4:1 to hexane:ethyl acetate=1:1) to obtain the title compound (3.7 g, yield 87%).

Oil.

$^1$H NMR (CDCl$_3$) δ 1.46-1.53 (18H, m), 2.68-2.85 (2H, m), 3.10-3.50 (4H, m), 3.52-3.60 (2H, m), 3.72-3.90 (3H, m), 7.17-7.31 (5H, m).

Reference Example 58

1,1-Dimethylethyl tetrahydro-3-oxo-8a-(phenylmethyl)-3H-oxazolo[3,4-a]pyrazine-7(1H)-carboxylate Bis(1,1-dimethylethyl)2-(hydroxymethyl)-2-(phenylmethyl)piperazine-1,4-dicarboxylate (3.6 g, 8.9 mmol) was dissolved in N,N-dimethylformamide (40 mL). 60% Sodium hydride (0.43 g, 11 mmol) was added thereto, and the mixture was stirred at room temperature for 3 hours. To the reaction solution was added a 0.5 M aqueous sodium hydrogen carbonate solution, and the resulting mixture was extracted with ethyl acetate. The extract was dried over anhydrous magnesium sulfate and concentrated under reduced pressure. To the residue was added diethyl ether, and the precipitated crystals were collected by filtration to obtain the title compound (2.6 g, yield 88%).

Melting point 188-190° C.

$^1$H NMR (CDCl$_3$) δ 1.52 (9H, m), 2.75-3.07 (4H, m), 3.20-3.30 (1H, m), 3.72 (1H, d, J=9.2 Hz), 3.81 (1H, dd, J=3.5 Hz, 13.6 Hz), 4.10-4.30 (3H, m), 7.21-7.36 (5H, m).

Reference Example 59

Ethyl 1,4-bis(phenylmethyl)-1,4-diazepane-2-carboxylate 1,3-Propanediamine (50 g, 0.67 mol) was dissolved in ethanol (500 mL), with ice cooling, benzaldehyde (140 g, 1.4 mol) was added thereto, and the mixture was stirred at 70° C. for 2 hours. The reaction solution was concentrated under reduced pressure. To the residue were added methanol (1000 mL) and ethanol (500 mL), with ice cooling, sodium borohydride (61 g, 1.6 mol) was added portionwise thereto over 1 hour, and the mixture was stirred at room temperature overnight. Then, the reaction solution was concentrated under reduced pressure, and water was added to the residue. The reaction solution was extracted with ethyl acetate and washed with an aqueous saturated sodium chloride solution. The extract was dried over anhydrous magnesium sulfate and concentrated under reduced pressure to obtain an oily matter (180 g). To 81 g of the obtained oily matter were added toluene (1000 mL), triethylamine (76 g, 0.75 mol) and ethyl 2,3-dibromopropionate (43 mL), and the mixture was stirred at 70° C. overnight. The reaction solution was cooled to room temperature and ethyl acetate was added thereto. The resulting mixture was washed with a 0.5 M aqueous sodium hydrogen carbonate solution, dried over anhydrous magnesium sulfate and concentrated under reduced pressure. The residue was purified with silica gel column chromatography (hexane:ethyl acetate=20:1 to hexane:ethyl acetate=9:1) to obtain the title compound (52 g, yield 49%).

Oil.

$^1$H NMR (CDCl$_3$) δ 1.20 (3H, t, J=7.1 Hz), 1.63-1.82 (2H, m), 2.60-2.82 (3H, m), 2.93-3.18 (2H, m), 3.22-3.32 (1H, m), 3.55-3.59 (1H, m), 3.66-3.77 (2H, m), 3.80-3.93 (2H, m), 4.08-4.18 (2H, m), 7.21-7.39 (10H, m).

Reference Example 60

Bis(1,1-dimethylethyl)2-[hydroxy(diphenyl)methyl]-1,4-diazepane-1,4-dicarboxylate Ethyl 1,4-bis(phenylmethyl)-1,4-diazepane-2-carboxylate (57 g, 0.16 mol) was dissolved in ethanol (300 mL). 10% Palladium carbon (7.0 g) was added thereto, and the mixture was stirred under hydrogen atmosphere at pressures of 3 bar, at room temperature for 1 week. The reaction solution was filtered through Celite, the Celite was washed with ethanol, and then the filtrate was concentrated under reduced pressure. To the residue was added tetrahydrofuran (400 mL), and the extract was filtered off. The filtrate was concentrated under reduced pressure to obtain an oily matter (26.6 g). 8.6 g of the obtained oily matter was dissolved in tetrahydrofuran (250 mL). A 1 M solution of phenylmagnesium bromide in tetrahydrofuran (250 mL) was added dropwise thereto over 1 hour, and the mixture was stirred at room temperature overnight. After ice cooling the reaction solution, water (500 mL) was added thereto, and the mixture was stirred for 1 hour with ice cooling. Di-tert-butyl dicarbonate (44 g, 0.2 mol) was added thereto, and the mixture was stirred at room temperature one whole day and night. To the reaction solution was added ethyl acetate (500 mL), and the resulting mixture was washed with an aqueous saturated ammonium chloride solution (500 mL). The organic layer was dried over anhydrous magnesium sulfate and concentrated under reduced pressure. The residue was subjected to silica gel column chromatography (hexane:ethyl acetate=9:1 to hexane:ethyl acetate=8:2) to obtain the title compound (1.4 g, yield 6%) as a crude product. Amorphous. The obtained compound was used in the next process without further purification.

Reference Example 61

1,1-Dimethylethyl tetrahydro-3-oxo-1,1-diphenyl-1H-[1,3]oxazolo[3,4-a][1,4]diazepine-8(5H)-carboxylate To bis(1,1-dimethylethyl)2-[hydroxy(diphenyl)methyl]-1,4-diazepane-1,4-dicarboxylate (crude product, 1.4 g, 2.8 mmol) obtained in Reference Example 60 were added N,N-dimethylformamide (30 mL) and 60% sodium hydride (0.11 g, 2.8 mmol), and the mixture was stirred at room temperature for 3 hours. To the reaction solution was added ethyl acetate, and the resulting mixture was washed with a 0.5 M aqueous sodium hydrogen carbonate solution, dried over anhydrous magnesium sulfate and concentrated under reduced pressure. The residue was purified with silica gel column chromatography (hexane:ethyl acetate=9:1 to hexane:ethyl acetate=1:1) to obtain the title compound (0.44 g, yield 38%).

Oil.

$^1$H NMR (CDCl$_3$) δ 1.55 (9H, s), 1.80-1.95 (1H, m), 2.13-2.34 (1H, m), 2.86-3.01 (2H, m), 3.12-3.18 (1H, m), 3.78-4.03 (3H, m), 4.42-4.54 (1H, m), 7.26-7.61 (10H, m).

Reference Example 62

Hexahydro-1,1-diphenyl-1H-[1,3]oxazolo[3,4-a][1,4]diazepin-3-one 1,1-Dimethylethyl tetrahydro-3-oxo-1,1-diphenyl-1H-[1,3]oxazolo[3,4-a][1,4]diazepine-8(5H)-carboxylate (0.30 g, 0.73 mmol) was dissolved in ethyl acetate (5 mL). A 4 M hydrogen chloride/ethyl acetate solution (4 mL) was added thereto, and the mixture was stirred at room temperature for 1 hour. The reaction solution was concentrated, and then ethyl acetate was added to the residue. The resulting mixture was washed with a 0.5 M aqueous sodium hydrogen carbonate solution, dried over anhydrous magnesium sulfate and concentrated under reduced pressure to obtain the title compound (0.16 g, yield 70%).

Oil.

$^1$H NMR (CDCl$_3$) δ 1.80-1.99 (2H, m), 2.04 (1H, dd, J=8.1 Hz, 14.1 Hz), 2.62-2.75 (1H, m), 2.81 (1H, dd, J=3.0 Hz, 14.1 Hz), 2.96-3.00 (1H, m), 3.36-3.39 (1H, m), 3.70-3.73 (1H, m), 4.56 (1H, dd, J=3.0 Hz, 8.0 Hz), 7.24-7.51 (10H, m).

Reference Example 63

(Phenylmethyl)octahydro-7,9-dioxo-6,6-diphenyl-2H-pyrazino[1,2-a]pyrazine-2-carboxylate Chloro(diphenyl)acetic acid (0.56 g, 2.3 mmol) was dissolved in acetonitrile (10 mL). Dicyclohexylcarbodiimide (0.41 g, 2.0 mmol) and ammonium 1H-1,2,3-benzotriazol-1-olate (0.30 g, 2.0 mmol) were added thereto, and the mixture was stirred at room temperature for 30 minutes. The precipitates were filtered off, and the filtrate was concentrated under reduced pressure. The residue was dissolved in ethyl acetate (20 mL), and the resulting mixture was washed with a 0.5 M aqueous sodium hydrogen carbonate solution, dried over anhydrous magnesium sulfate and concentrated under reduced pressure. The residue was dissolved in acetonitrile (10 mL). 3-Ethyl piperazine-1,3-dicarboxylate 1-benzyl (0.58 g, 2.0 mmol) and potassium carbonate (0.55 g, 4.0 mmol) were added thereto, and the mixture was stirred at 60° C. overnight. After cooling to room temperature, insolubles were filtered off, and the filtrate was concentrated under reduced pressure. The residue was purified with silica gel column chromatography (dichloromethane to dichloromethane:methanol=99:1) and recrystallized from methanol to obtain the title compound (0.16 g, yield 16%).

Melting point 151-152° C.

$^1$H NMR (CDCl$_3$) δ 2.67-2.87 (2H, m), 2.97-3.07 (1H, m), 3.97 (1H, dd, J=4.8 Hz, 10.8 Hz), 4.06-4.10 (1H, m), 4.18-4.31 (1H, m), 4.57-4.68 (1H, m), 5.16 (2H, s), 6.48 (1H, br), 7.26-7.40 (15H, m).

Reference Example 64

N-[(4-Fluorophenyl)methyl]-hexahydro-4-oxo-1,1-diphenylpyrazino[2,1-c][1,4]oxazine-8(1H)-carboxamide To 1,1-dimethylethyl hexahydro-4-oxo-1,1-diphenylpyrazino[2,1-c][1,4]oxazine-8(1H)-carboxylate (0.11 g, 0.26 mmol) was added trifluoroacetic acid (2.0 mL), and the mixture was stirred for 2 hours with ice cooling. The reaction solution was concentrated under reduced pressure, neutralized with a 0.5 M aqueous sodium hydrogen carbonate solution and extracted with ethyl acetate. The extract was dried over anhydrous magnesium sulfate and concentrated under reduced pressure. The residue was dissolved in toluene (2 mL). (4-Fluorophenyl)methyl isocyanate (61 mg, 0.4 mmol) was added thereto, and the mixture was stirred at 60° C. overnight. The reaction solution was concentrated under reduced pressure. Then, the residue was purified with silica gel column chromatography (hexane:ethyl acetate=1:1 to hexane:ethyl acetate=1:9) and powder was formed from diisopropyl ether to obtain the title compound (90 mg, yield 75%).

Amorphous.

$^1$H NMR (CDCl$_3$) δ 2.87-2.98 (3H, m), 3.20-3.25 (1H, m), 3.76 (1H, d, J=16.9 Hz), 3.90-3.94 (1H, m), 4.21-4.37 (5H, m), 4.71-4.75 (1H, m), 6.96-7.02 (2H, m), 7.15-7.37 (12H, m).

Reference Example 65

Hexahydro-8a-(phenylmethyl)-3H-oxazolo[3,4-a]pyrazin-3-one

To 1,1-dimethylethyl tetrahydro-3-oxo-8a-(phenylmethyl)-3H-oxazolo[3,4-a]pyrazine-7(1H)-carboxylate (2.8 g, 8.6 mmol) were added dichloromethane (40 mL) and trifluoroacetic acid (9.7 g, 86 mmol), and the mixture was stirred at room temperature for 2 hours. The reaction solution was concentrated under reduced pressure, and ethyl acetate was added to the residue. The resulting mixture was washed with a 0.5 M aqueous sodium hydrogen carbonate solution, dried over anhydrous magnesium sulfate and concentrated under reduced pressure to obtain the title compound (1.74 g, yield 88%).

Oil.

$^1$H NMR (CDCl$_3$) δ 2.65-2.82 (2H, m), 3.01-3.14 (3H, m), 3.23-3.36 (2H, m), 3.70-3.79 (2H, m), 4.28 (1H, d, J=8.8 Hz), 7.17-7.37 (5H, m).

Reference Example 66

N-[(4-Fluorophenyl)methyl]-tetrahydro-3-oxo-1,1-diphenyl-1H-oxazolo[3,4-a][1,4]diazepine-8(5H)-carboxamide To hexahydro-1,1-diphenyl-1H-oxazolo[3,4-a][1,4]diazepin-3-one (60 mg, 0.2 mmol) were added tetrahydrofuran (5 mL) and 4-fluorobenzyl isocyanate (59 mg, 0.39 mmol), and the mixture was stirred at 50° C. for 2 hours. The reaction solution was concentrated under reduced pressure. Then, the residue was purified with silica gel column chromatography (hexane:ethyl acetate=6:1 to hexane:ethyl acetate=1:4) and powder was formed from diethyl ether to obtain the title compound (73 mg, yield 82%).

Amorphous.

$^1$H NMR (CDCl$_3$) δ 1.97-2.05 (2H, m), 2.22-2.30 (1H, m), 2.91-2.99 (1H, m), 3.18-3.23 (1H, m), 3.46-3.50 (1H, m), 4.06-4.18 (2H, m), 4.35-4.52 (2H, m), 4.59-4.66 (2H, m), 6.99-7.04 (2H, m), 7.26-7.44 (10H, m), 7.64-7.67 (2H, m).

Reference Example 67

Phenyl tetrahydro-3-oxo-1,1-diphenyl-1H-oxazolo[3,4-a][1,4]diazepine-8(5H)-carboxylate To hexahydro-1,1-diphenyl-1H-oxazolo[3,4-a][1,4]diazepin-3-one (60 mg, 0.2 mmol) were added tetrahydrofuran (5 mL), triethylamine (60 mg, 0.59 mmol) and phenyl chlorocarbonate (69 mg, 0.44 mmol), and the mixture was stirred at room temperature for 2 hours. To the reaction solution was added ethyl acetate, and the resulting mixture was washed with a 0.5 M aqueous sodium hydrogen carbonate solution, dried over anhydrous magnesium sulfate and concentrated under reduced pressure. The residue was purified with silica gel column chromatography (hexane:ethyl acetate=9:1 to hexane:ethyl acetate=3:2) and powder was formed from diisopropyl ether to obtain the title compound (69 mg, yield 83%).

Amorphous.

$^1$H NMR (CDCl$_3$) δ 1.95-2.13 (2H, m), 2.33-2.50 (1H, m), 3.04-3.23 (2H, m), 4.03-4.14 (3H, m), 4.63-4.72 (1H, m), 7.10-7.61 (15H, m).

Reference Example 68

Hexahydro-7-(2-oxo-2-phenylethyl)-1,1-diphenyl-3H-oxazolo[3,4-a]pyrazin-3-one

To a solution of hexahydro-1,1-diphenyl-3H-oxazolo[3,4-a]pyrazin-3-one (0.10 g, 0.34 mmol) in tetrahydrofuran (2 mL) were sequentially added diisopropylethylamine (0.6 mL) and phenacyl bromide (0.10 g, 0.51 mmol), and the mixture was stirred at room temperature for 17 hours. To the reaction solution was added water, and the mixture was extracted with ethyl acetate. The extract was washed with water and concentrated under reduced pressure. The residue was purified with silica gel column chromatography (hexane:ethyl acetate=1:1), hexane was added thereto, and powder was formed to obtain the title compound (92 mg, yield 66%).

Amorphous.

$^1$H NMR (CDCl$_3$) δ 1.73 (1H, t, J=11.1 Hz), 2.20-2.27 (1H, m), 2.65 (1H, dd, J=2.5 Hz, 11.2 Hz), 2.88 (1H, dd, J=3.4 Hz, 11.4 Hz), 3.30 (1H, dt, J=3.7 Hz, 12.0 Hz), 3.80 (2H, d, J=6.5 Hz), 3.85-3.90 (1H, m), 4.68 (1H, dd, J=3.6 Hz, 11.0 Hz), 7.23-7.55 (13H, m), 7.88-7.90 (2H, m).

Reference Example 69

Hexahydro-1,1-diphenyl-7-[1-(phenylmethyl)-4-piperidinyl]-3H-oxazolo[3,4-a]pyrazin-3-one To a solution of hexahydro-1,1-diphenyl-3H-oxazolo[3,4-a]pyrazin-3-one (0.15 g, 0.51 mmol), acetic acid (0.045 mL, 0.79 mmol) and 1-benzyl-4-piperidone (0.12 g, 0.63 mmol) in tetrahydrofuran (5 mL) was added sodium triacetoxyborohydride (0.16 g, 0.75 mmol), and the mixture was stirred at room temperature for 16 hours. 1-Benzyl-4-piperidone (0.060 mL) and sodium triacetoxyborohydride (0.16 g) were added thereto, and the mixture was stirred at room temperature for 3 days. The reaction solution was diluted with water, and the mixture was extracted with ethyl acetate. The organic layer was washed with an aqueous saturated sodium hydrogen carbonate solution, water and saturated brine, and then dried over magnesium sulfate. The solid was filtered off, and the filtrate was concentrated. The residue was purified with amino silica gel column chromatography (hexane:ethyl acetate=98:2 to hexane:ethyl acetate=1:1) and recrystallized from ethyl acetate-hexane to obtain the title compound (70 mg, yield 29%).

Melting point 153-155° C.

$^1$H NMR (CDCl$_3$) δ 1.37-1.62 (4H, m), 1.73 (1H, t, J=11.1 Hz), 1.83-1.92 (2H, m), 2.20-2.29 (2H, m), 2.45-2.49 (1H, m), 2.70-2.74 (1H, m), 2.88 (2H, d, J=11.3 Hz), 3.04-3.13 (1H, m), 3.44 (2H, s), 3.83 (1H, dd, J=2.5 Hz, 13.0 Hz), 4.45 (1H, dd, J=3.5 Hz, 10.8 Hz), 7.23-7.36 (13H, m), 7.49-7.52 (2H, m).

Reference Example 70

7-(Benzoxazol-2-yl)-hexahydro-1,1-diphenyl-3H-oxazolo[3,4-a]pyrazin-3-one

To a solution of hexahydro-1,1-diphenyl-3H-oxazolo[3,4-a]pyrazin-3-one (60 mg, 0.2 mmol) in tetrahydrofuran (2 mL) were sequentially added diisopropylethylamine (0.3 mL) and 2-chlorobenzoxazole (45 mg, 0.29 mmol), and the mixture was stirred at room temperature for 3 hours. The reaction solution was concentrated under reduced pressure. Then, the residue was purified with silica gel column chromatography (hexane:ethyl acetate=3:1) and recrystallized from diisopropyl ether to obtain the title compound (51 mg, yield 62%).

Melting point 260° C.

$^1$H NMR (CDCl$_3$) δ 2.56 (1H, t, J=12.4 Hz), 3.09-3.25 (2H, m), 3.96-4.01 (1H, m), 4.10-4.15 (1H, m), 4.28 (1H, dd, J=3.8 Hz, 13.0 Hz), 4.57 (1H, dd, J=3.8 Hz, 11.3 Hz), 7.06-7.41 (12H, m), 7.53-7.56 (2H, m).

Reference Example 71

Phenyl(tetrahydro-3-oxo-1,1-diphenyl-3H-oxazolo[3,4-a]pyrazin-7(1H)-yl)acetate

To a solution of hexahydro-1,1-diphenyl-3H-oxazolo[3,4-a]pyrazin-3-one (60 mg, 0.2 mmol) in tetrahydrofuran (2 mL) were sequentially added diisopropylethylamine (0.3 mL) and phenyl bromoacetate (65 mg, 0.29 mmol), and the mixture was stirred at room temperature for 2 hours. The reaction solution was concentrated under reduced pressure. Then, the residue was purified with silica gel column chromatography (hexane:ethyl acetate=2:1) and recrystallized from diisopropyl ether to obtain the title compound (51 mg, yield 60%).

Melting point 172° C.

$^1$H NMR (CDCl$_3$) δ 1.86 (1H, t, J=11.1 Hz), 2.34-2.42 (1H, m), 2.64-2.69 (1H, m), 2.87 (1H, dd, J=3.7 Hz, 11.2 Hz), 3.22-3.29 (1H, m), 3.43 (2H, dd, J=3.0 Hz), 3.88 (1H, dd, J=2.6 Hz, 13.3 Hz), 4.62 (1H, dd, J=3.6 Hz, 10.9 Hz), 7.00-7.02 (2H, m), 7.24-7.40 (11H, m), 7.50-7.54 (2H, m).

Example 1

(1,1-Dimethylethyl)tetrahydro-3-oxo-1,1-diphenyl-3H-oxazolo[3,4-a]pyrazine-7(1H)-carboxylate To a solution of (1,1-dimethylethyl)3-(hydroxydiphenylmethyl)-1-piperazine carboxylate (9.6 g, 26 mmol) in N,N-dimethylformamide (180 mL) were added potassium carbonate (20 g, 0.14 mol) and ethyl chlorocarbonate (14 g, 0.26 mol), and the mixture was stirred at 50° C. for 16 hours. To the reaction solution were further added potassium carbonate (20 g, 0.14 mol) and ethyl chlorocarbonate (14 g, 0.26 mol), and the mixture was further stirred at 50° C. for 18 hours. To the reaction solution was added ice water, and the mixture was extracted with ethyl acetate. The extract was washed with water and concentrated under reduced pressure. The residue was purified with silica gel column chromatography (hexane:ethyl acetate=3:1) to obtain the title compound (6.9 g, yield 64%) as a solid.

Melting point 151-152° C.

$^1$H NMR (CDCl$_3$) δ 1.46 (9H, s), 2.15 (1H, t, J=12.6 Hz), 2.73 (1H, t, J=12.6 Hz), 3.03 (1H, dt, J=12.6 Hz, 3.7 Hz), 3.82 (1H, dd, J=12.6 Hz, 3.2 Hz), 4.00 (2H, m), 4.35 (1H, dd, J=11.3 Hz, 3.2 Hz), 7.27-7.42 (8H, m), 7.51 (2H, m).

Example 2

Phenyl tetrahydro-3-oxo-1,1-diphenyl-3H-oxazolo[3,4-a]pyrazine-7(1H)-carboxylate To a solution of (1,1-dimethylethyl)tetrahydro-3-oxo-1,1-diphenyl-3H-oxazolo[3,4-a]pyrazine-7(1H)-carboxylate (99 mg, 0.25 mmol) in dichloromethane (2 mL) was added trifluoroacetic acid (0.19 mL, 2.5 mmol), and the mixture was stirred at room temperature for 4 hours. The reaction solution was concentrated under reduced pressure, and the residue was dissolved in ethyl acetate. This solution was washed with sodium hydrogen carbonate, dried over anhydrous magnesium sulfate and concentrated under reduced pressure to obtain hexahydro-1,1-diphenyl-3H-oxazolo[3,4-a]pyrazin-3-one as a crude product. The product was dissolved in tetrahydrofuran (2 mL). Diisopropylethylamine (60 µL, 0.35 mmol) and phenyl chlorocarbonate (44 µL, 0.35 mmol) were added thereto, and the mixture was stirred at room temperature for 1 hour. To the reaction solution was added ethyl acetate, and the resulting mixture was washed with water and saturated brine, dried over anhydrous magnesium sulfate and concentrated under reduced pressure. The residue was crystallized from ethyl acetate-hexane to obtain the title compound (70 mg, yield 67%).

Melting point 189-191° C.

$^1$H NMR (CDCl$_3$) δ 2.22-2.54 (1H, m), 2.82-3.08 (1H, m), 3.17 (1H, dt, J=12.7 Hz, 3.6 Hz), 3.95 (1H, dd, J=13.2 Hz, 3.2 Hz), 4.08 (1H, br d, J=14.0 Hz), 4.27 (1H, br d, J=12.5 Hz), 4.49 (1H, dd, J=11.3 Hz, 3.5 Hz), 7.08 (2H, d, J=7.8 Hz), 7.26-7.43 (11H, m), 7.51-7.54 (2H, m).

Example 3

(4-Fluorophenyl)tetrahydro-3-oxo-1,1-diphenyl-3H-oxazolo[3,4-a]pyrazine-7(1H)-carboxylate To a solution of hexahydro-1,1-diphenyl-3H-oxazolo[3,4-a]pyrazin-3-one (50 mg, 0.17 mmol) in tetrahydrofuran (2 mL) were sequentially added diisopropylethylamine (0.30 mL, 1.7 mmol) and 4-fluorophenyl chlorocarbonate (45 mg, 0.26 mmol), and the mixture was stirred at room temperature for 2 hours. The reaction solution was concentrated, and the residue was purified with silica gel column chromatography (hexane:ethyl acetate=3:1) and crystallized from diisopropyl ether to obtain the title compound (58 mg, yield 79%).

Melting point 188-189° C.

$^1$H NMR (CDCl$_3$) δ 2.26-2.50 (1H, m), 2.80-3.03 (1H, m), 3.17 (1H, dt, J=12.5 Hz, 3.7 Hz), 3.95 (1H, dd, J=13.2 Hz, 3.0 Hz), 4.06 (1H, d, J=12.9 Hz), 4.26 (1H, d, J=12.9 Hz), 4.48 (1H, dd, J=11.2 Hz, 3.5 Hz), 7.05 (4H, d, J=6.3 Hz), 7.26-7.43 (8H, m), 7.52 (2H, m).

Example 4

Tetrahydro-3-oxo-N,1,1-triphenyl-3H-oxazolo[3,4-a]pyrazine-7(1H)-carboxamide

To a solution of hexahydro-1,1-diphenyl-3H-oxazolo[3,4-a]pyrazin-3-one (85 mg, 0.29 mmol) in toluene (3 mL) was added phenyl isocyanate (70 mg, 0.59 mmol), and the mixture was stirred at 60° C. for 4 hours. The reaction solution was concentrated. Then, the residue was purified with silica gel column chromatography (hexane:ethyl acetate=2:1) and crystallized from diisopropyl ether to obtain the title compound (0.12 g, yield 99%).

Melting point 117-118° C.

$^1$H NMR (CDCl$_3$) δ 2.22 (1H, dd, J=13.3 Hz, 11.3 Hz), 2.97 (1H, dt, J=10.4 Hz, 3.5 Hz), 3.13 (1H, dt, J=13.3 Hz, 3.5 Hz), 3.86 (2H, dt, J=12.6 Hz, 2.7 Hz), 4.05 (1H, m), 4.47 (1H, dd, J=11.3 Hz, 3.7 Hz), 6.53 (1H, s), 7.08 (1H, m), 7.26-7.41 (12H, m), 7.50 (2H, m).

Example 5

Tetrahydro-N-methyl-3-oxo-N,1,1-triphenyl-3H-oxazolo[3,4-a]pyrazine-7(1H)-carboxamide To a solution of tetrahydro-3-oxo-N,1,1-triphenyl-3H-oxazolo[3,4-a]pyrazine-7(1H)-carboxamide (60 mg, 0.15 mmol) in tetrahydrofuran (2 mL) was added 60% sodium hydride (10 mg, 0.25 mmol), and the mixture was stirred at room temperature for 1 hour. Next, methyl iodide (0.15 g, 1.1 mmol) was added thereto, and the mixture was stirred at room temperature for 4 hours. The reaction solution was concentrated. Then, the residue was purified with silica gel column chromatography (hexane:ethyl acetate=1:1) and crystallized from diisopropyl ether to obtain the title compound (30 mg, yield 48%).

Melting point 146-147° C.

$^1$H NMR (CDCl$_3$) δ 2.00 (1H, dd, J=13.2 Hz, 11.2 Hz), 2.57 (1H, dt, J=13.2 Hz, 3.6 Hz), 2.89 (1H, dt, J=13.2 Hz, 3.7 Hz), 3.20 (3H, s), 3.54 (1H, m), 3.74 (2H, dt, J=13.2 Hz, 2.7 Hz), 4.05 (1H, dd, J=11.2 Hz, 3.7 Hz), 7.06-7.15 (4H, m), 7.23-7.34 (9H, m), 7.41 (2H, m).

Example 6

Hexahydro-7-(1-oxo-3-phenyl-2-propenyl)-1,1-diphenyl-3H-oxazolo[3,4-a]pyrazin-3-one In the same manner as in Example 3, the title compound was obtained using cinnamoyl chloride instead of 4-fluorophenyl chlorocarbonate. Yield 79%.

Melting point 230-232° C. (recrystallized from dichloromethane-petroleum ether).

$^1$H NMR (CDCl$_3$) δ 2.00-2.27 (1H, m), 3.00-3.23 (2H, m), 3.87-4.25 (1H, m), 3.97 (1H, d, J=9.6 Hz), 4.43 (1H, dd, J=11.2 Hz, 3.4 Hz), 4.48-4.75 (1H, m), 6.80 (1H, d, J=15.4 Hz), 7.28-7.58 (15H, m), 7.71 (1H, d, J=15.4 Hz).

Example 7

Hexahydro-1,1-diphenyl-7-(2-pyridinylcarbonyl)-3H-oxazolo[3,4-a]pyrazin-3-one

In the same manner as in Example 3, the title compound was obtained using picolinic acid chloride hydrochloride instead of 4-fluorophenyl chlorocarbonate. Yield 51%.

Melting point 169-170° C. (crystallized from diisopropyl ether).

$^1$H NMR (CDCl$_3$) δ 2.24 (0.5H, t, J=12.6 Hz), 2.39 (0.5H, dd, J=13.1 Hz, 11.0 Hz), 2.77 (0.5H, m), 3.05 (0.5H, m), 3.25 (1H, m), 3.85 (0.5H, dd, J=13.0 Hz, 2.7 Hz), 4.00 (0.5H, dd, J=13.2 Hz, 3.5 Hz), 4.18 (1H, d, J=12.8 Hz), 4.57 (1H, m), 4.76 (0.5H, m), 4.94 (0.5H, dd, J=10.8 Hz, 3.2 Hz), 7.24-7.45 (9H, m), 7.55-7.85 (4H, m), 8.58 (0.5H, d, J=4.6 Hz), 8.70 (0.5H, d, J=4.6 Hz).

Example 8

Hexahydro-7-(1-oxo-3-phenylpropyl)-1,1-diphenyl-3H-oxazolo[3,4-a]pyrazin-3-one

In the same manner as in Example 3, the title compound was obtained using 3-phenylpropionyl chloride instead of 4-fluorophenyl chlorocarbonate. Yield 54%.

Melting point 129-130° C. (crystallized from diisopropyl ether).

$^1$H NMR (CDCl$_3$) δ 1.95 (0.7H, t, J=12.2 Hz), 2.35-2.75 (3.0H, m), 2.96 (2.7H, m), 3.32 (0.3H, m), 3.63-4.00 (1.9H, m), 4.27 (0.7H, dd, J=11.2, 3.6 Hz), 4.52 (0.7H, d, J=13.2 Hz), 4.18 (0.7H, d, J=12.8 Hz), 4.66 (0.3H, m), 7.18-7.42 (13H, m), 7.50 (2H, m).

Example 9

(4-Chlorophenyl)tetrahydro-3-oxo-1,1-diphenyl-3H-oxazolo[3,4-a]pyrazine-7(1H)-carboxylate In the same manner as in Example 3, the title compound was obtained using 4-chlorophenyl chlorocarbonate instead of 4-fluorophenyl chlorocarbonate. Yield 65%.

Melting point 205-206° C. (crystallized from diisopropyl ether).

$^1$H NMR (CDCl$_3$) δ 2.26-2.50 (1H, m), 2.80-3.03 (1H, m), 3.17 (1H, dt, J=12.5 Hz, 3.7 Hz), 3.95 (1H, dd, J=13.2 Hz, 3.0 Hz), 4.09 (1H, m), 4.25 (1H, d, J=13.2 Hz), 4.48 (1H, dd, J=11.3 Hz, 3.6 Hz), 7.03 (2H, m), 7.24-7.43 (10H, m), 7.52 (2H, m).

Example 10

Tetrahydro-3-oxo-1,1-diphenyl-3H-oxazolo[3,4-a]pyrazine-7(1H)-carboxylic acid 2-phenylhydrazide To a solution of hexahydro-1,1-diphenyl-3H-oxazolo[3,4-a]pyrazin-3-one (0.10 g, 0.34 mmol) in tetrahydrofuran (1 mL) were sequentially added diisopropylethylamine (0.15 mL) and bis(trichloromethyl)carbonate (0.10 g, 0.34 mmol), and the mixture was stirred at room temperature for 45 minutes. Next, phenylhydrazine (39 mg, 0.36 mmol) was added thereto, and the mixture was stirred at room temperature for 3 hours. To the reaction solution was added water, and the mixture was extracted with ethyl acetate. The extract was washed with water and concentrated under reduced pressure. The residue was purified with silica gel column chromatography (hexane:ethyl acetate=1:1) and crystallized from ethyl acetate-diisopropyl ether to obtain the title compound (44 mg, yield 30%).

Melting point 227-228° C.

$^1$H NMR (CDCl$_3$) δ 2.31 (1H, dd, J=13.2 Hz, 11.3 Hz), 2.93 (1H, dt, J=13.2 Hz, 3.5 Hz), 3.11 (1H, dt, J=12.4 Hz, 3.7 Hz), 3.83-3.92 (3H, m), 4.42 (1H, dd, J=11.3 Hz, 3.7 Hz), 5.97 (1H, s), 6.33 (1H, s), 6.85 (2H, d, J=7.7 Hz), 6.91 (1H, m), 7.21-7.37 (10H, m), 7.48 (2H, m).

Example 11

(4-Methoxyphenyl)tetrahydro-3-oxo-1,1-diphenyl-3H-oxazolo[3,4-a]pyrazine-7(1H)-carboxylate In the same manner as in Example 3, the title compound was obtained using 4-methoxyphenyl chlorocarbonate instead of 4-fluorophenyl chlorocarbonate. Yield 67%.

Melting point 198-199° C. (crystallized from diisopropyl ether).

$^1$H NMR (CDCl$_3$) δ 2.26-2.50 (1H, m), 2.80-3.03 (1H, m), 3.17 (1H, dt, J=12.5 Hz, 3.7 Hz), 3.80 (3H, s), 3.94 (1H, dd, J=13.2 Hz, 3.0 Hz), 4.07 (1H, d, J=11.9 Hz), 4.26 (1H, d, J=13.2 Hz), 4.48 (1H, dd, J=11.2 Hz, 3.6 Hz), 6.88 (2H, d, J=9.1 Hz), 6.99 (2H, d, J=9.1 Hz), 7.32-7.43 (8H, m), 7.52 (2H, m).

Example 12

(9H-Fluoren-9-ylmethyl)tetrahydro-3-oxo-1,1-diphenyl-3H-oxazolo[3,4-a]pyrazine-7(1H)-carboxylate In the same manner as in Example 3, the title compound was obtained using (9H-fluoren-9-ylmethyl)chlorocarbonate instead of 4-fluorophenyl chlorocarbonate. Yield 76%.

Melting point 168-169° C. (crystallized from diisopropyl ether).

$^1$H NMR (CDCl$_3$) δ 2.12 (1H, dd, J=13.2 Hz, 11.5 Hz), 2.66-2.90 (2H, m), 3.44 (0.5H, m), 3.75 (1.5H, m), 3.90-4.22 (3H, m), 4.52 (1.5H, m), 4.80 (0.5H, m), 7.14-7.40 (14H, m), 7.53 (2H, m), 7.76 (2H, t, J=7.7 Hz).

Example 13

(3-Trifluoromethylphenyl)tetrahydro-3-oxo-1,1-diphenyl-3H-oxazolo[3,4-a]pyrazine-7(1H)-carboxylate In the same manner as in Example 3, the title compound was obtained using 3-trifluoromethylphenyl chlorocarbonate instead of 4-fluorophenyl chlorocarbonate. Yield 46%.

Melting point 183-184° C. (crystallized from diisopropyl ether).

$^1$H NMR (CDCl$_3$) δ 2.28-2.52 (1H, m), 2.84-3.07 (1H, m), 3.19 (1H, dt, J=12.6 Hz, 3.7 Hz), 3.97 (1H, dd, J=13.2 Hz, 3.0 Hz), 4.07 (1H, d, J=12.2 Hz), 4.26 (1H, d, J=11.7 Hz), 4.50 (1H, dd, J=11.7 Hz, 2.9 Hz), 7.27-7.34 (10H, m), 7.51 (4H, m).

Example 14

(4-Nitrophenyl)tetrahydro-3-oxo-1,1-diphenyl-3H-oxazolo[3,4-a]pyrazine-7(1H)-carboxylate In the same manner as in Example 3, the title compound was obtained using 4-nitrophenyl chlorocarbonate instead of 4-fluorophenyl chlorocarbonate. Yield 69%.

Melting point 214-215° C. (crystallized from diisopropyl ether).

$^1$H NMR (CDCl$_3$) δ 2.31-2.53 (1H, m), 2.84-3.08 (1H, m), 3.20 (1H, dt, J=12.5 Hz, 3.7 Hz), 3.99 (1H, dd, J=13.2 Hz, 3.0 Hz), 4.06 (1H, m), 4.26 (1H, d, J=13.2 Hz), 4.50 (1H, m), 7.26-7.44 (10H, m), 7.52 (2H, m), 8.27 (2H, d, J=9.1 Hz).

Example 15

Hexahydro-7-(phenoxyacetyl)-1,1-diphenyl-3H-oxazolo[3,4-a]pyrazin-3-one

In the same manner as in Example 3, the title compound was obtained using phenoxyacetyl chloride instead of 4-fluorophenyl chlorocarbonate. Yield 68%.

Melting point 119-120° C. (crystallized from diisopropyl ether).

¹H NMR (CDCl₃) δ 2.06 (0.7H, m), 2.46-2.66 (1H, m), 2.96-3.08 (1.4H, m), 3.84-4.07 (1.9H, m), 4.29-4.45 (1.6H, m), 4.55-4.74 (2.4H, m), 6.92 (1H, d, J=8.1 Hz), 6.98-7.11 (2H, m), 7.26-7.39 (11H, m), 7.48 (1H, m).

Example 16

N-(4-Fluorophenyl)-tetrahydro-3-oxo-1,1-diphenyl-3H-oxazolo[3,4-a]pyrazine-7(1H)-carboxamide In the same manner as in Example 4, the title compound was obtained using 4-fluorophenyl isocyanate instead of phenyl isocyanate. Yield 71%.

Melting point 110-111° C. (crystallized from diisopropyl ether).

¹H NMR (CDCl₃) δ 2.24 (1H, dd, J=13.3 Hz, 11.3 Hz), 3.01 (1H, dt, J=12.8 Hz, 3.2 Hz), 3.15 (1H, dt, J=12.6 Hz, 3.6 Hz), 3.82 (1H, d, J=12.8 Hz), 3.91 (1H, dd, J=13.3 Hz, 2.6 Hz), 4.04 (1H, dd, J=13.3 Hz, 2.6 Hz), 4.47 (1H, dd, J=11.3 Hz, 3.6 Hz), 6.39 (1H, br s), 6.99 (2H, t, J=8.5 Hz), 7.02-7.39 (10H, m), 7.51 (2H, m).

Example 17

Tetrahydro-3-oxo-1,1-diphenyl-N-(phenylmethyl)-3H-oxazolo[3,4-a]pyrazine-7(1H)-carboxamide In the same manner as in Example 4, the title compound was obtained using benzyl isocyanate instead of phenyl isocyanate. Yield 71%.

Melting point 98-99° C. (crystallized from diisopropyl ether).

¹H NMR (CDCl₃) δ 2.17 (1H, dd, J=13.3 Hz, 11.3 Hz), 2.90 (1H, dt, J=13.1 Hz, 3.5 Hz), 3.08 (1H, dt, J=12.8 Hz, 3.6 Hz), 3.64 (1H, m), 3.84 (1H, dd, J=12.8 Hz, 2.6 Hz), 4.04 (1H, dd, J=13.3 Hz, 2.6 Hz), 4.39-4.43 (3H, m), 4.75 (1H, m), 7.24-7.39 (13H, m), 7.51 (2H, m).

Example 18

(2-Methoxyphenyl)tetrahydro-3-oxo-1,1-diphenyl-3H-oxazolo[3,4-a]pyrazine-7(1H)-carboxylate In the same manner as in Example 3, the title compound was obtained using 2-methoxyphenyl chlorocarbonate instead of 4-fluorophenyl chlorocarbonate. Yield 40%.

Melting point 99-100° C. (crystallized from diisopropyl ether).

¹H NMR (CDCl₃) δ 2.31-2.43 (1H, m), 2.80-3.08 (1H, m), 3.21 (1H, m), 3.82 (3H, s), 3.92 (1H, dd, J=13.0 Hz, 3.0 Hz), 4.11 (1H, m), 4.27 (1H, m), 4.51 (1H, m), 6.96 (2H, d, J=7.8 Hz), 7.10-7.44 (10H, m), 7.54 (2H, m).

Example 19

(E)-7-[3-(4-Fluorophenyl)-1-oxo-2-propenyl]-hexahydro-1,1-diphenyl-3H-oxazolo[3,4-a]pyrazin-3-one To a solution of 4-fluorocinnamic acid (50 mg, 0.30 mmol) in tetrahydrofuran (1 mL) were sequentially added oxalyl chloride (46 mg, 0.36 mmol) and N,N-dimethylformamide (one drop), and the mixture was stirred at room temperature for 1 hour. The reaction solution was concentrated under reduced pressure. A solution of hexahydro-1,1-diphenyl-3H-oxazolo[3,4-a]pyrazin-3-one (60 mg, 0.20 mmol) in tetrahydrofuran (1.5 mL) and diisopropylethylamine (0.3 mL) were sequentially added thereto, and the mixture was stirred at room temperature for 3 hours. To the reaction solution was added an aqueous saturated sodium hydrogen carbonate solution, and the mixture was extracted with ethyl acetate. The extract was washed with water and concentrated under reduced pressure. The residue was purified with silica gel column chromatography (hexane:ethyl acetate=1:1) and crystallized from ethyl acetate-diisopropyl ether to obtain the title compound (32 mg, yield 36%).

Melting point 250-251° C.

¹H NMR (CDCl₃) δ 2.12 (1H, m), 3.10 (2H, m), 3.97 (1H, d, J=10.8 Hz), 4.11 (1H, m), 4.42 (1H, dd, J=11.3 Hz, 3.5 Hz), 4.61 (1H, m), 6.73 (1H, d, J=13.8 Hz), 7.08 (2H, t, J=8.6 Hz), 7.32-7.52 (12H, m), 7.66 (1H, d, J=15.6 Hz).

Example 20

Hexahydro-7-(1-oxo-4-phenylbutyl)-1,1-diphenyl-3H-oxazolo[3,4-a]pyrazin-3-one

In the same manner as in Example 19, the title compound was obtained using 4-phenylbutyric acid instead of 4-fluorocinnamic acid. Yield 34%.

Melting point 128-129° C. (crystallized from ethanol).

¹H NMR (CDCl₃) δ 1.97 (2H, m), 2.21-2.35 (2H, m), 2.45 (1H, m), 2.67 (2H, m), 2.96 (2H, m), 3.38 (0.3H, d, J=12.6 Hz), 3.65 (0.7H, m), 3.87 (1H, d, J=9.8 Hz), 4.29 (1H, m), 4.52 (0.7H, d, J=13.1 Hz), 4.63 (0.3H, d, J=12.9 Hz), 7.15-7.39 (13H, m), 7.52 (2H, m).

Example 21

N-(3-Fluorophenyl)-tetrahydro-3-oxo-1,1-diphenyl-3H-oxazolo[3,4-a]pyrazine-7(1H)-carboxamide In the same manner as in Example 4, the title compound was obtained using 3-fluorophenyl isocyanate instead of phenyl isocyanate. Yield 49%.

Melting point 112-113° C. (crystallized from diisopropyl ether).

¹H NMR (CDCl₃) δ 2.24 (1H, dd, J=13.3 Hz, 11.2 Hz), 3.01 (1H, m), 3.15 (1H, m), 3.82 (1H, d, J=13.1 Hz), 3.91 (1H, d, J=13.1 Hz), 4.04 (1H, dd, J=13.3 Hz, 2.4 Hz), 4.47 (1H, dd, J=11.2 Hz, 3.5 Hz), 6.50 (1H, m), 6.76 (1H, dt, J=8.3 Hz, 2.4 Hz), 7.00 (1H, m), 7.22-7.39 (10H, m), 7.50 (2H, m).

Example 22

N-(2-Fluorophenyl)-tetrahydro-3-oxo-1,1-diphenyl-3H-oxazolo[3,4-a]pyrazine-7(1H)-carboxamide In the same manner as in Example 4, the title compound was obtained using 2-fluorophenyl isocyanate instead of phenyl isocyanate. Yield 50%.

Melting point 105-106° C. (crystallized from diisopropyl ether).

¹H NMR (CDCl₃) δ 2.28 (1H, dd, J=13.3 Hz, 11.3 Hz), 3.05 (1H, dt, J=12.6 Hz, 3.0 Hz), 3.18 (1H, dt, J=12.6 Hz, 3.3 Hz), 3.85 (1H, d, J=13.0 Hz), 3.94 (1H, m), 4.05 (1H, dd, J=13.4 Hz, 2.5 Hz), 4.50 (1H, dd, J=11.2 Hz, 3.6 Hz), 6.54 (1H, m), 7.00-7.11 (3H, m), 7.32-7.51 (8H, m), 7.52 (2H, m), 7.98 (1H, m).

Example 23

Methyl 4-[[(tetrahydro-3-oxo-1,1-diphenyl-3H-oxazolo[3,4-a]pyrazin-7(1H)-yl)carbonyl]amino]benzoate In the same manner as in Example 4, the title compound was obtained using methyl 4-isocyanatobenzoate instead of phenyl isocyanate. Yield 70%.

Melting point 145-146° C. (crystallized from diisopropyl ether).

$^1$H NMR (CDCl$_3$) δ 2.26 (1H, dd, J=13.3 Hz, 11.3 Hz), 3.04 (1H, dt, J=12.5 Hz, 3.0 Hz), 3.16 (1H, dt, J=12.6 Hz, 3.0 Hz), 3.84-3.94 (2H, m), 3.89 (3H, s), 4.06 (1H, dd, J=13.2 Hz, 2.4 Hz), 4.49 (1H, dd, J=11.3 Hz, 3.6 Hz), 6.68 (1H, s), 7.31-7.52 (12H, m), 7.98 (2H, d, J=8.7 Hz).

Example 24

Methyl 3-[[(tetrahydro-3-oxo-1,1-diphenyl-3H-oxazolo[3,4-a]pyrazin-7(1H)-yl)carbonyl]amino]benzoate In the same manner as in Example 4, the title compound was obtained using methyl 3-isocyanatobenzoate instead of phenyl isocyanate. Yield 70%.

Melting point 105-106° C. (crystallized from diisopropyl ether).

$^1$H NMR (CDCl$_3$) δ 2.26 (1H, dd, J=13.3 Hz, 11.2 Hz), 3.01 (1H, dt, J=12.7 Hz, 3.3 Hz), 3.15 (1H, dt, J=12.6 Hz, 3.4 Hz), 3.85-3.94 (2H, m), 3.89 (3H, s), 4.04 (1H, dd, J=13.3 Hz, 2.4 Hz), 4.48 (1H, dd, J=11.2 Hz, 3.6 Hz), 6.64 (1H, s), 7.30-7.40 (9H, m), 7.50 (2H, m), 7.65-7.75 (2H, m), 7.88 (1H, m).

Example 25

N-[(4-Fluorophenyl)methyl]-tetrahydro-3-oxo-1,1-diphenyl-3H-oxazolo[3,4-a]pyrazine-7(1H)-carboxamide In the same manner as in Example 4, the title compound was obtained using 4-fluorobenzyl isocyanate instead of phenyl isocyanate. Yield 72%.

Melting point 105-106° C. (crystallized from diisopropyl ether).

$^1$H NMR (CDCl$_3$) δ 2.16 (1H, dd, J=13.3 Hz, 11.3 Hz), 2.91 (1H, dt, J=12.9 Hz, 3.3 Hz), 3.07 (1H, dt, J=12.8 Hz, 3.4 Hz), 3.62 (1H, m), 3.84 (1H, dd, J=12.8 Hz, 2.4 Hz), 4.02 (1H, dd, J=13.3 Hz, 2.4 Hz), 4.36 (2H, m), 4.42 (1H, dd, J=11.2 Hz, 3.5 Hz), 4.78 (1H, t, J=5.2 Hz), 7.00 (2H, m), 7.22-7.39 (10H, m), 7.50 (2H, m).

Example 26

N-[(2-Fluorophenyl)methyl]-tetrahydro-3-oxo-1,1-diphenyl-3H-oxazolo[3,4-a]pyrazine-7(1H)-carboxamide In the same manner as in Example 4, the title compound was obtained using 2-fluorobenzyl isocyanate instead of phenyl isocyanate. Yield 64%.

Melting point 109-110° C. (crystallized from diisopropyl ether).

$^1$H NMR (CDCl$_3$) δ 2.15 (1H, dd, J=13.3 Hz, 11.2 Hz), 2.89 (1H, dt, J=13.0 Hz, 3.4 Hz), 3.07 (1H, dt, J=12.9 Hz, 3.4 Hz), 3.61 (1H, m), 3.84 (1H, dd, J=13.0 Hz, 2.4 Hz), 3.99 (1H, dd, J=13.3 Hz, 2.4 Hz), 4.40 (1H, dd, J=11.3 Hz, 3.6 Hz), 4.45 (2H, m), 4.89 (1H, t, J=5.2 Hz), 7.00-7.15 (2H, m), 7.25-7.38 (10H, m), 7.50 (2H, m).

Example 27

(Phenylmethyl)tetrahydro-1,1-dimethyl-3-oxo-3H-oxazolo[3,4-a]pyrazine-7(1H)-carboxylate Bis(phenylmethyl)2-(1-hydroxy-1-methylethyl)-1,4-piperazinedicarboxylate (1.7 g, 4.2 mmol) was dissolved in N,N-dimethylformamide (20 mL). 60% Sodium hydride (0.25 g, 6.3 mmol) was added thereto, and the mixture was stirred at room temperature for 2 hours. The reaction solution was diluted with ethyl acetate (200 ml), and then washed with an aqueous sodium hydrogen carbonate solution. The extract was washed with water, dried over magnesium sulfate and concentrated under reduced pressure. The residue was purified with silica gel column chromatography (hexane:ethyl acetate=3:1 to 1:1) and recrystallized from ethyl acetate-hexane to obtain the title compound (0.97 g, yield 76%).

Melting point 86-88° C.

$^1$H NMR (CDCl$_3$) δ 1.36 (3H, s), 1.47 (3H, s), 2.76-2.98 (3H, m), 3.25-3.35 (1H, m), 3.75-3.83 (1H, m), 4.09-4.18 (2H, m), 5.16 (2H, s), 7.33-7.37 (5H, m).

Example 28

N-[(3-Fluorophenyl)methyl]-tetrahydro-3-oxo-1,1-diphenyl-3H-oxazolo[3,4-a]pyrazine-7(1H)-carboxamide In the same manner as in Example 4, the title compound was obtained using 3-fluorobenzyl isocyanate instead of phenyl isocyanate. Yield 64%.

Melting point 110-111° C. (crystallized from diisopropyl ether).

$^1$H NMR (CDCl$_3$) δ 2.18 (1H, dd, J=13.3 Hz, 11.3 Hz), 2.93 (1H, dt, J=12.8 Hz, 3.4 Hz), 3.09 (1H, dt, J=12.8 Hz, 3.4 Hz), 3.66 (1H, m), 3.86 (1H, dd, J=12.9 Hz, 2.5 Hz), 4.02 (1H, dd, J=13.3 Hz, 2.5 Hz), 4.38-4.46 (3H, m), 4.83 (1H, t, J=5.3 Hz), 6.96-7.06 (2H, m), 7.25-7.39 (10H, m), 7.51 (2H, m).

Example 29

Tetrahydro-N-[(4-methylphenyl)methyl]-3-oxo-1,1-diphenyl-3H-oxazolo[3,4-a]pyrazine-7(1H)-carboxamide In the same manner as in Example 4, the title compound was obtained using 4-methylbenzyl isocyanate instead of phenyl isocyanate. Yield 31%.

Melting point 112-113° C. (crystallized from diisopropyl ether).

$^1$H NMR (CDCl$_3$) δ 2.16 (1H, dd, J=13.3 Hz, 11.3 Hz), 2.33 (3H, s), 2.89 (1H, dt, J=12.9 Hz, 3.5 Hz), 3.07 (1H, dt, J=12.9 Hz, 3.5 Hz), 3.62 (1H, m), 3.83 (1H, dd, J=13.0 Hz, 2.4 Hz), 4.02 (1H, dd, J=13.3 Hz, 2.4 Hz), 4.36 (2H, t, J=5.4 Hz), 4.42 (1H, dd, J=11.2 Hz, 3.7 Hz), 4.69 (1H, m), 7.15 (4H, m), 7.27-7.39 (8H, m), 7.51 (2H, m).

Example 30

Tetrahydro-3-oxo-1,1-diphenyl-N-(2-thienylmethyl)-3H-oxazolo[3,4-a]pyrazine-7(1H)-carboxamide In the same manner as in Example 10, the title compound was obtained using thiophene-2-methylamine instead of phenylhydrazine. Yield 58%.

Melting point 94-95° C. (crystallized from diisopropyl ether).

$^1$H NMR (CDCl$_3$) δ 2.18 (1H, dd, J=13.3 Hz, 11.3 Hz), 2.90 (1H, dt, J=13.1 Hz, 3.5 Hz), 3.08 (1H, dt, J=12.9 Hz, 3.5 Hz), 3.64 (1H, m), 3.84 (1H, dd, J=13.1 Hz, 2.6 Hz), 4.00 (1H, m), 4.42 (1H, dd, J=11.3 Hz, 3.6 Hz), 4.58 (2H, m), 4.81 (1H, m), 6.96 (2H, m), 7.21-7.39 (9H, m), 7.51 (2H, m).

Example 31

Tetrahydro-3-oxo-1,1-diphenyl-N-(2-pyridinylmethyl)-3H-oxazolo[3,4-a]pyrazine-7(1H)-carboxamide In the same manner as in Example 10, the title compound was obtained using 2-(aminomethyl)pyridine instead of phenylhydrazine. Yield 58%.

Melting point 65-66° C. (crystallized from diisopropyl ether).

$^1$H NMR (CDCl$_3$) δ 2.20 (1H, dd, J=13.3 Hz, 11.3 Hz), 2.93 (1H, dt, J=13.3 Hz, 3.6 Hz), 3.10 (1H, dt, J=12.9 Hz, 3.6 Hz), 3.85 (2H, dt, J=12.9 Hz, 2.6 Hz), 4.04 (1H, m), 4.44 (1H, dd, J=11.2 Hz, 2.4 Hz), 4.51 (2H, t, J=4.5 Hz), 6.02 (1H, t, J=4.5 Hz), 7.25-7.38 (10H, m), 7.52 (2H, m), 7.75 (1H, m), 8.52 (1H, d, J=4.4 Hz).

Example 32

Hexahydro-1,1-diphenyl-7-[(1,2,3,4-tetrahydroisoquinolin-2-yl)carbonyl]-3H-oxazolo[3,4-a]pyrazin-3-one In the same manner as in Example 10, the title compound was obtained using 1,2,3,4-tetrahydroisoquinoline instead of phenylhydrazine. Yield 49%.

Melting point 93-94° C. (crystallized from diisopropyl ether).

$^1$H NMR (CDCl$_3$) δ 2.23 (1H, dd, J=13.3 Hz, 11.3 Hz), 2.86-2.95 (3H, m), 3.14 (1H, dt, J=12.9 Hz, 3.5 Hz), 3.43 (1H, m), 3.52-3.65 (3H, m), 3.84 (1H, dd, J=13.0 Hz, 2.8 Hz), 4.43 (2H, m), 4.59 (1H, dd, J=11.2 Hz, 3.4 Hz), 7.08-7.19 (4H, m), 7.25-7.39 (8H, m), 7.52 (2H, m).

Example 33

Tetrahydro-3-oxo-1,1-diphenyl-N-[[4-(trifluoromethyl)phenyl]methyl]-3H-oxazolo[3,4-a]pyrazine-7(1H)-carboxamide In the same manner as in Example 10, the title compound was obtained using 4-(trifluoromethyl)benzylamine instead of phenylhydrazine. Yield 55%.

Melting point 109-110° C. (crystallized from diisopropyl ether).

$^1$H NMR (CDCl$_3$) δ 2.19 (1H, dd, J=13.3 Hz, 11.3 Hz), 2.94 (1H, dt, J=12.8 Hz, 3.3 Hz), 3.07 (1H, dt, J=12.8 Hz, 3.5 Hz), 3.65 (1H, m), 3.86 (1H, dd, J=13.0 Hz, 2.6 Hz), 4.02 (1H, dd, J=13.3 Hz, 2.4 Hz), 4.40-4.54 (3H, m), 4.88 (1H, m), 7.26-7.41 (10H, m), 7.50 (2H, m), 7.58 (2H, d, J=8.1 Hz).

Example 34

N-[(4-Chlorophenyl)methyl]-tetrahydro-3-oxo-1,1-diphenyl-3H-oxazolo[3,4-a]pyrazine-7(1H)-carboxamide In the same manner as in Example 10, the title compound was obtained using 4-chlorobenzylamine instead of phenylhydrazine. Yield 45%.

Melting point 110-111° C. (crystallized from diisopropyl ether).

$^1$H NMR (CDCl$_3$) δ 2.17 (1H, dd, J=13.3 Hz, 11.3 Hz), 2.91 (1H, dt, J=12.8 Hz, 3.3 Hz), 3.08 (1H, dt, J=12.8 Hz, 3.5 Hz), 3.64 (1H, m), 3.85 (1H, dd, J=12.8 Hz, 2.6 Hz), 4.02 (1H, m), 4.34-4.43 (3H, m), 4.79 (1H, m), 7.20-7.39 (12H, m), 7.51 (2H, m).

Example 35

N-[[4-(Dimethylamino)phenyl]methyl]-tetrahydro-3-oxo-1,1-diphenyl-3H-oxazolo[3,4-a]pyrazine-7(1H)-carboxamide In the same manner as in Example 10, the title compound was obtained using 4-(dimethylamino)benzylamine instead of phenylhydrazine. Yield 26%.

Melting point 100-101° C. (crystallized from diisopropyl ether).

$^1$H NMR (CDCl$_3$) δ 2.14 (1H, dd, J=13.3 Hz, 11.3 Hz), 2.91 (1H, m), 2.93 (6H, s), 3.06 (1H, dt, J=12.8 Hz, 3.5 Hz), 3.60 (1H, m), 3.82 (1H, dd, J=13.0 Hz, 2.6 Hz), 4.03 (1H, dd, J=13.3 Hz, 2.4 Hz), 4.30 (2H, m), 4.42 (1H, dd, J=11.2 Hz, 3.6 Hz), 4.58 (1H, m), 6.69 (2H, d, J=4.4 Hz), 7.16 (2H, d, J=4.4 Hz), 7.25-7.39 (8H, m), 7.51 (2H, m).

Example 36

Tetrahydro-N-[[4-(methylsulfonyl)phenyl]methyl]-3-oxo-1,1-diphenyl-3H-oxazolo[3,4-a]pyrazine-7(1H)-carboxamide In the same manner as in Example 10, the title compound was obtained using 4-(methylsulfonyl)benzylamine instead of phenylhydrazine. Yield 33%.

Melting point 147-148° C. (crystallized from diisopropyl ether).

$^1$H NMR (CDCl$_3$) δ 2.19 (1H, dd, J=13.3 Hz, 11.3 Hz), 2.92 (1H, dt, J=12.9 Hz, 3.3 Hz), 3.01 (3H, s), 3.08 (1H, m), 3.71 (1H, m), 3.84 (1H, dd, J=12.8 Hz, 2.4 Hz), 4.03 (1H, dd, J=13.3 Hz, 2.4 Hz), 4.43 (1H, dd, J=11.2 Hz, 3.7 Hz), 4.49 (2H, m), 5.23 (1H, t, J=5.8 Hz), 7.26-7.44 (10H, m), 7.51 (2H, m), 7.82 (2H, d, J=8.4 Hz).

Example 37

N-[(4-Fluorophenyl)methyl]-tetrahydro-1,1-dimethyl-3-oxo-3H-oxazolo[3,4-a]pyrazine-7(1H)-carboxamide (Phenylmethyl)tetrahydro-3-oxo-1,1-dimethyl-3H-oxazolo[3,4-a]pyrazine-7(1H)-carboxylate (0.12 g, 0.39 mmol) was dissolved in ethanol (10 mL). 10% Palladium carbon (12 mg) was added thereto, and the mixture was stirred under hydrogen atmosphere at room temperature overnight. The reaction solution was filtered through Celite, the Celite was washed with ethanol, and the filtrate was concentrated under reduced pressure. The residue was dissolved in tetrahydrofuran (10 mL). 4-Fluorobenzyl isocyanate (0.20 mL, 1.6 mmol) was added thereto, and the mixture was stirred at 50° C. for 4 hours. The reaction solution was concentrated under reduced pressure, and the residue was purified with silica gel column chromatography (hexane:ethyl acetate=2:1 to 1:9) to obtain the title compound (0.11 g, yield 86%).

Oil.

$^1$H NMR (CDCl$_3$) δ 1.37 (3H, s), 1.48 (3H, s), 2.65-2.73 (1H, m), 2.95-3.03 (2H, m), 3.34-3.39 (1H, m), 3.66-3.83 (2H, m), 4.17-4.23 (1H, m), 4.40 (2H, d, J=5.5 Hz), 4.77 (1H, br s), 6.99-7.05 (2H, m), 7.25-7.30 (2H, m).

Example 38

Phenyl tetrahydro-1,1-dimethyl-3-oxo-3H-oxazolo [3,4-a]pyrazine-7(1H)-carboxylate Hexahydro-1,1-dimethyl-3H-oxazolo[3,4-a]pyrazin-3-one (0.10 g, 0.59 mmol) was dissolved in tetrahydrofuran (10 mL). Triethylamine (0.17 mL, 1.2 mmol) and phenyl chlorocarbonate (0.11 mL, 0.88 mmol) were added, and the mixture was stirred at room temperature for 2 hours. To the reaction solution was added water, and the mixture was extracted with ethyl acetate. The extract was washed with an aqueous sodium hydrogen carbonate solution, dried over magnesium sulfate and concentrated under reduced pressure. The residue was purified with silica gel column chromatography (hexane: ethyl acetate=3:1 to 1:2). After purification, the crystals, which were precipitated while concentrating under reduced pressure, were collected by filtration to obtain the title compound (0.14 g, yield 80%).

Melting point 144-145° C.

$^1$H NMR (CDCl$_3$) δ 1.41 (3H, s), 1.51 (3H, s), 2.74-3.16 (3H, m), 3.43-3.47 (1H, m), 3.88-3.91 (1H, m), 4.19-4.31 (2H, m), 7.09-7.41 (5H, m).

Example 39

N-(4-Fluorophenyl)-tetrahydro-1,1-dimethyl-3-oxo-3H-oxazolo[3,4-a]pyrazine-7(1H)-carboxamide Hexahydro-1,1-dimethyl-3H-oxazolo[3,4-a]pyrazin-3-one (0.10 g, 0.59 mmol) was dissolved in tetrahydrofuran (10 mL). 4-Fluorophenyl isocyanate (0.12 g, 0.88 mmol) was added thereto, and the mixture was stirred at 50° C. for 4 hours. The reaction solution was concentrated under reduced pressure. The residue was purified with silica gel column chromatography (hexane:ethyl acetate=1:1 to 1:9). After purification, the crystals, which were precipitated while concentrating under reduced pressure, were collected by filtration to obtain the title compound (136 mg, yield 75%).

Melting point 199-201° C.

$^1$H NMR (CDCl$_3$) δ 1.41 (3H, s), 1.50 (3H, s), 2.73-2.81 (1H, m), 3.07-3.11 (2H, m), 3.42-3.46 (1H, m), 3.79-3.91 (2H, m), 4.24-4.28 (1H, m), 6.32 (1H, br s), 6.99-7.04 (2H, m), 7.26-7.31 (2H, m).

Example 40

N-(2-Furylmethyl)-tetrahydro-3-oxo-1,1-diphenyl-3H-oxazolo[3,4-a]pyrazine-7(1H)-carboxamide In the same manner as in Example 10, the title compound was obtained using furfurylamine instead of phenylhydrazine. Yield 55%.

Melting point 120-121° C. (crystallized from diisopropyl ether).

$^1$H NMR (CDCl$_3$) δ 2.16 (1H, dd, J=13.2 Hz, 11.3 Hz), 2.90 (1H, dt, J=12.8 Hz, 3.3 Hz), 3.08 (1H, dt, J=12.8 Hz, 3.5 Hz), 3.64 (1H, m), 3.84 (1H, dd, J=13.0 Hz, 2.8 Hz), 4.00 (1H, dd, J=13.1 Hz, 2.3 Hz), 4.41 (3H, m), 4.77 (1H, m), 6.22 (1H, d, J=3.1 Hz), 6.31 (1H, m), 7.27-7.41 (9H, m), 7.51 (2H, m).

Example 41

(Phenylmethyl)tetrahydro-3-oxo-1,1-diphenyl-3H-oxazolo[3,4-a]pyrazine-7(1H)-carboxylate In the same manner as in Example 3, the title compound was obtained using benzyl chlorocarbonate instead of 4-fluorophenyl chlorocarbonate. Yield 75%.

Melting point 157-158° C. (crystallized from diisopropyl ether).

$^1$H NMR (CDCl$_3$) δ 2.23 (1H, m), 2.80 (1H, m), 3.04 (1H, dt, J=12.8 Hz, 10.3 Hz), 3.85 (1H, dd, J=13.2 Hz, 3.1 Hz), 4.01-4.14 (2H, m), 4.36 (1H, d, J=10.3 Hz), 5.16 (2H, m), 7.28-7.40 (13H, m), 7.47 (2H, m).

Example 42

Tetrahydro-3-oxo-1,1-diphenyl-N-(2-phenylethyl)-3H-oxazolo[3,4-a]pyrazine-7(1H)-carboxamide In the same manner as in Example 10, the title compound was obtained using 2-phenethylamine instead of phenylhydrazine. Yield 26%.

Melting point 75-76° C. (crystallized from diisopropyl ether).

$^1$H NMR (CDCl$_3$) δ 2.13 (1H, dd, J=13.3 Hz, 11.3 Hz), 2.78-2.87 (3H, m), 3.00 (1H, dt, J=12.8 Hz, 3.5 Hz), 3.45-3.55 (3H, m), 3.80 (1H, dd, J=12.8 Hz, 2.6 Hz), 3.89 (1H, m), 4.36 (2H, m), 7.18-7.48 (13H, m), 7.49 (2H, m).

Example 43

N-(2,3-Dihydro-1H-inden-1-yl)-tetrahydro-3-oxo-1, 1-diphenyl-3H-oxazolo[3,4-a]pyrazine-7(1H)-carboxamide In the same manner as in Example 10, the title compound was obtained using 1-aminoindane instead of phenylhydrazine. Yield 29%.

Melting point 133-134° C. (crystallized from diisopropyl ether).

$^1$H NMR (CDCl$_3$) δ 1.77 (1H, m), 2.16 (1H, m), 2.62 (1H, m), 2.86-3.10 (4H, m), 3.60 (1H, m), 3.85 (1H, d, J=12.9 Hz), 4.08 (1H, m), 4.48 (1H, m), 4.63 (1H, d, J=8.0 Hz), 5.37 (1H, m), 7.24-7.40 (12H, m), 7.52 (2H, m).

Example 44

Tetrahydro-3-oxo-1,1-diphenyl-N-(1-phenylethyl)-3H-oxazolo[3,4-a]pyrazine-7(1H)-carboxamide In the same manner as in Example 10, the title compound was obtained using 1-phenethylamine instead of phenylhydrazine. Yield 60%.

Melting point 120-121° C. (crystallized from diisopropyl ether).

$^1$H NMR (CDCl$_3$) δ 1.48 (3H, dd, J=6.7 Hz, 5.8 Hz), 2.12 (1H, m), 2.91 (1H, m), 3.05 (1H, m), 3.59 (1H, m), 3.84 (1H, d, J=12.6 Hz), 4.03 (1H, m), 4.40 (1H, dt, J=11.3 Hz, 3.7 Hz), 4.64 (1H, t, J=7.0 Hz), 4.97 (1H, quintet, J=7.0 Hz), 7.22-7.40 (13H, m), 7.50 (2H, m).

Example 45

(Phenylmethyl) 1,1-dicyclopropyl-tetrahydro-3-oxo-3H-oxazolo[3,4-a]pyrazine-7(1H)-carboxylate Bis(phenylmethyl)2-(dicyclopropylhydroxymethyl)-1,4-piperazinedicarboxylate (1.4 g, 3.0 mmol) was dissolved in N,N-dimethylformamide (15 mL). 60% Sodium hydride (0.13 g, 3.3 mmol) was added thereto, and the mixture was stirred at room temperature for 2 hours. The reaction solution was diluted with ethyl acetate (100 mL), and then washed with an aqueous sodium hydrogen carbonate solution. The extract was washed with water, dried over magnesium sulfate and concentrated under reduced pressure. The residue was purified with silica gel column chromatography (hexane:ethyl acetate=7:1 to 3:1) to obtain the title compound (0.62 g, yield 58%).

Oil.

$^1$H NMR (CDCl$_3$) δ 0.44-0.60 (8H, m), 0.85-0.92 (1H, m), 1.03-1.11 (1H, m), 2.82-3.13 (3H, m), 3.43-3.48 (1H, m), 3.73-3.78 (1H, m), 4.09-4.20 (2H, m), 5.17 (2H, s), 7.26 (2H, s), 7.37 (3H, s).

Example 46

Tetrahydro-3-oxo-1,1-diphenyl-N-(3-pyridinylmethyl)-3H-oxazolo[3,4-a]pyrazine-7(1H)-carboxamide In the same manner as in Example 10, the title compound was obtained using 3-(aminomethyl)pyridine instead of phenylhydrazine. Yield 41%.

Melting point 191-192° C. (crystallized from diisopropyl ether).

$^1$H NMR (CDCl$_3$) δ 2.18 (1H, dd, J=13.3 Hz, 11.3 Hz), 2.92 (1H, dt, J=13.0 Hz, 3.3 Hz), 3.08 (1H, dt, J=12.9 Hz, 3.5 Hz), 3.66 (1H, m), 3.86 (1H, dd, J=12.9 Hz, 2.6 Hz), 4.00 (1H, d, J=13.3 Hz, 2.4 Hz), 4.42 (3H, m), 4.92 (1H, m), 7.25-7.39 (10H, m), 7.51 (2H, m), 7.64 (1H, m), 8.52 (1H, s).

Example 47

N-(2,4-Difluorophenyl)-tetrahydro-3-oxo-1,1-diphenyl-3H-oxazolo[3,4-a]pyrazine-7(1H)-carboxamide In the same manner as in Example 4, the title compound was obtained using 2,4-difluorophenyl isocyanate instead of phenyl isocyanate. Yield 51%.

Melting point 98-99° C. (crystallized from diisopropyl ether).

$^1$H NMR (CDCl$_3$) δ 2.28 (1H, dd, J=13.3 Hz, 11.3 Hz), 3.05 (1H, dt, J=12.8 Hz, 3.0 Hz), 3.18 (1H, dt, J=12.7 Hz, 3.0 Hz), 3.83 (1H, d, J=13.0 Hz), 3.94 (1H, dd, J=13.3 Hz, 2.4 Hz), 4.03 (1H, dd, J=13.3 Hz, 2.4 Hz), 4.49 (1H, dd, J=11.3 Hz, 3.6 Hz), 6.38 (1H, br s), 6.86 (2H, m), 7.30-7.42 (8H, m), 7.52 (2H, m), 7.89 (1H, m).

Example 48

N-(4-Chlorophenyl)-tetrahydro-3-oxo-1,1-diphenyl-3H-oxazolo[3,4-a]pyrazine-7(1H)-carboxamide In the same manner as in Example 4, the title compound was obtained using 4-chlorophenyl isocyanate instead of phenyl isocyanate. Yield 70%.

Melting point 121-122° C. (crystallized from diisopropyl ether).

$^1$H NMR (CDCl$_3$) δ 2.23 (1H, dd, J=13.3 Hz, 11.3 Hz), 3.01 (1H, dt, J=12.7 Hz, 2.9 Hz), 3.14 (1H, dt, J=12.7 Hz, 3.0 Hz), 3.82 (1H, d, J=13.0 Hz), 3.91 (1H, dd, J=13.0 Hz, 2.6 Hz), 4.03 (1H, dd, J=13.3 Hz, 2.5 Hz), 4.47 (1H, dd, J=11.3 Hz, 3.6 Hz), 6.43 (1H, br s), 7.23-7.42 (12H, m), 7.52 (2H, m).

Example 49

Tetrahydro-N-(4-methoxyphenyl)-3-oxo-1,1-diphenyl-3H-oxazolo[3,4-a]pyrazine-7(1H)-carboxamide In the same manner as in Example 4, the title compound was obtained using 4-methoxyphenyl isocyanate instead of phenyl isocyanate. Yield 80%.

Melting point 241-242° C. (crystallized from diisopropyl ether).

$^1$H NMR (CDCl$_3$) δ 2.22 (1H, dd, J=13.3 Hz, 11.3 Hz), 2.98 (1H, dt, J=12.9 Hz, 3.0 Hz), 3.14 (1H, dt, J=12.8 Hz, 3.0 Hz), 3.78 (3H, s), 3.87-3.92 (2H, m), 4.02 (1H, dd, J=13.3 Hz, 3.0 Hz), 4.46 (1H, dd, J=11.3 Hz, 3.6 Hz), 6.25 (1H, br s), 6.85 (2H, d, J=9.0 Hz), 7.20 (2H, d, J=9.0 Hz), 7.29-7.39 (8H, m), 7.50 (2H, m).

Example 50

Tetrahydro-N-(2-naphthylmethyl)-3-oxo-1,1-diphenyl-3H-oxazolo[3,4-a]pyrazine-7(1H)-carboxamide In the same manner as in Example 10, the title compound was obtained using 2-(aminomethyl)naphthalene instead of phenylhydrazine. Yield 43%.

Melting point 163-164° C. (crystallized from diisopropyl ether).

$^1$H NMR (CDCl$_3$) δ 2.16 (1H, dd, J=13.3 Hz, 11.3 Hz), 2.85 (1H, dt, J=12.9 Hz, 3.3 Hz), 3.03 (1H, dt, J=12.8 Hz, 3.4 Hz), 3.56 (1H, m), 3.78 (1H, dd, J=13.0 Hz, 2.8 Hz), 4.03 (1H, dd, J=13.3 Hz, 2.4 Hz), 4.41 (1H, dd, J=11.3 Hz, 3.6 Hz), 4.76 (1H, t, J=4.6 Hz), 4.87 (2H, m), 7.25-7.54 (14H, m), 7.80 (1H, m), 7.87 (1H, m), 8.01 (1H, m).

Example 51

1,1-Dicyclopropyl-N-[(4-fluorophenyl)methyl]-tetrahydro-3-oxo-3H-oxazolo[3,4-a]pyrazine-7(1H)-carboxamide (Phenylmethyl)1,1-dicyclopropyl-tetrahydro-3-oxo-3H-oxazolo[3,4-a]pyrazine-7(1H)-carboxylate (0.18 g, 0.50 mmol) was dissolved in ethanol (10 mL). 10% Palladium carbon (17 mg) was added thereto, and the mixture was stirred under hydrogen atmosphere at room temperature overnight. The reaction solution was filtered through Celite, the Celite was washed with ethanol, and the filtrate was concentrated under reduced pressure. The resulting 1,1-dicyclopropyl-hexahydro-3H-oxazolo[3,4-a]pyrazin-3-one was dissolved in tetrahydrofuran (10 mL). (4-Fluoro)benzyl isocyanate (0.25 mL, 2.0 mmol) was added thereto, and the mixture was stirred at 50° C. for 4 hours. The reaction solution was concentrated under reduced pressure, and the residue was purified with silica gel column chromatography (hexane:ethyl acetate=1:1 to 1:4) to obtain the title compound (0.16 g, 87% yield from (phenylmethyl) 1,1-dicyclopropyl-tetrahydro-3-oxo-3H-oxazolo[3,4-a]pyrazine-7(1H)-carboxylate).

Oil.

$^1$H NMR (CDCl$_3$) δ 0.44-0.61 (8H, m), 0.87-0.91 (1H, m), 1.07-1.12 (1H, m), 2.92-3.10 (3H, m), 3.53 (1H, dd, J=3.6 Hz, 11.2 Hz), 3.70-3.79 (2H, m), 4.27-4.42 (3H, m), 4.76 (1H, br s), 7.03 (2H, t, J=8.6 Hz), 7.26-7.31 (2H, m).

Example 52

1,1-Dicyclopropyl-N-(4-fluorophenyl)-tetrahydro-3-oxo-3H-oxazolo[3,4-a]pyrazine-7(1H)-carboxamide In the same manner as in Example 51, the title compound (0.15 g, 83% yield from (phenylmethyl) 1,1-dicyclopropyl-tetrahydro-3-oxo-3H-oxazolo[3,4-a]pyrazine-7(1H)-carboxylate) was obtained from 1,1-dicyclopropyl-hexahydro-3H-oxazolo[3,4-a]pyrazin-3-one, which was obtained from (phenylmethyl) 1,1-dicyclopropyl-tetrahydro-3-oxo-3H-oxazolo[3,4-a]pyrazine-7(1H)-carboxylate, and (4-fluoro)phenyl isocyanate.

Oil.

$^1$H NMR (CDCl$_3$) δ 0.46-0.62 (8H, m), 0.89-0.93 (1H, m), 1.13-1.28 (1H, m), 3.03-3.13 (3H, m), 3.60 (1H, dd, J=3.7 Hz, 11.3 Hz), 3.83-3.90 (2H, m), 4.33-4.37 (1H, m), 6.35 (1H, br s), 6.99 (2H, t, J=8.7 Hz), 7.26-7.32 (2H, m).

Example 53

Phenyl 1,1-dicyclopropyl-tetrahydro-3-oxo-3H-oxazolo[3,4-a]pyrazine-7(1H)-carboxylate (Phenylmethyl) 1,1-dicyclopropyl-tetrahydro-3-oxo-3H-oxazolo[3,4-a]pyrazine-7(1H)-carboxylate (0.18 g, 0.50 mmol) was dissolved in ethanol (10 mL). 10% Palladium carbon (17 mg) was added thereto, and the mixture was stirred under hydrogen atmosphere at room temperature overnight. The reaction solution was filtered through Celite, the Celite was washed with ethanol, and the filtrate was concentrated under reduced pressure. The resulting 1,1-dicyclopropyl-hexahydro-3H-oxazolo[3,4-a]pyrazin-3-one was dissolved in tetrahydrofuran (10 mL). Triethylamine (0.14 mL, 0.99 mmol) and phenyl chlorocarbonate (90 μL, 0.74 mmol) were added thereto, and the mixture was stirred at room temperature for 2 hours. To the reaction solution was added water, and the mixture was extracted with ethyl acetate. The extract was washed with an aqueous saturated sodium hydrogen carbonate solution, dried over magnesium sulfate and concentrated under reduced pressure. The residue was purified with silica gel column chromatography (hexane:ethyl acetate=7:1 to 1:1) and recrystallized from diisopropyl ether-hexane to obtain the title compound (0.15 g, 88% yield (phenylmethyl) 1,1-dicyclopropyl-tetrahydro-3-oxo-3H-oxazolo[3,4-a]pyrazine-7(1H)-carboxylate).

Melting point 102-104° C.

$^1$H NMR (CDCl$_3$) δ 0.47-0.60 (8H, m), 0.89-0.92 (1H, m), 1.10-1.18 (1H, m), 2.80-3.10 (3H, m), 3.62 (1H, dd, J=3.7 Hz, 11.3 Hz), 3.84-3.88 (1H, m), 4.20-4.26 (2H, m), 7.12 (2H, d, J=7.9 Hz), 7.21-7.26 (1H, m), 7.39 (2H, t, J=7.9 Hz).

Example 54

Hexahydro-1,1-diphenyl-7-(phenylsulfonyl)-3H-oxazolo[3,4-a]pyrazin-3-one

To a solution of hexahydro-1,1-diphenyl-3H-oxazolo[3,4-a]pyrazin-3-one (50 mg, 0.17 mmol) in chloroform (2 mL) were sequentially added pyridine (0.5 mL) and benzenesulfonyl chloride (43 mg, 0.24 mmol), and the mixture was stirred at room temperature for 2 hours. The reaction solution was concentrated under reduced pressure. The residue was purified with silica gel column chromatography (hexane:ethyl acetate=1:1) and crystallized from diisopropyl ether to obtain the title compound (27 mg, yield 37%).

Melting point 236-237° C.

$^1$H NMR (CDCl$_3$) δ 1.70 (1H, t, J=11.4 Hz), 2.22 (1H, dt, J=12.0 Hz, 3.6 Hz), 3.23 (1H, m), 3.43 (1H, m), 3.69 (1H, dd, J=11.9 Hz, 3.6 Hz), 3.90 (1H, dd, J=13.5 Hz, 2.6 Hz), 4.57 (1H, dd, J=11.1 Hz, 3.7 Hz), 7.27-7.51 (14H, m), 7.60 (1H, m).

Example 55

1,1-Dicyclohexyl-N-(2,4-difluorophenyl)-tetrahydro-3-oxo-3H-oxazolo[3,4-a]pyrazine-7(1H)-carboxamide 1,1-Dicyclohexyl-hexahydro-3H-oxazolo[3,4-a]pyrazin-3-one (0.13 g, 0.42 mmol) was dissolved in toluene (1.5 mL). 2,4-Difluorophenyl isocyanate (0.10 g, 0.64 mmol) was added thereto, and the mixture was stirred at 60° C. for 14 hours. The reaction solution was concentrated under reduced pressure. The residue was purified with silica gel column chromatography (hexane:ethyl acetate=3:2) and crystallized from hexane to obtain the title compound (0.12 g, yield 59%).

Amorphous.

$^1$H NMR (CDCl$_3$) δ 0.88 (2H, m), 1.00 (2H, m), 1.17-1.41 (9H, m), 1.70-2.04 (9H, m), 2.99 (1H, dt, J=12.3 Hz, 3.2 Hz), 3.10 (2H, m), 3.66 (1H, dd, J=11.3 Hz, 3.6 Hz), 3.84 (1H, dd, J=12.8 Hz, 2.2 Hz), 3.93 (1H, m), 4.18 (1H, m), 6.46 (1H, br s), 6.88 (2H, m), 7.93 (1H, m).

Example 56

1,1-Dicyclohexyl-N-[(4-fluorophenyl)methyl]-tetrahydro-3-oxo-3H-oxazolo[3,4-a]pyrazine-7(1H)-carboxamide In the same manner as in Example 55, the title compound was obtained using 4-fluorobenzyl isocyanate instead of 2,4-difluorophenyl isocyanate. Yield 58%.

Amorphous.

$^1$H NMR (CDCl$_3$) δ 0.88 (2H, m), 0.99 (2H, m), 1.17-1.45 (8H, m), 1.53 (1H, m), 1.68-2.04 (9H, m), 2.90-2.99 (3H, m), 3.60 (1H, dd, J=11.4 Hz, 3.7 Hz), 3.74 (2H, m), 4.13 (1H, m), 4.41 (2H, dq, J=17.2 Hz, 5.3 Hz), 4.80 (1H, t, J=5.3 Hz), 7.03 (2H, t, J=8.6 Hz), 7.28 (2H, m).

Example 57

Phenyl 1,1-dicyclohexyl-tetrahydro-3-oxo-3H-oxazolo[3,4-a]pyrazine-7(1H)-carboxylate To a solution of 1,1-dicyclohexyl-hexahydro-3H-oxazolo[3,4-a]pyrazin-3-one (0.13 g, 0.42 mmol) in tetrahydrofuran (1 mL) were sequentially added diisopropylethylamine (0.5 mL) and phenyl chlorocarbonate (0.10 g, 0.64 mmol), and the mixture was stirred at room temperature for 14 hours. The reaction solution was concentrated. The residue was purified with silica gel column chromatography (hexane:ethyl acetate=7:3), crystallized from diisopropyl ether and dried to obtain the title compound (88 mg, yield 49%).

Melting point 171.2-172.2° C.

$^1$H NMR (CDCl$_3$) δ 1.00 (2H, m), 1.15-1.35 (7H, m), 1.40-1.60 (3H, m), 1.72-2.05 (10H, m), 2.95-3.35 (3H, m), 3.67 (1H, m), 3.84 (1H, m), 4.21 (1H, dd, J=12.9 Hz, 3.2 Hz), 4.35 (1H, m), 7.12 (2H, d, J=7.7 Hz), 7.21 (1H, m), 7.39 (2H, t, J=7.7 Hz).

Example 58

Tetrahydro-3-oxo-1,1-diphenyl-N-(2-pyridinyl)-3H-oxazolo[3,4-a]pyrazine-7(1H)-carboxamide To a solution of hexahydro-1,1-diphenyl-3H-oxazolo[3,4-a]pyrazin-3-one (0.10 g, 0.34 mmol) in tetrahydrofuran (1 mL) were sequentially added diisopropylethylamine (0.4 mL) and bis(trichloromethyl)carbonate (0.10 g, 0.34 mmol), and the mixture was stirred at room temperature for 1 hour. Next, 2-aminopyridine (48 mg, 0.51 mmol) was added thereto, and the mixture was stirred at room temperature for 15 hours. To the reaction solution was added water, and the mixture was extracted with ethyl acetate. The extract was washed with water and concentrated under reduced pressure. The residue was subjected to silica gel column chromatography (hexane:ethyl acetate=1:4), purified with alumina column chromatography (hexane:ethyl acetate=1:1) and then powder was formed from diisopropyl ether to obtain the title compound (4.0 mg, yield 3%).

Amorphous.

$^1$H NMR (CDCl$_3$) δ 2.27 (1H, dd, J=13.2 Hz, 11.3 Hz), 2.77 (1H, dt, J=13.2 Hz, 3.7 Hz), 3.08 (1H, dt, J=12.6 Hz, 3.7 Hz), 3.77 (1H, dd, J=13.3 Hz, 3.1 Hz), 4.05 (2H, m), 4.43 (1H, dd, J=11.3 Hz, 3.6 Hz), 7.04 (2H, d, J=8.0 Hz), 7.07 (1H, m), 7.19-7.39 (10H, m), 7.66 (1H, t, J=8.0 Hz), 8.40 (1H, d, J=4.7 Hz).

Example 59

N-Benzoyl-tetrahydro-3-oxo-1,1-diphenyl-3H-oxazolo[3,4-a]pyrazine-7(1H)-carboxamide Benzamide (1.0 g, 8.3 mmol) was dissolved in 1,2-dichloroethane (5 mL), oxalyl dichloride (1.2 g, 9.1 mmol) was added thereto, and the mixture was stirred at 90° C. for 30 hours. The reaction solution was concentrated under reduced pressure. Toluene (4 mL) was added thereto and dissolved. Hexahydro-1,1-diphenyl-3H-oxazolo[3,4-a]pyrazin-3-one (0.20 g, 0.68 mmol) was added thereto, and the mixture was stirred at 60° C. for 6 hours. The reaction solution was concentrated under reduced pressure to a half its original volume, and the precipitated crystals were filtered off. The residue was purified with silica gel column chromatography (hexane:ethyl acetate=1:1), and toluene (4 mL) was added thereto. The precipitated crystals were filtered off, and the filtrate was concentrated. The residue was further purified with silica gel column chromatography (hexane:ethyl acetate=1:1) and crystallized from diisopropyl ether to obtain the title compound (70 mg, yield 23%).

Melting point 170-171° C.

$^1$H NMR (CDCl$_3$) δ 2.38 (1H, m), 2.96 (1H, m), 3.32 (1H, m), 3.80 (1H, m), 3.93 (1H, dd, J=13.3 Hz, 3.3 Hz), 4.05 (1H, m), 4.85 (1H, m), 7.25-7.62 (13H, m), 7.86 (2H, d, J=7.3 Hz), 8.01 (1H, m).

Example 60

1,1-Bis(4-fluorophenyl)-N-(2,4-difluorophenyl)-tetrahydro-3-oxo-3H-oxazolo[3,4-a]pyrazine-7(1H)-carboxamide In the same manner as in Example 55, the title compound was obtained using 1,1-bis(4-fluorophenyl)-hexahydro-3H-oxazolo[3,4-a]pyrazin-3-one instead of 1,1-dicyclohexyl-hexahydro-3H-oxazolo[3,4-a]pyrazin-3-one as a raw material. Yield 34%.

Amorphous.

$^1$H NMR (CDCl$_3$) δ 2.24 (1H, dd, J=13.3 Hz, 11.3 Hz), 3.08 (1H, dt, J=12.3 Hz, 3.0 Hz), 3.19 (1H, dt, J=12.0 Hz, 3.1 Hz), 3.81 (1H, d, J=12.2 Hz), 3.94 (1H, dd, J=13.2 Hz, 3.0 Hz), 4.03 (1H, m), 4.43 (1H, dd, J=11.3 Hz, 3.6 Hz), 6.39 (1H, s), 6.87 (2H, t, J=8.2 Hz), 7.03-7.12 (4H, m), 7.26-7.31 (2H, m), 7.47 (2H, m), 7.87 (1H, m).

Example 61

1,1-Bis(4-fluorophenyl)-N-[(4-fluorophenyl)methyl]-tetrahydro-3-oxo-3H-oxazolo[3,4-a]pyrazine-7(1H)-carboxamide In the same manner as in Example 55, the title compound was obtained using 1,1-bis(4-fluorophenyl)-hexahydro-3H-oxazolo[3,4-a]pyrazin-3-one instead of 1,1-dicyclohexyl-hexahydro-3H-oxazolo[3,4-a]pyrazin-3-one, and using 4-fluorobenzyl isocyanate instead of 2,4-difluorophenyl isocyanate. Yield 52%.

Amorphous.

$^1$H NMR (CDCl$_3$) δ 2.13 (1H, dd, J=13.3 Hz, 11.3 Hz), 2.94 (1H, dt, J=13.1 Hz, 3.3 Hz), 3.09 (1H, dt, J=12.9 Hz, 3.3 Hz), 3.59 (1H, m), 3.86 (1H, dd, J=13.1 Hz, 3.0 Hz), 4.03 (1H, m), 4.30-4.45 (3H, m), 4.76 (1H, m), 7.01-7.11 (6H, m), 7.22-7.28 (4H, m), 7.46 (2H, m).

Example 62

Phenyl 1,1-bis(4-fluorophenyl)-tetrahydro-3-oxo-3H-oxazolo[3,4-a]pyrazine-7(1H)-carboxylate In the same manner as in Example 57, the title compound was obtained using 1,1-bis(4-fluorophenyl)-hexahydro-3H-oxazolo[3,4-a]pyrazin-3-one instead of 1,1-dicyclohexyl-hexahydro-3H-oxazolo[3,4-a]pyrazin-3-one. Yield 52%.

Melting point 140-141° C.

$^1$H NMR (CDCl$_3$) δ 2.20-2.50 (1H, m), 2.80-3.10 (1H, m), 3.19 (1H, dt, J=12.6 Hz, 3.7 Hz), 3.95 (1H, dd, J=13.3 Hz, 3.2 Hz), 4.04 (1H, d, J=11.5 Hz), 4.30 (1H, d, J=12.5 Hz), 4.44 (1H, dd, J=11.3 Hz, 3.3 Hz), 7.03-7.12 (6H, m), 7.20-7.31 (3H, m), 7.38 (2H, m), 7.47 (2H, m).

Example 63

Ethyl N-[(tetrahydro-3-oxo-1,1-diphenyl-3H-oxazolo[3,4-a]pyrazin-7(1H)-yl)carbonyl]-β-alanine In the same manner as in Example 55, the title compound was obtained using hexahydro-1,1-diphenyl-3H-oxazolo[3,4-a]pyrazin-3-one instead of 1,1-dicyclohexyl-hexahydro-3H-oxazolo[3,4-a]pyrazin-3-one, and using ethyl 3-isocyanatopropionate instead of 2,4-difluorophenyl isocyanate. Yield 45%.
Amorphous.
$^1$H NMR (CDCl$_3$) δ 1.26 (3H, t, J=7.1 Hz), 2.15 (1H, dd, J=13.4 Hz, 11.3 Hz), 2.53 (2H, m), 2.87 (1H, dt, J=13.1 Hz, 3.6 Hz), 3.06 (1H, dt, J=13.0 Hz, 3.6 Hz), 3.48 (2H, m), 3.64 (1H, m), 3.84 (1H, dd, J=13.0 Hz, 2.7 Hz), 3.97 (1H, m), 4.15 (2H, q, J=7.1 Hz), 4.40 (1H, dd, J=11.3 Hz, 3.6 Hz), 5.29 (1H, t, J=5.7 Hz), 7.27-7.42 (8H, m), 7.51 (2H, m).

Example 64

Tetrahydro-N-[2-(4-morpholinyl)ethyl]-3-oxo-1,1-diphenyl-3H-oxazolo[3,4-a]pyrazine-7(1H)-carboxamide Hexahydro-1,1-diphenyl-3H-oxazolo[3,4-a]pyrazin-3-one (0.17 g, 0.58 mmol) was dissolved in toluene (1.5 mL). 2-Bromoethyl isocyanate (0.10 g, 0.67 mmol) was added thereto, and the mixture was stirred at room temperature for 2 hours. The reaction solution was concentrated under reduced pressure. The residue was subjected to silica gel column chromatography (ethyl acetate), and the fractions were collected and concentrated. The residue was dissolved in N,N-dimethylformamide (2 mL), morpholine (0.20 g, 3.9 mmol) was added thereto, and the mixture was stirred at 60° C. for 16 hours. To the reaction solution was added ice water, and the mixture was extracted with ethyl acetate. The organic layer was washed with water and concentrated under reduced pressure. The residue was purified with amino silica gel column chromatography (ethyl acetate), and crystallized from hexane to obtain the title compound (66 mg, yield 26%).
Melting point 174-175° C.
$^1$H NMR (CDCl$_3$) δ 2.18 (1H, dd, J=13.2 Hz, 11.3 Hz), 2.44 (4H, m), 2.49 (2H, t, J=5.4 Hz), 2.89 (1H, dt, J=13.1 Hz, 3.6 Hz), 3.09 (1H, dt, J=13.0 Hz, 3.6 Hz), 3.31 (2H, m), 3.65-3.70 (5H, m), 3.89 (2H, m), 4.42 (1H, dd, J=11.3 Hz, 3.6 Hz), 5.12 (1H, m), 7.30-7.41 (8H, m), 7.51 (2H, m).

Example 65

Tetrahydro-3-oxo-1,1-diphenyl-N-[(4-pyridinyl)methyl]-3H-oxazolo[3,4-a]pyrazine-7(1H)-carboxamide 4-(Aminomethyl)pyridine (0.50 g, 4.6 mmol) was dissolved in tetrahydrofuran (5 mL). With ice cooling, diisopropylethylamine (1.5 mL) and 4-nitrophenyl chloroformate (1.0 g, 5.0 mmol) were added thereto, and the mixture was stirred at 0° C. for 30 minutes. Next, hexahydro-1,1-diphenyl-3H-oxazolo[3,4-a]pyrazin-3-one (0.15 g, 0.51 mmol) was added thereto, and the resulting mixture was stirred for 16 hours while elevating the temperature from 0° C. to room temperature. The reaction solution was concentrated under reduced pressure, an aqueous saturated sodium hydrogen carbonate solution was added thereto, and the mixture was extracted with ethyl acetate. The organic layer was washed with an aqueous saturated sodium hydrogen carbonate solution and water, and concentrated under reduced pressure. The residue was purified with amino silica gel column chromatography (ethyl acetate) and powder was formed from hexane to obtain the title compound (0.12 g, yield 56%).
Amorphous.
$^1$H NMR (CDCl$_3$) δ 2.20 (1H, dd, J=13.3 Hz, 11.3 Hz), 2.96 (1H, dt, J=13.0 Hz, 3.3 Hz), 3.11 (1H, dt, J=12.8 Hz, 3.5 Hz), 3.69 (1H, m), 3.88 (1H, dd, J=13.0 Hz, 2.7 Hz), 4.02 (1H, m), 4.31-4.47 (3H, m), 5.02 (1H, t, J=5.7 Hz), 7.18 (2H, d, J=6.0 Hz), 7.27-7.40 (8H, m), 7.51 (2H, m), 8.54 (2H, d, J=6.0 Hz).

Example 66

Tetrahydro-N-[(1-oxide-4-pyridinyl)methyl]-3-oxo-1,1-diphenyl-3H-oxazolo[3,4-a]pyrazine-7(1H)-carboxamide Tetrahydro-3-oxo-1,1-diphenyl-N-[(4-pyridinyl)methyl]-3H-oxazolo[3,4-a]pyrazine-7(1H)-carboxamide (60 mg, 0.14 mmol) was dissolved in dichloromethane (1 mL). m-Chloroperbenzoic acid (40 mg, 0.23 mmol) was added thereto, and the mixture was stirred at room temperature for 5 hours. The reaction solution was concentrated under reduced pressure, an aqueous saturated sodium hydrogen carbonate solution was added thereto, and the resulting mixture was extracted with ethyl acetate. The organic layer was washed with an aqueous saturated sodium hydrogen carbonate solution and water, and concentrated under reduced pressure. To the residue was added hexane, and powdered and dried to obtain the title compound (34 mg, yield 55%).
Amorphous.
$^1$H NMR (CDCl$_3$) δ 2.21 (1H, dd, J=13.3 Hz, 11.3 Hz), 2.92 (1H, m), 3.10 (1H, dt, J=13.0 Hz, 3.5 Hz), 3.88 (2H, m), 4.06 (1H, m), 4.34-4.46 (3H, m), 5.83 (1H, t, J=5.9 Hz), 7.14 (2H, d, J=7.0 Hz), 7.27-7.39 (8H, m), 7.53 (2H, m), 7.96 (2H, d, J=7.0 Hz).

Example 67

N-[(2-Cyano-4-pyridinyl)methyl]-tetrahydro-3-oxo-1,1-diphenyl-3H-oxazolo[3,4-a]pyrazine-7(1H)-carboxamide Tetrahydro-N-[(1-oxide-4-pyridinyl)methyl]-3-oxo-1,1-diphenyl-3H-oxazolo[3,4-a]pyrazine-7(1H)-carboxamide (34 mg, 0.08 mmol) was dissolved in acetanilide (1 mL). Trimethylsilyl cyanide (15 mg, 0.15 mmol) and dimethylcarbamyl chloride (16 mg, 0.15 mmol) were added thereto, and the mixture was stirred at room temperature for 20 hours. The reaction solution was concentrated under reduced pressure. The residue was purified with silica gel column chromatography (ethyl acetate), hexane was added thereto, and powdered to obtain the title compound (6 mg, yield 17%).
Amorphous.
$^1$H NMR (CDCl$_3$) δ 2.23 (1H, dd, J=13.3 Hz, 11.3 Hz), 2.98 (1H, dt, J=13.0 Hz, 3.2 Hz), 3.13 (1H, dt, J=12.9 Hz, 3.5 Hz), 3.70 (1H, m), 3.91 (1H, dd, J=13.0 Hz, 2.7 Hz), 3.97 (1H, m), 4.35-4.50 (3H, m), 5.16 (1H, t, J=5.8 Hz), 7.27-7.41 (9H, m), 7.51 (2H, m), 7.60 (1H, s), 8.63 (1H, d, J=5.7 Hz).

Example 68

Tetrahydro-N-[2-(4-methyl-1-piperazinyl)ethyl]-3-oxo-1,1-diphenyl-3H-oxazolo[3,4-a]pyrazine-7(1H)-carboxamide In the same manner as in Example 64, the title compound was obtained using 1-methylpiperazine instead of morpholine. Yield 15%.
Amorphous.
$^1$H NMR (CDCl$_3$) δ 2.17 (1H, dd, J=13.3 Hz, 11.3 Hz), 2.29 (3H, s), 2.35-2.52 (10H, m), 2.88 (1H, dt, J=13.2 Hz, 3.5 Hz), 3.08 (1H, dt, J=12.9 Hz, 3.7 Hz), 3.30 (2H, m), 3.68 (1H, m), 3.86 (1H, dd, J=13.2 Hz, 2.9 Hz), 3.91 (1H, m), 4.42 (1H, dd, J=11.3 Hz, 3.6 Hz), 5.23 (1H, t, J=4.1 Hz), 7.30-7.41 (8H, m), 7.52 (2H, m).

Example 69

1,1-Dimethylethyl [[3-[[[(tetrahydro-3-oxo-1,1-diphenyl-3H-oxazolo[3,4-a]pyrazin-7(1H)-yl)carbonyl]amino]methyl]phenyl]methyl]carbamate In the same manner as in Example 65, the title compound was obtained using 1,1-dimethylethyl [[3-(aminomethyl)phenyl]methyl]carbamate instead of 4-(aminomethyl)pyridine. Yield 63%.
Amorphous.
$^1$H NMR (CDCl$_3$) δ 1.44 (9H, s), 2.15 (1H, dd, J=13.3 Hz, 11.3 Hz), 2.87 (1H, dt, J=13.0 Hz, 3.4 Hz), 3.06 (1H, dt, J=12.9 Hz, 3.6 Hz), 3.66 (1H, m), 3.81 (1H, dd, J=13.0 Hz, 2.7 Hz), 4.03 (1H, dd, J=13.3 Hz, 2.7 Hz), 4.28 (2H, d, J=5.9 Hz), 4.31-4.44 (3H, m), 4.88 (1H, br s), 4.94 (1H, t, J=5.4 Hz), 7.17 (3H, m), 7.25-7.39 (9H, m), 7.51 (2H, m).

Example 70

N-[[3-(Aminomethyl)phenyl]methyl]-tetrahydro-3-oxo-1,1-diphenyl-3H-oxazolo[3,4-a]pyrazine-7(1H)-carboxamide trifluoroacetate To 1,1-dimethylethyl [[3-[[[(tetrahydro-3-oxo-1,1-diphenyl-3H-oxazolo[3,4-a]pyrazin-7(1H)-yl)carbonyl]amino]methyl]phenyl]methyl]carbamate (0.12 g, 0.22 mmol) was added trifluoroacetic acid (1.5 mL), and the mixture was stirred at room temperature for 2 hours. To the reaction solution was added diisopropyl ether, the precipitated powder was collected by filtration and dried to obtain the title compound (0.11 g, yield 84%).
Amorphous.
$^1$H NMR (DMSO-d$_6$) δ 2.08 (1H, dd, J=13.1 Hz, 11.3 Hz), 2.69 (1H, dt, J=13.0 Hz, 3.0 Hz), 3.05 (1H, dt, J=12.9 Hz, 2.9 Hz), 3.54-3.65 (2H, m), 3.87-4.02 (4H, m), 4.27 (2H, m), 4.50 (1H, dd, J=11.1 Hz, 3.5 Hz), 7.25-7.46 (12H, m), 7.56 (2H, m), 8.10 (2H, br s).

Example 71

Ethyl N-[(tetrahydro-3-oxo-1,1-diphenyl-3H-oxazolo[3,4-a]pyrazin-7(1H)-yl)carbonyl]glycine In the same manner as in Example 55, the title compound was obtained using ethyl isocyanatoacetate instead of 2,4-difluorophenyl isocyanate. Yield 99%.
Amorphous.
$^1$H NMR (CDCl$_3$) δ 1.29 (3H, t, J=7.1 Hz), 2.21 (1H, dd, J=13.4 Hz, 11.3 Hz), 2.93 (1H, dt, J=13.1 Hz, 3.4 Hz), 3.11 (1H, dt, J=12.9 Hz, 3.6 Hz), 3.75 (1H, m), 3.87 (1H, dd, J=12.9 Hz, 2.8 Hz), 3.92-3.99 (3H, m), 4.22 (2H, q, J=7.1 Hz), 4.43 (1H, dd, J=11.3 Hz, 3.6 Hz), 4.95 (1H, m), 7.27-7.40 (8H, m), 7.51 (2H, m).

Example 72

N-[(Tetrahydro-3-oxo-1,1-diphenyl-3H-oxazolo[3,4-a]pyrazin-7(1H)-yl)carbonyl]glycine Ethyl N-[(tetrahydro-3-oxo-1,1-diphenyl-3H-oxazolo[3,4-a]pyrazin-7(1H)-yl)carbonyl]glycine (1.5 g, 3.6 mmol) was dissolved in ethanol (10 mL) and tetrahydrofuran (2 mL). With ice cooling, a 4 M aqueous sodium hydroxide solution (1.0 mL, 4.0 mmol) was added thereto, and the mixture was stirred at 0° C. for 3 hours. The reaction solution was concentrated under reduced pressure, and diethyl ether and water were added to the residue. The aqueous layer was neutralized with 4 M hydrochloric acid, which was extracted with ethyl acetate. The organic layer was concentrated under reduced pressure, and hexane was added to the residue. The resulting mixture was powdered and dried to obtain the title compound (1.2 g, yield 84%).
Amorphous.
$^1$H NMR (CDCl$_3$) δ 2.22 (1H, dd, J=13.3 Hz, 11.3 Hz), 2.91 (1H, dt, J=13.0 Hz, 3.3 Hz), 3.10 (1H, dt, J=12.8 Hz, 3.4 Hz), 3.75 (1H, m), 3.85 (1H, dd, J=13.2 Hz, 2.8 Hz), 3.92 (1H, dd, J=13.4 Hz, 2.9 Hz), 3.98 (2H, d, J=5.3 Hz), 4.44 (1H, dd, J=11.3 Hz, 3.6 Hz), 5.22 (1H, t, J=5.3 Hz), 7.27-7.39 (8H, m), 7.51 (2H, m).

Example 73

Tetrahydro-N-[2-(4-morpholinyl)-2-oxoethyl]-3-oxo-1,1-diphenyl-3H-oxazolo[3,4-a]pyrazine-7(1H)-carboxamide N-[(Tetrahydro-3-oxo-1,1-diphenyl-3H-oxazolo[3,4-a]pyrazin-7(1H)-yl)carbonyl]glycine (0.15 g, 0.38 mmol) was dissolved in N,N-dimethylformamide (3 mL). Morpholine (0.14 g, 1.2 mmol), 1-ethyl-3-(3-dimethylaminopropyl)carbodiimide hydrochloride (0.15 g, 0.76 mmol) and 1-hydroxybenzotriazole (0.11 g, 0.77 mmol) were added thereto, and the mixture was stirred at room temperature for 20 hours. To the reaction solution was added ice water, and the mixture was extracted with ethyl acetate. The organic layer was washed with water, an aqueous saturated sodium hydrogen carbonate solution and water and then concentrated under reduced pressure. The residue was purified with silica gel column chromatography (ethyl acetate:methanol=95:5) and powder was formed from hexane to obtain the title compound (90 mg, yield 51%).
Amorphous.
$^1$H NMR (CDCl$_3$) δ 2.20 (1H, dd, J=13.3 Hz, 11.3 Hz), 2.90 (1H, dt, J=13.3 Hz, 3.0 Hz), 3.09 (1H, dt, J=13.0 Hz, 3.2 Hz), 3.44 (2H, m), 3.64-3.71 (6H, m), 3.84 (2H, m), 3.94-4.02 (3H, m), 4.41 (1H, dd, J=11.3 Hz, 3.5 Hz), 5.59 (1H, m), 7.28-7.41 (8H, m), 7.51 (2H, m).

Example 74

7-[[(4-Fluorophenyl)amino]acetyl]-hexahydro-1,1-diphenyl-3H-oxazolo[3,4-a]pyrazin-3-one Hexahydro-1,1-diphenyl-3H-oxazolo[3,4-a]pyrazin-3-one (0.20 g, 0.68 mmol) was dissolved in tetrahydrofuran (3 mL). With ice cooling, diisopropylethylamine (1 mL) and chloroacetyl chloride (70 μL, 0.82 mmol) were added thereto, and the mixture was stirred at room temperature for 3 hours. Next, 4-fluoroaniline (0.13 mL, 1.4 mmol) was added thereto, and the mixture was stirred at 50° C. for 16 hours. To the reaction solution was added water, and the mixture was extracted with ethyl acetate. The organic layer was washed with water and concentrated under reduced pressure. The residue was purified with silica gel column chromatography (hexane:ethyl acetate=1:1) and crystallized from hexane to obtain the title compound (45 mg, yield 15%).

Melting point 203-204° C.

$^1$H NMR (CDCl$_3$) δ 2.11 (1H, m), 3.09 (2H, m), 3.73 (1H, m), 3.83-4.00 (3H, m), 4.38 (1H, dd, J=11.4 Hz, 3.3 Hz), 4.50 (1H, m), 4.60 (1H, m), 6.55 (2H, m), 6.91 (2H, t, J=8.3 Hz), 7.33-7.43 (8H, m), 7.50 (2H, m).

Example 75

Tetrahydro-N-[2-(1H-imidazol-1-yl)ethyl]-3-oxo-1,1-diphenyl-3H-oxazolo[3,4-a]pyrazine-7(1H)-carboxamide In the same manner as in Example 64, the title compound was obtained using imidazole instead of morpholine. Yield 34%.

Amorphous.

$^1$H NMR (CDCl$_3$) δ 2.17 (1H, dd, J=13.3 Hz, 11.3 Hz), 2.84 (1H, m), 3.03 (1H, dt, J=12.8 Hz, 3.5 Hz), 3.52 (2H, m), 3.69 (1H, m), 3.82 (1H, d, J=13.1 Hz), 3.93 (1H, m), 4.10 (2H, m), 4.38 (1H, dd, J=11.2 Hz, 3.6 Hz), 5.25 (1H, m), 6.86 (1H, s), 7.00 (1H, m), 7.11 (1H, s), 7.28-7.42 (8H, m), 7.51 (2H, m).

Example 76

Methyl α-[[(tetrahydro-3-oxo-1,1-diphenyl-3H-oxazolo[3,4-a]pyrazin-7(1H)-yl)carbonyl]amino]benzeneacetate In the same manner as in Example 65, the title compound was obtained using methyl phenylglycine instead of 4-(aminomethyl)pyridine. Yield 78%.

Amorphous.

$^1$H NMR (CDCl$_3$) δ 2.16 (1H, q, J=12.4 Hz), 2.90-3.16 (2H, m), 3.70 (1H, m), 3.73 (3H, s), 3.87 (1H, m), 4.02 (1H, dd, J=13.4 Hz, 2.5 Hz), 4.41 (1H, dd, J=11.3 Hz, 3.6 Hz), 5.42-5.50 (2H, m), 7.27-7.40 (13H, m), 7.49 (2H, m).

Example 77

N-(Benzoylmethyl)-tetrahydro-3-oxo-1,1-diphenyl-3H-oxazolo[3,4-a]pyrazine-7(1H)-carboxamide In the same manner as in Example 124, the title compound was obtained using 2-aminoacetophenone (2-aminoacetophenone hydrochloride was neutralized with an equivalent amount of diisopropylethylamine) instead of 1,1-dimethylethyl 4-amino-1H-benzimidazole-1-carboxylate. Yield 33%.

Melting point 99-102° C.

$^1$H NMR (CDCl$_3$) δ 2.20-2.28 (1H, m), 2.92-3.01 (1H, m), 3.11-3.18 (1H, m), 3.85-3.93 (2H, m), 3.98-4.04 (1H, m), 4.45 (1H, dd, J=3.5 Hz, 11.2 Hz), 4.74-4.80 (2H, m), 5.60 (1H, br s), 7.26-7.40 (8H, m), 7.49-7.55 (4H, m), 7.61-7.65 (1H, m), 7.97-8.01 (2H, m).

Example 78

Tetrahydro-N-(2-hydroxy-1-phenylethyl)-3-oxo-1,1-diphenyl-3H-oxazolo[3,4-a]pyrazine-7(1H)-carboxamide Methyl α-[[(tetrahydro-3-oxo-1,1-diphenyl-3H-oxazolo[3,4-a]pyrazin-7(1H)-yl)carbonyl]amino]benzeneacetate (0.15 g, 0.31 mmol) was dissolved in tetrahydrofuran (2 mL). Lithium borohydride (14 mg, 0.64 mmol) was added thereto, and the mixture was stirred at room temperature for 2 hours. To the reaction solution was added water, and the mixture was extracted with ethyl acetate. The organic layer was washed with water, and then concentrated under reduced pressure. The residue was purified with silica gel column chromatography (ethyl acetate) and powder was formed from hexane to obtain the title compound (0.13 g, yield 90%).

Amorphous.

$^1$H NMR (CDCl$_3$) δ 2.14 (1H, m), 2.42 (1H, m), 2.96 (1H, m), 3.08 (1H, m), 3.67 (1H, m), 3.87 (3H, m), 4.05 (1H, dd, J=13.4 Hz, 3.5 Hz), 4.41 (1H, m), 4.93 (1H, m), 5.17 (1H, m), 7.27-7.38 (13H, m), 7.49 (2H, m).

Example 79

α-[[(Tetrahydro-3-oxo-1,1-diphenyl-3H-oxazolo[3,4-a]pyrazin-7(1H)-yl)carbonyl]amino]benzeneacetic acid In the same manner as in Example 72, the title compound was obtained using methyl α-[[(tetrahydro-3-oxo-1,1-diphenyl-3H-oxazolo[3,4-a]pyrazin-7(1H)-yl)carbonyl]amino]benzeneacetate instead of ethyl N-[(tetrahydro-3-oxo-1,1-diphenyl-3H-oxazolo[3,4-a]pyrazin-7(1H)-yl)carbonyl]glycine. Yield 96%.

Amorphous.

$^1$H NMR (CDCl$_3$) δ 2.16 (1H, q, J=11.3 Hz), 2.85-3.08 (2H, m), 3.65 (1H, m), 3.84 (1H, m), 3.98 (1H, m), 4.41 (1H, m), 5.43 (2H, m), 7.28-7.39 (13H, m), 7.47 (2H, m).

Example 80

Tetrahydro-3-oxo-1,1-diphenyl-N-[2-(1-piperidinyl)ethyl]-3H-oxazolo[3,4-a]pyrazine-7(1H)-carboxamide In the same manner as in Example 64, the title compound was obtained using piperidine instead of morpholine. Yield 67%.

Melting point 139-140° C.

$^1$H NMR (CDCl$_3$) δ 1.44-1.54 (5H, m), 1.70 (2H, m), 2.18 (1H, dd, J=13.3 Hz, 11.3 Hz), 2.36 (3H, m), 2.43 (2H, t, J=6.0 Hz), 2.86 (1H, dt, J=13.1 Hz, 3.5 Hz), 3.08 (1H, dt, J=12.9 Hz, 3.7 Hz), 3.27 (2H, m), 3.73 (1H, m), 3.87 (2H, m), 4.42 (1H, dd, J=11.3 Hz, 3.6 Hz), 5.36 (1H, m), 7.29-7.39 (8H, m), 7.52 (2H, m).

Example 81

Tetrahydro-N-[2-[(2-methoxyethyl)methylamino]ethyl]-3-oxo-1,1-diphenyl-3H-oxazolo[3,4-a]pyrazine-7(1H)-carboxamide In the same manner as in Example 64, the title compound was obtained using N-(2-methoxyethyl)-N-methylamine instead of morpholine. Yield 67%.

Amorphous.

$^1$H NMR (CDCl$_3$) δ 2.12 (1H, dd, J=13.3 Hz, 11.3 Hz), 2.28 (3H, s), 2.51 (2H, t, J=5.8 Hz), 2.57 (2H, t, J=5.3 Hz), 2.85 (1H, dt, J=13.1 Hz, 3.5 Hz), 3.07 (1H, dt, J=12.9 Hz, 3.7 Hz), 3.25 (2H, m), 3.29 (3H, s), 3.43 (2H, t, J=5.3 Hz), 3.71 (1H, m), 3.83 (1H, dd, J=13.1 Hz, 2.7 Hz), 4.08 (1H, m), 4.40 (1H, dd, J=11.2 Hz, 3.6 Hz), 5.57 (1H, t, J=4.3 Hz), 7.29-7.39 (8H, m), 7.52 (2H, m).

Example 82

[[[(Tetrahydro-3-oxo-1,1-diphenyl-3H-oxazolo[3,4-a]pyrazin-7(1H)-yl)carbonyl]amino]methyl]carbamic azide N-[(Tetrahydro-3-oxo-1,1-diphenyl-3H-oxazolo[3,4-a]pyrazin-7(1H)-yl)carbonyl]glycine (0.30 g, 0.76 mmol) was dissolved in tetrahydrofuran (5 mL). Oxalyl dichloride (0.11 g, 0.85 mmol) and N,N-dimethylformamide (one drop) were added thereto, and the mixture was stirred at room temperature for 1 hour. The reaction solution was concentrated under reduced pressure. The residue was dissolved in N,N-dimethylformamide (3 mL), sodium azide (0.12 g, 1.9 mmol) was added thereto, and the mixture was stirred at room temperature for 2 hours. To the reaction solution was added water, and the resulting mixture was extracted with ethyl acetate. The organic layer was washed with water and then concentrated under reduced pressure. The residue was purified with silica gel column chromatography (hexane:ethyl acetate=1:9) and powder was formed from hexane to obtain the title compound (0.11 g, yield 31%).

Amorphous.

$^1$H NMR (CDCl$_3$) δ 2.21 (1H, dd, J=13.3 Hz, 11.3 Hz), 2.86 (1H, dt, J=13.1 Hz, 3.5 Hz), 3.07 (1H, dt, J=13.0 Hz, 3.6 Hz), 3.72 (1H, m), 3.85 (2H, m), 4.39 (1H, dd, J=11.3 Hz, 3.6 Hz), 4.56 (2H, t, J=6.4 Hz), 5.55 (1H, t, J=6.2 Hz), 6.20 (1H, t, J=6.0 Hz), 7.29-7.40 (8H, m), 7.50 (2H, m).

Example 83

N-[[(Aminocarbonyl)amino]methyl]-tetrahydro-3-oxo-1,1-diphenyl-3H-oxazolo[3,4-a]pyrazine-7(1H)-carboxamide

[[[(Tetrahydro-3-oxo-1,1-diphenyl-3H-oxazolo[3,4-a]pyrazin-7(1H)-yl)carbonyl]amino]methyl]carbamic azide (68 mg, 0.16 mmol) was dissolved in methanol (3 mL). Nickel (II) chloride hexahydrate (77 mg, 0.32 mmol) and sodium borohydride (12 mg, 0.32 mmol) were added thereto, and the mixture was stirred at room temperature for 4 hours. To the reaction solution was added water, and the mixture was extracted with ethyl acetate. The organic layer was washed with water and then concentrated under reduced pressure. The precipitated powder was washed with diisopropyl ether and dried to obtain the title compound (52 mg, yield 81%).

Amorphous.

$^1$H NMR (DMSO-d$_6$) δ 2.05 (1H, dd, J=13.3 Hz, 11.3 Hz), 2.58 (1H, m), 3.00 (1H, dt, J=12.8 Hz, 3.4 Hz), 3.58 (1H, m), 3.85 (1H, m), 3.94 (1H, m), 4.28 (2H, t, J=5.9 Hz), 4.48 (1H, dd, J=11.0 Hz, 3.4 Hz), 5.60 (2H, m), 6.42 (1H, t, J=6.2 Hz), 6.52 (1H, s), 7.30-7.45 (8H, m), 7.57 (2H, m).

Example 84

Tetrahydro-N-[2-(4-methyl-1-piperidinyl)ethyl]-3-oxo-1,1-diphenyl-3H-oxazolo[3,4-a]pyrazine-7(1H)-carboxamide In the same manner as in Example 64, the title compound was obtained using 4-methylpiperidine instead of morpholine. Yield 54%.

Melting point 136-137° C.

$^1$H NMR (CDCl$_3$) δ 0.93 (3H, d, J=6.5 Hz), 1.12 (2H, m), 1.37 (1H, m), 1.63 (2H, m), 1.96 (2H, m), 2.17 (1H, dd, J=13.2 Hz, 11.3 Hz), 2.45 (2H, t, J=5.9 Hz), 2.78-2.90 (3H, m), 3.08 (1H, dt, J=12.9 Hz, 3.6 Hz), 3.27 (2H, m), 3.72 (1H, m), 3.88 (2H, m), 4.42 (1H, dd, J=11.3 Hz, 3.6 Hz), 5.33 (1H, m), 7.27-7.42 (8H, m), 7.52 (2H, m).

Example 85

N-[2-(3,6-Dihydropyridin-1(2H)-yl)ethyl]-tetrahydro-3-oxo-1,1-diphenyl-3H-oxazolo[3,4-a]pyrazine-7(1H)-carboxamide In the same manner as in Example 64, the title compound was obtained using 1,2,3,6-tetrahydropyridine instead of morpholine. Yield 34%.

Melting point 142-143° C.

$^1$H NMR (CDCl$_3$) δ 2.15 (3H, m), 2.56 (4H, t, J=5.6 Hz), 2.85 (1H, dt, J=13.2 Hz, 3.5 Hz), 2.96 (2H, m), 3.07 (1H, dt, J=13.0 Hz, 3.7 Hz), 3.32 (2H, m), 3.71 (1H, m), 3.84 (1H, dd, J=13.3 Hz, 3.0 Hz), 3.92 (1H, m), 4.40 (1H, dd, J=11.3 Hz, 3.6 Hz), 5.27 (1H, m), 5.67 (1H, m), 5.74 (1H, m), 7.27-7.39 (8H, m), 7.51 (2H, m).

Example 86

N-[2-(Diethylamino)ethyl]-tetrahydro-3-oxo-1,1-diphenyl-3H-oxazolo[3,4-a]pyrazine-7(1H)-carboxamide In the same manner as in Example 64, the title compound was obtained using diethylamine instead of morpholine. Yield 9%.

Melting point 97-98° C.

$^1$H NMR (CDCl$_3$) δ 0.98 (6H, t, J=7.1 Hz), 2.17 (1H, dd, J=13.3 Hz, 11.3 Hz), 2.46-2.55 (6H, m), 2.85 (1H, dt, J=13.2 Hz, 3.5 Hz), 3.08 (1H, dt, J=13.0 Hz, 3.8 Hz), 3.23 (2H, m), 3.72 (1H, m), 3.87 (2H, m), 4.41 (1H, dd, J=11.3 Hz, 3.6 Hz), 5.34 (1H, m), 7.27-7.39 (8H, m), 7.51 (2H, m).

Example 87

N-[2-(3,4-Dihydroisoquinolin-2(1H)-yl)ethyl]-tetrahydro-3-oxo-1,1-diphenyl-3H-oxazolo[3,4-a]pyrazine-7(1H)-carboxamide In the same manner as in Example 64, the title compound was obtained using 1,2,3,4-tetrahydroisoquinoline instead of morpholine. Yield 66%.

Amorphous.

$^1$H NMR (CDCl$_3$) δ 2.14 (1H, dd, J=13.3 Hz, 11.3 Hz), 2.67 (2H, t, J=5.9 Hz), 2.72-2.88 (5H, m), 3.05 (1H, dt, J=12.9 Hz, 3.7 Hz), 3.40 (2H, m), 3.64 (2H, s), 3.73 (1H, m), 3.83 (2H, m), 4.38 (1H, dd, J=11.3 Hz, 3.6 Hz), 5.27 (1H, t, J=4.3 Hz), 7.04 (1H, m), 7.13-7.37 (11H, m), 7.48 (2H, m).

Example 88

Tetrahydro-3-oxo-1,1-diphenyl-N-[2-(1-pyrrolidinyl)ethyl]-3H-oxazolo[3,4-a]pyrazine-7(1H)-carboxamide In the same manner as in Example 64, the title compound was obtained using pyrrolidine instead of morpholine. Yield 30%.
Melting point 153-154° C.
$^1$H NMR (CDCl$_3$) δ 1.74-1.78 (4H, m), 2.15 (1H, dd, J=13.3 Hz, 11.3 Hz), 2.45-2.55 (4H, m), 2.59 (2H, t, J=5.9 Hz), 2.87 (1H, dt, J=13.1 Hz, 3.6 Hz), 3.08 (1H, dt, J=12.9 Hz, 3.7 Hz), 3.31 (2H, m), 3.70 (1H, m), 3.85 (1H, dd, J=13.1 Hz, 2.7 Hz), 3.97 (1H, m), 4.41 (1H, dd, J=11.3 Hz, 3.6 Hz), 5.22 (1H, m), 7.27-7.41 (8H, m), 7.53 (2H, m).

Example 89

Tetrahydro-3-oxo-1,1-diphenyl-N-[2-(4-thiomorpholinyl)ethyl]-3H-oxazolo[3,4-a]pyrazine-7(1H)-carboxamide In the same manner as in Example 64, the title compound was obtained using thiomorpholine instead of morpholine. Yield 64%.
Melting point 177-178° C.
$^1$H NMR (CDCl$_3$) δ 2.19 (1H, dd, J=13.2 Hz, 11.3 Hz), 2.50 (2H, t, J=6.0 Hz), 2.63 (4H, m), 2.69 (4H, m), 2.87 (1H, dt, J=13.1 Hz, 3.5 Hz), 3.09 (1H, dt, J=12.9 Hz, 3.7 Hz), 3.29 (2H, m), 3.72 (1H, m), 3.86 (2H, m), 4.42 (1H, dd, J=11.3 Hz, 3.7 Hz), 5.10 (1H, t, J=4.3 Hz), 7.30-7.42 (8H, m), 7.52 (2H, m).

Example 90

Tetrahydro-3-oxo-1,1-diphenyl-N-[3-(1-piperidinyl)propyl]-3H-oxazolo[3,4-a]pyrazine-7(1H)-carboxamide In the same manner as in Example 64, the title compound was obtained using 3-chloropropyl isocyanate instead of 2-bromoethyl isocyanate, and using piperidine instead of morpholine. Yield 45%.
Amorphous.
$^1$H NMR (CDCl$_3$) δ 1.40-1.54 (4H, m), 1.62-1.70 (4H, m), 2.10 (1H, dd, J=13.3 Hz, 11.3 Hz), 2.37-2.45 (6H, m), 2.89 (1H, dt, J=13.1 Hz, 3.5 Hz), 3.07 (1H, dt, J=13.0 Hz, 3.5 Hz), 3.32 (2H, m), 3.70 (1H, m), 3.85 (1H, dd, J=12.9 Hz, 2.8 Hz), 4.15 (1H, m), 4.41 (1H, dd, J=11.2 Hz, 3.7 Hz), 7.06 (1H, m), 7.27-7.41 (8H, m), 7.52 (2H, m).

Example 91

N-[3-(3,6-Dihydropyridin-1(2H)-yl)propyl]-tetrahydro-3-oxo-1,1-diphenyl-3H-oxazolo[3,4-a]pyrazine-7(1H)-carboxamide In the same manner as in Example 64, the title compound was obtained using 3-chloropropyl isocyanate instead of 2-bromoethyl isocyanate, and using 1,2,3,6-tetrahydropyridine instead of morpholine. Yield 72%.
Amorphous.
$^1$H NMR (CDCl$_3$) δ 1.71 (2H, m), 2.03 (1H, dd, J=13.2 Hz, 11.3 Hz), 2.14 (2H, m), 2.50-2.65 (4H, m), 2.77 (1H, dt, J=13.3 Hz, 3.6 Hz), 2.89-3.10 (3H, m), 3.36 (2H, m), 3.50 (1H, m), 3.75 (1H, dd, J=13.1 Hz, 2.8 Hz), 4.19 (1H, m), 4.36 (1H, dd, J=11.2 Hz, 3.7 Hz), 5.70 (2H, m), 7.24-7.38 (8H, m), 7.52 (3H, m).

Example 92

Ethyl [(tetrahydro-3-oxo-1,1-diphenyl-3H-oxazolo[3,4-a]pyrazin-7(1H)-yl)carbonyl]carbamate In the same manner as in Example 55, the title compound was obtained using ethyl isocyanatoformate instead of 2,4-difluorophenyl isocyanate. Yield 40%.
Amorphous.
$^1$H NMR (CDCl$_3$) δ 1.31 (3H, t, J=7.1 Hz), 2.31 (1H, dd, J=13.2 Hz, 11.2 Hz), 2.91 (1H, dt, J=13.1 Hz, 3.6 Hz), 3.20 (1H, dt, J=13.2 Hz, 3.8 Hz), 3.77 (1H, m), 3.87-3.99 (2H, m), 4.22 (2H, q, J=7.1 Hz), 4.69 (1H, dd, J=11.2 Hz, 3.4 Hz), 6.53 (1H, s), 7.27-7.42 (8H, m), 7.56 (2H, m).

Example 93

Tetrahydro-N-(1-naphthyl)-3-oxo-1,1-diphenyl-3H-oxazolo[3,4-a]pyrazine-7(1H)-carboxamide In the same manner as in Example 55, the title compound was obtained using 1-naphthyl isocyanate instead of 2,4-difluorophenyl isocyanate. Yield 40%.
Amorphous.
$^1$H NMR (CDCl$_3$) δ 2.26 (1H, dd, J=13.3 Hz, 11.4 Hz), 3.02 (1H, dt, J=13.1 Hz, 3.4 Hz), 3.20 (1H, dt, J=12.9 Hz, 3.4 Hz), 3.94 (3H, m), 4.41 (1H, dd, J=11.3 Hz, 3.5 Hz), 6.49 (1H, s), 7.17-7.56 (13H, m), 7.72-7.91 (4H, m).

Example 94

7-[[(E)-2-(4-Fluorophenyl)ethenyl]sulfonyl]-hexahydro-1,1-diphenyl-3H-oxazolo[3,4-a]pyrazin-3-one To a solution of hexahydro-1,1-diphenyl-3H-oxazolo[3,4-a]pyrazin-3-one (50 mg, 0.17 mmol) in chloroform (2 mL) were sequentially added pyridine (0.5 mL) and (E)-2-(4-fluorophenyl)vinylsulfonyl chloride (43 mg, 0.24 mmol), and the mixture was stirred at room temperature for 2 hours. The reaction solution was concentrated under reduced pressure. The residue was purified with silica gel column chromatography (hexane:ethyl acetate=1:1) and crystallized from diisopropyl ether to obtain the title compound (27 mg, yield 64%).
Melting point 248-249° C.
$^1$H NMR (CDCl$_3$) δ 2.11 (1H, dd, J=11.9 Hz, 11.3 Hz), 2.64 (1H, dt, J=12.2 Hz, 3.6 Hz), 3.25 (1H, dt, J=13.4 Hz, 3.9 Hz), 3.51 (1H, m), 3.68 (1H, dd, J=12.2 Hz, 3.9 Hz), 3.96 (1H, dd, J=13.3 Hz, 2.8 Hz), 4.59 (1H, dd, J=11.0 Hz, 3.7 Hz), 6.40 (1H, d, J=15.5 Hz), 7.10 (2H, t, J=8.5 Hz), 7.26-7.43 (11H, m), 7.51 (2H, m).

Example 95

Hexahydro-1,1-diphenyl-7-[(phenylmethyl)sulfonyl]-3H-oxazolo[3,4-a]pyrazin-3-one In the same manner as in Example 94, the title compound was obtained using benzylsulfonyl chloride instead of (E)-2-(4-fluorophenyl)vinylsulfonyl chloride. Yield 52%.
Melting point 153-154° C.
$^1$H NMR (CDCl$_3$) δ 1.85 (1H, dd, J=12.8 Hz, 11.1 Hz), 2.56 (1H, dt, J=12.5 Hz, 3.5 Hz), 3.07 (1H, dt, J=13.3 Hz, 3.9

Hz), 3.20 (1H, m), 3.56 (1H, dd, J=12.8 Hz, 3.9 Hz), 3.81 (1H, dd, J=13.4 Hz, 2.8 Hz), 4.16 (2H, s), 4.31 (1H, dd, J=11.1 Hz, 3.8 Hz), 7.17-7.39 (15H, m).

Example 96

Tetrahydro-3-oxo-1,1-diphenyl-N-[(3-thienyl)methyl]-3H-oxazolo[3,4-a]pyrazine-7(1H)-carboxamide In the same manner as in Example 65, the title compound was obtained using 3-thienylmethylamine instead of 4-(aminomethyl)pyridine. Yield 73%.
Amorphous.
$^1$H NMR (CDCl$_3$) δ 2.17 (1H, dd, J=13.3 Hz, 11.3 Hz), 2.90 (1H, dt, J=12.8 Hz, 3.4 Hz), 3.08 (1H, dt, J=12.8 Hz, 3.5 Hz), 3.63 (1H, m), 3.85 (1H, dd, J=12.9 Hz, 2.8 Hz), 4.02 (1H, m), 4.30-4.50 (3H, m), 4.69 (1H, m), 7.02 (1H, m), 7.12 (1H, s), 7.27-7.40 (9H, m), 7.51 (2H, m).

Example 97

N-[(3,4-Difluorophenyl)methyl]-tetrahydro-3-oxo-1,1-diphenyl-3H-oxazolo[3,4-a]pyrazine-7(1H)-carboxamide In the same manner as in Example 58, the title compound was obtained using 3,4-difluorobenzylamine instead of 2-aminopyridine. Yield 44%.
Amorphous.
$^1$H NMR (CDCl$_3$) δ 2.18 (1H, dd, J=13.3 Hz, 11.3 Hz), 2.93 (1H, dt, J=12.9 Hz, 3.4 Hz), 3.09 (1H, dt, J=12.8 Hz, 3.4 Hz), 3.64 (1H, m), 3.87 (1H, dd, J=13.0 Hz, 2.6 Hz), 4.02 (1H, dd, J=13.4 Hz, 2.4 Hz), 4.35 (2H, m), 4.42 (1H, dd, J=11.3 Hz, 3.6 Hz), 4.84 (1H, t, J=5.3 Hz), 7.00 (1H, m), 7.10 (2H, m), 7.27-7.40 (8H, m), 7.51 (2H, m).

Example 98

Tetrahydro-N-[2-[methyl(phenylmethyl)amino]ethyl]-3-oxo-1,1-diphenyl-3H-oxazolo[3,4-a]pyrazine-7(1H)-carboxamide In the same manner as in Example 64, the title compound was obtained using N-methylbenzylamine instead of morpholine. Yield 62%.
Amorphous.
$^1$H NMR (CDCl$_3$) δ 2.11 (1H, dd, J=13.2 Hz, 11.3 Hz), 2.24 (3H, s), 2.50 (2H, m), 2.85 (1H, dt, J=12.9 Hz, 3.4 Hz), 3.02 (1H, dt, J=12.9 Hz, 3.5 Hz), 3.27 (2H, q, J=5.6 Hz), 3.45-3.55 (3H, m), 3.83 (1H, dd, J=12.9 Hz, 2.7 Hz), 3.98 (1H, m), 4.37 (1H, dd, J=11.3 Hz, 3.6 Hz), 5.10 (1H, m), 7.21-7.38 (13H, m), 7.52 (2H, m).

Example 99

1,1-Dimethylethyl 1,1-bis(phenylmethyl)-tetrahydro-3-oxo-3H-oxazolo[3,4-a]pyrazine-7(1H)-carboxylate Bis(1,1-dimethylethyl)2-[1-hydroxy-2-phenyl-1-(phenylmethyl)ethyl]-1,4-piperazinedicarboxylate (2.0 g, 4.0 mmol) was dissolved in N,N-dimethylformamide (20 mL). 60% Sodium hydride (0.19 g, 4.8 mmol) was added thereto, and the mixture was stirred at room temperature for 6 hours. The resulting mixture was extracted with ethyl acetate, washed with a 0.5 M aqueous sodium hydrogen carbonate solution, dried over anhydrous magnesium sulfate, and concentrated under reduced pressure. To the residue was added diisopropyl ether, and the obtained crystals were collected by filtration and washed with diisopropyl ether to obtain the title compound (1.4 g, yield 82%).
Melting point 188-189° C.
$^1$H NMR (CDCl$_3$) δ 1.47 (9H, s), 2.59-2.98 (6H, m), 3.26 (1H, d, J=14.3 Hz), 3.48-3.56 (2H, m), 3.95-4.10 (2H, m), 7.13-7.38 (10H, m).

Example 100

1,1-Bis(phenylmethyl)-N-[(4-fluorophenyl)methyl]-tetrahydro-3-oxo-3H-oxazolo[3,4-a]pyrazine-7(1H)-carboxamide To 1,1-bis(phenylmethyl)-hexahydro-3H-oxazolo[3,4-a]pyrazin-3-one (0.16 g, 0.50 mmol) were added tetrahydrofuran (10 mL) and 4-fluorobenzyl isocyanate (0.30 g, 2.0 mmol), and the mixture was stirred at 50° C. for 4 hours. The reaction solution was concentrated, and then the residue was purified with silica gel column chromatography (hexane:ethyl acetate=1:1 to ethyl acetate). The fractions were collected and concentrated. To the residue was added diisopropyl ether, and the obtained solid matter was collected by filtration and washed with diisopropyl ether to obtain the title compound (0.17 g, yield 70%).
Amorphous.
$^1$H NMR (CDCl$_3$) δ 2.65-2.95 (6H, m), 3.26 (1H, d, J=14.3 Hz), 3.55-3.71 (3H, m), 3.94-3.98 (1H, m), 4.37-4.39 (2H, m), 4.58 (1H, br s), 7.01-7.37 (14H, m).

Example 101

1,1-Bis(phenylmethyl)-N-(4-fluorophenyl)-tetrahydro-3-oxo-3H-oxazolo[3,4-a]pyrazine-7(1H)-carboxamide In the same manner as in Example 100, the title compound was obtained using 4-fluorophenyl isocyanate instead of 4-fluorobenzyl isocyanate. Yield 49%.
Melting point 165-166° C. (crystallized from diethyl ether).
$^1$H NMR (CDCl$_3$) δ 2.74-2.98 (6H, m), 3.27-3.32 (1H, m), 3.60-3.66 (2H, m), 3.75-3.82 (1H, m), 4.00-4.08 (1H, m), 6.10-6.16 (1H, m), 7.00-7.39 (14H, m).

Example 102

Phenyl 1,1-bis(phenylmethyl)-tetrahydro-3-oxo-3H-oxazolo[3,4-a]pyrazine-7(1H)-carboxylate To a solution of 1,1-bis(phenylmethyl)-hexahydro-3H-oxazolo[3,4-a]pyrazin-3-one (0.16 g, 0.50 mmol) in tetrahydrofuran (10 mL) were sequentially added triethylamine (0.14 mL) and phenyl chlorocarbonate (0.12 g, 0.75 mmol), and the mixture was stirred at room temperature for 3 hours. To the reaction solution was added water, and the mixture was extracted with ethyl acetate. The extract was washed with a 0.5 M aqueous sodium hydrogen carbonate solution, dried over anhydrous magnesium sulfate and concentrated under reduced pressure. The residue was purified with silica gel column chromatography (hexane:ethyl acetate=10:1 to ethyl acetate). The fractions were concentrated, and to the obtained crystals was added diisopropyl ether, collected by filtration and washed with diisopropyl ether to obtain the title compound (0.19 g, yield 85%).

Melting point 140-141° C.

$^1$H NMR (CDCl$_3$) δ 2.74-3.01 (6H, m), 3.29-3.33 (1H, m), 3.64-3.68 (2H, m), 4.20-4.30 (2H, m), 7.09-7.39 (15H, m).

Example 103

1,1-Dimethylethyl tetrahydro-3-oxo-1-phenyl-3H-oxazolo[3,4-a]pyrazine-7(1H)-carboxylate Bis(1,1-dimethylethyl)2-benzoyl-1,4-piperazinedicarboxylate (0.10 g, 0.26 mmol) was dissolved in methanol (2 mL), sodium borohydride (19 mg, 0.51 mmol) was added thereto, and the mixture was stirred at room temperature for 2 hours. To the reaction solution was added ethyl acetate, and the resulting mixture was washed with a 0.5 M aqueous sodium hydrogen carbonate solution, dried over anhydrous magnesium sulfate and concentrated under reduced pressure. The residue was dissolved in N,N-dimethylformamide (3 mL), 60% sodium hydride (12 mg, 0.30 mmol) was added thereto, and the mixture was stirred at room temperature for 1 hour. The resulting mixture was extracted with ethyl acetate, washed with a 0.5 M aqueous sodium hydrogen carbonate solution, dried over anhydrous magnesium sulfate and concentrated under reduced pressure. The residue was purified with silica gel column chromatography (hexane:ethyl acetate=9:1 to 1:1) to obtain the title compound (47 mg, yield 57%) as a diastereomer mixture. Diastereomer ratio (α:β=1:5).

Melting point 133-135° C.

$^1$H NMR (CDCl$_3$) δ 1.42 (9H of α, 9H of β, s), 2.10-2.20 (1H of α, 1H of β, m), 2.62-3.09 (2H of α, 2H of β, m), 3.50-4.10 (4H of α, 4H of β, m), 5.03-5.06 (1H of α, m), 5.68-5.71 (1H of β, m), 7.27-7.38 (5H of α, 5H of β, m).

Example 104

N-(4-Fluorophenyl)-tetrahydro-3-oxo-1-phenyl-3H-oxazolo[3,4-a]pyrazine-7(1H)-carboxamide To a solution of 1,1-dimethylethyl tetrahydro-3-oxo-1-phenyl-3H-oxazolo[3,4-a]pyrazine-7(1H)-carboxylate (94 mg, 0.30 mmol) in dichloromethane (5 mL) was added trifluoroacetic acid (0.5 mL), and the mixture was stirred at room temperature for 4 hours. The reaction solution was concentrated, and then ethyl acetate was added to the residue. The resulting mixture was washed with a 0.5 M aqueous sodium hydrogen carbonate solution (50 mL), dried over anhydrous magnesium sulfate and concentrated under reduced pressure. To the residue were added tetrahydrofuran (5 mL) and 4-fluorophenyl isocyanate (0.10 g, 0.73 mmol), and the mixture was stirred at 50° C. for 1 hour. The reaction solution was concentrated, and then the residue was purified with silica gel column chromatography (hexane:ethyl acetate=1:1 to ethyl acetate) to obtain the title compound (20 mg, yield 19%) as a diastereomer mixture. Diastereomer ratio (α:β=3:1).

Amorphous.

$^1$H NMR (CDCl$_3$) δ 2.31 (1H of α, t, J=13.3 Hz), 2.95-3.18 (2H of α, 3H of β, m), 3.58-3.62 (1H of α), 3.68-3.78 (1H of β, m), 3.83-3.96 (2H of α, 2H of β, m), 4.04-4.14 (1H of α, m), 4.43-4.48 (1H of β, m), 5.10 (1H of β, d, J=6.4 Hz), 5.73 (1H of α, d, J=8.2 Hz), 6.18 (1H of α, br), 6.32 (1H of β, br s), 6.95-7.03 (2H of α, 2H of β, m), 7.20-7.43 (7H of α, 7H of β, m).

Example 105

N-[(4-Fluorophenyl)methyl]-tetrahydro-3-oxo-1-phenyl-3H-oxazolo[3,4-a]pyrazine-7(1H)-carboxamide In the same manner as in Example 104, the title compound was obtained as a diastereomer mixture using 4-fluorobenzyl isocyanate instead of 4-fluorophenyl isocyanate. Yield 91%. Diastereomer ratio (α:β=5:2).

Amorphous.

$^1$H NMR (CDCl$_3$) δ 2.21 (1H of α, t, J=12.2 Hz), 2.82-2.90 (1H of α, 1H of β, m), 2.99-3.13 (1H of α, 2H of β, m), 3.56-3.72 (2H of α, 1H of β, m), 3.81-3.88 (1H of α, 2H of β, m), 3.96-4.03 (1H of α, m), 4.31-4.42 (2H of α, 3H of β, m), 4.72 (1H of α, br s), 4.82 (1H of β, br s), 5.06 (1H of β, d, J=7.1 Hz), 5.68 (1H of α, d, J=8.2 Hz), 6.96-7.01 (2H of α, 1H of β, m), 7.20-7.40 (7H of α, 8H of β, m).

Example 106

Phenyl tetrahydro-3-oxo-1-phenyl-3H-oxazolo[3,4-a]pyrazine-7(1H)-carboxylate

To a solution of 1,1-dimethylethyl tetrahydro-3-oxo-1-phenyl-3H-oxazolo[3,4-a]pyrazine-7(1H)-carboxylate (0.12 g, 0.38 mmol) in dichloromethane (5 mL) was added trifluoroacetic acid (1 mL), and the mixture was stirred at room temperature for 4 hours. The reaction solution was concentrated, and then ethyl acetate was added to the residue. The resulting mixture was washed with a 0.5 M aqueous sodium hydrogen carbonate solution, dried over anhydrous magnesium sulfate and concentrated under reduced pressure. To the residue were added tetrahydrofuran (5 mL), triethylamine (0.10 ml, 0.75 mmol) and phenyl chlorocarbonate (88 mg, 0.56 mmol), and the mixture was stirred at room temperature for 2 hours. To the reaction solution was added ethyl acetate, and the resulting mixture was washed with a 0.5 M aqueous sodium hydrogen carbonate solution, dried over magnesium sulfate and concentrated under reduced pressure. The residue was purified with silica gel column chromatography (hexane:ethyl acetate=9:1 to ethyl acetate) to obtain the title compound (0.10 g, yield 80%) as a diastereomer mixture. Diastereomer ratio (α:β=3:1).

Amorphous.

$^1$H NMR (CDCl$_3$) δ 2.28-2.56 (1H of α, m), 2.82-3.32 (2H of α, 3H of β, m), 3.71-3.77 (1H of α, 1H of β, m), 3.94-3.98 (1H of α, 1H of β, m), 4.07-4.11 (1H of α, m), 4.23-4.40 (1H of α, 1H of β, m), 4.53-4.58 (1H of β, m), 5.11 (1H of β, d, J=6.3 Hz), 5.74 (1H of α, d, J=8.3 Hz), 7.02-7.40 (10H of α, 10H of β, m).

Example 107

Tetrahydro-3-oxo-1,1-diphenyl-N-(8-quinolinyl)-3H-oxazolo[3,4-a]pyrazine-7(1H)-carboxamide 8-Quinolinecarboxylic acid (0.17 g, 1.0 mmol) was suspended in toluene (5 mL). With ice cooling, triethylamine (0.14 mL, 1.0 mmol) and diphenylphosphoryl azide (0.28 g, 1.0 mmol) were sequentially added thereto, and the mixture was stirred at room temperature for 1 hour and then at 80° C. for 3 hour. After cooling to 50° C., tetrahydrofuran (5 mL) and hexahydro-1,1-diphenyl-3H-oxazolo[3,4-a]pyrazin-3-one (88 mg, 0.30 mmol) were added thereto, and the mixture was stirred at 50° C. overnight. The reaction solution was cooled to room temperature and ethyl acetate was added thereto. The resulting mixture was washed with a 0.5 M aqueous sodium hydrogen carbonate solution, dried over anhydrous magnesium sulfate and concentrated under reduced pressure. The residue was purified with silica gel column chromatography (hexane:ethyl acetate=4:1 to ethyl acetate) to obtain the title compound (46 mg, yield 33%).

Amorphous.
$^1$H NMR (CDCl$_3$) δ 2.18-2.30 (1H, m), 2.82-3.10 (2H, m), 3.90-4.14 (2H, m), 4.40-4.82 (2H, m), 6.77-8.33 (16H, m), 14.48 (1H, br s).

Example 108

Tetrahydro-3-oxo-1,1-diphenyl-N-(4-quinolinyl)-3H-oxazolo[3,4-a]pyrazine-7(1H)-carboxamide In the same manner as in Example 107, the title compound was obtained using 4-quinolinecarboxylic acid instead of 8-quinolinecarboxylic acid. Yield 66%.
Melting point 238-241° C.
$^1$H NMR (CDCl$_3$) δ 2.37 (1H, t, J=12.1 Hz), 3.17-3.25 (2H, m), 3.94-4.11 (3H, m), 4.54 (1H, dd, J=3.3 Hz, 11.2 Hz), 7.08 (1H, br s), 7.35-7.41 (8H, m), 7.52-7.76 (5H, m), 7.93 (1H, d, J=5.0 Hz), 8.14 (1H, d, J=8.5 Hz), 8.82 (1H, d, J=5.1 Hz).

Example 109

Tetrahydro-N-(1H-indol-3-yl)-3-oxo-1,1-diphenyl-3H-oxazolo[3,4-a]pyrazine-7(1H)-carboxamide In the same manner as in Example 107, the title compound was obtained using 3-indolecarboxylic acid instead of 8-quinolinecarboxylic acid. Yield 60%.
Melting point 239-243° C.
$^1$H NMR (CDCl$_3$) δ 2.27 (1H, t, J=12.8 Hz), 3.01-3.24 (2H, m), 3.92 (2H, t, J=11.3 Hz), 4.05 (1H, d, J=14.0 Hz), 4.43-4.46 (1H, m), 6.24 (1H, s), 7.12-7.49 (14H, m), 7.95 (1H, br s).

Example 110

Tetrahydro-N-(2-hydroxy-3-pyridinyl)-3-oxo-1,1-diphenyl-3H-oxazolo[3,4-a]pyrazine-7(1H)-carboxamide In the same manner as in Example 107, the title compound was obtained using 2-hydroxynicotinic acid instead of 8-quinolinecarboxylic acid. Yield 69%.
Melting point 277-278° C.
$^1$H NMR (CDCl$_3$) δ 2.27 (1H, t, J=11.8 Hz), 2.99-3.20 (2H, m), 3.90-3.96 (2H, m), 4.09 (1H, t, J=6.8 Hz), 4.44-4.49 (1H, m), 6.32 (1H, t, J=6.8 Hz), 6.95 (1H, d, J=6.5 Hz), 7.26-7.47 (8H, m), 7.52-7.55 (2H, m), 7.77 (1H, s), 8.16 (1H, d, J=7.4 Hz), 10.61 (1H, br s).

Example 111

Tetrahydro-3-oxo-N-[5-oxo-2-pyrrolidinyl]-1,1-diphenyl-3H-oxazolo[3,4-a]pyrazine-7(1H)-carboxamide In the same manner as in Example 107, the title compound was obtained using DL-pyroglutamic acid instead of 8-quinolinecarboxylic acid. Yield 36%.

Amorphous.
$^1$H NMR (CDCl$_3$) δ 1.56-2.48 (6H, m), 2.78-3.08 (2H, m), 3.74-3.95 (3H, m), 4.39-4.42 (1H, m), 5.40-5.53 (1H, m), 6.49-6.63 (1H, m), 7.26-7.50 (10H, m).

Example 112

N-(Benzo[b]thien-3-yl)-tetrahydro-3-oxo-1,1-diphenyl-3H-oxazolo[3,4-a]pyrazine-7(1H)-carboxamide In the same manner as in Example 107, the title compound was obtained using 3-benzothiophenecarboxylic acid instead of 8-quinolinecarboxylic acid. Yield 41%.
Melting point 228-230° C.
$^1$H NMR (CDCl$_3$) δ 2.30 (1H, t, J=12.3 Hz), 3.09-3.22 (2H, m), 3.87-4.08 (3H, m), 4.49 (1H, dd, J=3.6 Hz, 11.3 Hz), 6.59 (1H, br s), 7.32-7.52 (13H, m), 7.61 (1H, s), 7.84-7.86 (1H, m).

Example 113

Tetrahydro-N-(1H-indol-2-yl)-3-oxo-1,1-diphenyl-3H-oxazolo[3,4-a]pyrazine-7(1H)-carboxamide In the same manner as in Example 107, the title compound was obtained using 2-indolecarboxylic acid instead of 8-quinolinecarboxylic acid. Yield 32%.

Amorphous.
$^1$H NMR (CDCl$_3$) δ 2.13-2.36 (1H, m), 2.62-2.90 (1H, m), 3.03-3.11 (1H, m), 3.80-3.90 (2H, m), 4.31-4.51 (2H, m), 4.69-4.83 (1H, m), 6.89-7.67 (15H, m), 11.20 (1H, br s).

Example 114

Tetrahydro-N-(1H-indol-4-yl)-3-oxo-1,1-diphenyl-3H-oxazolo[3,4-a]pyrazine-7(1H)-carboxamide In the same manner as in Example 107, the title compound was obtained using 4-indolecarboxylic acid instead of 8-quinolinecarboxylic acid. Yield 61%.
Melting point 143-145° C.
$^1$H NMR (CDCl$_3$) δ 2.26 (1H, t, J=12.6 Hz), 2.95-3.21 (2H, m), 3.88-4.01 (3H, m), 4.41 (1H, dd, J=3.4 Hz, 11.1 Hz), 6.41-6.44 (2H, m), 7.16-7.46 (14H, m), 8.28 (1H, br s).

Example 115

Tetrahydro-N-(1H-indole-5-yl)-3-oxo-1,1-diphenyl-3H-oxazolo[3,4-a]pyrazine-7(1H)-carboxamide In the same manner as in Example 107, the title compound was obtained using 5-indolecarboxylic acid instead of 8-quinolinecarboxylic acid. Yield 76%.
Melting point 263-265° C.
$^1$H NMR (CDCl$_3$) δ 2.22 (1H, t, J=11.5 Hz), 2.88-3.17 (2H, m), 3.84-3.92 (2H, m), 4.00-4.05 (1H, m), 4.45 (1H, dd, J=3.4 Hz, 11.2 Hz), 6.30 (1H, s), 6.51 (1H, s), 7.04-7.55 (14H, m), 8.16 (1H, br s).

Example 116

Tetrahydro-N-(1H-indol-6-yl)-3-oxo-1,1-diphenyl-3H-oxazolo[3,4-a]pyrazine-7(1H)-carboxamide In the same manner as in Example 107, the title compound was obtained using 6-indolecarboxylic acid instead of 8-quinolinecarboxylic acid. Yield 50%.

Melting point 258-260° C.

$^1$H NMR (CDCl$_3$) δ 2.15 (1H, t, J=11.1 Hz), 2.70-2.77 (1H, m), 3.08-3.16 (1H, m), 3.61-3.66 (1H, m), 3.93-4.11 (2H, m), 4.58-4.63 (1H, m), 6.30 (1H, s), 6.94 (1H, d, J=8.5 Hz), 7.18-7.20 (1H, m), 7.33-7.43 (9H, m), 7.57-7.60 (3H, m), 8.57 (1H, br), 10.87 (1H, br s).

Example 117

N-(2,3-Dihydro-3-oxo-1H-isoindol-1-yl)-tetrahydro-3-oxo-1,1-diphenyl-3H-oxazolo[3,4-a]pyrazine-7(1H)-carboxamide In the same manner as in Example 107, the title compound was obtained as a diastereomer mixture using 2,3-dihydro-3-oxo-1H-isoindole-1-carboxylic acid instead of 8-quinolinecarboxylic acid. Yield 32%. Diastereomer ratio (α:β=1:1).

Melting point 152-156° C.

$^1$H NMR (CDCl$_3$) δ 2.18-2.27 (1H of α, 1H of β, m), 2.80-2.89 (1H of α, 1H of β, m), 3.04-3.13 (1H of α, 1H of β, m), 3.80-3.89 (2H of α, 2H of β, m), 4.03-4.15 (1H of α, 1H of β, m), 4.36-4.41 (1H of α or β, m), 4.48-4.54 (1H of α or β, m), 5.71-5.74 (1H of α or β, m), 5.83 (1H of α or β, br), 6.29-6.38 (1H of α, 1H of β, 1H of α or β, m), 6.82 (1H of α or β, br), 7.26-7.39 (9H of α, 9H of β, m), 7.49-7.59 (5H of α, 5H of β, m).

Example 118

Tetrahydro-N-(6-hydroxy-2-pyridinyl)-3-oxo-1,1-diphenyl-3H-oxazolo[3,4-a]pyrazine-7(1H)-carboxamide In the same manner as in Example 107, the title compound was obtained using 6-hydroxypicolinic acid instead of 8-quinolinecarboxylic acid. Yield 55%.

Melting point 260-263° C.

$^1$H NMR (DMSO-d$_6$) δ 2.24-2.32 (1H, m), 2.73-2.85 (1H, m), 3.11-3.18 (1H, m), 3.63-3.67 (1H, m), 3.84-3.87 (1H, m), 4.01-4.07 (1H, m), 4.67-4.71 (1H, m), 6.02 (1H, br s), 7.34-7.46 (9H, m), 7.59-7.62 (2H, m), 9.27 (1H, br s), 10.30 (1H, br s), 11.44 (1H, br s).

Example 119

Tetrahydro-N-(6-hydroxy-3-pyridinyl)-3-oxo-1,1-diphenyl-3H-oxazolo[3,4-a]pyrazine-7(1H)-carboxamide In the same manner as in Example 107, the title compound was obtained using 6-hydroxynicotinic acid instead of 8-quinolinecarboxylic acid. Yield 26%.

Melting point 259° C.

$^1$H NMR (DMSO-d$_6$) δ 2.07-2.18 (1H, m), 2.71-2.79 (1H, m), 3.06-3.13 (1H, m), 3.59-3.64 (1H, m), 3.86-4.00 (2H, m), 4.55-4.60 (1H, m), 6.27 (1H, d, J=9.7 Hz), 7.09-7.17 (1H, m), 7.30-7.44 (9H, m), 7.55-7.58 (2H, m), 8.98 (1H, br s), 11.29 (1H, br s).

Example 120

Tetrahydro-γ,3-dioxo-1,1-diphenyl-3H-oxazolo[3,4-a]pyrazine-7(1H)-butanoic acid

To a solution of hexahydro-1,1-diphenyl-3H-oxazolo[3,4-a]pyrazin-3-one (0.15 g, 0.50 mmol) in tetrahydrofuran (10 mL) were added triethylamine (0.14 mL, 1.0 mmol) and succinic anhydride (55 mg, 0.55 mmol), and the mixture was stirred at room temperature for 2 hours. To the reaction solution was added ethyl acetate, and the resulting mixture was washed with 2 M hydrochloric acid, dried over anhydrous magnesium sulfate and concentrated under reduced pressure. The residue was purified with silica gel column chromatography (hexane:ethyl acetate=1:1 to ethyl acetate). The fractions were concentrated, and to the residue was added diethyl ether. The resulting crystals were collected by filtration and washed with diethyl ether to obtain the title compound (99 mg, yield 50%).

Melting point 158-164° C.

Amide rotamer ratio (α:β=7:3).

$^1$H NMR (CDCl$_3$) δ 1.99-2.07 (1H of α, m), 2.42-2.46 (1H of β, m), 2.52-2.72 (4H of α, 5H of β, m), 3.06-3.10 (2H of α, 1H of β, m), 3.50-3.52 (1H of β, m), 3.78-3.96 (2H of α, 1H of β, m), 4.33-4.38 (1H of α, m), 4.45-4.49 (1H of α, 1H of β, m), 4.59-4.64 (1H of β, m), 7.17-7.52 (10H of α, 10H of β, m).

Example 121

Hexahydro-7-[(4-morpholinyl)acetyl]-1,1-diphenyl-3H-oxazolo[3,4-a]pyrazin-7(1H)-3-one To a solution of hexahydro-1,1-diphenyl-3H-oxazolo[3,4-a]pyrazin-3-one (0.15 g, 0.50 mmol) in tetrahydrofuran (10 mL) were sequentially added triethylamine (0.14 mL, 1.0 mmol) and chloroacetyl chloride (62 mg, 0.55 mmol), and the mixture was stirred at room temperature for 30 minutes. Morpholine (0.87 g, 10 mmol) and sodium iodide (0.15 g, 1.0 mmol) were added thereto, and the mixture was further stirred at room temperature for 5 hours. To the reaction solution was added ethyl acetate, and the resulting mixture was washed with a 0.5 M aqueous sodium hydrogen carbonate solution, dried over anhydrous magnesium sulfate and concentrated under reduced pressure. The residue was purified with silica gel column chromatography (hexane:ethyl acetate=1:1 to ethyl acetate). The fractions were concentrated, and to the residue was added diethyl ether-ethyl acetate. The resulting crystals were collected by filtration and washed with diethyl ether to obtain the title compound (0.16 g, yield 76%).

Melting point 175-177° C.

Amide rotamer ratio (α:β=1:1).

$^1$H NMR (CDCl$_3$) δ 1.95-2.04 (1H of α, m), 2.45-2.77 (5H of α, 5H of β, m), 2.95-3.28 (3H of α, 4H of β, m), 3.70-3.94 (5H of α, 6H of β, m), 4.11-4.15 (1H of α, m), 4.26-4.31 (1H of α, m), 4.42-4.55 (1H of α, 2H of β, m), 7.26-7.56 (10H of α, 10H of β, m).

Example 122

7-Acetyl-hexahydro-1,1-diphenyl-3H-oxazolo[3,4-a]pyrazin-7(1H)-3-one

In the same manner as in Example 120, the title compound was obtained using anhydrous acetic acid instead of succinic anhydride. Yield 58%.

Melting point 226-227° C.

Amide rotamer ratio (α:β=7:3).

$^1$H NMR (CDCl$_3$) δ 1.93-2.01 (1H of α, 1H of β, m), 2.06 (3H of β, s), 2.13 (3H of α, s), 2.53-2.61 (1H of α, m), 2.98-3.13 (1H of α, 2H of β, m), 3.38-3.42 (1H of β, m), 3.73-3.77 (1H of α, m), 3.88-3.93 (1H of α, 1H of β, m), 4.31-4.39 (1H of α, 1H of β, m), 4.49-4.54 (1H of α, m), 4.60-4.65 (1H of β), 7.26-7.61 (10H of α, 10H of β, m).

Example 123

Hexahydro-7-[3-(4-morpholinyl)-1-oxopropyl]-1,1-diphenyl-3H-oxazolo[3,4-a]pyrazin-7(1H)-3-one In the same manner as in Example 121, the title compound was obtained using 3-chloropropionyl chloride instead of chloroacetyl chloride. Yield 68%.

Melting point 173-175° C.

Amide rotamer ratio (α:β=7:3).

$^1$H NMR (CDCl$_3$) δ 1.95-2.05 (1H of α, m), 2.47-2.56 (6H of α, 8H of β, m), 2.68-2.70 (2H of α, 2H of β, m), 2.98-3.06 (2H of α, 1H of β), 3.47-3.50 (1H of β, m), 3.68-3.70 (4H of α, 4H of β, m), 3.75-3.80 (1H of α, m), 3.83-3.95 (1H of α, 1H of β, m), 4.31-4.35 (1H of α, 1H of β, m), 4.49-4.54 (1H of α, m), 4.62-4.66 (1H of β), 7.26-7.52 (10H of α, 10H of β, m).

Example 124

1,1-Dimethylethyl 4-[[(tetrahydro-3-oxo-1,1-diphenyl-3H-oxazolo[3,4-a]pyrazin-7(1H)-yl)carbonyl]amino]-1H-benzimidazole-1-carboxylate To a solution of 1,1-dimethylethyl 4-amino-1H-benzimidazole-1-carboxylate (0.12 g, 0.50 mmol) in tetrahydrofuran (10 ml) were added diisopropylethylamine (90 μL, 0.50 mmol) and 4-nitrophenyl chloroformate (0.11 g, 0.50 mmol), and the mixture was stirred at room temperature for 4 hours. Hexahydro-1,1-diphenyl-3H-oxazolo[3,4-a]pyrazin-3-one (88 mg, 0.30 mmol) and diisopropylethylamine (90 μL, 0.50 mmol) were sequentially added thereto, and the mixture was stirred at room temperature overnight. To the reaction solution were added ethyl acetate (50 mL) and a 0.5 M aqueous sodium hydrogen carbonate solution (50 mL), and the obtained crystals were collected by filtration. The crude crystals were sequentially washed with a 0.5 M aqueous sodium hydrogen carbonate solution, water and ethyl acetate to obtain the title compound (0.11 g, yield 65%).

Melting point 183-185° C.

$^1$H NMR (CDCl$_3$) δ 1.71 (9H, s), 2.25-2.34 (1H, m), 3.10-3.26 (2H, m), 3.94-4.00 (2H, m), 4.17-4.21 (1H, m), 4.50-4.55 (1H, m), 7.26-7.36 (9H, m), 7.52-7.55 (3H, m), 7.69-7.71 (1H, m), 8.00-8.02 (1H, m), 8.32-8.35 (1H, m).

Example 125

N-(1H-Benzimidazole-4-yl)-tetrahydro-3-oxo-1,1-diphenyl-3H-oxazolo[3,4-a]pyrazine-7(1H)-carboxamide hydrochloride 1,1-Dimethylethyl 4-[[(tetrahydro-3-oxo-1,1-diphenyl-3H-oxazolo[3,4-a]pyrazin-7(1H)-yl)carbonyl]amino]-1H-benzimidazole-1-carboxylate (74 mg, 0.13 mmol) was suspended in ethyl acetate (5 mL). A 4 M hydrogen chloride/ethyl acetate solution (6 mL) was added thereto, and the mixture was stirred at room temperature overnight. The reaction solution was concentrated, and then ethyl acetate was added to the residue. The obtained crystals were collected by filtration and washed with ethyl acetate to obtain the title compound (51 mg, yield 79%).

Melting point 201-203° C.

$^1$H NMR (DMSO-d$_6$) δ 2.30 (1H, t, J=11.8 Hz), 2.88-2.92 (1H, m), 3.21-3.26 (1H, m), 3.69-3.74 (1H, m), 3.98-4.16 (2H, m), 4.79-4.83 (1H, m), 7.28-7.65 (13H, m), 9.43 (2H, s).

Example 126

Hexahydro-7-[4-(4-morpholinyl)-1-oxobutyl]-1,1-diphenyl-3H-oxazolo[3,4-a]pyrazin-7(1H)-3-one In the same manner as in Example 121, the title compound was obtained using 4-chlorobutyryl chloride instead of chloroacetyl chloride. Yield 32%.

Melting point 138-139° C.

Amide rotamer ratio (α:β=1:3).

$^1$H NMR (CDCl$_3$) δ 1.80-1.85 (2H of α, 2H of β, m), 1.94-2.05 (1H of β, m), 2.34-2.54 (10H of α, 8H of β, m), 3.01-3.08 (1H of α, 2H of β, m), 3.51-3.68 (5H of α, 4H of β, m), 3.84-3.94 (1H of α, 2H of β, m), 4.31-4.34 (1H of α, 1H of β, m), 4.50-4.54 (1H of β, m), 4.58-4.63 (1H of α, m), 7.25-7.39 (8H of α, 8H of β, m), 7.50-7.52 (2H of α, 2H of β, m).

Example 127

1,1-Dimethylethyl methyl [[3-[(tetrahydro-3-oxo-1,1-diphenyloxazolo[3,4-a]pyrazin-7(1H)-yl)carbonyl]phenyl]methyl]carbamate To a solution of 1,1-dimethylethyl [[3-[(tetrahydro-3-oxo-1,1-diphenyloxazolo[3,4-a]pyrazin-7(1H)-yl)carbonyl]phenyl]methyl]carbamate (0.20 g, 0.38 mmol) in N,N-dimethylformamide (5 mL) was added 60% sodium hydride (15 mg, 0.38 mmol) under argon atmosphere, and the mixture was stirred at room temperature for 30 minutes. Methyl iodide (54 mg, 0.38 mmol) was added thereto, and the resulting mixture was stirred at room temperature overnight. To the reaction solution was added ethyl acetate, and the resulting mixture was washed with a 0.5 M aqueous sodium hydrogen carbonate solution, dried over anhydrous magnesium sulfate and concentrated under reduced pressure. To the residue was added hexane-ethyl acetate, and then the obtained crystals were collected by filtration and washed with hexane to obtain the title compound (0.17 g, yield 82%).

Melting point 194-195° C.

$^1$H NMR (CDCl$_3$) δ 1.46 (9H, s), 2.15-2.20 (1H, m), 2.80-2.83 (3H, m), 2.91-3.02 (2H, m), 3.81-3.90 (2H, m), 4.40-4.50 (4H, m), 7.26-7.52 (14H, m).

Example 128

1,1-Dimethylethyl [[4-[(tetrahydro-3-oxo-1,1-diphenyloxazolo[3,4-a]pyrazin-7(1H)-yl)carbonyl]phenyl]methyl]carbamate In the same manner as in Example 144, the title compound was obtained using 4-[[(tert-butoxycarbonyl)amino]methyl]benzoic acid instead of 3-[[(tert-butoxycarbonyl)amino]methyl]benzoic acid. Yield 74%.

Amorphous.

$^1$H NMR (CDCl$_3$) δ 1.47 (9H, s), 2.18-2.24 (1H, m), 2.95-3.03 (2H, m), 3.72-3.85 (2H, m), 4.35-4.54 (4H, m), 4.90 (1H, br s), 7.30-7.51 (14H, m).

Example 129

N-(2,3-Dihydro-2-oxo-1H-indol-4-yl)-tetrahydro-3-oxo-1,1-diphenyl-3H-oxazolo[3,4-a]pyrazine-7(1H)-carboxamide In the same manner as in Example 124, the title compound was obtained using 4-amino-1,3-dihydro-2H-indol-2-one instead of 1,1-dimethylethyl 4-amino-1H-benzimidazole-1-carboxylate. Yield 34%.
Melting point 200-201° C.
¹H NMR (CDCl₃) δ 2.24-2.32 (1H, m), 3.03-3.17 (2H, m), 3.43 (2H, s), 3.81-4.00 (3H, m), 4.46-4.51 (1H, m), 6.16 (1H, s), 6.66 (1H, d, J=7.7 Hz), 6.96 (1H, d, J=8.1 Hz), 7.10-7.40 (9H, m), 7.50-7.58 (3H, m).

Example 130

3-[(Hexahydro-3-oxo-1,1-diphenyl-3H-oxazolo[3,4-a]pyrazin-7(1H)-yl)carbonyl]-N-methylbenzenemethanamine hydrochloride In the same manner as in Example 125, the title compound was obtained using 1,1-dimethylethyl methyl [[3-[(tetrahydro-3-oxo-1,1-diphenyloxazolo[3,4-a]pyrazin-7(1H)-yl)carbonyl]phenyl]methyl]carbamate instead of 1,1-dimethylethyl 4-[[[tetrahydro-3-oxo-1,1-diphenyl-3H-oxazolo[3,4-a]pyrazin-7(1H)-yl]carbonyl]amino]-1H-benzimidazole-1-carboxylate. Yield 86%.
Melting point 241-242° C.
¹H NMR (DMSO-d₆) δ 2.28-2.34 (1H, m), 2.54 (3H, s), 2.95-3.05 (1H, m), 3.18-3.26 (1H, m), 3.55-3.63 (1H, m), 4.10-4.23 (4H, m), 4.78-4.84 (1H, m), 7.35-7.67 (14H, m), 8.84 (2H, br s).

Example 131

4-[(Hexahydro-3-oxo-1,1-diphenyl-3H-oxazolo[3,4-a]pyrazin-7(1H)-yl)carbonyl]benzenemethanamine hydrochloride In the same manner as in Example 125, the title compound was obtained using 1,1-dimethylethyl [[4-[(tetrahydro-3-oxo-1,1-diphenyloxazolo[3,4-a]pyrazin-7(1H)-yl)carbonyl]phenyl]methyl]carbamate instead of 1,1-dimethylethyl 4-[[[tetrahydro-3-oxo-1,1-diphenyl-3H-oxazolo[3,4-a]pyrazin-7(1H)-yl]carbonyl]amino]-1H-benzimidazole-1-carboxylate. Yield 64%.
Melting point 237-240° C.
¹H NMR (DMSO-d₆) δ 2.26-2.32 (1H, m), 2.92-3.45 (3H, m), 3.54-3.62 (1H, m), 4.00-4.29 (3H, m), 4.77-4.85 (1H, m), 7.35-7.59 (14H, m), 8.20 (2H, br s).

Example 132

Hexahydro-7-[5-(4-morpholinyl)-1-oxopentyl]-1,1-diphenyl-3H-oxazolo[3,4-a]pyrazin-7(1H)-3-one Hexahydro-1,1-diphenyl-3H-oxazolo[3,4-a]pyrazin-3-one (0.15 g, 0.50 mmol) was dissolved in tetrahydrofuran (10 mL). 1-Ethyl-3-(3-dimethylaminopropyl)carbodiimide hydrochloride (0.12 g, 0.60 mmol), 1-hydroxybenzotriazole (81 mg, 0.60 mmol) and 5-bromovaleric acid (0.11 g, 0.60 mmol) were added thereto, and the mixture was stirred at room temperature overnight. To the reaction solution was added ethyl acetate, and the resulting mixture was washed with 1 M hydrochloric acid, dried over anhydrous magnesium sulfate and concentrated under reduced pressure. The residue was dissolved in tetrahydrofuran (10 mL). Diisopropylethylamine (0.17 mL, 1.0 mmol) and morpholine (0.87 g, 10 mmol) were added thereto, and the mixture was stirred at room temperature for 2 days. To the reaction solution was added ethyl acetate, and the resulting mixture was washed with a 0.5 M aqueous sodium hydrogen carbonate solution, dried over anhydrous magnesium sulfate and concentrated under reduced pressure. The residue was purified with amino silica gel column chromatography (hexane:ethyl acetate=9:1 to ethyl acetate). The fractions were concentrated, and to the residue was added hexane-ethyl acetate. The obtained crystals were collected by filtration and washed with hexane to obtain the title compound (0.11 g, yield 46%).
Melting point 92-96° C.
Amide rotamer ratio (α:β=1:3.2).
¹H NMR (CDCl₃) δ 1.50-1.72 (4H of α, 4H of β, m), 1.97 (1H of β, t, J=11.9 Hz), 2.28-2.54 (10H of α, 8H of β, m), 2.98-3.06 (1H of α, 2H of β, m), 3.44-3.47 (1H of α, m), 3.68-3.71 (4H of α, 4H of β, m), 3.76-3.80 (1H of β, m), 3.88-3.95 (1H of α, 1H of β, m), 4.30-4.35 (1H of α, 1H of β, m), 4.50-4.54 (1H of β, m), 4.61-4.66 (1H of α, m), 7.32-7.61 (10H of α, 10H of β, m).

Example 133

Hexahydro-7-[1-oxo-4-(1-piperidinyl)butyl]-1,1-diphenyl-3H-oxazolo[3,4-a]pyrazin-7(1H)-3-one In the same manner as in Example 121, the title compound was obtained using 4-chlorobutyryl chloride instead of chloroacetyl chloride, and using piperidine instead of morpholine. Yield 50%.
Melting point 129-130° C.
Amide rotamer ratio (α:β=1:3).
¹H NMR (CDCl₃) δ 1.41-1.56 (6H of α, 6H of β, m), 1.76-1.85 (2H of α, 2H of β, m), 1.97 (1H of β, t, J=12.5 Hz), 2.27-2.39 (8H of α, 8H of β, m), 2.47-2.53 (2H of α, m), 2.97-3.08 (1H of α, 2H of β, m), 3.49-3.58 (1H of α, m), 3.86-3.93 (1H of α, 2H of β, m), 4.30-4.35 (1H of α, 1H of β, m), 4.49-4.55 (1H of β, m), 4.61-4.67 (1H of α, m), 7.31-7.61 (10H of α, 10H of β, m).

Example 134

7-(4-Chloro-1-oxobutyl)-hexahydro-1,1-diphenyl-3H-oxazolo[3,4-a]pyrazin-7(1H)-3-one Hexahydro-1,1-diphenyl-3H-oxazolo[3,4-a]pyrazin-3-one (1.0 g, 3.4 mmol) was dissolved in tetrahydrofuran (50 mL). Triethylamine (0.96 mL, 6.8 mmol) and 4-chlorobutyryl chloride (0.42 mL, 3.7 mmol) were added thereto, and the mixture was stirred at room temperature for 1 hour. To the reaction solution was added ethyl acetate, and the resulting mixture was washed with a 0.5 M aqueous sodium hydrogen carbonate solution, dried over anhydrous magnesium sulfate and concentrated under reduced pressure. To the residue was added hexane-ethyl acetate. Then, the obtained crystals were collected by filtration and washed with hexane to obtain the title compound (1.2 g, yield 85%).
Melting point 144-145° C.
Amide rotamer ratio (α:β=1:2.4).
¹H NMR (CDCl₃) δ 1.99 (1H of β, t, J=12.5 Hz), 2.10-2.16 (2H of α, 2H of β, m), 2.32-2.37 (1H of α, m), 2.48-2.60 (3H of α, 2H of β, m), 2.99-3.12 (1H of α, 2H of β, m), 3.52-3.65 (3H of α, 2H of β, m), 3.83-3.96 (1H of α, 2H of β, m), 4.31-4.40 (1H of α, 1H of β, m), 4.48-4.53 (1H of β, m), 4.62-4.66 (1H of α, m), 7.28-7.52 (10H of α, 10H of β, m).

Example 135

Hexahydro-7-[6-(4-morpholinyl)-1-oxohexyl]-1,1-diphenyl-3H-oxazolo[3,4-a]pyrazin-7(1H)-3-one In the same manner as in Example 132, the title compound was obtained using 6-bromohexanoic acid instead of 5-bromovaleric acid. Yield 38%.
Melting point 112° C.
Amide rotamer ratio (α:β=1:3.4).
$^1$H NMR (CDCl$_3$) δ 1.34-1.37 (2H of α, 2H of β, m), 1.45-1.67 (4H of α, 4H of β, m), 1.93-2.01 (1H of β, m), 2.20-2.57 (10H of α, 8H of β, m), 2.95-3.03 (1H of α, 2H of β, m), 3.45-3.48 (1H of α, m), 3.70-3.78 (4H of α, 5H of β, m), 3.91-3.95 (1H of α, 1H of β, m), 4.31-4.35 (1H of α, 1H of β, m), 4.50-4.55 (1H of β, m), 4.62-4.66 (1H of α, m), 7.32-7.50 (10H of α, 10H of β, m).

Example 136

Hexahydro-7-[1-oxo-5-(1-piperidinyl)pentyl]-1,1-diphenyl-3H-oxazolo[3,4-a]pyrazin-7(1H)-3-one In the same manner as in Example 132, the title compound was obtained using piperidine instead of morpholine. Yield 18%.
Melting point 93-94° C.
Amide rotamer ratio (α:β=1:3).
$^1$H NMR (CDCl$_3$) δ 1.42-1.67 (10H of α, 10H of β, m), 1.96 (1H of β, t, J=11.7 Hz), 2.22-2.58 (10H of α, 8H of β, m), 2.97-3.08 (1H of α, 2H of β, m), 3.47-3.51 (1H of α, m), 3.82-3.94 (1H of α, 2H of β, m), 4.30-4.35 (1H of α, 1H of β, m), 4.50-4.54 (1H of β, m), 4.61-4.66 (1H of α, m), 7.32-7.61 (10H of α, 10H of β, m).

Example 137

7-[5-(3,6-Dihydropyridin-1(2H)-yl)-1-oxopentyl]-hexahydro-1,1-diphenyl-3H-oxazolo[3,4-a]pyrazin-7(1H)-3-one In the same manner as in Example 132, the title compound was obtained using 1,2,3,6-tetrahydropyridine instead of morpholine. Yield 46%.
Amorphous.
Amide rotamer ratio (α:β=1:3.3).
$^1$H NMR (CDCl$_3$) δ 1.55-1.67 (4H of α, 4H of β, m), 1.96 (1H of β, t, J=11.9 Hz), 2.13-2.17 (2H of α, 2H of β, m), 2.26-2.43 (4H of α, 4H of β, m), 2.50-2.54 (4H of α, 2H of β, m), 2.93-2.95 (2H of α, 2H of β, m), 3.00-3.04 (1H of α, 2H of β, m), 3.45-3.51 (1H of α, m), 3.83-3.93 (1H of α, 2H of β, m), 4.29-4.34 (1H of α, 1H of β, m), 4.49-4.55 (1H of β, m), 4.61-4.66 (1H of α, m), 5.63-5.75 (2H of α, 2H of β, m), 7.30-7.50 (10H of α, 10H of β, m).

Example 138

7-[4-(3,6-Dihydropyridin-1(2H)-yl)-1-oxobutyl]-hexahydro-1,1-diphenyl-3H-oxazolo[3,4-a]pyrazin-7(1H)-3-one In the same manner as in Example 121, the title compound was obtained using 4-chlorobutyryl chloride instead of chloroacetyl chloride, and using 1,2,3,6-tetrahydropyridine instead of morpholine. Yield 27%.
Amorphous.
Amide rotamer ratio (α:β=1:4).
$^1$H NMR (CDCl$_3$) δ 1.83-2.01 (2H of α, 3H of β, m), 2.12-2.16 (2H of α, 2H of β, m), 2.26-2.52 (8H of α, 6H of β, m), 2.93-3.08 (3H of α, 4H of β, m), 3.54-3.59 (1H of α, m), 3.85-3.92 (1H of α, 2H of β, m), 4.31-4.35 (1H of α, 1H of β, m), 4.51-4.55 (1H of β, m), 4.62-4.66 (1H of α, m), 5.63-5.71 (2H of α, 2H of β, m), 7.31-7.66 (10H of α, 10H of β, m).

Example 139

Hexahydro-7-[1-oxo-4-(1-pyrrolidinyl)butyl]-1,1-diphenyl-3H-oxazolo[3,4-a]pyrazin-7(1H)-3-one In the same manner as in Example 121, the title compound was obtained using 4-chlorobutyryl chloride instead of chloroacetyl chloride, and using pyrrolidine instead of morpholine. Yield 26%.
Melting point 87-89° C.
Amide rotamer ratio (α:β=1:2.6).
$^1$H NMR (CDCl$_3$) δ 1.73-1.88 (6H of α, 6H of β, m), 1.97 (1H of β, t, J=12.2 Hz), 2.32-2.49 (10H of α, 8H of β, m), 2.97-3.08 (1H of α, 2H of β, m), 3.55-3.59 (1H of α, m), 3.82-3.93 (1H of α, 2H of β, m), 4.30-4.35 (1H of α, 1H of β, m), 4.50-4.55 (1H of β, m), 4.63-4.67 (1H of α, m), 7.27-7.52 (10H of α, 10H of β, m).

Example 140

1,1-Dimethylethyl 4-[[(tetrahydro-3-oxo-1,1-diphenyl-3H-oxazolo[3,4-a]pyrazin-7(1H)-yl)carbonyl]amino]-1-piperidinecarboxylate In the same manner as in Example 124, the title compound was obtained using 1,1-dimethylethyl 4-amino-1-piperidinecarboxylate instead of 1,1-dimethylethyl 4-amino-1H-benzimidazole-1-carboxylate. Yield 42%.
Melting point 208-209° C.
$^1$H NMR (CDCl$_3$) δ 1.22-1.30 (2H, m), 1.45 (9H, s), 1.90-1.95 (2H, m), 2.09-2.17 (1H, m), 2.79-2.95 (3H, m), 3.04-3.14 (1H, m), 3.55-3.61 (1H, m), 3.71-3.88 (2H, m), 3.97-4.07 (3H, m), 4.22-4.26 (1H, m), 4.41 (1H, dd, J=3.7 Hz, 11.3 Hz), 7.27-7.41 (8H, m), 7.50-7.61 (2H, m).

Example 141

Tetrahydro-3-oxo-1,1-diphenyl-N-(4-piperidinyl)-3H-oxazolo[3,4-a]pyrazine-7(1H)-carboxamide hydrochloride In the same manner as in Example 125, the title compound was obtained using 1,1-dimethylethyl 4-[[(tetrahydro-3-oxo-1,1-diphenyl-3H-oxazolo[3,4-a]pyrazin-7(1H)-yl)carbonyl]amino]-1-piperidinecarboxylate instead of 1,1-dimethylethyl 4-[[(tetrahydro-3-oxo-1,1-diphenyl-3H-oxazolo[3,4-a]pyrazin-7(1H)-yl)carbonyl]amino]-1H-benzimidazole-1-carboxylate. Yield 60%.
Melting point 206-210° C.
$^1$H NMR (DMSO-d$_6$) δ 1.55-1.64 (2H, m), 1.81-1.91 (2H, m), 1.97-2.08 (1H, m), 2.60-2.71 (1H, m), 2.87-3.06 (3H, m), 3.22-3.38 (2H, m), 3.56-3.65 (2H, m), 3.84-3.92 (2H, m), 4.45-4.50 (1H, m), 6.67 (1H, br s), 7.30-7.45 (8H, m), 7.55-7.57 (2H, m), 8.51 (1H, br s).

Example 142

7-[(2,3-Dihydro-3-oxo-1H-isoindol-1-yl)carbonyl]-hexahydro-1,1-diphenyl-3H-oxazolo[3,4-a]pyrazin-3-one (Single Diastereomer)

In the same manner as in Reference Example 19, the reaction was performed using 2,3-dihydro-3-oxo-1H-isoindole-1-carboxylic acid instead of 1,4-bis(phenylmethyl)-2-piperazine carboxylic acid, and using hexahydro-1,1-diphenyl-3H-oxazolo[3,4-a]pyrazin-3-one instead of N,O-dimethylhydroxylamine hydrochloride and triethylamine. The reaction solution was extracted with ethyl acetate, washed with a 0.5 M aqueous sodium hydrogen carbonate solution, dried over anhydrous magnesium sulfate and concentrated under reduced pressure. To the residue was added hexane-ethyl acetate. Then, the obtained crystals were collected by filtration and washed with hexane to obtain the title compound. Yield 14%.

Melting point 227-228° C.

Amide rotamer ratio (α:β=1:1).

$^1$H NMR (DMSO-d$_6$) δ 2.14-2.27 (2H of α or β, m), 2.65-2.72 (1H of α or β, m), 2.82-2.91 (1H of α or β, m), 3.00-3.09 (1H of α or β, m), 3.40-3.49 (1H of α or β, m), 3.69-3.82 (2H of α or β, m), 3.91-3.95 (1H of α or β, m), 4.06-4.10 (1H of α or β, m), 4.27-4.32 (1H of α or β, m), 4.39-4.43 (1H of α or β, m), 4.60-4.65 (2H of α or β, m), 5.83 (1H of α or β, s), 5.90 (1H of α or β, s), 7.13-7.69 (14H of α, 14H of β, m), 8.65 (1H of α or β, br s), 8.88 (1H of α or β, br s).

Example 143

7-[(2,3-Dihydro-3-oxo-1H-isoindol-1-yl)carbonyl]-hexahydro-1,1-diphenyl-3H-oxazolo[3,4-a]pyrazin-3-one (Diastereomer Mixture)

The mother liquor, which was used during the crystallization process of Example 142, was purified with silica gel column chromatography (hexane:ethyl acetate=9:1 to ethyl acetate). Hexane-diisopropyl ether was added thereto. Then, the obtained crystals were collected by filtration and washed with hexane to obtain the title compound. Yield 36%.

Melting point 200-202° C.

Diastereomer A (identical with the compound of Example 142):diastereomer B=1:2.

Amide rotamer ratio of diastereomer A (α:β=1:1).

Amide rotamer ratio of diastereomer B (α':β'=1:2).

$^1$H NMR (DMSO-d$_6$) δ 2.17-4.81 (7H of α, 7H of α, 7H of α', 7H of β', m), 5.70 (1H of α', s), 5.81 (1H of α or β, s), 5.88 (1H of α or β, s), 5.91 (1H of β', s), 7.11-7.64 (14H of α, 14H of β, 14H of α', 14H of β', m), 8.64-8.67 (1H of α or β, 1H of β', br s), 8.87 (1H of α or β, br), 9.00 (1H of α', br s).

Example 144

1,1-Dimethylethyl [[3-[(tetrahydro-3-oxo-1,1-diphenyl-3H-oxazolo[3,4-a]pyrazin-7(1H)-yl)carbonyl]phenyl]methyl]carbamate

To a solution of hexahydro-1,1-diphenyl-3H-oxazolo[3,4-a]pyrazin-3-one (0.20 g, 0.67 mmol), 3-[[(tert-butoxycarbonyl)amino]methyl]benzoic acid (0.17 g, 0.67 mmol), 1-hydroxybenzotriazole (0.10 g, 0.74 mmol) and triethylamine (69 mg, 0.68 mmol) in acetonitrile (10 mL) was added 1-ethyl-3-(3-dimethylaminopropyl)carbodiimide hydrochloride (0.20 g, 1.0 mmol), and the mixture was stirred at room temperature for 15 hours. To the reaction solution were added ethyl acetate and water. The separated organic layer was washed with saturated brine, dried over sodium sulfate, and then concentrated. The residue was purified with silica gel column chromatography (hexane:ethyl acetate=3:1 to 3:7) to obtain the title compound (0.27 g, yield 75%).

Amorphous.

$^1$H-NMR (CDCl$_3$) δ 1.45 (9H, s), 2.22 (1H, br s), 2.87-3.10 (2H, m), 3.60-3.95 (2H, m), 4.33 (2H, d, J=6.0 Hz), 4.30-4.60 (2H, m), 4.85 (1H, br s), 7.20-7.60 (14H, m).

Example 145

3-[(Hexahydro-3-oxo-1,1-diphenyl-3H-oxazolo[3,4-a]pyrazin-7(1H)-yl)carbonyl]benzenemethanamine hydrochloride

To 1,1-dimethylethyl [[3-[(tetrahydro-3-oxo-1,1-diphenyl-3H-oxazolo[3,4-a]pyrazin-7(1H)-yl)carbonyl]phenyl]methyl]carbamate (0.25 g, 0.46 mmol) was added a 4 M hydrogen chloride/ethyl acetate solution (10 mL), and the mixture was stirred at room temperature for 2 hours. The reaction solution was concentrated and crystallized from 2-propanol and ethyl acetate to obtain the title compound (0.19 g, yield 90%).

Melting point 270-271° C.

$^1$H NMR (DMSO-d$_6$) δ 2.20-2.40 (1H, m), 3.05 (1H, br s), 3.26 (1H, m), 3.40-3.70 (2H, m), 4.06 (2H, s), 4.05-4.30 (1H, m), 4.81 (1H, br s), 7.10-7.70 (14H, m), 8.54 (3H, br s).

Example 146

Tetrahydro-N-[1-(1-methylethyl)-4-piperidinyl]-3-oxo-1,1-diphenyl-3H-oxazolo[3,4-a]pyrazine-7(1H)-carboxamide

To tetrahydro-3-oxo-1,1-diphenyl-N-(4-piperidinyl)-3H-oxazolo[3,4-a]pyrazine-7(1H)-carboxamide hydrochloride (0.23 g, 0.50 mmol) were added N,N-dimethylformamide (5 mL), triethylamine (0.14 mL, 1.0 mmol), acetone (58 mg, 1.0 mmol) and sodium triacetoxyborohydride (0.32 g, 1.5 mmol), and the mixture was stirred at room temperature for 14 hours. To the reaction solution was added ethyl acetate, and the resulting mixture was washed with a 0.5 M aqueous sodium hydrogen carbonate solution, dried over anhydrous magnesium sulfate and concentrated under reduced pressure. The residue was purified with amino silica gel column chromatography (hexane:ethyl acetate=9:1 to ethyl acetate), and powder was formed from diisopropyl ether to obtain the title compound (64 mg, yield 28%).

Amorphous.

$^1$H NMR (CDCl$_3$) δ 1.01-1.04 (6H, m), 1.34-1.37 (2H, m), 1.93-1.97 (2H, m), 2.08-2.27 (2H, m), 2.69-2.94 (4H, m), 3.02-3.12 (1H, m), 3.57-3.62 (2H, m), 3.83-3.87 (1H, m), 3.95-4.00 (1H, m), 4.20-4.24 (1H, m), 4.38-4.43 (1H, m), 7.26-7.40 (8H, m), 7.50-7.53 (2H, m).

Example 147

N-[2-(Hexahydro-1H-azepin-1-yl)ethyl]tetrahydro-3-oxo-1,1-diphenyl-3H-oxazolo[3,4-a]pyrazine-7(1H)-carboxamide

In the same manner as in Example 64, the title compound was obtained using hexahydro-1H-azepine instead of morpholine. Yield 12%.

Melting point 118-120° C.

$^1$H NMR (CDCl$_3$) δ 1.55-1.58 (8H, m), 2.18 (1H, t, J=13.4 Hz), 2.58-2.61 (6H, m), 2.83-2.91 (1H, m), 3.04-3.13 (1H, m), 3.21-3.25 (2H, m), 3.70-3.75 (1H, m), 3.84-3.94 (2H, m), 4.39-4.44 (1H, m), 5.42 (1H, br), 7.26-7.41 (8H, m), 7.50-7.54 (2H, m).

Example 148

Hexahydro-1,1-diphenyl-7-[[4-(1-piperidinyl)-1-piperidinyl]carbonyl]-3H-oxazolo[3,4-a]pyrazin-7(1H)-3-one To a solution of 4-piperidinopiperidine (0.17 g, 1.0 mmol) in tetrahydrofuran (10 mL) was added bis(trichloromethyl) carbonate (0.10 g, 0.34 mmol), and the mixture was stirred at room temperature for 30 minutes. To the reaction solution were sequentially added hexahydro-1,1-diphenyl-3H-oxazolo[3,4-a]pyrazin-3-one (0.29 g, 1.0 mmol) and diisopropylethylamine (0.36 mL, 2.0 mmol), and the mixture was stirred at room temperature for 14 hours. To the reaction solution was added ethyl acetate, and the resulting mixture was washed with a 0.5 M aqueous sodium hydrogen carbonate solution, dried over anhydrous magnesium sulfate and concentrated under reduced pressure. The residue was subjected to amino silica gel column chromatography (hexane:ethyl acetate=9:1 to ethyl acetate), purified with silica gel column chromatography (ethyl acetate to ethyl acetate:methanol=1:9), and crystallized from diethyl ether to obtain the title compound (0.16 g, yield 32%).

Melting point 147-149° C.

$^1$H NMR (CDCl$_3$) δ 1.40-1.57 (9H, m), 1.78-1.82 (2H, m), 2.18 (1H, t, J=13.3 Hz), 2.32-2.48 (4H, m), 2.67-2.93 (3H, m), 3.05-3.13 (1H, m), 3.46-3.55 (2H, m), 3.67-3.83 (3H, m), 4.52-4.57 (1H, m), 7.26-7.40 (8H, m), 7.53-7.60 (2H, m).

Example 149

N-[2-(Dimethylamino)-1-phenylethyl]-tetrahydro-3-oxo-1,1-diphenyl-3H-oxazolo[3,4-a]pyrazine-7(1H)-carboxamide In the same manner as in Example 124, the title compound was obtained using 2-(dimethylamino)-1-phenylethylamine instead of 1,1-dimethylethyl 4-amino-1H-benzimidazole-1-carboxylate. Yield 33%. Diastereomer mixture (α:β=1:1).

Amorphous.

$^1$H NMR (CDCl$_3$) δ2.10-2.16 (1H, m), 2.25 (6H, s), 2.32-2.38 (1H, m), 2.47-2.55 (1H, m), 2.95-3.02 (1H, m), 3.04-3.14 (1H, m), 3.72-3.82 (1H, m), 3.84-3.91 (1H, m), 3.95-4.04 (1H, m), 4.35-4.40 (1H, m), 4.60-4.65 (1H, m), 5.79 [0.5H (1H of a), s], 5.83 [0.5H (1H of P), s], 7.27-7.40 (8H, m), 7.48-7.52 (2H, m).

Example 150

Tetrahydro-N-[2-(4-morpholinyl)-1-phenylethyl]-3-oxo-1,1-diphenyl-3H-oxazolo[3,4-a]pyrazine-7(1H)-carboxamide In the same manner as in Example 124, the title compound was obtained using 2-(4-morpholinyl)-1-phenylethylamine instead of 1,1-dimethylethyl 4-amino-1H-benzimidazole-1-carboxylate. Yield 62%. Diastereomer mixture (α:β=1:1).

Melting point 112-113° C.

$^1$H NMR (CDCl$_3$) δ 2.11-2.19 (1H, m), 2.36-2.39 (2H, m), 2.51-2.58 (4H, m), 2.88-3.13 (2H, m), 3.53-3.75 (5H, m), 3.88-4.02 (2H, m), 4.37-4.43 (1H, m), 4.63-4.72 (1H, m), 5.74 [0.5H (1H of a), br], 5.78 [0.5H (1H of β), br], 7.25-7.37 (8H, m), 7.47-7.53 (2H, m).

Example 151

7-[4-(3,6-Dihydropyridin-1(2H)-ylmethyl)benzoyl]-hexahydro-1,1-diphenyl-3H-oxazolo[3,4-a]pyrazin-3-one To a solution of 4-[(tetrahydro-3-oxo-1,1-diphenyl-3H-oxazolo[3,4-a]pyrazin-7(1H)-yl)carbonyl]benzaldehyde (0.15 g, 0.35 mmol) and 1,2,3,6-tetrahydropyridine (44 mg, 0.53 mmol) in tetrahydrofuran (4 mL) was added sodium triacetoxyborohydride (0.11 g, 0.52 mmol), and the mixture was stirred at room temperature for 27 hours. The reaction solution was diluted with water and then extracted with ethyl acetate. The organic layer was washed with water and saturated brine and dried over magnesium sulfate. The solid was filtered off, and the filtrate was concentrated. The residue was purified with silica gel column chromatography (ethyl acetate to ethyl acetate:methanol=4:1) and crystallized from diisopropyl ether to obtain the title compound (70 mg, yield 41%).

Melting point 189-191° C.

$^1$H NMR (CDCl$_3$) δ 2.18 (2H, t, J=2.6 Hz), 2.26 (1H, br s), 2.57 (2H, t, J=5.6 Hz), 2.98 (2H, t, J=2.6 Hz), 2.99 (2H, br s), 3.61 (2H, s), 3.84 (2H, br s), 4.40-4.70 (2H, m), 5.65-5.68 (1H, m), 5.75-5.79 (1H, m), 7.26-7.44 (12H, m), 7.52 (2H, br s).

Example 152

7-[3-(3,6-Dihydropyridin-1(2H)-ylmethyl)benzoyl]-hexahydro-1,1-diphenyl-3H-oxazolo[3,4-a]pyrazin-3-one In the same manner as in Example 151, the title compound was obtained using 3-[(tetrahydro-3-oxo-1,1-diphenyl-3H-oxazolo[3,4-a]pyrazin-7(1H)-yl)carbonyl]benzaldehyde instead of 4-[(tetrahydro-3-oxo-1,1-diphenyl-3H-oxazolo[3,4-a]pyrazin-7(1H)-yl)carbonyl]benzaldehyde. Yield 42%.

Melting point 170-172° C.

$^1$H NMR (CDCl$_3$) δ 2.15-2.35 (3H, m), 2.55 (2H, t, J=5.5 Hz), 2.96 (4H, br s), 3.60 (2H, s), 3.83 (2H, br s), 4.49 (2H, br s), 5.65 (1H, d, J=10.0 Hz), 5.76 (1H, d, J=10.0 Hz), 7.24-7.61 (14H, m).

Example 153

Tetrahydro-3-oxo-1,1-diphenyl-N-[2-(1H-pyrrol-1-yl)ethyl]-3H-oxazolo[3,4-a]pyrazine-7(1H)-carboxamide Hexahydro-1,1-diphenyl-3H-oxazolo[3,4-a]pyrazin-3-one (0.20 g, 0.68 mmol) was dissolved in tetrahydrofuran (7 mL). 2-Bromoethyl isocyanate (0.07 mL, 0.77 mmol) was added thereto at 0° C., and the mixture was stirred for 1 hour without modification. The reaction solution was concentrated under reduced pressure and dissolved in N-methyl-2-pyrrolidinone (7 mL). 3-Pyrroline (0.21 mL, 2.7 mmol) was added thereto, and the mixture was stirred at 60° C. for 25 hours. To the reaction solution was added water, and the mixture was extracted with ethyl acetate. Then, the organic layer was washed with an aqueous saturated sodium hydrogen carbonate solution, water and saturated brine, and dried over magnesium sulfate. The solid was filtered off, and the filtrate was concentrated under reduced pressure. The residue was purified with amino silica gel column chromatography (hexane:ethyl acetate=1:1 to ethyl acetate) and silica gel column chromatography (hexane:ethyl acetate=8:2 to ethyl acetate) to obtain the title compound (0.21 g, yield 72%) as amorphous.

$^1$H NMR (CDCl$_3$) δ 2.16 (1H, dd, J=11.1 Hz, 13.2 Hz), 2.76-2.86 (1H, m), 2.97-3.06 (1H, m), 3.44-3.67 (3H, m), 3.81 (2H, dd, J=3.0 Hz, 13.2 Hz), 4.02 (2H, t, J=5.7 Hz), 4.36 (1H, dd, J=3.6 Hz, 11.1 Hz), 4.46 (1H, t, J=5.7 Hz), 6.17 (2H, t, J=2.1 Hz), 6.62 (2H, t, J=2.1 Hz), 7.28-7.43 (8H, m), 7.49-7.52 (2H, m).

Example 154

7-[2-(3,6-Dihydropyridin-1(2H)-ylmethyl)benzoyl]-hexahydro-1,1-diphenyl-3H-oxazolo[3,4-a]pyrazin-3-one 2-Formylbenzoic acid (0.15 g, 1.0 mmol) was dissolved in thionyl chloride (1 mL), one drop of pyridine was added thereto, and the mixture was stirred at room temperature for 30 minutes. The reaction solution was concentrated, and the residue was dissolved in tetrahydrofuran (5 mL). This solution was added dropwise to a solution of triethylamine (0.19 mL, 1.4 mmol) and hexahydro-1,1-diphenyl-3H-oxazolo[3,4-a]pyrazin-3-one (0.20 g, 0.68 mmol) in tetrahydrofuran (3 mL), and the mixture was stirred at room temperature for 24 hours. The reaction solution was diluted with water and then extracted with ethyl acetate. The organic layer was sequentially washed with 1 N hydrochloric acid, an aqueous saturated sodium hydrogen carbonate solution, water and saturated brine, and dried over magnesium sulfate. The solid was filtered off, and the filtrate was concentrated. The residue was purified with silica gel column chromatography (hexane:ethyl acetate=1:1 to ethyl acetate). The fractions were collected and concentrated. The residue was dissolved in tetrahydrofuran (4 mL). 1,2,3,6-Tetrahydropyridine (0.08 mL, 0.88 mmol) and sodium triacetoxyborohydride (0.13 g, 0.61 mmol) were sequentially added thereto, and the mixture was stirred at room temperature for 25 hours. The reaction solution was diluted with water and then extracted with ethyl acetate. The organic layer was washed with water and saturated brine, and dried over magnesium sulfate. The solid was filtered off, and the filtrate was concentrated. The residue was purified with amino silica gel column chromatography (ethyl acetate:hexane=2:98 to ethyl acetate:hexane=1:1) and silica gel column chromatography (ethyl acetate:hexane=1:1 to ethyl acetate), and then recrystallized from diisopropyl ether to obtain the title compound (68 mg, yield 14%).

Melting point 155-157° C.

$^1$H NMR (CDCl$_3$) δ 1.84 (1H, br s), 1.96-2.04 (1H, m), 2.17-2.89 (5H, m), 3.00-3.58 (4H, m), 3.74-3.87 (1H, m), 4.22-4.35 (1H, m), 4.41-4.49 (1H, m), 4.57-4.67 (1H, m), 5.45-5.68 (2H, m), 7.04-7.58 (14H, m).

Example 155

2-[4-[(Tetrahydro-3-oxo-1,1-diphenyl-3H-oxazolo[3,4-a]pyrazin-7(1H)-yl)carbonyl]-1-piperidinyl]acetamide A solution of hexahydro-1,1-diphenyl-7-[(4-piperidinyl)carbonyl]-3H-oxazolo[3,4-a]pyrazin-3-one hydrochloride (0.15 g, 0.34 mmol), potassium carbonate (0.12 g, 0.87 mmol), sodium iodide (51 mg, 0.34 mmol) and 2-chloroacetamide (38 mg, 0.41 mmol) in N,N-dimethylacetamide (3 mL) was stirred at room temperature for 26 hours. The reaction solution was diluted with water, and the mixture was extracted with ethyl acetate-tetrahydrofuran. The organic layer was washed with water and saturated brine, and dried over magnesium sulfate. The solid was filtered off, and the filtrate was concentrated and dried to a solid. The residue was recrystallized from ethanol to obtain the title compound (80 mg, yield 50%).

Melting point 253-255° C.

$^1$H NMR (CDCl$_3$) δ 1.62-2.03 (5H, m), 2.16-2.26 (2H, m), 2.47 (1H, br s), 2.92-3.12 (6H, m), 3.83 (1H, d, J=10.3 Hz), 3.96 (1H, d, J=10.0 Hz), 4.33 (1H, dd, J=3.5 Hz, 11.3 Hz), 4.52 (1H, d, J=12.8 Hz), 5.39 (1H, br s), 7.01 (1H, br s), 7.26-7.61 (10H, m).

Example 156

Hexahydro-1,1-diphenyl-7-(quinolin-6-ylcarbonyl)-3H-oxazolo[3,4-a]pyrazin-3-one

Hexahydro-1,1-diphenyl-3H-oxazolo[3,4-a]pyrazin-3-one (0.15 g, 0.51 mmol), quinoline-6-carboxylic acid (0.11 g, 0.63 mmol), 1-hydroxybenzotriazole (0.10 g, 0.74 mmol) were dissolved in N,N-dimethylformamide (5 mL). 1-Ethyl-3-(3-dimethylaminopropyl)carbodiimide hydrochloride (0.15 g, 0.78 mmol) was added thereto, and the mixture was stirred at room temperature for 2 hours and 30 minutes. The reaction solution was diluted with water, and the mixture was extracted with ethyl acetate. The organic layer was washed with a 1 N aqueous sodium hydroxide solution, water and saturated brine, and dried over magnesium sulfate. The solid was filtered off, and the filtrate was concentrated. The residue was purified with amino silica gel column chromatography (hexane:ethyl acetate=1:1 to ethyl acetate) and concentrated. The residue was recrystallized from ethyl acetate-hexane to obtain the title compound (0.13 g, yield 57%).

Melting point 190-192° C.

$^1$H NMR (CDCl$_3$) δ 2.04 (1H, br s), 3.08 (2H, br s), 3.86 (2H, br s), 4.51 (2H, br s), 7.26-7.61 (11H, m), 7.68 (1H, dd, J=1.8 Hz, 8.7 Hz), 7.90 (1H, d, J=1.6 Hz), 8.17-8.22 (2H, m), 9.01 (1H, d, J=2.8 Hz).

Example 157

Hexahydro-7-[[1-(2-hydroxyethyl)piperidin-4-yl]carbonyl]-1,1-diphenyl-3H-oxazolo[3,4-a]pyrazin-3-one To a solution of ethyl [4-[(tetrahydro-3-oxo-1,1-diphenyl-3H-oxazolo[3,4-a]pyrazin-7(1H)-yl)carbonyl]piperidin-1-yl]acetate (0.13 g, 0.26 mmol) in tetrahydrofuran (3 mL) was added aluminum lithium hydride (10 mg, 0.26 mmol) at 0° C., and the mixture was stirred at 0° C. for 30 minutes. An excessive amount of ethyl acetate was added thereto, and the mixture was further stirred at 0° C. for 5 minutes. The reaction solution was diluted with water and then extracted with ethyl acetate. The organic layer was washed with a 1 N aqueous sodium hydroxide solution, water and saturated brine, and dried over magnesium sulfate. The solid was filtered off, and the filtrate was concentrated. The residue was purified with amino silica gel column chromatography (ethyl acetate to ethyl acetate:methanol=9:1), and then recrystallized from diisopropyl ether-ethyl acetate to obtain the title compound (25 mg, yield 21%).

Melting point 160-162° C.

$^1$H NMR (CDCl$_3$) δ 1.67-2.29 (7H, m), 2.43-2.55 (3H, m), 2.93-3.12 (4H, m), 3.60 (2H, t, J=5.3 Hz), 3.83 (1H, d, J=10.3 Hz), 3.95 (1H, d, J=9.8 Hz), 4.33 (1H, dd, J=3.5 Hz, 11.3 Hz), 4.53 (1H, d, J=12.2 Hz), 7.26-7.42 (8H, m), 7.50-7.52 (2H, m).

Example 158

1-[(Tetrahydro-3-oxo-1,1-diphenyl-3H-oxazolo[3,4-a]pyrazin-7(1H)-yl)carbonyl]-2,3-dihydroquinolin-4(1H)-one To a solution of 2,3-dihydroquinolin-4(1H)-one (75 mg, 0.51 mmol) and diisopropylethylamine (0.25 mL) in tetrahydrofuran (3 mL) was added triphosgene (0.15 g, 0.51 mmol), and the mixture was stirred at room temperature for 20 minutes. Hexahydro-1,1-diphenyl-3H-oxazolo[3,4-a]pyrazin-3-one (0.15 g, 0.51 mmol) was added thereto, and the resulting mixture was stirred at room temperature for 24 hours. The reaction solution was diluted with water and then extracted with ethyl acetate. The organic layer was washed with water and saturated brine, and dried over magnesium sulfate. The solid was filtered off, and the filtrate was concentrated. The residue was purified with amino silica gel column chromatography (hexane:ethyl acetate=1:1 to ethyl acetate), and then recrystallized from diisopropyl ether to obtain the title compound (25 mg, yield 10%).
Melting point 202-205° C.
$^1$H NMR (CDCl$_3$) δ 2.25 (1H, dd, J=11.4 Hz, 13.2 Hz), 2.74-2.79 (2H, m), 2.82-2.91 (1H, m), 3.04-3.14 (1H, m), 3.72-3.89 (4H, m), 4.04-4.12 (1H, m), 4.49 (1H, dd, J=3.4 Hz, 11.2 Hz), 6.72-7.46 (13H, m), 8.02-8.05 (1H, m).

Example 159

Hexahydro-7-[[1-[2-(4-morpholinyl)-2-oxoethyl]piperidin-4-yl]carbonyl]-1,1-diphenyl-3H-oxazolo[3,4-a]pyrazin-3-one In the same manner as in Example 155, using 4-(chloroacetyl)morpholine instead of 2-chloroacetamide, the reaction mixture was purified with amino silica gel column chromatography (ethyl acetate to ethyl acetate:methanol=9:1) to obtain the title compound. Yield 66%.
Amorphous.
$^1$H NMR (CDCl$_3$) δ 1.79-2.13 (7H, m), 2.45 (1H, br s), 2.92-3.12 (4H, m), 3.17 (2H, s), 3.61-3.65 (8H, m), 3.83 (1H, d, J=9.3 Hz), 3.95 (1H, d, J=9.6 Hz), 4.32 (1H, d, J=10.7 Hz), 4.51 (1H, d, J=12.2 Hz), 7.27-7.39 (8H, m), 7.49 (2H, br s).

Example 160

Ethyl [4-[(tetrahydro-3-oxo-1,1-diphenyl-3H-oxazolo[3,4-a]pyrazin-7(1H)-yl)carbonyl]piperidin-1-yl]acetate To a solution of hexahydro-1,1-diphenyl-7-[(4-piperidinyl)carbonyl]-3H-oxazolo[3,4-a]pyrazin-3-one hydrochloride (0.20 g, 0.45 mmol) and potassium carbonate (0.16 g, 1.2 mmol) in tetrahydrofuran (5 mL) was added ethyl bromoacetate (0.055 mL, 0.50 mmol) at 0° C., and the mixture was stirred at 0° C. for 2 hours and at room temperature for 20 hours. The reaction solution was diluted with water and then extracted with ethyl acetate. The organic layer was washed with saturated brine and dried over magnesium sulfate. The solid was filtered off, and the filtrate was concentrated and dried to a solid. The residue was purified with silica gel column chromatography (ethyl acetate to ethyl acetate:methanol=9:1) to obtain the title compound (0.20 g, yield 90%).
Amorphous.
$^1$H NMR (CDCl$_3$) δ 1.27 (3H, t, J=7.1 Hz), 1.62-1.70 (2H, m), 1.80-2.01 (3H, m), 2.27-2.48 (3H, m), 2.94-3.11 (4H, m), 3.24 (2H, s), 3.81-3.96 (2H, m), 4.18 (2H, q, J=7.1 Hz), 4.33 (1H, dd, J=3.6 Hz, 11.3 Hz), 4.52 (1H, d, J=13.2 Hz), 7.27-7.41 (8H, m), 7.51 (2H, d, J=7.2 Hz).

Example 161

Tetrahydro-3-oxo-1,1-diphenyl-N-(5-quinolinyl)-3H-oxazolo[3,4-a]pyrazine-7(1H)-carboxamide To a solution of hexahydro-1,1-diphenyl-3H-oxazolo[3,4-a]pyrazin-3-one (0.15 g, 0.51 mmol) and 1,8-diazabicyclo[5.4.0]undec-7-ene (0.19 g, 1.3 mmol) in acetonitrile (6 mL) was added 2,2,2-trichloro-N-(5-quinolinyl)acetamide (0.16 g, 0.55 mmol), and the mixture was heated under reflux for 6 hours. The reaction solution was diluted with water and then extracted with ethyl acetate. The organic layer was washed twice with water, once with saturated brine, and dried over magnesium sulfate. The solid was filtered off, and the filtrate was concentrated. The residue was purified with silica gel column chromatography (hexane:ethyl acetate=1:1 to ethyl acetate), and then recrystallized from hexane-ethyl acetate to obtain the title compound (78 mg, yield 33%).
Melting point 234-236° C.
$^1$H NMR (CDCl$_3$) δ 2.27 (1H, dd, J=11.3 Hz, 13.2 Hz), 2.98-3.08 (1H, m), 3.14-3.23 (1H, m), 3.89-4.10 (3H, m), 4.46 (1H, dd, J=3.6 Hz, 11.3 Hz), 6.73 (1H, br s), 7.22-7.50 (12H, m), 7.67 (1H, t, J=8.4 Hz), 8.00 (1H, d, J=8.5 Hz), 8.15 (1H, d, J=8.5 Hz), 8.92 (1H, dd, J=1.5 Hz, 4.2 Hz).

Example 162

Tetrahydro-3-oxo-1,1-diphenyl-N-(3-pyridinyl)-3H-oxazolo[3,4-a]pyrazine-7(1H)-carboxamide In the same manner as in Example 161, the title compound was obtained using 2,2,2-trichloro-N-(3-pyridinyl)acetamide instead of 2,2,2-trichloro-N-(5-quinolinyl)acetamide. Yield 66%.
Melting point 196-198° C. (recrystallized from hexane-ethyl acetate).
$^1$H NMR (CDCl$_3$) δ 2.26 (1H, dd, J=11.3 Hz, 13.3 Hz), 2.96-3.06 (1H, m), 3.10-3.20 (1H, m), 3.88-3.93 (2H, m), 4.03-4.13 (1H, m), 4.48 (1H, dd, J=3.6 Hz, 11.3 Hz), 6.92 (1H, br s), 7.22-7.41 (9H, m), 7.48-7.52 (2H, m), 7.90-7.94 (1H, m), 8.28 (1H, dd, J=1.4 Hz, 4.7 Hz), 8.44 (1H, d, J=2.5 Hz).

Example 163

Tetrahydro-3-oxo-1,1-diphenyl-N-(4-pyridinyl)-3H-oxazolo[3,4-a]pyrazine-7(1H)-carboxamide In the same manner as in Example 161, the title compound was obtained using 2,2,2-trichloro-N-(4-pyridinyl)acetamide instead of 2,2,2-trichloro-N-(5-quinolinyl)acetamide. Yield 76%.
Melting point 157-159° C. (recrystallized from hexane-ethyl acetate).
$^1$H NMR (CDCl$_3$) δ 2.26 (1H, dd, J=11.4 Hz, 13.2 Hz), 2.97-3.18 (2H, m), 3.88-3.92 (2H, m), 4.04-4.09 (1H, m), 4.49 (1H, dd, J=3.6 Hz, 11.3 Hz), 7.07 (1H, br s), 7.26-7.43 (10H, m), 7.49-7.52 (2H, m), 8.40-8.42 (2H, m).

Example 164

7-[[1-(Cyclopropylmethyl)piperidin-4-yl]carbonyl]-hexahydro-1,1-diphenyl-3H-oxazolo[3,4-a]pyrazin-3-one In the same manner as in Example 160, the title compound was obtained using (bromomethyl)cyclopropane instead of ethyl bromoacetate. Yield 48%.

Melting point 145-147° C. (recrystallized from hexane-ethyl acetate).

$^1$H NMR (CDCl$_3$) δ 0.06-0.11 (2H, m), 0.48-0.54 (2H, m), 0.82-0.90 (1H, m), 1.64-2.04 (7H, m), 2.25 (2H, d, J=6.5 Hz), 2.42 (1H, br s), 2.97-3.11 (4H, m), 3.82-3.96 (2H, m), 4.33 (1H, dd, J=3.6 Hz, 11.3 Hz), 4.52 (1H, d, J=13.2 Hz), 7.32-7.52 (10H, m).

Example 165

Hexahydro-1,1-diphenyl-7-[[1-(2-propenyl)piperidin-4-yl]carbonyl]-3H-oxazolo[3,4-a]pyrazin-3-one hydrochloride In the same manner as in Example 160, the title compound was synthesized using allyl bromide instead of ethyl bromoacetate. The free base of the resulting title compound was taken as hydrochloride using an excessive amount of a 4 M hydrogen chloride/ethyl acetate solution, and crystallized from diethyl ether to obtain the title compound. Yield 11%.

Melting point 161-163° C.

$^1$H NMR (DMSO-d$_6$) δ 1.62-2.07 (5H, m), 2.88-3.39 (7H, m), 3.67 (3H, br s), 3.93-4.14 (2H, m), 4.54-4.67 (1H, m), 5.49-5.54 (2H, m), 5.97 (1H, br s), 7.36-7.57 (10H, m), 10.49 (1H, br s).

Example 166

Tetrahydro-N-(isoquinolin-6-yl)-3-oxo-1,1-diphenyl-3H-oxazolo[3,4-a]pyrazine-7(1H)-carboxamide In the same manner as in Example 161, the title compound was obtained using 2,2,2-trichloro-N-(isoquinolin-6-yl)acetamide instead of 2,2,2-trichloro-N-(5-quinolinyl)acetamide. Yield 55%.

Melting point 176-178° C. (recrystallized from hexane-ethyl acetate).

$^1$H NMR (CDCl$_3$) δ 2.29 (1H, dd, J=11.4 Hz, 13.2 Hz), 3.01-3.22 (2H, m), 3.90-3.97 (2H, m), 4.09-4.16 (1H, m), 4.52 (1H, dd, J=3.6 Hz, 11.3 Hz), 7.10 (1H, br s), 7.28-7.42 (8H, m), 7.47-7.54 (4H, m), 7.87 (1H, d, J=8.8 Hz), 7.97 (1H, d, J=1.5 Hz), 8.43 (1H, d, J=5.8 Hz), 9.11 (1H, s).

Example 167

Tetrahydro-N-(isoquinolin-5-yl)-3-oxo-1,1-diphenyl-3H-oxazolo[3,4-a]pyrazine-7(1H)-carboxamide In the same manner as in Example 161, the title compound was obtained using 2,2,2-trichloro-N-(isoquinolin-5-yl)acetamide instead of 2,2,2-trichloro-N-(5-quinolinyl)acetamide. Yield 59%.

Melting point 204-206° C. (recrystallized from hexane-ethyl acetate).

$^1$H NMR (CDCl$_3$) δ 2.30 (1H, dd, J=11.3 Hz, 13.3 Hz), 3.03-3.12 (1H, m), 3.17-3.26 (1H, m), 3.92-3.97 (2H, m), 4.02-4.07 (1H, m), 4.50 (1H, dd, J=3.6 Hz, 11.3 Hz), 6.74 (1H, s), 7.24-7.41 (8H, m), 7.48-7.51 (2H, m), 7.54-7.61 (2H, m), 7.78-7.84 (2H, m), 8.54 (1H, d, J=6.0 Hz), 9.26 (1H, s).

Example 168

1,1-Bis(4-methylphenyl)-N-(2,4-difluorophenyl)-tetrahydro-3-oxo-3H-oxazolo[3,4-a]pyrazine-7(1H)-carboxamide To a solution of 1,1-bis(4-methylphenyl)-hexahydro-3H-oxazolo[3,4-a]pyrazin-3-one (0.20 g, 0.62 mmol) in tetrahydrofuran (6 mL) was added 2,4-difluorophenyl isocyanate (0.090 mL, 0.76 mmol) at 0° C., and the mixture was stirred at 0° C. for 1 hour. The reaction solution was diluted with water and then extracted with ethyl acetate. The organic layer was washed with water and saturated brine, and dried over magnesium sulfate. The solid was filtered off, and the filtrate was concentrated. The residue was purified with silica gel column chromatography (hexane:ethyl acetate=98:2 to hexane:ethyl acetate=1:1), and then recrystallized from diisopropyl ether to obtain the title compound (0.20 g, yield 68%).

Melting point 120-122° C.

$^1$H NMR (CDCl$_3$) δ 2.28 (1H, dd, J=11.4 Hz, 13.4 Hz), 2.32 (3H, s), 2.34 (3H, s), 2.98-3.21 (2H, m), 3.81-3.85 (1H, m), 3.90-4.01 (2H, m), 4.44 (1H, dd, J=3.6 Hz, 11.3 Hz), 6.38-6.39 (1H, m), 6.82-6.89 (2H, m), 7.13-7.21 (6H, m), 7.38 (2H, d, J=8.3 Hz), 7.84-7.92 (1H, m).

Example 169

1,1-Bis(4-methylphenyl)-N-[2-(3,6-dihydropyridin-1(2H)-yl)ethyl]-tetrahydro-3-oxo-3H-oxazolo[3,4-a]pyrazine-7(1H)-carboxamide In the same manner as in Example 153, the title compound was obtained using 1,1-bis(4-methylphenyl)-hexahydro-3H-oxazolo[3,4-a]pyrazin-3-one instead of hexahydro-1,1-diphenyl-3H-oxazolo[3,4-a]pyrazin-3-one, and using 1,2,3,6-tetrahydropyridine instead of 3-pyrroline. Yield 61%.

Melting point 155-157° C. (recrystallized from ethyl acetate-hexane).

$^1$H NMR (CDCl$_3$) δ 2.21-2.20 (3H, m), 2.30 (3H, s), 2.33 (3H, s), 2.53-2.57 (4H, m), 2.79-2.88 (1H, m), 2.95-2.97 (2H, m), 3.01-3.11 (1H, m), 3.29-3.38 (2H, m), 3.69-3.74 (1H, m), 3.80-3.89 (2H, m), 4.35 (1H, dd, J=3.6 Hz, 11.3 Hz), 5.27 (1H, t, J=4.3 Hz), 5.64-5.68 (1H, m), 5.73-5.78 (1H, m), 7.10-7.19 (6H, m), 7.38 (2H, d, J=8.3 Hz).

Example 170

1,1-Bis(4-methylphenyl)-tetrahydro-3-oxo-N-[2-(1-piperidinyl)ethyl]-3H-oxazolo[3,4-a]pyrazine-7(1H)-carboxamide In the same manner as in Example 153, the title compound was obtained using 1,1-bis(4-methylphenyl)-hexahydro-3H-oxazolo[3,4-a]pyrazin-3-one instead of hexahydro-1,1-diphenyl-3H-oxazolo[3,4-a]pyrazin-3-one, and using piperidine instead of 3-pyrroline. Yield 51%.

Amorphous.

$^1$H NMR (CDCl$_3$) δ 1.43-1.55 (6H, m), 2.18 (1H, dd, J=11.3 Hz, 13.2 Hz), 2.30 (3H, s), 2.34 (3H, s), 2.37 (4H, br s), 2.44 (2H, t, J=5.9 Hz), 2.78-2.88 (1H, m), 3.02-3.11 (1H, m), 3.25-3.30 (2H, m), 3.74-3.87 (3H, m), 4.36 (1H, dd, J=3.7 Hz, 11.3 Hz), 5.44 (1H, br s), 7.11-7.20 (6H, m), 7.39 (2H, d, J=8.3 Hz).

Example 171

N-[2-[Cyclopropyl[(2-nitrophenyl)sulfonyl]amino]ethyl]-tetrahydro-3-oxo-1,1-diphenyl-3H-oxazolo[3,4-a]pyrazine-7(1H)-carboxamide To a solution of N-(2-aminoethyl)-N-cyclopropyl-2-nitrobenzenesulfonamide (0.47 g, 1.7 mmol) and diisopropylethylamine (0.71 mL, 4.1 mmol) in tetrahydrofuran (15 mL) was added 4-nitrophenyl chloroformate (0.33 g, 1.7 mmol) at 0° C., and the mixture was stirred at room temperature for 1 hour. Hexahydro-1,1-diphenyl-3H-oxazolo[3,4-a]pyrazin-3-one (0.40 g, 1.4 mmol) was added thereto, and the mixture was stirred at room temperature for 60 hours. To the reaction solution was added ethyl acetate, and the resulting mixture was washed with 1 N hydrochloric acid, a 1 N aqueous sodium hydroxide solution, water and saturated brine, and dried over magnesium sulfate. The solid was filtered off, and the filtrate was concentrated. The residue was purified with silica gel column chromatography (hexane:ethyl acetate=98:2 to ethyl acetate). The fractions were collected and concentrated. The residue was washed with diethyl ether and collected by filtration to obtain the title compound (0.76 g, yield 92%).

Melting point 136-138° C.

$^1$H NMR (CDCl$_3$) δ 0.49-0.56 (2H, m), 0.65-0.74 (2H, m), 2.28 (1H, dd, J=11.3 Hz, 13.4 Hz), 2.64-2.68 (1H, m), 2.77-2.86 (1H, m), 3.13-3.22 (1H, m), 3.43-3.67 (4H, m), 3.79-3.84 (2H, m), 4.49 (1H, d, J=10.4 Hz), 4.57 (1H, dd, J=3.6 Hz, 11.2 Hz), 4.95 (1H, br s), 7.24-7.38 (8H, m), 7.55-7.59 (2H, m), 7.65-7.78 (3H, m), 8.13-8.17 (1H, m).

Example 172

N-[2-(Cyclopropylamino)ethyl]-tetrahydro-3-oxo-1,1-diphenyl-3H-oxazolo[3,4-a]pyrazine-7(1H)-carboxamide hydrochloride To a solution of N-[2-[cyclopropyl[(2-nitrophenyl)sulfonyl]amino]ethyl]-tetrahydro-3-oxo-1,1-diphenyl-3H-oxazolo[3,4-a]pyrazine-7(1H)-carboxamide (0.60 g, 0.99 mmol) and potassium carbonate (0.41 g, 3.0 mmol) in N,N-dimethylformamide (10 mL) was added thiophenol (0.12 mL, 1.2 mmol), and the mixture was stirred at room temperature for 90 minutes. Thiophenol (0.010 mL, 0.097 mmol) was added thereto, and the mixture was stirred at room temperature for 30 minutes. To the reaction solution was added water, and the mixture was extracted twice with ethyl acetate. The organic layers were combined and dried over magnesium sulfate. The solid was filtered off, and the filtrate was concentrated. To the residue was added ethyl acetate, and the mixture was extracted three times with 1 N hydrochloric acid. The aqueous layers were combined, sodium hydroxide (pellet) was added thereto, and the mixture was adjusted to pH 12. The resulting mixture was extracted with ethyl acetate. The organic layer was washed with saturated brine and dried over magnesium sulfate. The solid was filtered off, and the filtrate was concentrated. An excessive amount of a 4 M hydrogen chloride/ethyl acetate solution was added thereto, and concentrated. The residue was crystallized from diethyl ether to obtain the title compound (0.30 g, yield 66%).

Melting point 140-142° C.

$^1$H NMR (DMSO-d$_6$) δ 0.70-0.77 (2H, m), 0.85-0.90 (2H, m), 2.10 (1H, t, J=12.4 Hz), 2.60-2.73 (2H, m), 3.00-3.08 (3H, m), 3.32-3.42 (2H, m), 3.60 (1H, dd, J=2.4 Hz, 12.8 Hz), 3.87-3.97 (2H, m), 4.55 (1H, dd, J=3.3 Hz, 11.1 Hz), 7.11 (1H, t, J=5.2 Hz), 7.30-7.45 (8H, m), 7.60 (2H, d, J=7.1 Hz), 9.06 (2H, br s).

Example 173

Tetrahydro-N-[2-[[(2-nitrophenyl)sulfonyl](2-propenyl)amino]ethyl]-3-oxo-1,1-diphenyl-3H-oxazolo[3,4-a]pyrazine-7(1H)-carboxamide In the same manner as in Example 171, the title compound was obtained using N-allyl-N-(2-aminoethyl)-2-nitrobenzenesulfonamide instead of N-(2-aminoethyl)-N-cyclopropyl-2-nitrobenzenesulfonamide. Yield 89%.

Melting point 145-147° C.

$^1$H NMR (CDCl$_3$) δ 2.24 (1H, dd, J=11.3 Hz, 13.4 Hz), 2.74-2.83 (1H, m), 3.08-3.18 (1H, m), 3.29-3.54 (4H, m), 3.76-3.85 (2H, m), 3.92-3.97 (3H, m), 4.50 (1H, dd, J=3.6 Hz, 11.2 Hz), 5.07 (1H, br s), 5.16-5.26 (2H, m), 5.56-5.69 (1H, m), 7.24-7.39 (8H, m), 7.54-7.57 (2H, m), 7.64-7.76 (3H, m), 8.01-8.04 (1H, m).

Example 174

N-[2-[Cyclopropyl(ethyl)amino]ethyl]-tetrahydro-3-oxo-1,1-diphenyl-3H-oxazolo[3,4-a]pyrazine-7(1H)-carboxamide hydrochloride To a solution of N-[2-(cyclopropylamino)ethyl]-tetrahydro-3-oxo-1,1-diphenyl-3H-oxazolo[3,4-a]pyrazine-7(1H)-carboxamide hydrochloride (0.15 g, 0.33 mmol), triethylamine (67 mg, 0.66 mmol) and 90% acetaldehyde (0.040 mL, 0.64 mmol) in 1,2-dichloroethane (5 mL) was added sodium triacetoxyborohydride (0.14 g, 0.66 mmol), and the mixture was stirred at room temperature for 13 hours. The reaction solution was diluted with water and then extracted with ethyl acetate. The organic layer was washed with water and saturated brine and dried over magnesium sulfate. The solid was filtered off, and the filtrate was concentrated. The residue was purified with amino silica gel column chromatography (hexane:ethyl acetate=1:1 to ethyl acetate) and concentrated. A 4 M hydrogen chloride/ethyl acetate solution (5 mL) was added thereto, and then concentrated. The residue was crystallized from diethyl ether to obtain the title compound (54 mg, yield 34%).

Melting point 138-140° C.

$^1$H NMR (DMSO-d$_6$) δ 0.83-0.86 (2H, m), 1.00-1.20 (2H, m), 1.28 (3H, t, J=7.2 Hz), 2.11 (1H, t, J=12.8 Hz), 2.62-2.73 (1H, m), 2.82 (1H, br s), 2.98-3.07 (1H, m), 3.24-3.30 (4H, m), 3.42-3.46 (2H, m), 3.58-3.63 (1H, m), 3.86-3.96 (2H, m), 4.53 (1H, dd, J=3.3 Hz, 11.1 Hz), 7.14 (1H, br s), 7.30-7.45 (8H, m), 7.60 (2H, d, J=8.1 Hz), 10.15 (1H, br s).

Example 175

Tetrahydro-3-oxo-1,1-diphenyl-N-[2-[(2-propenyl)amino]ethyl]-3H-oxazolo[3,4-a]pyrazine-7(1H)-carboxamide hydrochloride In the same manner as in Example 172, the title compound was obtained using tetrahydro-N-[2-[[(2-nitrophenyl)sulfonyl](2-propenyl)amino]ethyl]-3-oxo-1,1-diphenyl-3H-oxazolo[3,4-a]pyrazine-7(1H)-carboxamide instead of N-[2-[cyclopropyl[(2-nitrophenyl)sulfonyl]amino]ethyl]-tetrahydro-3-oxo-1,1-diphenyl-3H-oxazolo[3,4-a]pyrazine-7(1H)-carboxamide. Yield 78%.

Melting point 139-141° C.

$^1$H NMR (DMSO-d$_6$) δ 2.10 (1H, t, J=12.6 Hz), 2.60-2.70 (1H, m), 2.93 (2H, br s), 3.00-3.10 (1H, m), 3.26-3.37 (2H, m), 3.57-3.63 (3H, m), 3.87-3.97 (2H, m), 4.56 (1H, dd, J=3.7 Hz, 11.1 Hz), 5.40 (1H, d, J=10.4 Hz), 5.46 (1H, dd, J=1.1 Hz, 17.3 Hz), 5.83-5.97 (1H, m), 7.16 (1H, t, J=5.2 Hz), 7.30-7.45 (8H, m), 7.60 (2H, d, J=7.1 Hz), 9.00 (2H, br s).

Example 176

Tetrahydro-N-(1-methyl-4-piperidinyl)-3-oxo-1,1-diphenyl-3H-oxazolo[3,4-a]pyrazine-7(1H)-carboxamide To tetrahydro-3-oxo-1,1-diphenyl-N-(4-piperidinyl)-3H-oxazolo[3,4-a]pyrazine-7(1H)-carboxamide hydrochloride (0.14 g, 0.30 mmol) were added N,N-dimethylformamide (5 mL) and potassium carbonate (0.14 g, 1.0 mmol), and the mixture was stirred at room temperature for 1 hour. To the reaction solution was added methyl iodide (43 mg, 0.30 mmol), and the mixture was stirred at room temperature for 24 hours. To the reaction solution was added ethyl acetate, and the resulting mixture was washed with a 0.5 M aqueous sodium hydrogen carbonate solution, dried over anhydrous magnesium sulfate and concentrated under reduced pressure. The residue was purified with amino silica gel column chromatography (hexane:ethyl acetate=9:1 to ethyl acetate), and then the powder was formed from diisopropyl ether to obtain the title compound (18 mg, yield 14%).

Amorphous.

$^1$H NMR (CDCl$_3$) δ 1.37-1.47 (2H, m), 1.92-2.13 (4H, m), 2.22-2.24 (3H, m), 2.77-3.09 (4H, m), 3.56-3.61 (2H, m), 3.85-4.00 (2H, m), 4.18-4.42 (2H, m), 7.27-7.51 (10H, m).

Example 177

1,1-Dimethylethyl 4-[(tetrahydro-3-oxo-1,1-diphenyl-3H-oxazolo[3,4-a]pyrazin-7(1H)-yl)carbonyl]-1-piperidinecarboxylate In the same manner as in Example 144, the title compound was obtained using 1-(tert-butoxycarbonyl)piperidine-4-carboxylic acid instead of 3-[[(tert-butoxycarbonyl)amino]methyl]benzoic acid. Yield 90%.

Amorphous.

$^1$H NMR (CDCl$_3$) δ 1.47 (9H, s), 1.63-2.06 (4H, m), 2.60-2.82 (4H, m), 3.03-3.06 (2H, m), 3.82-3.97 (2H, m), 4.04-4.12 (2H, m), 4.33-4.52 (2H, m), 7.28-7.51 (10H, m).

Example 178

Tetrahydro-3-oxo-1,1-diphenyl-N-(1-propyl-4-piperidinyl)-3H-oxazolo[3,4-a]pyrazine-7(1H)-carboxamide In the same manner as in Example 146, the title compound was obtained using propionaldehyde instead of acetone. Yield 69%.

Amorphous.

$^1$H NMR (CDCl$_3$) δ 0.89 (3H, t, J=7.3 Hz), 1.45-1.53 (4H, m), 1.91-2.16 (5H, m), 2.25-2.32 (2H, m), 2.82-2.91 (3H, m), 3.07-3.11 (1H, m), 3.56-3.61 (2H, m), 3.83-3.87 (1H, m), 3.97-4.02 (1H, m), 4.21-4.23 (1H, m), 4.41 (1H, dd, J=3.5 Hz, 11.2 Hz), 7.26-7.42 (8H, m), 7.50-7.53 (2H, m).

Example 179

Hexahydro-1,1-diphenyl-7-[(4-piperidinyl)carbonyl]-3H-oxazolo[3,4-a]pyrazine-3-one hydrochloride In the same manner as in Example 125, the title compound was obtained using 1,1-dimethylethyl 4-[(tetrahydro-3-oxo-1,1-diphenyl-3H-oxazolo[3,4-a]pyrazin-7(1H)-yl)carbonyl]-1-piperidinecarboxylate instead of 1,1-dimethylethyl 4-[[(tetrahydro-3-oxo-1,1-diphenyl-3H-oxazolo[3,4-a]pyrazin-7(1H)-yl)carbonyl]amino]-1H-benzimidazole-1-carboxylate. Yield 94%.

Melting point 186-190° C.

Amide rotamer ratio (α:β=1:3.7).

$^1$H NMR (DMSO-d$_6$) δ 1.58-1.82 (4H of α, 4H of β, m), 2.03 (1H of β, t, J=12.2 Hz), 2.49-2.51 (1H of α, m), 2.85-3.30 (7H of α, 7H of β, m), 3.62-3.78 (2H of α, 1H of β, m), 3.94-4.15 (2H of β, m), 4.32-4.38 (1H of α, m), 4.53-4.62 (1H of α, 1H of β, m), 7.33-7.43 (8H of α, 8H of β, m), 7.56-7.60 (2H of α, 2H of β, m), 8.68 (1H of α, 1H of β, m), 8.98 (1H of β, br), 9.18 (1H of α, br).

Example 180

Hexahydro-7-[[1-(1-methylethyl)-4-piperidinyl]carbonyl]-1,1-diphenyl-3H-oxazolo[3,4-a]pyrazin-3-one In the same manner as in Example 146, the title compound was obtained using hexahydro-1,1-diphenyl-7-[(4-piperidinyl)carbonyl]-3H-oxazolo[3,4-a]pyrazin-3-one hydrochloride instead of tetrahydro-3-oxo-1,1-diphenyl-N-(4-piperidinyl)-3H-oxazolo[3,4-a]pyrazine-7(1H)-carboxamide hydrochloride. Yield 18%.

Melting point 161-162° C.

$^1$H NMR (CDCl$_3$) δ 1.03-1.05 (6H, m), 1.59-1.97 (5H, m), 2.09-2.18 (2H, m), 2.35-3.39 (1H, m), 2.67-2.74 (1H, m), 2.82-3.04 (4H, m), 3.82-3.95 (2H, m), 4.30-4.35 (1H, m), 4.50-4.55 (1H, m), 7.25-7.39 (8H, m), 7.49-7.51 (2H, m).

Example 181

4-[(Tetrahydro-3-oxo-1,1-diphenyl-3H-oxazolo[3,4-a]pyrazin-7(1H)-yl)carbonyl]-1-piperidinecarboxaldehyde While the reaction was carried out in Example 180, the title compound was obtained as a by-product. Yield 39%.

Melting point 133-136° C.

$^1$H NMR (CDCl$_3$) δ 1.70-1.75 (4H, m), 1.98-2.02 (1H, m), 2.52-2.78 (2H, m), 2.98-3.14 (3H, m), 3.64-3.82 (2H, m), 3.96-3.99 (1H, m), 4.32-4.48 (3H, m), 7.26-7.42 (8H, m), 7.49-7.52 (2H, m), 8.03 (1H, s).

Example 182

N-[2-(3,6-Dihydropyridin-1(2H)-yl)ethyl]-tetrahydro-N-methyl-3-oxo-1,1-diphenyl-3H-oxazolo[3,4-a]pyrazine-7(1H)-carboxamide In the same manner as in Example 10, the title compound was obtained using N-[2-(3,6-dihydropyridin-1(2H)-yl)ethyl]-N-methylamine instead of phenylhydrazine. Yield 41%.

Amorphous.
Amide rotamer ratio (α:β=1:5.3).
$^1$H NMR (CDCl$_3$) δ 2.11-2.22 (3H of α, 3H of β, m), 2.54-2.63 (4H of α, 4H of β, m), 2.82-3.15 (7H of α, 7H of β, m), 3.28-3.55 (4H of α, 4H of β, m), 3.62-3.64 (1H of α, m), 3.77-3.82 (1H of β, m), 4.58 (1H of β, dd, J=3.5 Hz, 11.2 Hz), 4.92-4.96 (1H of α, m), 5.60-5.76 (2H of α, 2H of β, m), 7.26-7.39 (8H of α, 8H of β, m), 7.51-7.54 (2H of α, 2H of β, m).

Example 183

Hexahydro-1,1-diphenyl-7-[(1-propyl-4-piperidinyl)carbonyl]-3H-oxazolo[3,4-a]pyrazin-3-one In the same manner as in Example 146, the title compound was obtained using hexahydro-1,1-diphenyl-7-[(4-piperidinyl)carbonyl]-3H-oxazolo[3,4-a]pyrazin-3-one hydrochloride instead of tetrahydro-3-oxo-1,1-diphenyl-N-(4-piperidinyl)-3H-oxazolo[3,4-a]pyrazine-7(1H)-carboxamide hydrochloride, and using propionaldehyde instead of acetone. Yield 40%.
Melting point 151° C.
$^1$H NMR (CDCl$_3$) δ 0.89 (3H, t, J=7.3 Hz), 1.49-1.68 (4H, m), 1.72-2.02 (5H, m), 2.25-2.42 (3H, m), 2.94-3.04 (4H, m), 3.82-3.96 (2H, m), 4.32 (1H, dd, J=3.6 Hz, 11.3 Hz), 4.50-4.55 (1H, m), 7.26-7.42 (8H, m), 7.49-7.52 (2H, m).

Example 184

[2-(3,6-Dihydropyridin-1(2H)-yl)ethyl]tetrahydro-3-oxo-1,1-diphenyl-3H-oxazolo[3,4-a]pyrazine-7(1H)-carboxylate Hexahydro-1,1-diphenyl-3H-oxazolo[3,4-a]pyrazin-3-one (0.15 g, 0.50 mmol) was dissolved in tetrahydrofuran (5 mL). Triethylamine (0.14 mL, 1.0 mmol) and 2-bromoethyl chlorocarbonate (0.10 g, 0.55 mmol) were added thereto, and the mixture was stirred at room temperature for 1 hour. Diisopropylamine (0.36 mL, 2.0 mmol), N,N-dimethylformamide (5 mL) and 1,2,3,6-tetrahydropyridine (0.23 mL, 2.5 mmol) were sequentially added thereto, and the mixture was stirred at room temperature for 24 hours. To the reaction solution was added ethyl acetate, and the resulting mixture was washed with a 0.5 M aqueous sodium hydrogen carbonate solution, dried over anhydrous magnesium sulfate and concentrated under reduced pressure. The residue was purified with amino silica gel column chromatography (hexane:ethyl acetate=9:1 to ethyl acetate), and then crystallized from diisopropyl ether to obtain the title compound (0.13 g, yield 59%).
Melting point 107-108° C.
$^1$H NMR (CDCl$_3$) δ 2.10-2.28 (3H, m), 2.59-2.83 (5H, m), 3.02-3.10 (3H, m), 3.82-3.86 (1H, m), 3.95-4.11 (2H, m), 4.25-4.29 (2H, m), 4.37 (1H, dd, J=3.4 Hz, 11.1 Hz), 5.63-5.76 (2H, m), 7.26-7.42 (8H, m), 7.49-7.51 (2H, m).

Example 185

Hexahydro-1,1-diphenyl-7-[(4-propyl-1-piperazinyl)carbonyl]-3H-oxazolo[3,4-a]pyrazin-3-one In the same manner as in Example 10, using 1,1-dimethylethyl piperazine carboxylate instead of phenylhydrazine, 1,1-dimethylethyl 4-[(tetrahydro-3-oxo-1,1-diphenyl-3H-oxazolo[3,4-a]pyrazin-7(1H)-yl)carbonyl]-1-piperazine carboxylate was obtained as a crude product. In the same manner as in Example 125, hexahydro-1,1-diphenyl-7-[(piperazin-4-yl)carbonyl]-3H-oxazolo[3,4-a]pyrazin-3-one hydrochloride was obtained as a crude product from 1,1-dimethylethyl 4-[(tetrahydro-3-oxo-1,1-diphenyl-3H-oxazolo[3,4-a]pyrazin-7(1H)-yl)carbonyl]-1-piperazine carboxylate. Further, in the same manner as in Example 146, the title compound was obtained from hexahydro-1,1-diphenyl-7-[(piperazin-4-yl)carbonyl]-3H-oxazolo[3,4-a]pyrazin-3-one hydrochloride using propionaldehyde instead of acetone. Yield 18%.
Melting point 125-127° C.
$^1$H NMR (CDCl$_3$) δ 0.90 (3H, t, J=7.3 Hz), 1.46-1.55 (2H, m), 2.18 (1H, t, J=11.8 Hz), 2.22-2.40 (6H, m), 2.84-2.94 (1H, m), 3.09 (1H, dt, J=3.9 Hz, 12.8 Hz), 3.20-3.35 (4H, m), 3.47-3.56 (2H, m), 3.79-3.83 (1H, m), 4.55 (1H, dd, J=3.1 Hz, 11.0 Hz), 7.26-7.41 (8H, m), 7.51-7.54 (2H, m).

Example 186

Hexahydro-7-[(1-pentyl-4-piperidinyl)carbonyl]-1,1-diphenyl-3H-oxazolo[3,4-a]pyrazin-3-one In the same manner as in Example 146, the title compound was obtained using hexahydro-1,1-diphenyl-7-[(4-piperidinyl)carbonyl]-3H-oxazolo[3,4-a]pyrazin-3-one hydrochloride instead of tetrahydro-3-oxo-1,1-diphenyl-N-(4-piperidinyl)-3H-oxazolo[3,4-a]pyrazine-7(1H)-carboxamide hydrochloride, and using pentanal instead of acetone. Yield 72%.
Melting point 115-117° C.
$^1$H NMR (CDCl$_3$) δ 0.89 (3H, t, J=7.1 Hz), 1.24-1.31 (4H, m), 1.43-1.68 (4H, m), 1.75-2.01 (5H, m), 2.27-2.42 (3H, m), 2.94-3.04 (4H, m), 3.82-3.96 (2H, m), 4.32 (1H, dd, J=3.6 Hz, 11.3 Hz), 4.50-4.55 (1H, m), 7.31-7.41 (8H, m), 7.50-7.53 (2H, m).

Example 187

N-[2-(3,6-Dihydropyridin-1(2H)-yl)-1,1-dimethylethyl]-tetrahydro-3-oxo-1,1-diphenyl-3H-oxazolo[3,4-a]pyrazine-7(1H)-carboxamide In the same manner as in Example 124, the title compound was obtained using N-[2-(3,6-dihydropyridin-1(2H)-yl)-1,1-dimethylethyl]amine dihydrochloride instead of 1,1-dimethylethyl 4-amino-1H-benzimidazole-1-carboxylate. Yield 57%.
Melting point 154-155° C.
$^1$H NMR (CDCl$_3$) δ 1.34 (6H, s), 2.08-2.16 (3H, m), 2.45 (2H, s), 2.69 (2H, t, J=5.5 Hz), 2.82 (1H, dt, J=3.3 Hz, 12.9 Hz), 3.01-3.09 (3H, m), 3.61-3.65 (1H, m), 3.81-3.95 (2H, m), 4.39 (1H, dd, J=3.5 Hz, 11.1 Hz), 5.62-5.76 (3H, m), 7.26-7.41 (8H, m), 7.50-7.53 (2H, m).

Example 188

N-[2-(3,6-Dihydropyridin-1(2H)-yl)-1-oxoethyl]-tetrahydro-3-oxo-1,1-diphenyl-3H-oxazolo[3,4-a]pyrazine-7(1H)-carboxamide Hexahydro-1,1-diphenyl-3H-oxazolo[3,4-a]pyrazin-3-one (0.22 g, 0.75 mmol) was dissolved in tetrahydrofuran (7.5 mL). 2-Chloroacetyl isocyanate (0.10 g, 0.83 mmol) was added thereto, and the mixture was stirred at −20° C. for 1 hour. 1,2,3,6-Tetrahydropyridine (0.27 mL, 3.0 mmol) was added thereto, and the mixture was stirred at room temperature for 24 hours. To the reaction solution was added ethyl acetate, and the resulting mixture was washed with a 0.5 M aqueous sodium hydrogen carbonate solution, dried over anhydrous magnesium sulfate and concentrated under reduced pressure. The residue was purified with silica gel column chromatography (hexane:ethyl acetate=1:1 to ethyl acetate), and then crystallized from ethyl acetate-hexane to obtain the title compound (0.25 g, yield 72%).

Melting point 156-157° C.

$^1$H NMR (CDCl$_3$) δ 2.17-2.20 (2H, m), 2.33 (1H, t, J=11.9 Hz), 2.60-2.70 (2H, m), 2.87-2.95 (1H, m), 3.06-3.26 (5H, m), 3.62-4.08 (3H, m), 4.72-4.78 (1H, m), 45.62-5.66 (1H, m), 5.76-5.80 (1H, m), 7.29-7.42 (8H, m), 7.56-7.59 (2H, m), 9.06 (1H, br).

Example 189

N-[2-(3,6-Dihydropyridin-1(2H)-yl)-2,2-dimethylethyl]-tetrahydro-3-oxo-1,1-diphenyl-3H-oxazolo[3,4-a]pyrazine-7(1H)-carboxamide In the same manner as in Example 124, the title compound was obtained using N-[2-(3,6-dihydropyridin-1(2H)-yl)-2,2-dimethylethyl]amine dihydrochloride instead of 1,1-dimethylethyl 4-amino-1H-benzimidazole-1-carboxylate. Yield 48%.

Melting point 196-198° C.

$^1$H NMR (CDCl$_3$) δ 1.06 (6H, s), 2.05 (2H, s), 2.17 (1H, t, J=13.2 Hz), 2.53-2.57 (2H, m), 2.79-2.88 (1H, m), 3.02-3.51 (5H, m), 3.70-3.90 (3H, m), 4.37-4.42 (1H, m), 5.53-5.73 (3H, m), 7.26-7.39 (8H, m), 7.50-7.52 (2H, m).

Example 190

N-[1-[(3,6-Dihydropyridin-1(2H)-yl)methyl]cyclopropyl]-tetrahydro-3-oxo-1,1-diphenyl-3H-oxazolo[3,4-a]pyrazine-7(1H)-carboxamide In the same manner as in Example 124, the title compound was obtained using N-[1-[(3,6-dihydropyridin-1(2H)-yl)methyl]cyclopropyl]amine dihydrochloride instead of 1,1-dimethylethyl 4-amino-1H-benzimidazole-1-carboxylate. Yield 20%.

Amorphous.

$^1$H NMR (CDCl$_3$) δ 0.63-0.65 (2H, m), 0.86-0.90 (2H, m), 2.04-2.16 (3H, m), 2.44 (1H, d, J=12.9 Hz), 2.57-2.64 (3H, m), 2.82-2.92 (1H, m), 3.00-3.12 (3H, m), 3.59-3.66 (1H, m), 3.78-3.83 (1H, m), 3.93-3.97 (1H, m), 4.40 (1H, dd, J=3.6 Hz, 11.2 Hz), 5.12 (1H, br), 5.66-5.72 (2H, m), 7.26-7.42 (8H, m), 7.50-7.53 (2H, m).

Example 191

1,1-Bis(4-fluorophenyl)-N-[2-(3,6-dihydropyridin-1(2H)-yl)ethyl]-tetrahydro-3-oxo-3H-oxazolo[3,4-a]pyrazine-7(1H)-carboxamide In the same manner as in Example 64, the title compound was obtained using 1,2,3,6-tetrahydropyridine instead of morpholine, and using 1,1-bis(4-fluorophenyl)-hexahydro-3H-oxazolo[3,4-a]pyrazin-3-one instead of hexahydro-1,1-diphenyl-3H-oxazolo[3,4-a]pyrazin-3-one. Yield 65%.

Melting point 153-154° C.

$^1$H NMR (CDCl$_3$) δ 2.09-2.17 (3H, m), 2.55-2.64 (4H, m), 2.82-3.13 (4H, m), 3.32-3.35 (2H, m), 3.66-3.71 (1H, m), 3.82-3.93 (2H, m), 4.35 (1H, dd, J=3.6 Hz, 11.2 Hz), 5.29 (1, br), 5.64-5.76 (2H, m), 7.00-7.11 (4H, m), 7.26-7.28 (1H, m), 7.44-7.49 (2H, m).

Example 192

1,1-Bis(4-fluorophenyl)-tetrahydro-3-oxo-N-[2-(1-piperidinyl)ethyl]-3H-oxazolo[3,4-a]pyrazine-7(1H)-carboxamide In the same manner as in Example 64, the title compound was obtained using piperidine instead of morpholine, and using 1,1-bis(4-fluorophenyl)-hexahydro-3H-oxazolo[3,4-a]pyrazin-3-one instead of hexahydro-1,1-diphenyl-3H-oxazolo[3,4-a]pyrazin-3-one. Yield 52%.

Melting point 161° C.

$^1$H NMR (CDCl$_3$) δ 1.49-1.55 (6H, m), 2.14 (1H, t, J=12.3 Hz), 2.36-2.44 (6H, m), 2.89 (1H, dt, J=3.4 Hz, 13.2 Hz), 3.10 (1H, dt, J=3.5 Hz, 13.0 Hz), 3.26-3.28 (2H, m), 3.66-3.71 (1H, m), 3.83-3.92 (2H, m), 4.36 (1H, dd, J=3.5 Hz, 11.1 Hz), 5.36 (1H, br), 7.01-7.11 (4H, m), 7.26-7.29 (2H, m), 7.45-7.49 (2H, m).

Example 193

1,1-Bis(3-fluorophenyl)-N-[2-(3,6-dihydropyridin-1(2H)-yl)ethyl]-tetrahydro-3-oxo-3H-oxazolo[3,4-a]pyrazine-7(1H)-carboxamide In the same manner as in Example 64, the title compound was obtained using 1,2,3,6-tetrahydropyridine instead of morpholine, and using 1,1-bis(3-fluorophenyl)-hexahydro-3H-oxazolo[3,4-a]pyrazin-3-one instead of hexahydro-1,1-diphenyl-3H-oxazolo[3,4-a]pyrazin-3-one. Yield 74%.

Melting point 146° C.

$^1$H NMR (CDCl$_3$) δ 2.14-2.22 (3H, m), 2.54-2.58 (4H, m), 2.84-3.14 (4H, m), 3.31-3.34 (2H, m), 3.65-3.70 (1H, m), 3.82-3.97 (2H, m), 4.36 (1H, dd, J=3.4 Hz, 11.0 Hz), 5.27 (1H, br), 5.65-5.78 (2H, m), 6.98-7.08 (4H, m), 7.26-7.40 (4H, m).

Example 194

1,1-Bis(3-fluorophenyl)-tetrahydro-3-oxo-N-[2-(1-piperidinyl)ethyl]-3H-oxazolo[3,4-a]pyrazine-7(1H)-carboxamide In the same manner as in Example 64, the title compound was obtained using piperidine instead of morpholine, and using 1,1-bis(3-fluorophenyl)-hexahydro-3H-oxazolo[3,4-a]pyrazin-3-one instead of hexahydro-1,1-diphenyl-3H-oxazolo[3,4-a]pyrazin-3-one. Yield 43%.

Melting point 138-141° C.

$^1$H NMR (CDCl$_3$) δ 1.50-1.58 (6H, m), 2.20 (1H, t, J=12.3 Hz), 2.33-2.46 (6H, m), 2.85-2.94 (1H, m), 3.05-3.14 (1H, m), 3.24-3.27 (2H, m), 3.67-3.72 (1H, m), 3.84-3.96 (2H, m), 4.35-4.39 (1H, m), 5.36 (1H, br), 7.02-7.10 (4H, m), 7.24-7.40 (4H, m).

Example 195

1,1-Bis(3-fluorophenyl)-N-[(4-fluorophenyl)methyl]-tetrahydro-3-oxo-3H-oxazolo[3,4-a]pyrazine-7(1H)-carboxamide 1,1-Bis(3-fluorophenyl)-hexahydro-3H-oxazolo[3,4-a]pyrazin-3-one (0.18 g, 0.55 mmol) was dissolved in tetrahydrofuran (5 mL). (4-Fluorophenyl)methyl isocyanate (0.15 g, 1.0 mmol) was added thereto, and the mixture was stirred at room temperature for 1 hour. The reaction solution was concentrated under reduced pressure. The residue was purified with silica gel column chromatography (hexane:ethyl acetate=50:1 to ethyl acetate) to obtain the title compound (0.25 g, yield 96%).
Amorphous.
$^1$H NMR (CDCl$_3$) δ 2.17 (1H, t, J=12.3 Hz), 2.92-3.13 (2H, m), 3.61-3.65 (1H, m), 3.81-3.86 (1H, m), 4.03-4.12 (1H, m), 4.34-4.35 (3H, m), 4.88 (1H, br), 6.97-7.08 (6H, m), 7.19-7.39 (6H, m).

Example 196

Ethyl 1-[2-[[(tetrahydro-3-oxo-1,1-diphenyl-3H-oxazolo[3,4-a]pyrazin-7(1H)-yl)carbonyl]amino]ethyl]-4-piperidinecarboxylate In the same manner as in Example 64, the title compound was obtained using ethyl isonipecotate instead of morpholine. Yield 91%.
Amorphous.
$^1$H NMR (CDCl$_3$) δ 1.26 (3H, t, J=7.1 Hz), 1.62-1.72 (2H, m), 1.88-1.92 (2H, m), 2.00-2.07 (2H, m), 2.17 (1H, t, J=13.2 Hz), 2.26-2.30 (1H, m), 2.44-2.48 (2H, m), 2.80-2.91 (3H, m), 3.04-3.11 (1H, m), 3.26-3.29 (2H, m), 3.68-3.72 (1H, m), 3.85-3.89 (2H, m), 4.10-4.18 (2H, m), 4.39-4.43 (1H, m), 5.20 (1H, br), 7.28-7.41 (8H, m), 7.50-7.53 (2H, m).

Example 197

Phenyl 1,1-bis(3-fluorophenyl)-tetrahydro-3-oxo-3H-oxazolo[3,4-a]pyrazine-7(1H)-carboxylate In the same manner as in Example 3, the title compound was obtained using phenyl chlorocarbonate instead of 4-fluorophenyl chlorocarbonate, and using 1,1-bis(3-fluorophenyl)-hexahydro-3H-oxazolo[3,4-a]pyrazin-3-one instead of hexahydro-1,1-diphenyl-3H-oxazolo[3,4-a]pyrazin-3-one. Yield 84%.
Melting point 159-160° C.
$^1$H NMR (CDCl$_3$) δ 2.28-2.52 (1H, m), 2.82-3.06 (1H, m), 3.20 (1H, dt, J=2.9 Hz, 12.7 Hz), 3.93-3.97 (1H, m), 4.05-4.10 (1H, m), 4.27-4.32 (1H, m), 4.44 (1H, dd, J=3.4 Hz, 11.3 Hz), 7.03-7.10 (6H, m), 7.21-7.44 (7H, m).

Example 198

1,1-Bis(3-fluorophenyl)-N-(4-fluorophenyl)-tetrahydro-3-oxo-3H-oxazolo[3,4-a]pyrazine-7(1H)-carboxamide In the same manner as in Example 195, the title compound was obtained using 4-fluorophenyl isocyanate instead of (4-fluorophenyl)methyl isocyanate. Yield 88%.
Amorphous.
$^1$H NMR (CDCl$_3$) δ 2.26 (1H, t, J=12.3 Hz), 3.06-3.23 (2H, m), 3.76-3.80 (1H, m), 3.90-3.96 (1H, m), 4.04-4.09 (1H, m), 4.43 (1H, dd, J=3.5 Hz, 11.2 Hz), 6.28 (1H, br), 6.98-7.10 (6H, m), 7.19-7.39 (6H, m).

Example 199

(+)-N-[(4-Fluorophenyl)methyl]-tetrahydro-3-oxo-1,1-diphenyl-3H-oxazolo[3,4-a]pyrazine-7(1H)-carboxamide Racemate (320 mg) of N-[(4-fluorophenyl)methyl]-tetrahydro-3-oxo-1,1-diphenyl-3H-oxazolo[3,4-a]pyrazine-7(1H)-carboxamide was resolved with the following HPLC conditions.
Preparative HPLC Conditions:
Column; CHIRALPAK AD 50 mmID×500 mL (manufactured by Daicel Chemical Industries, Ltd.)
Mobile phase; hexane/2-propanol=90/10
Flow rate; 80 mL/min
Temperature; 30° C.
Detection; UV 220 nm
Loading dose; 160 mg
Each fraction was concentrated under reduced pressure, and hexane was added thereto. As an enantiomer having a long retention time, the title compound (158 mg, yield 49%, 99.9% ee) was obtained as powder. $^1$H NMR of the above obtained compound corresponded with the compound obtained in Example 25.
[α]$^{20}_D$ +158.00 (c 0.991, chloroform).

Example 200

(−)-N-[(4-Fluorophenyl)methyl]-tetrahydro-3-oxo-1,1-diphenyl-3H-oxazolo[3,4-a]pyrazine-7(1H)-carboxamide While the operation was carried out in Example 199, as an enantiomer having a short retention time, the title compound (158 mg, yield 49%, 99.9% ee) was obtained as powder. $^1$H NMR of the above obtained compound corresponded with the compound obtained in Example 25.
[α]$^{20}_D$ −159.1° (c 0.871, chloroform).

Example 201

(+)-N-[2-(3,6-Dihydropyridin-1(2H)-yl)ethyl]-tetrahydro-3-oxo-1,1-diphenyl-3H-oxazolo[3,4-a]pyrazine-7(1H)-carboxamide Racemate (2.0 g) of N-[2-(3,6-dihydropyridin-1(2H)-yl)ethyl]-tetrahydro-3-oxo-1,1-diphenyl-3H-oxazolo[3,4-a]pyrazine-7(1H)-carboxamide was resolved with the following HPLC conditions.
Preparative HPLC Conditions:
Column; CHIRALPAK AD 50 mmID×500 mL (manufactured by Daicel Chemical Industries, Ltd.)
Mobile phase; hexane/ethanol=93/7
Flow rate; 70 mL/min
Temperature; 35° C.
Detection; UV 220 nm
Loading dose; 100 mg
Each fraction was concentrated under reduced pressure, and redissolved in ethanol. Then, insolubles were removed by a membrane filter. After concentration under reduced pressure, hexane was added thereto. As an enantiomer having a long retention time, the title compound (957 mg, yield 48%, 99.4% ee) was obtained as powder. $^1$H NMR of the above obtained compound corresponded with the compound obtained in Example 85.
[α]$^{20}_D$ +165.3° (c 1.010, chloroform).
Further, in the same manner as in Example 64, the title compound was obtained using (+)-hexahydro-1,1-diphenyl-3H-oxazolo[3,4-a]pyrazin-3-one instead of hexahydro-1,1-diphenyl-3H-oxazolo[3,4-a]pyrazin-3-one, and using 1,2,3,6-tetrahydropyridine instead of morpholine. Yield 44%, 99.9% ee. $^1$H NMR of the above obtained compound corresponded with the compound obtained in Example 85.
Melting point 177-179° C
[α]$^{20}_D$ +165.9° (c 0.930, chloroform). .

Example 202

(−)-N-[2-(3,6-Dihydropyridin-1(2H)-yl)ethyl]-tetrahydro-3-oxo-1,1-diphenyl-3H-oxazolo[3,4-a]pyrazine-7(1H)-carboxamide While the operation was carried out in Example 199, as an enantiomer having a short retention time, the title compound (970 mg, yield 49%, 99.9% ee) was obtained as powder. $^1$H NMR of the above obtained compound corresponded with the compound obtained in Example 85.

$[\alpha]^{20}_D$ −159.4° (c 0.929, chloroform).

Further, in the same manner as in Example 64, the title compound was obtained using (−)-hexahydro-1,1-diphenyl-3H-oxazolo[3,4-a]pyrazin-3-one instead of hexahydro-1,1-diphenyl-3H-oxazolo[3,4-a]pyrazin-3-one, and using 1,2,3,6-tetrahydropyridine instead of morpholine. Yield 51%, 99.9% ee. $^1$H NMR of the above obtained compound corresponded with the compound obtained in Example 85.

Melting point 177-178° C.

$[\alpha]^{20}_D$ −165.5° (c 0.791, chloroform).

Example 203

(−)-N-(4-Bromophenyl)-tetrahydro-3-oxo-1,1-diphenyl-3H-oxazolo[3,4-a]pyrazine-7(1H)-carboxamide In the same manner as in Example 4, the title compound was obtained using (−)-hexahydro-1,1-diphenyl-3H-oxazolo[3,4-a]pyrazin-3-one instead of hexahydro-1,1-diphenyl-3H-oxazolo[3,4-a]pyrazin-3-one, and using 4-bromophenyl isocyanate instead of phenyl isocyanate. Yield 96%.

Melting point 244-246° C.

$^1$H NMR (CDCl$_3$) δ 2.25 (1H, t, J=11.5 Hz), 2.99-3.21 (2H, m), 3.78-3.82 (1H, m), 3.90-3.95 (1H, m), 4.01-4.06 (1H, m), 4.47 (1H, dd, J=3.6 Hz, 11.3 Hz), 6.29 (1H, br), 7.20-7.42 (12H, m), 7.50-7.53 (2H, m).

$[\alpha]^{20}_D$ −119.3° (c 0.850, chloroform).

Example 204

Tetrahydro-N-[2-(4-hydroxy-4-methyl-1-piperidinyl)ethyl]-3-oxo-1,1-diphenyl-3H-oxazolo[3,4-a]pyrazine-7(1H)-carboxamide In the same manner as in Example 64, the title compound was obtained using 4-hydroxy-4-methylpiperidine instead of morpholine. Yield 52%.

Melting point 154° C.

$^1$H NMR (CDCl$_3$) δ 1.25 (3H, s), 1.58-1.65 (4H, m), 2.16 (1H, t, J=12.9 Hz), 2.36-2.52 (6H, m), 2.88-2.92 (1H, m), 3.07 (1H, dt, J=2.5 Hz, 12.9 Hz), 3.27-3.30 (2H, m), 3.66-3.70 (1H, m), 3.84-3.96 (2H, m), 4.41 (1H, dd, J=2.4 Hz, 11.2 Hz), 5.22 (1H, br), 7.26-7.41 (8H, m), 7.50-7.53 (2H, m).

Example 205

Hexahydro-1,1-diphenyl-7-(4-piperidinylacetyl)-3H-oxazolo[3,4-a]pyrazin-3-one hydrochloride In the same manner as in Example 144, 1,1-dimethylethyl 4-[2-oxo-2-(tetrahydro-3-oxo-1,1-diphenyl-3H-oxazolo[3,4-a]pyrazin-7(1H)-yl)ethyl]-1-piperidinecarboxylate was obtained using t-butyl 4-(carboxymethyl)piperidine-1-carboxylate instead of 3-[[(tert-butoxycarbonyl)amino]methyl]benzoic acid as a crude product. In the same manner as in Example 125, the title compound was obtained from 1,1-dimethylethyl 4-[2-oxo-2-(tetrahydro-3-oxo-1,1-diphenyl-3H-oxazolo[3,4-a]pyrazin-7(1H)-yl)ethyl]-1-piperidinecarboxylate. Yield 69%.

Melting point 180-182° C.

Amide rotamer ratio (α:β=1:2).

$^1$H NMR (DMSO-d$_6$) δ 1.32-1.36 (2H of α, 2H of β, m), 1.78-2.02 (4H of α, 4H of β, m), 2.14-2.35 (2H of α, 2H of β, m), 2.73-3.21 (6H of α, 4H of β, m), 3.60-3.64 (2H of β, m), 3.75-3.89 (2H of α, 1H of β, m), 4.13-4.17 (1H of β, m), 4.31-4.39 (1H of α, 1H of β, m), 4.51-4.54 (1H of β, m), 4.69-4.72 (1H of α, m), 7.35-7.42 (8H of α, 8H of β, m), 7.54-7.63 (2H of α, 2H of β, m), 8.74 (2H of α, 2H of β, br).

Example 206

1,1-Bis(3-fluorophenyl)-N-[2-[cyclopropyl[(2-nitrophenyl)sulfonyl]amino]ethyl]-tetrahydro-3-oxo-3H-oxazolo[3,4-a]pyrazine-7(1H)-carboxamide To a solution of N-(2-aminoethyl)-N-cyclopropyl-2-nitrobenzenesulfonamide (0.51 g, 1.8 mmol) and diisopropylethylamine (0.80 mL, 4.5 mmol) in tetrahydrofuran (20 mL) was added 4-nitrophenyl chloroformate (0.36 g, 1.8 mmol) with ice cooling, and the mixture was stirred at room temperature for 1 hour. 1,1-Bis(3-fluorophenyl)-hexahydro-3H-oxazolo[3,4-a]pyrazin-3-one (0.50 g, 1.5 mmol) was added thereto, and the mixture was stirred at room temperature overnight. To the reaction solution was added ethyl acetate, and the resulting mixture was sequentially washed with 1 N hydrochloric acid and a 1 N aqueous sodium hydroxide solution and water, dried over anhydrous magnesium sulfate, and concentrated under reduced pressure. The residue was purified with silica gel column chromatography (hexane:ethyl acetate=49:1 to ethyl acetate), and then crystallized from ethyl acetate-diethyl ether to obtain the title compound (0.24 g, yield 25%).

Melting point 203° C.

$^1$H NMR (CDCl$_3$) δ 0.50 (2H, s), 0.70-0.72 (2H, m), 2.35 (1H, t, J=11.4 Hz), 2.69-2.87 (2H, m), 3.21 (1H, t, J=12.3 Hz), 3.40-3.79 (6H, m), 4.03 (1H, d, J=12.9 Hz), 4.56-4.60 (1H, m), 4.91 (1H, br), 6.98-7.00 (2H, m), 7.13-7.16 (2H, m), 7.26-7.35 (4H, m), 7.68-7.76 (3H, m), 8.18-8.20 (1H, m).

Example 207

N-[2-[(Cyclopropylmethyl)[(2-nitrophenyl)sulfonyl]amino]ethyl]-tetrahydro-3-oxo-1,1-diphenyl-3H-oxazolo[3,4-a]pyrazine-7(1H)-carboxamide In the same manner as in Example 206, the title compound was obtained using N-(2-aminoethyl)-N-(cyclopropylmethyl)-2-nitrobenzenesulfonamide instead of N-(2-aminoethyl)-N-cyclopropyl-2-nitrobenzenesulfonamide, and using hexahydro-1,1-diphenyl-3H-oxazolo[3,4-a]pyrazin-3-one instead of 1,1-bis(3-fluorophenyl)-hexahydro-3H-oxazolo[3,4-a]pyrazin-3-one. Yield 85%.

Melting point 174-175° C.

$^1$H NMR (CDCl$_3$) δ 0.16-0.21 (2H, m), 0.49-54 (2H, m), 0.85-0.90 (1H, m), 2.24 (1H, t, J=12.6 Hz), 2.77 (1H, dt, J=3.6 Hz, 13.2 Hz), 3.07-3.22 (3H, m), 3.36-3.48 (1H, m), 3.54-3.62 (3H, m), 3.76-3.85 (2H, m), 3.93-3.97 (1H, m), 4.49 (1H, dd, J=3.6 Hz, 11.1 Hz), 5.11 (1H, br), 7.26-7.40 (8H, m), 7.54-7.56 (2H, m), 7.64-7.73 (3H, m), 8.00-8.04 (1H, m).

Example 208

1,1-Bis(3-fluorophenyl)-N-[2-(cyclopropylamino)ethyl]-tetrahydro-3-oxo-3H-oxazolo[3,4-a]pyrazine-7(1H)-carboxamide hydrochloride To a solution of 1,1-bis(3-fluorophenyl)-N-[2-[cyclopropyl[(2-nitrophenyl)sulfonyl]amino]ethyl]-tetrahydro-3-oxo-3H-oxazolo[3,4-a]pyrazine-7(1H)-carboxamide (0.19 g, 0.3 mmol) and potassium carbonate (0.12 g, 0.9 mmol) in N,N-dimethylformamide (5 mL) was added thiophenol (50 mg, 0.45 mmol), and the mixture was stirred at room temperature for 3 hours. To the reaction solution was added ethyl acetate, and the resulting mixture was washed with water, dried over anhydrous magnesium sulfate, and concentrated under reduced pressure. The residue was purified with silica gel column chromatography (ethyl acetate to ethyl acetate: methanol=1:1). A 4 M hydrogen chloride/ethyl acetate solution (1.0 mL) was added thereto, and the mixture was stirred at room temperature for 10 minutes. The reaction solution was concentrated under reduced pressure, and then to the residue was added diethyl ether, and powder was formed to obtain the title compound (0.10 g, yield 66%).

Amorphous.

$^1$H NMR (DMSO-$d_6$) δ 0.69-0.81 (4H, m), 2.15-2.27 (1H, m), 2.66-2.73 (2H, m), 3.01-3.10 (3H, m), 3.30-3.40 (2H, m), 3.58-3.62 (1H, m), 3.86-3.95 (2H, m), 4.59 (1H, dd, J=3.3 Hz, 11.1 Hz), 7.03 (1H, br), 7.17-7.27 (4H, m), 7.44-7.54 (4H, m), 8.84 (2H, br).

Example 209

N-[2-[(Cyclopropylmethyl)amino]ethyl]-tetrahydro-3-oxo-1,1-diphenyl-3H-oxazolo[3,4-a]pyrazine-7(1H)-carboxamide hydrochloride In the same manner as in Example 208, the title compound was obtained using N-[2-[(cyclopropylmethyl)[(2-nitrophenyl)sulfonyl]amino]ethyl]-tetrahydro-3-oxo-1,1-diphenyl-3H-oxazolo[3,4-a]pyrazine-7(1H)-carboxamide instead of 1,1-bis(3-fluorophenyl)-N-[2-[cyclopropyl[(2-nitrophenyl)sulfonyl]amino]ethyl]-tetrahydro-3-oxo-3H-oxazolo[3,4-a]pyrazine-7(1H)-carboxamide. Yield 40%.

Amorphous.

$^1$H NMR (DMSO-$d_6$) δ 0.32-0.38 (2H, m), 0.52-0.58 (2H, m), 1.02-1.08 (1H, m), 2.06-2.14 (1H, m), 2.66-2.74 (1H, m), 2.80 (2H, d, J=7.2 Hz), 2.94-3.08 (3H, m), 3.30-3.40 (2H, m), 3.59-3.63 (1H, m), 3.86-3.92 (2H, m), 4.53 (1H, dd, J=3.6 Hz, 11.1 Hz), 7.10 (1H, br), 7.30-7.45 (8H, m), 7.58-7.60 (2H, m), 8.57 (2H, br).

Example 210

N-[2-[Acetyl(2-propenyl)amino]ethyl]-tetrahydro-3-oxo-1,1-diphenyl-3H-oxazolo[3,4-a]pyrazine-7(1H)-carboxamide To tetrahydro-3-oxo-1,1-diphenyl-N-[2-[(2-propenyl)amino]ethyl]-3H-oxazolo[3,4-a]pyrazine-7(1H)-carboxamide hydrochloride (0.13 g, 0.29 mmol) was added a 0.5 M aqueous sodium hydrogen carbonate solution (20 mL), and the mixture was extracted with ethyl acetate. The extract was dried over anhydrous magnesium sulfate and concentrated under reduced pressure. The residue was dissolved in tetrahydrofuran (5 mL). Triethylamine (58 mg, 0.57 mmol) and acetic anhydride (32 mg, 0.31 mmol) were sequentially added thereto, and the mixture was stirred at room temperature for 2 hours. To the reaction solution was added ethyl acetate, and the resulting mixture was washed with a 0.5 M aqueous sodium hydrogen carbonate solution, dried over anhydrous magnesium sulfate and concentrated under reduced pressure. The residue was recrystallized from diisopropyl ether to obtain the title compound (90 mg, yield 68%).

Melting point 104-105° C.

$^1$H NMR (CDCl$_3$) δ 2.05-2.18 (4H, m), 2.77 (1H, dt, J=3.6 Hz, 13.2 Hz), 3.02 (1H, dt, J=3.9 Hz, 12.6 Hz), 3.28-3.67 (4H, m), 3.78-3.98 (5H, m), 4.37 (1H, dd, J=3.6 Hz, 11.1 Hz), 5.15-5.28 (2H, m), 5.73-5.84 (1H, m), 6.25 (1H, br), 7.26-7.41 (8H, m), 7.55-7.58 (2H, m).

Example 211

Tetrahydro-N-[2-[methylsulfonyl(2-propenyl)amino]ethyl]-3-oxo-1,1-diphenyl-3H-oxazolo[3,4-a]pyrazine-7(1H)-carboxamide In the same manner as in Example 210, the title compound was obtained using methanesulfonyl chloride instead of acetic anhydride. Yield 77%.

Melting point 131° C.

$^1$H NMR (CDCl$_3$) δ 2.21 (1H, t, J=11.4 Hz), 2.79 (1H, dt, J=3.6 Hz, 13.2 Hz), 2.90 (3H, s), 3.09 (1H, dt, J=2.4 Hz, 12.6 Hz), 3.26-3.45 (4H, m), 3.80-3.91 (5H, m), 4.43 (1H, dd, J=3.6 Hz, 11.4 Hz), 5.29-5.35 (3H, m), 5.75-5.87 (1H, m), 7.26-7.41 (8H, m), 7.54-7.56 (2H, m).

Example 212

N-[2-[Ethyl(2-propenyl)amino]ethyl]-tetrahydro-3-oxo-1,1-diphenyl-3H-oxazolo[3,4-a]pyrazine-7(1H)-carboxamide hydrochloride To tetrahydro-3-oxo-1,1-diphenyl-N-[2-[(2-propenyl)amino]ethyl]-3H-oxazolo[3,4-a]pyrazine-7(1H)-carboxamide hydrochloride (0.13 g, 0.29 mmol) was added a 0.5 M aqueous sodium hydrogen carbonate solution (20 mL), and the mixture was extracted with ethyl acetate. The extract was dried over anhydrous magnesium sulfate and concentrated under reduced pressure. The residue was dissolved in a 1,2-dichloroethane solution (5 mL). Acetaldehyde (25 mg, 0.57 mmol) and sodium triacetoxyborohydride (0.12 g, 0.57 mmol) were sequentially added thereto, and the mixture was stirred at room temperature for 8 hours. To the reaction solution was added ethyl acetate, and the resulting mixture was washed with a 0.5 M aqueous sodium hydrogen carbonate solution, dried over anhydrous magnesium sulfate and concentrated under reduced pressure. To the residue was added a 4M hydrogen chloride/ethyl acetate solution (1.0 mL), and the mixture was stirred at room temperature for 10 minutes. The reaction solution was concentrated under reduced pressure, and then the residue formed powder from 2-propanol-ethyl acetate to obtain the title compound (77 mg, yield 56%).

Amorphous.

$^1$H NMR (DMSO-$d_6$) δ 1.18-1.22 (3H, m), 2.04-2.12 (1H, m), 2.62-2.70 (2H, m), 3.00-3.18 (4H, m), 3.31-3.42 (2H, m), 3.60-3.63 (1H, m), 3.75-3.92 (4H, m), 4.51-4.54 (1H, m), 5.50-5.60 (2H, m), 5.85-6.01 (1H, m), 7.12 (1H, br), 7.33-7.45 (8H, m), 7.57-7.60 (2H, m), 9.89 (1H, br).

Example 213

N-[2-[Acetyl(cyclopropyl)amino]ethyl]-tetrahydro-3-oxo-1,1-diphenyl-3H-oxazolo[3,4-a]pyrazine-7(1H)-carboxamide In the same manner as in Example 210, the title compound was obtained using N-[2-(cyclopropylamino)ethyl]-tetrahydro-3-oxo-1,1-diphenyl-3H-oxazolo[3,4-a]pyrazine-7(1H)-carboxamide hydrochloride instead of tetrahydro-3-oxo-1,1-diphenyl-N-[2-[(2-propenyl)amino]ethyl]-3H-oxazolo[3,4-a]pyrazine-7(1H)-carboxamide hydrochloride. Yield 70%.

Amorphous.

¹H NMR (CDCl₃) δ 0.79-0.81 (2H, m), 0.91-0.93 (2H, m), 2.09-2.22 (4H, m), 2.72-2.81 (2H, m), 2.97-3.07 (1H, m), 3.26-3.68 (4H, m), 3.73-3.96 (3H, m), 4.37 (1H, dd, J=3.3 Hz, 11.1 Hz), 6.11 (1H, br), 7.26-7.41 (8H, m), 7.54-7.57 (2H, m).

Example 214

N-[2-[Cyclopropyl(methanesulfonyl)amino]ethyl]-tetrahydro-3-oxo-1,1-diphenyl-3H-oxazolo[3,4-a]pyrazine-7(1H)-carboxamide In the same manner as in Example 210, the title compound was obtained using N-[2-(cyclopropylamino)ethyl]-tetrahydro-3-oxo-1,1-diphenyl-3H-oxazolo[3,4-a]pyrazine-7(1H)-carboxamide hydrochloride instead of tetrahydro-3-oxo-1,1-diphenyl-N-[2-[(2-propenyl)amino]ethyl]-3H-oxazolo[3,4-a]pyrazine-7(1H)-carboxamide hydrochloride, and using methanesulfonyl chloride instead of acetic anhydride. Yield 86%.

Melting point 168-169° C.

¹H NMR (CDCl₃) δ 0.84-0.86 (4H, m), 2.21 (1H, t, J=13.2 Hz), 2.51-2.57 (1H, m), 2.79 (1H, dt, J=3.6 Hz, 13.5 Hz), 2.94 (3H, s), 3.10 (1H, dt, J=2.4 Hz, 13.2 Hz), 3.35-3.53 (4H, m), 3.80-3.92 (3H, m), 4.45 (1H, dd, J=3.3 Hz, 11.4 Hz), 5.27 (1H, br), 7.26-7.41 (8H, m), 7.54-7.57 (2H, m).

Example 215

3-[(Tetrahydro-3-oxo-1,1-diphenyl-3H-oxazolo[3,4-a]pyrazin-7(1H)-yl)carbonyl]benzaldehyde 3-Formylbenzoic acid (0.10 g, 0.67 mmol) was dissolved in toluene (7 mL). Thionyl chloride (0.80 g, 6.7 mmol) was added thereto, and the mixture was heated under reflux for 1 hour. The reaction solution was concentrated, and the residue was dissolved in tetrahydrofuran (5 mL). The resulting solution was added dropwise to a solution of triethylamine (69 mg, 0.68 mmol) and hexahydro-1,1-diphenyl-3H-oxazolo[3,4-a]pyrazin-3-one (0.20 g, 0.68 mmol) in tetrahydrofuran (3 mL) at 0° C., and the mixture was stirred at room temperature for 1 hour. The reaction solution was diluted with water and then extracted with ethyl acetate. The organic layer was sequentially washed with 1 N hydrochloric acid, an aqueous saturated sodium hydrogen carbonate solution, water and saturated brine, and dried over magnesium sulfate. The solid was filtered off, and the filtrate was concentrated. The residue was purified with silica gel column chromatography (hexane: ethyl acetate=1:1 to ethyl acetate), and the fractions were collected and concentrated. The residue was collected by filtration and washed with diisopropyl ether to obtain the title compound (0.19 g, yield 66%).

Melting point 174-176° C.

¹H NMR (CDCl₃) δ 2.30 (1H, br s), 3.06 (2H, br s), 3.60-3.69 (1H, m), 3.89 (1H, br s), 4.49-4.52 (2H, m), 7.26-7.65 (12H, m), 7.91 (1H, s), 7.97-8.00 (1H, m), 10.06 (1H, s).

Example 216

4-[(Tetrahydro-3-oxo-1,1-diphenyl-3H-oxazolo[3,4-a]pyrazin-7(1H)-yl)carbonyl]benzaldehyde In the same manner as in Example 215, the title compound was obtained using 4-formylbenzoic acid instead of 3-formylbenzoic acid. Yield 63%.

Melting point 210-212° C.

¹H NMR (CDCl₃) δ 2.26 (1H, br s), 3.04 (2H, br s), 3.61-3.67 (1H, m), 3.88 (1H, br s), 4.52 (2H, br s), 7.17-7.64 (12H, m), 7.96 (2H, d, J=8.1 Hz), 10.07 (1H, s).

The chemical structural formulae of Compound obtained in Examples 1 to 216 are shown in Tables 1 to 23.

TABLE 1

| Example No. | R¹ | R² | R³ |
|---|---|---|---|
| 1 | OC(O)C(Me)₂OC(=O)- (tert-butoxycarbonyl) | phenyl | phenyl |
| 2 | phenyl carbamate | phenyl | phenyl |
| 3 | 4-fluorophenyl carbamate | phenyl | phenyl |

TABLE 1-continued
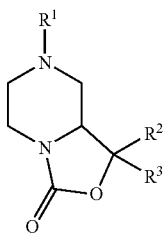
| Example No. | R¹ | R² | R³ |
|---|---|---|---|
| 4 | acetanilide-CH2- | Ph | Ph |
| 5 | -Ph) | Ph | Ph |
| 6 | cinnamoyl | Ph | Ph |
| 7 | | Ph | Ph |
| 8 | | Ph | Ph |
| 9 | | Ph | Ph |
| 10 | | Ph | Ph |
| 11 | | Ph | Ph |

TABLE 1-continued
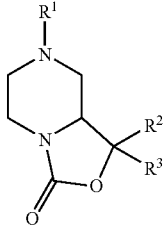
| Example No. | R¹ | R² | R³ |
|---|---|---|---|
| 12 | 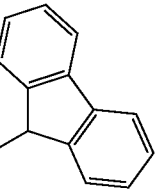 | 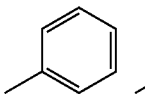 |  |
TABLE 2
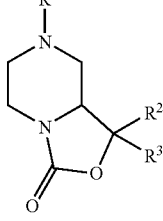
| Example No. | R¹ | R² | R³ |
|---|---|---|---|
| 13 | 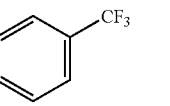 | 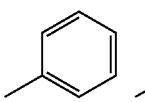 |  |
| 14 | 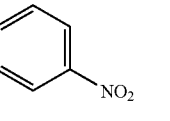 | 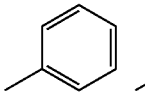 |  |
| 15 | 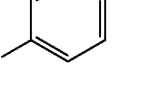 | 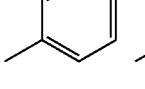 |  |
| 16 | 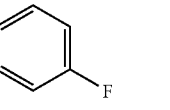 | 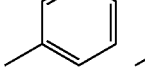 |  |
| 17 | 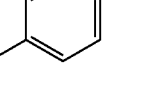 | 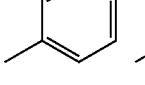 |  |

TABLE 2-continued

| Example No. | R¹ | R² | R³ |
|---|---|---|---|
| 18 | acetoxy-2-methoxyphenyl (O=C-O-C₆H₃(OMe)) | phenyl | phenyl |
| 19 | (E)-4-(4-fluorophenyl)-3-buten-1-oyl | phenyl | phenyl |
| 20 | 5-phenylpentanoyl | phenyl | phenyl |
| 21 | N-(3-fluorophenyl)acetamido | phenyl | phenyl |
| 22 | N-(2-fluorophenyl)acetamido | phenyl | phenyl |
| 23 | N-(4-(methoxycarbonyl)phenyl)acetamido | phenyl | phenyl |
| 24 | N-(3-(methoxycarbonyl)phenyl)acetamido | phenyl | phenyl |
| 25 | N-(4-fluorobenzyl)acetamido | phenyl | phenyl |

TABLE 3
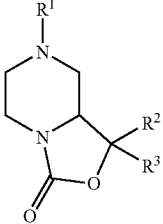
| Example No. | R¹ | R² | R³ |
|---|---|---|---|
| 26 | 2-F-benzyl-NHC(O)CH₂- | Ph | Ph |
| 27 | benzyl-OC(O)CH₂- | Me | Me |
| 28 | 3-F-benzyl-NHC(O)CH₂- | Ph | Ph |
| 29 | 4-Me-benzyl-NHC(O)CH₂- | Ph | Ph |
| 30 | (thiophen-2-yl)methyl-NHC(O)CH₂- | Ph | Ph |
| 31 | (pyridin-2-yl)methyl-NHC(O)CH₂- | Ph | Ph |
| 32 | 1,2,3,4-tetrahydroisoquinolin-2-yl-C(O)CH₂- | Ph | Ph |
| 33 | 4-CF₃-benzyl-NHC(O)CH₂- | Ph | Ph |

TABLE 3-continued
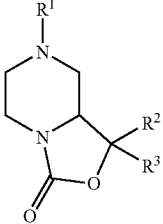
| Example No. | R¹ | R² | R³ |
|---|---|---|---|
| 34 | 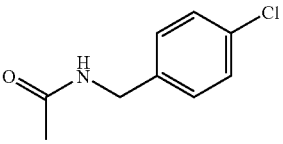 | 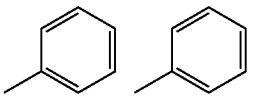 | 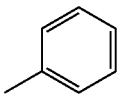 |
| 35 | 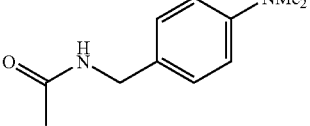 | 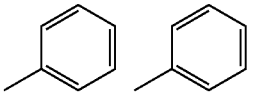 | 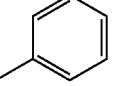 |
| 36 | 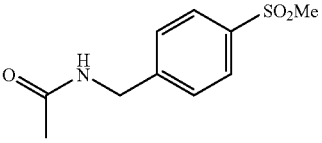 | 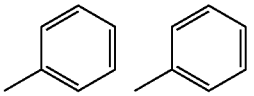 | 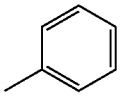 |
| 37 | 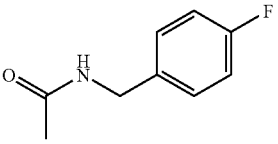 | Me | Me |
TABLE 4
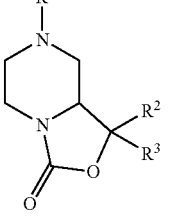
| Example No. | R¹ | R² | R³ |
|---|---|---|---|
| 38 | 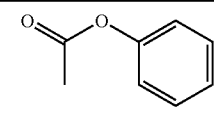 | Me | Me |
| 39 | 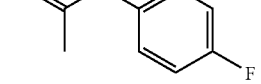 | Me | Me |

TABLE 4-continued
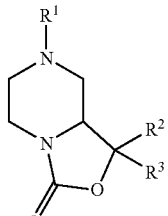

TABLE 4-continued
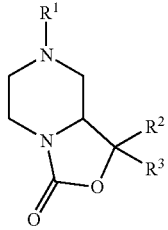
| Example No. | R¹ | R² | R³ |
|---|---|---|---|
| 49 | 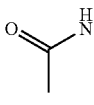 | 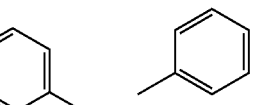 | 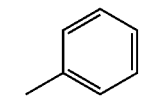 |
TABLE 5
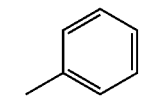
| Example No. | R¹ | R² | R³ |
|---|---|---|---|
| 50 | 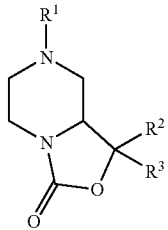 | 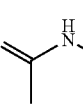 | 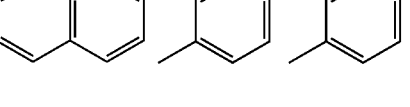 |
| 51 | 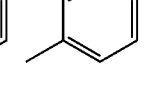 | 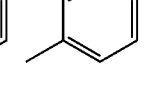 | 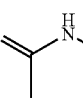 |
| 52 | 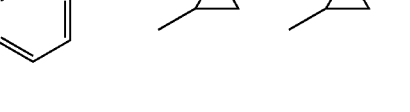 | 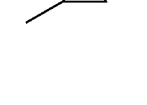 | 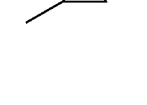 |
| 53 | 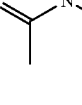 |  |  |
| 54 |  | 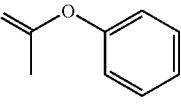 |  |

TABLE 6

| Example No. | R¹ | R² | R³ |
|---|---|---|---|
| 55 | acetyl-NH-(2,4-difluorophenyl) | cyclohexyl | cyclohexyl |
| 56 | acetyl-NH-CH₂-(4-fluorophenyl) | cyclohexyl | cyclohexyl |
| 57 | acetyl-O-phenyl | cyclohexyl | cyclohexyl |
| 58 | acetyl-NH-(pyridin-2-yl) | phenyl | phenyl |
| 59 | acetyl-NH-C(O)-(pyridin-3-yl) | phenyl | phenyl |
| 60 | acetyl-NH-(2,4-difluorophenyl) | 4-fluorophenyl | 4-fluorophenyl |

TABLE 7
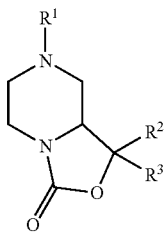
| Example No. | R¹ | R² | R³ |
|---|---|---|---|
| 61 | 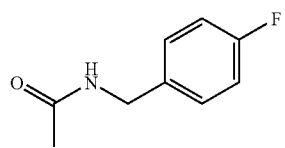 | 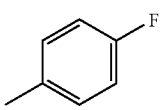 | 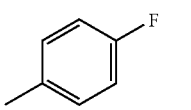 |
| 62 | 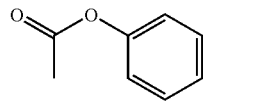 | 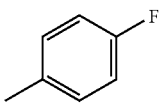 | 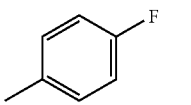 |
| 63 | 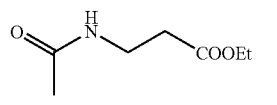 | 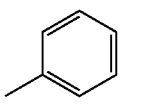 | 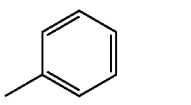 |
| 64 | 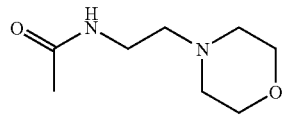 | 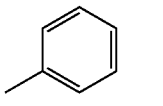 | 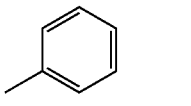 |
| 65 | 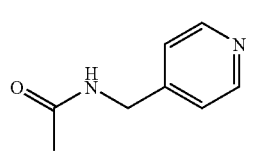 | 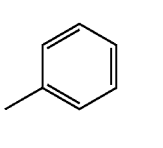 | 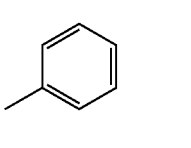 |
| 66 | 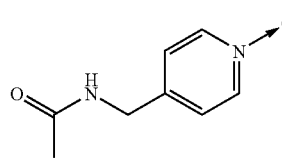 | 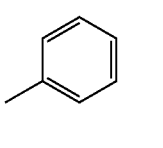 | 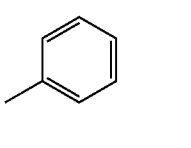 |
| 67 | 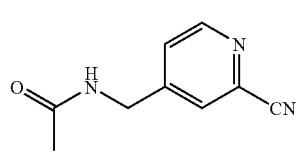 | 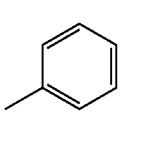 | 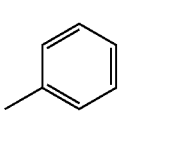 |
| 68 | 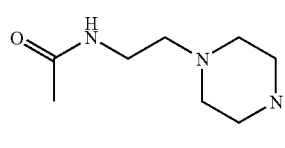 | 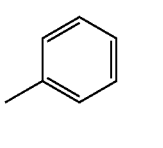 | 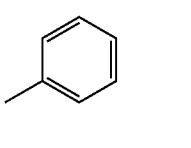 |
| 69 | 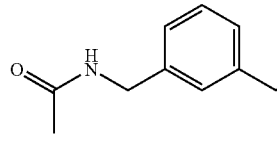 | 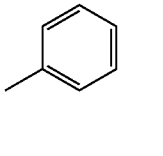 | 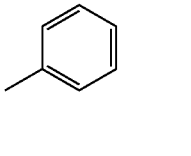 |

TABLE 7-continued
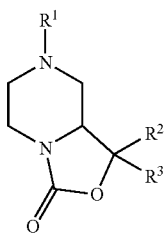
| Example No. | R¹ | R² | R³ |
|---|---|---|---|
| 70 |  ·CF₃COOH |  |  |
TABLE 8
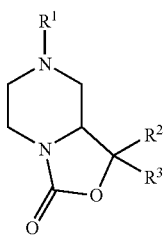
| Example No. | R¹ | R² | R³ |
|---|---|---|---|
| 71 | 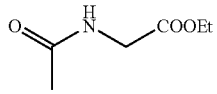 | 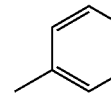 | 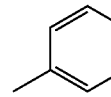 |
| 72 | 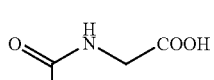 | 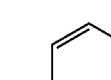 | 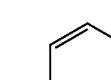 |
| 73 | 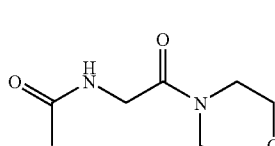 | 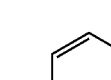 | 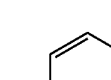 |
| 74 | 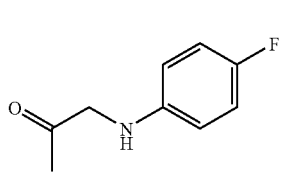 | 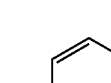 | 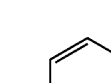 |

TABLE 8-continued
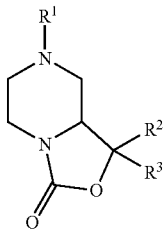
| Example No. | R¹ | R² | R³ |
|---|---|---|---|
| 75 | 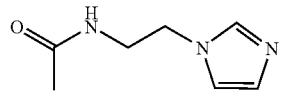 | 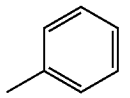 | 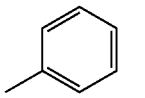 |
| 76 | 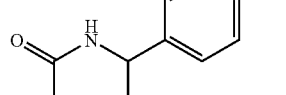 | 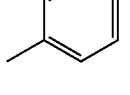 | 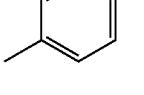 |
| 77 | 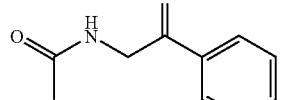 | 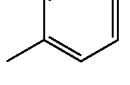 | 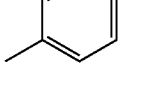 |
| 78 | 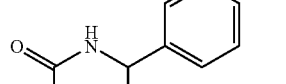 | 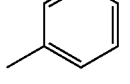 | 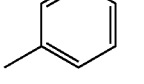 |
| 79 | 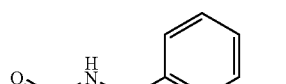 | 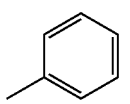 | 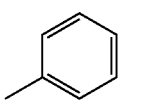 |
| 80 | 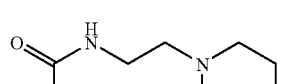 | 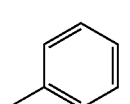 |  |

TABLE 9
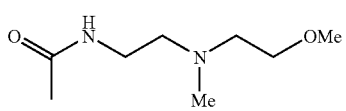
| Example No. | R¹ | R² | R³ |
|---|---|---|---|
| 81 | 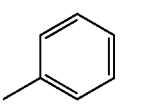 | 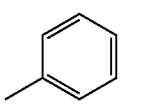 |  |
| 82 | 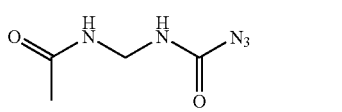 | 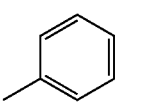 | 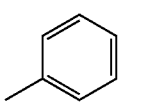 |
| 83 |  | 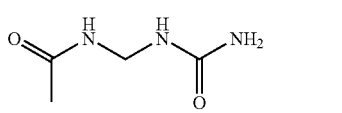 | 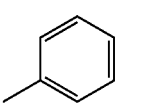 |
| 84 | 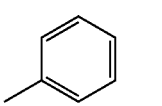 |  | 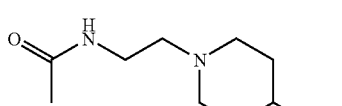 |
| 85 | 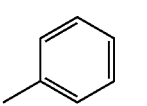 | 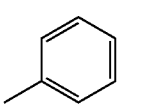 |  |
| 86 | 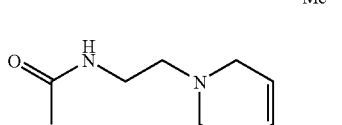 | 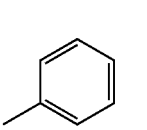 | 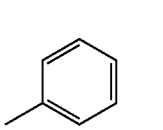 |
| 87 |  | 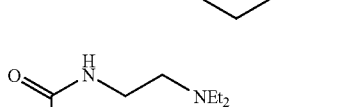 | 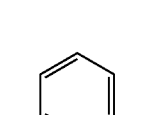 |
| 88 |  |  | 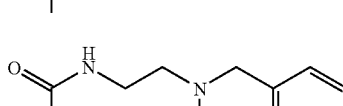 |
| 89 | 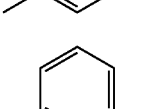 | 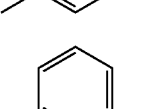 |  |
| 90 | 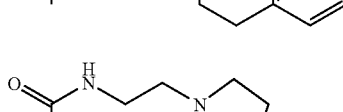 | 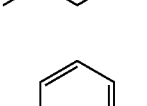 | 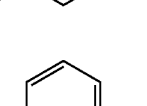 |

TABLE 10
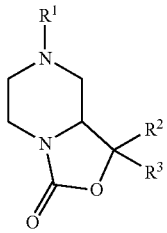

TABLE 10-continued
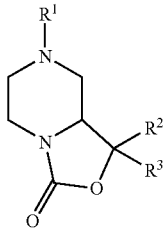
| Example No. | R¹ | R² | R³ |
|---|---|---|---|
| 100 | 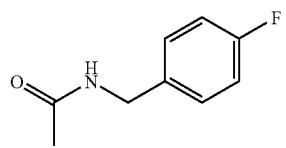 | 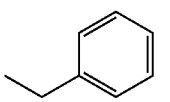 | 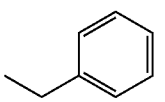 |
TABLE 11
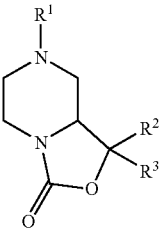
| Example No. | R¹ | R² | R³ |
|---|---|---|---|
| 101 | 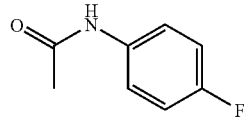 | 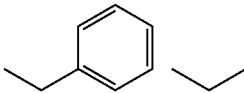 |  |
| 102 | 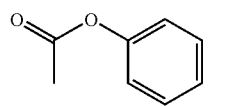 | 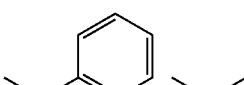 |  |
| 103 | 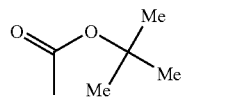 | H | 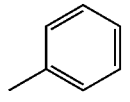 |
| 104 | 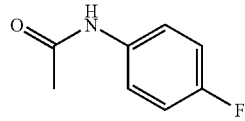 | H | 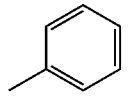 |
| 105 | 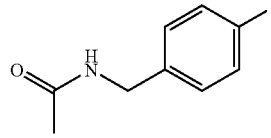 | H | 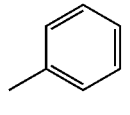 |
| 106 | 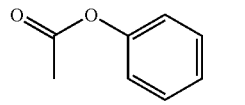 | H | 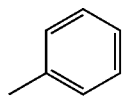 |

TABLE 11-continued
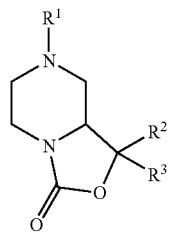
| Example No. | R¹ | R² | R³ |
|---|---|---|---|
| 107 | 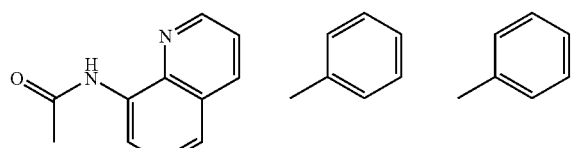 | 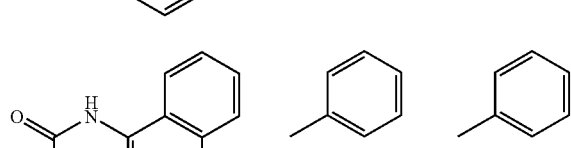 | 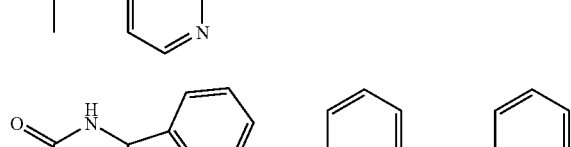 |
| 108 | 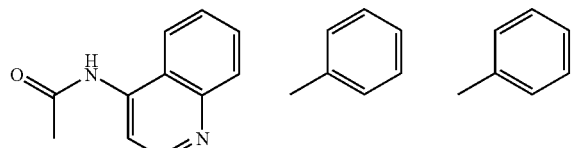 | 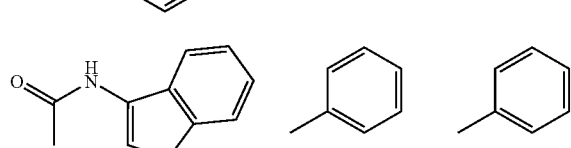 | 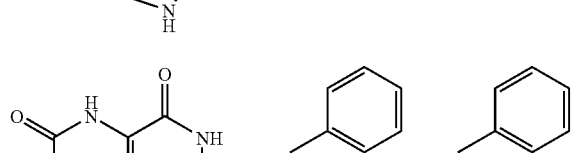 |
| 109 | 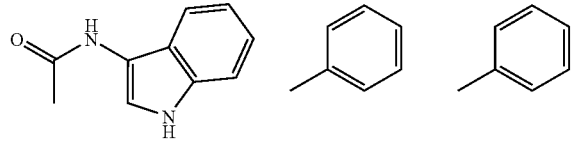 | 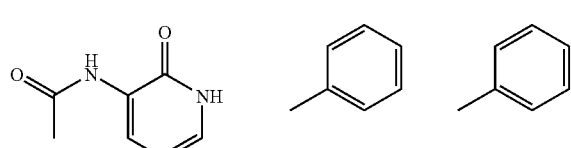 | 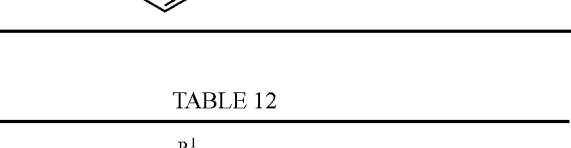 |
| 110 | 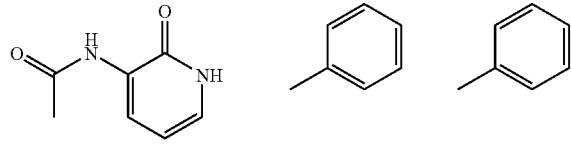 | 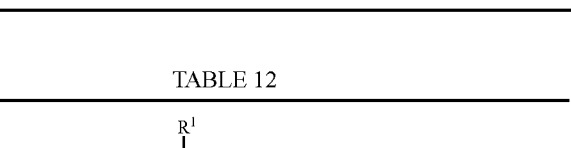 | 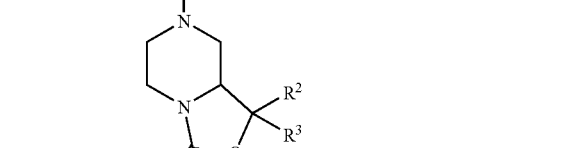 |
TABLE 12
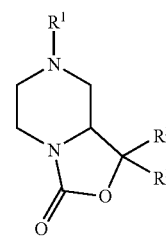
| Example No. | R¹ | R² | R³ |
|---|---|---|---|
| 111 | 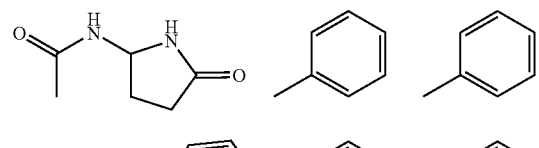 | 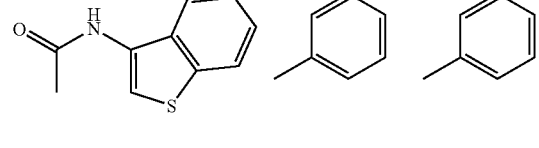 |  |
| 112 | 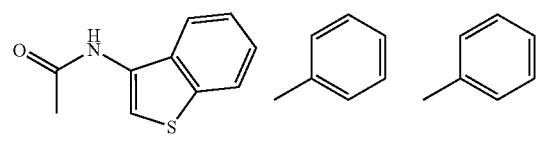 |  | |

TABLE 12-continued
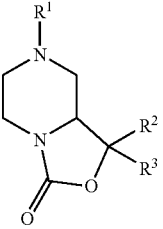
| Example No. | R¹ | R² | R³ |
|---|---|---|---|
| 113 | 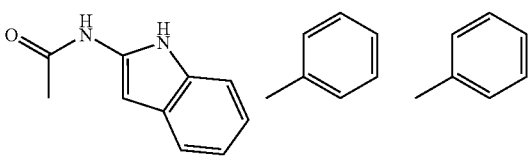 |  |  |
| 114 | 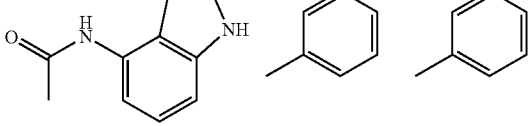 |  |  |
| 115 | 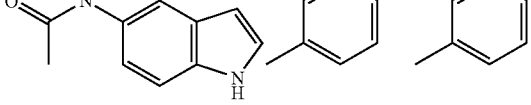 |  |  |
| 116 | 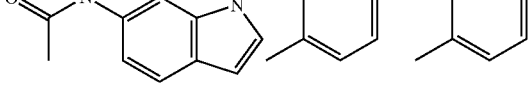 |  |  |
| 117 | 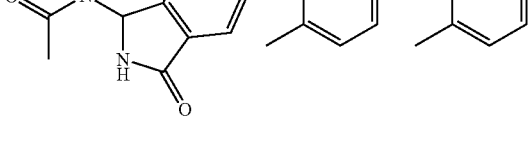 |  |  |
| 118 | 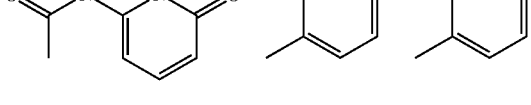 |  |  |
| 119 | 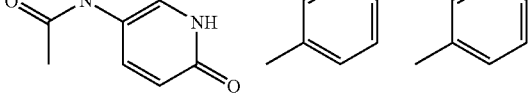 |  |  |
| 120 | 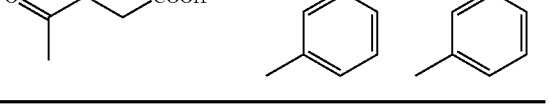 |  |  |

TABLE 13
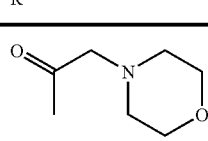
| Example No. | R¹ | R² | R³ |
|---|---|---|---|
| 121 | 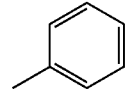 |  | 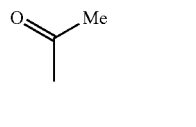 |
| 122 | 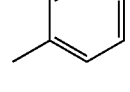 |  | 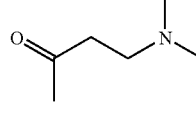 |
| 123 | 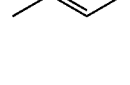 |  | 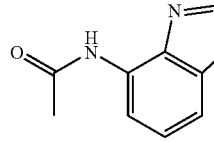 |
| 124 | 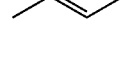 |  | 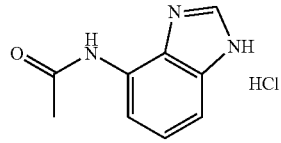 |
| 125 | 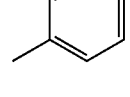 HCl |  | 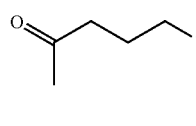 |
| 126 | 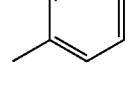 |  | 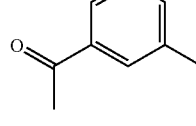 |
| 127 | 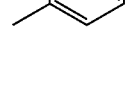 |  | 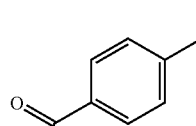 |
| 128 | 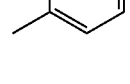 |  | |

TABLE 13-continued
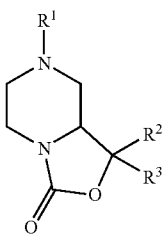
| Example No. | R¹ | R² | R³ |
| --- | --- | --- | --- |
| 129 | 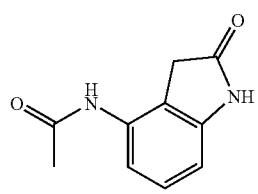 | 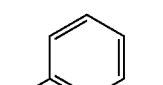 |  |
| 130 | 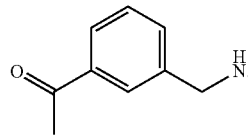 HCl | 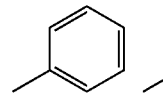 |  |
TABLE 14
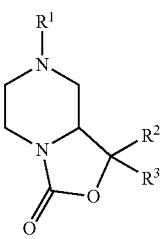
| Example No. | R¹ | R² | R³ |
| --- | --- | --- | --- |
| 131 | 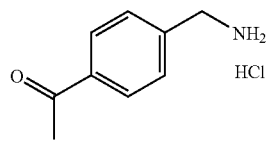 HCl | 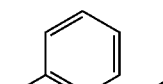 | 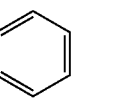 |
| 132 | 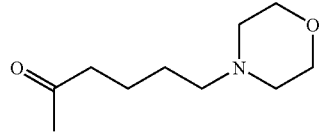 | 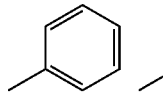 | 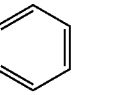 |
| 133 | 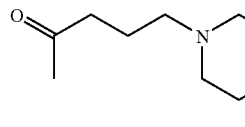 | 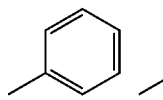 | 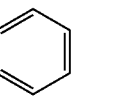 |
| 134 | 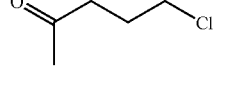 | 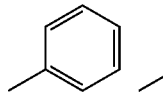 | 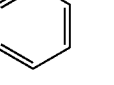 |

TABLE 14-continued

| Example No. | R¹ | R² | R³ |
|---|---|---|---|
| 135 | 4-(6-oxohexyl)morpholine group | phenyl | phenyl |
| 136 | 5-(piperidin-1-yl)pentan-1-one group | phenyl | phenyl |
| 137 | 5-(3,6-dihydropyridin-1(2H)-yl)pentan-1-one group | phenyl | phenyl |
| 138 | 4-(3,6-dihydropyridin-1(2H)-yl)butan-1-one group | phenyl | phenyl |
| 139 | 4-(pyrrolidin-1-yl)butan-1-one group | phenyl | phenyl |
| 140 | 4-acetamido-1-Boc-piperidine group | phenyl | phenyl |

TABLE 15

| Example No. | R¹ | R² | R³ |
|---|---|---|---|
| 141 | 4-acetamidopiperidine·HCl | phenyl | phenyl |

TABLE 15-continued
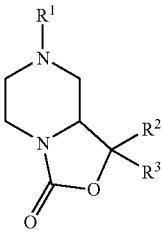
| Example No. | R¹ | R² | R³ | |
|---|---|---|---|---|
| 142 | 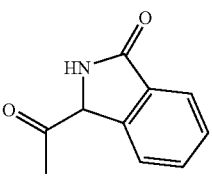 | 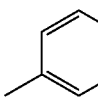 | 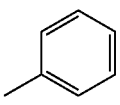 | single diastereomer |
| 143 | 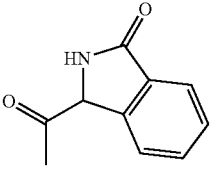 | 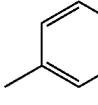 | 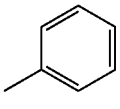 | diastereomer mixture |
| 144 | 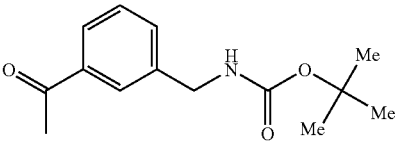 | 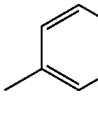 | 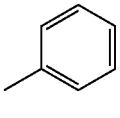 | |
| 145 | 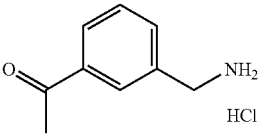 HCl | 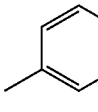 | 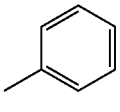 | |
| 146 | 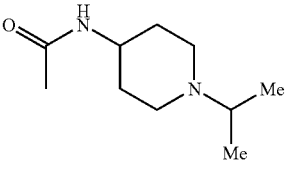 | 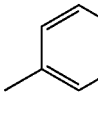 | 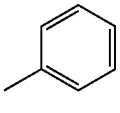 | |
| 147 | 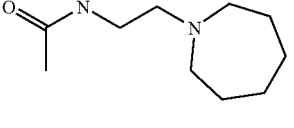 | 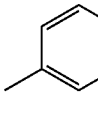 | 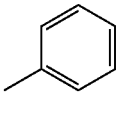 | |
| 148 | 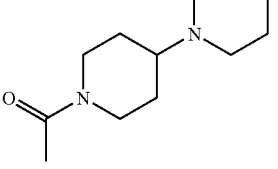 | 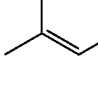 | 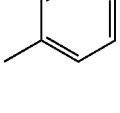 | |

TABLE 15-continued

| Example No. | R¹ | R² | R³ |
|---|---|---|---|
| 149 | acetamido-(phenyl)-CH-CH₂-NMe₂ | phenyl | phenyl |
| 150 | acetamido-(phenyl)-CH-CH₂-morpholinyl | phenyl | phenyl |

TABLE 16

| Example No. | R¹ | R² | R³ |
|---|---|---|---|
| 151 | acetyl-(4-((tetrahydropyridin-1-yl)methyl)phenyl) | phenyl | phenyl |
| 152 | acetyl-(3-((tetrahydropyridin-1-yl)methyl)phenyl) | phenyl | phenyl |
| 153 | acetamido-CH₂CH₂-(pyrrol-1-yl) | phenyl | phenyl |

TABLE 16-continued

| Example No. | R¹ | R² | R³ |
|---|---|---|---|
| 154 | 2-((3,6-dihydro-2H-pyridin-1-yl)methyl)benzoyl | phenyl | phenyl |
| 155 | 4-(2-amino-2-oxoethyl)piperidine-1-carbonyl... (1-(carbamoylmethyl)piperidin-4-yl)carbonyl | phenyl | phenyl |
| 156 | quinolin-6-ylcarbonyl | phenyl | phenyl |
| 157 | 1-(2-hydroxyethyl)piperidin-4-ylcarbonyl | phenyl | phenyl |
| 158 | 4-oxo-3,4-dihydroquinolin-1(2H)-ylcarbonyl | phenyl | phenyl |
| 159 | 1-(2-morpholino-2-oxoethyl)piperidin-4-ylcarbonyl | phenyl | phenyl |
| 160 | 1-(2-ethoxy-2-oxoethyl)piperidin-4-ylcarbonyl | phenyl | phenyl |

TABLE 17
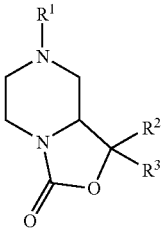
| Example No. | R¹ | R² | R³ |
|---|---|---|---|
| 161 | 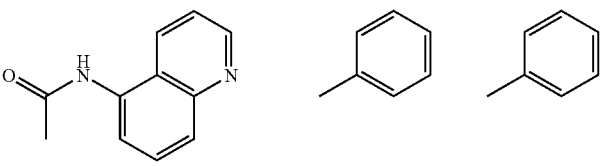 | 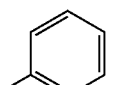 |  |
| 162 | 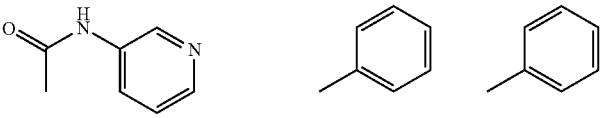 | 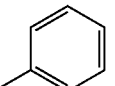 |  |
| 163 | 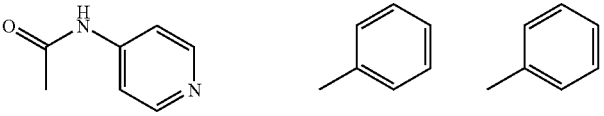 | 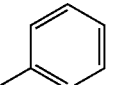 |  |
| 164 | 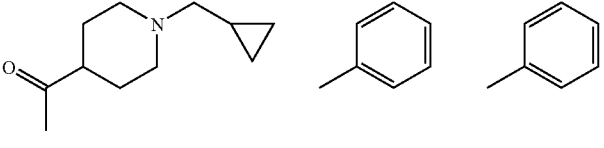 | 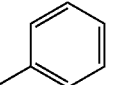 |  |
| 165 | 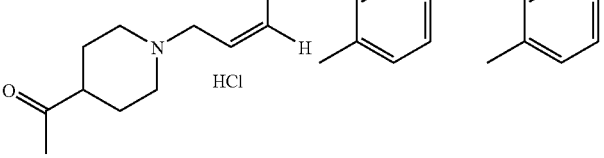 HCl | 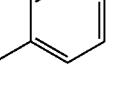 |  |
| 166 | 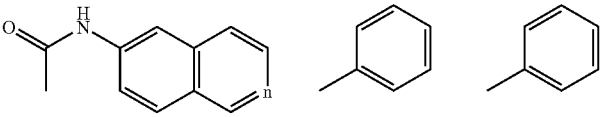 | 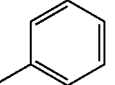 |  |
| 167 | 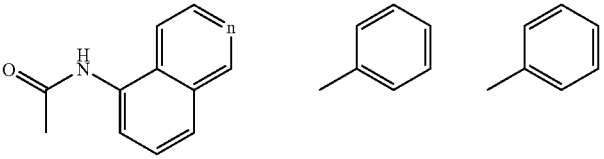 | 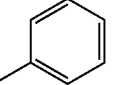 |  |
| 168 | 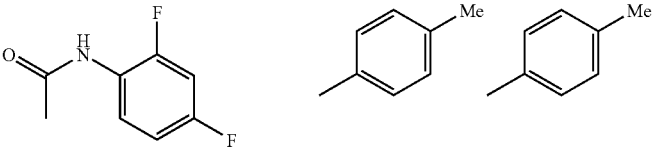 | 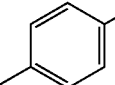 |  |

TABLE 17-continued
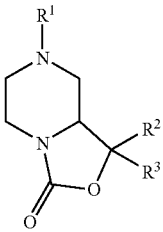
| Example No. | R¹ | R² | R³ |
|---|---|---|---|
| 169 | 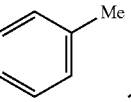 | 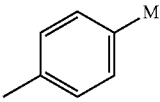 Me | 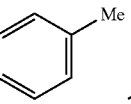 Me |
| 170 | 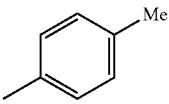 | 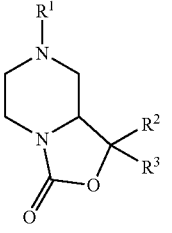 Me | 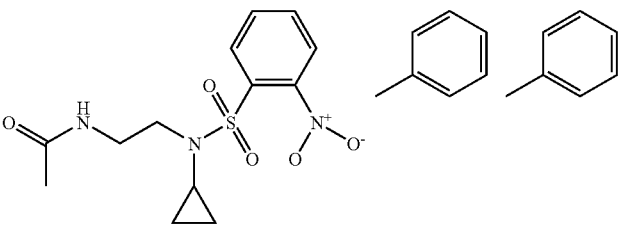 Me |
TABLE 18
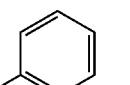
| Example No. | R¹ | R² | R³ |
|---|---|---|---|
| 171 | 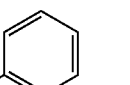 |  | 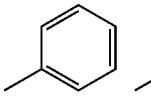 |
| 172 | 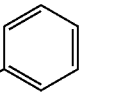 HCl | 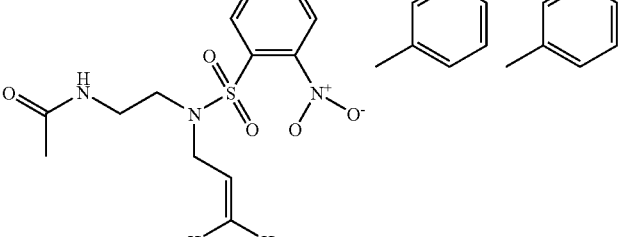 | 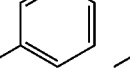 |
| 173 | 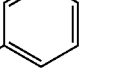 | | |

TABLE 18-continued
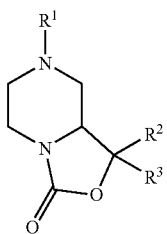
| Example No. | R¹ | R² | R³ |
| --- | --- | --- | --- |
| 174 | acetyl-NH-CH₂CH₂-N(Et)(cyclopropyl)·HCl | phenyl | phenyl |
| 175 | acetyl-NH-CH₂CH₂-NH-CH₂-CH=CH₂·HCl | phenyl | phenyl |
| 176 | acetyl-NH-(1-Me-piperidin-4-yl) | phenyl | phenyl |
| 177 | 1-Boc-piperidin-4-yl-C(O)- | phenyl | phenyl |
| 178 | acetyl-NH-(1-propyl-piperidin-4-yl) | phenyl | phenyl |
| 179 | piperidin-4-yl-C(O)-·HCl | phenyl | phenyl |
| 180 | 1-(isopropyl)piperidin-4-yl-C(O)- | phenyl | phenyl |

TABLE 19
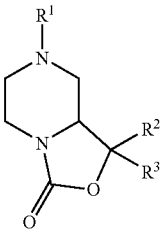
| Example No. | R¹ | R² | R³ |
|---|---|---|---|
| 181 | 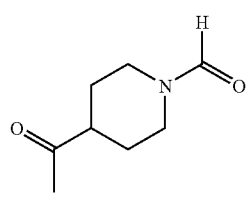 | 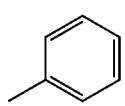 | 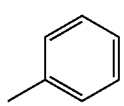 |
| 182 | 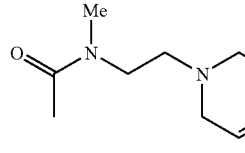 | 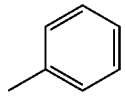 | 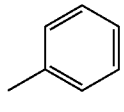 |
| 183 | 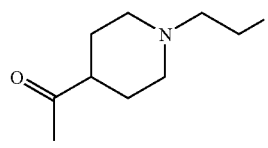 | 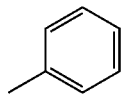 | 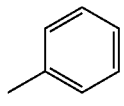 |
| 184 | 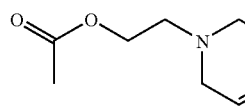 | 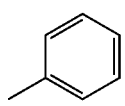 | 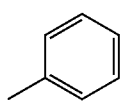 |
| 185 | 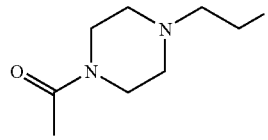 | 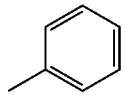 | 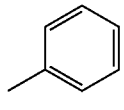 |
| 186 | 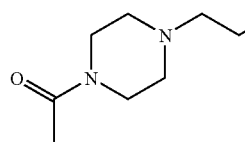 | 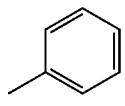 | 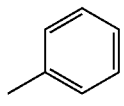 |
| 187 | 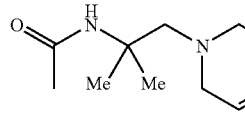 | 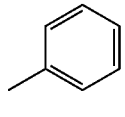 | 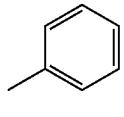 |
| 188 | 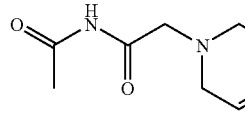 | 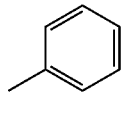 | 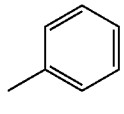 |

TABLE 19-continued
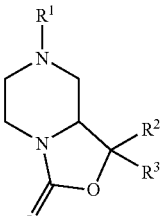
| Example No. | R¹ | R² | R³ |
|---|---|---|---|
| 189 | 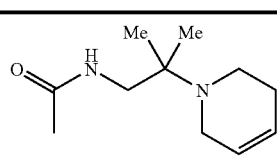 | 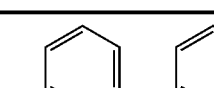 |  |
| 190 | 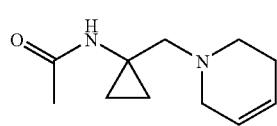 | 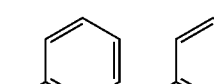 |  |
TABLE 20
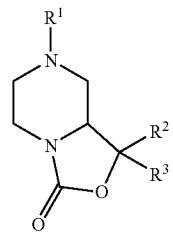
| Example No. | R¹ | R² | R³ |
|---|---|---|---|
| 191 | 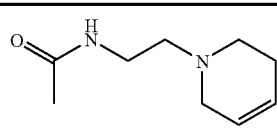 | 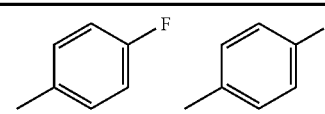 |  |
| 192 | 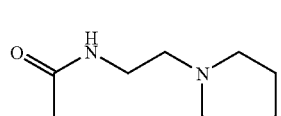 | 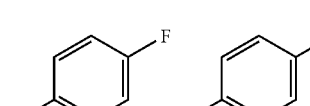 | 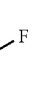 |
| 193 | 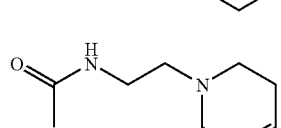 | 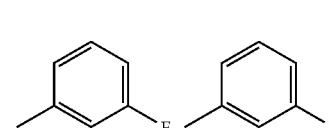 |  |
| 194 | 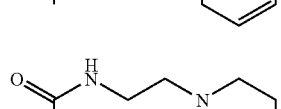 | 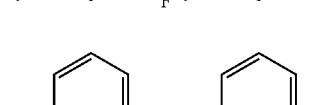 |  |
| 195 | 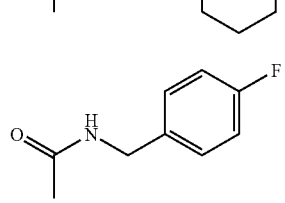 | 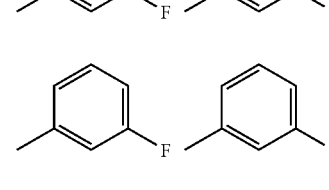 |  |

TABLE 20-continued

| Example No. | R¹ | R² | R³ |
|---|---|---|---|
| 196 | acetamidoethyl-piperidine-4-carboxylic acid 1-methylethyl ester | phenyl | phenyl |
| 197 | phenyl acetate | 3-fluorophenyl | 3-fluorophenyl |
| 198 | N-(4-fluorophenyl)acetamide | 3-fluorophenyl | 3-fluorophenyl |

TABLE 22

| Example No. | R¹ | R² | R³ | Optical Rotation |
|---|---|---|---|---|
| 199 | N-(4-fluorobenzyl)acetamide | phenyl | phenyl | (+) |
| 200 | N-(4-fluorobenzyl)acetamide | phenyl | phenyl | (−) |
| 201 | N-(2-(3,6-dihydro-2H-pyridin-1-yl)ethyl)acetamide | phenyl | phenyl | (+) |

TABLE 22-continued

| Example No. | R¹ | R² | R³ | Optical Rotation |
|---|---|---|---|---|
| 202 | CH₃C(O)NH-CH₂CH₂-N(tetrahydropyridine) | phenyl | phenyl | (−) |
| 203 | CH₃C(O)NH-(4-bromophenyl) | phenyl | phenyl | (−) |

TABLE 22

| Example No. | R¹ | R² | R³ |
|---|---|---|---|
| 204 | CH₃C(O)NH-CH₂CH₂-N(4-methyl-4-hydroxypiperidine) | phenyl | phenyl |
| 205 | CH₃C(O)CH₂-(4-piperidinyl)·HCl | phenyl | phenyl |
| 206 | CH₃C(O)NH-CH₂CH₂-N(cyclopropyl)-SO₂-(2-nitrophenyl) | 3-fluorophenyl | 3-fluorophenyl |

TABLE 22-continued
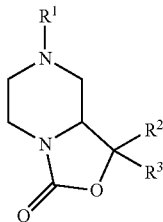
| Example No. | R¹ | R² | R³ |
|---|---|---|---|
| 207 | 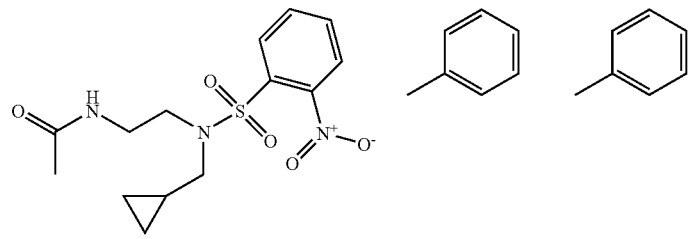 | 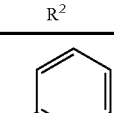 | 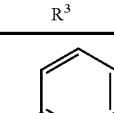 |
| 208 | 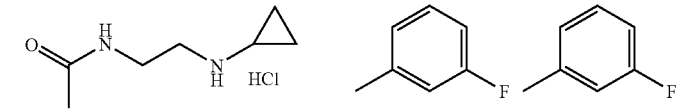 HCl | 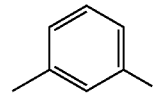 | 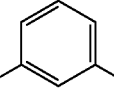 |
| 209 |  HCl | 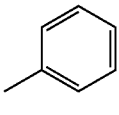 | 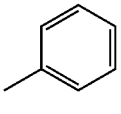 |
| 210 | 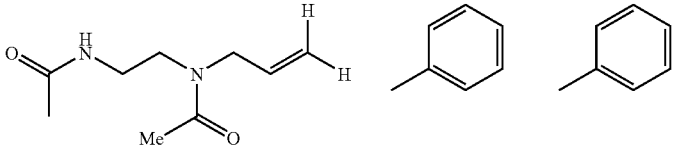 | 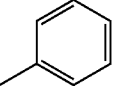 | 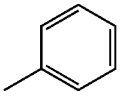 |
| 211 | 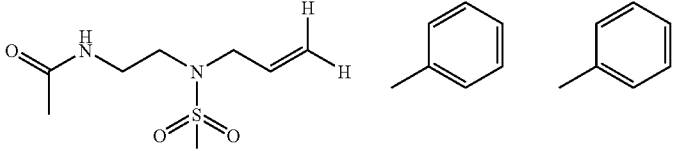 | 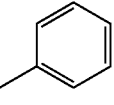 | 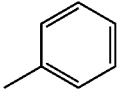 |
| 212 | 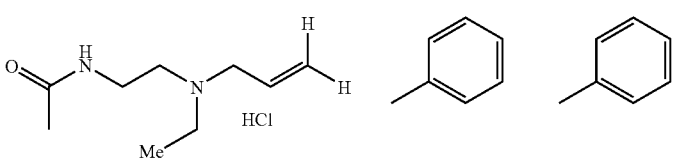 HCl | 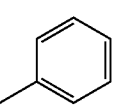 | 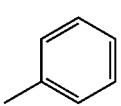 |
| 213 | 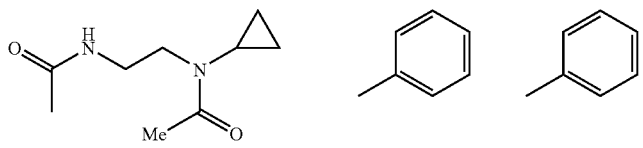 | 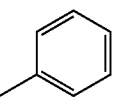 | 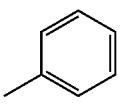 |
| 214 | 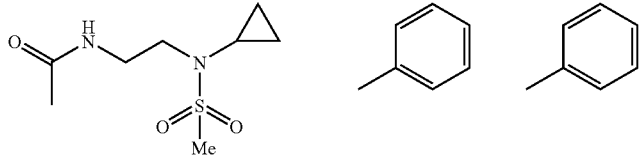 | 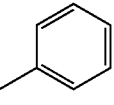 | 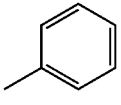 |

TABLE 23

| Example No. | R¹ | R² | R³ |
|---|---|---|---|
| 215 | 3-acetylbenzaldehyde group | phenyl | phenyl |
| 216 | 4-acetylbenzaldehyde group | phenyl | phenyl |

Experimental Example 1

Binding Inhibitory Test

A peptide having cysteine added at the carboxyl terminal of a TGR23 ligand [a human TGR23-2 ligand (1-20) represented by the SEQ ID NO: 23 in WO 03/25179 was used] via amide bonding, and further having Cy-5 (Anygen Co., Ltd., South Korea) introduced via the thiol group of the added cysteine, was obtained by a synthesis technique under the possession of Anygen Co., Ltd. (hereinafter, may be referred to as Cy-5 labeled TGR23 ligand), and the following binding inhibition test was carried out.

CHO cells expressing TGR23-2 (Example 1 of WO 03/25179) were incubated in a MEM-α medium containing 10% dialyzed serum (not including nucleic acid). The medium was removed, the adhered cells were washed with PBS, and then the cells were removed from flask by pipetting a PBS containing 5 mM EDTA. After centrifugation, the cells were suspended in a buffer for measurement (10 mM HEPES, pH 7.4; 140 mM NaCl, 2.5 mM $CaCl_2$, 3 mM $MgCl_2$, 0.5% BSA, and 0.01% $NaN_3$) to a concentration of $2.22 \times 10^5$ cells/mL, and the Cy-5 labeled TGR23 ligand was added thereto to a final concentration of 1 nM. To each well of a 96-well black/clear bottom plate (Applied Biosystems, Inc.), there were added 10 μL of the buffer for measurement containing 1% dimethyl sulfoxide to examine the total binding, 10 μM of a non-labeled peptide [a human TGR23-2 ligand (1-20) represented by SEQ ID NO: 23 in WO 03/25179] solution diluted with the buffer for measurement to examine non-specific binding, and 10 μL of the test compound diluted with the buffer for measurement to examine the binding inhibitory activity of the test compound, respectively. Also, 90 μL each of the cell suspension was added to each well. After one hour, the amount of the Cy-5 labeled TGR23 ligand bound to the cells was measured with a FMAT 8100 HTS system (Applied Biosystems, Inc.). The specific binding is defined as the value obtained by subtracting non-specific binding from the total binding. The binding inhibitory activity of the test compound is expressed as a ratio of the value obtained by subtracting the measured value obtained upon addition of the test compound from the total binding, to the specific binding. The concentration of the compound representing 50% of the binding inhibitory activity ($IC_{50}$ value) was calculated from a dose response curve.

In the present test system, the compounds obtained in Examples 2 to 4, 6, 10, 16 to 19, 21, 22, 25, 26, 28 to 31, 34, 40, 43, 44, 46, 47, 59 to 61, 64, 65, 70, 76 to 78, 80, 84 to 86, 88 to 93, 96, 97, 109, 112, 114, 115, 117, 126, 129, 132, 133, 137 to 139, 147, 148, 150, 154, 157, 161, 162, 164, 165, 167, 169, 171 to 176, 178 to 180, 182 to 185, 187 to 195, 197 to 199, 201, 204 and 206 to 214 exhibited $IC_{50}$ values of not more than 100 nM.

Experimental Example 2

Measurement of Antagonist Activity

Using CHO cells expressing TGR23-2 (Example 1 of WO 03/25179), the inhibition of the activity of a TGR23 ligand [a human TGR23-2 ligand (1-20) represented by SEQ ID NO: 23 in WO 03/25179 was used] to increase the Ca ion concentration in cells, by addition of the test compound was measured with a FLIPR (Molecular Devices Corp.), in order to evaluate the antagonist activity of the test compound.

CHO cells expressing human TGR23-2 were suspended in an RPMI medium containing 10% dialyzed fetal bovine serum to a concentration of $3 \times 10^5$ cells/mL, and 100 μL of the suspension was added to each well ($3 \times 10^4$ cells/100 μL/well) of a 96-well plate for FLIPR (black plate clear bottom, Coaster Corp.) using a 8-channeled multichannel pipette. The plated cells were incubated overnight at 37° C. in a carbon dioxide gas incubator (5% $CO_2$) and then were used in the assay (hereinafter, this plate will be referred to as the cell plate). To a mixture comprising 10 mL of HANKS'/HBSS [9.8 g of Nissui Hanks 2 (Nissui Pharmaceutical Co., Ltd.), 0.35 g of sodium hydrogen carbonate and 4.77 g of HEPES (Dojindo Laboratories) were dissolved in 1 L of distilled water, adjusted to pH 7.4 with a 5 M sodium hydroxide solution, and sterilized by filtering], 100 μL of 250 mM Probenecid (Sigma Chemical Co.) and 100 μL of fetal bovine serum (FBS), a mixture obtained by dissolving one vial (50 μg) of Fluo 3-AM (Dojindo Laboratories) in 20 μL of dimethyl sulfoxide and 20 μL of 20% pluronic acid (Molecular Probe Inc.) was added and blended, and 100 μL each of the resulting mixture was added to each well of the cell plate which was removed of the culture solution, using a 8-channeled pipette. The cell plate was incubated at 37° C. for 1 hour in a carbon dioxide incubator (5% $CO_2$), and a dye was loaded onto the cells. After completion of dye loading onto the cell plate, the cell plate was washed 4 times with a washing buffer comprising HANKS'/HBSS containing 2.5 mM Probenecid, using a plate washer, and after washing, 100 μL of HANKS'/HBSS containing 2.5 mM Probenecid was added to each well. 50 μL of the solutions of test compound (final concentrations: 0, 0.3, 1, 3, 10, 30, 100, 300, 1000, 3000, 10000 nM) were added to the cells, a pretreatment was carried out for 30 seconds, and subsequently 50 μL of a human TGR23 ligand solution (final concentration: 1 nM) was added. After addition of the human TGR23 ligand, the change of fluorescence intensity associated with the calcium concentration change within the cells was measured with a FLIPR for 3 minutes. A dosage response curve was produced for the test compound concentration with respect to the maximum fluorescence intensity values obtained for 3 minutes for each concentration of the test compound, and the compound concentration inhibiting the increase of fluorescence intensity to 50% upon non-addition of compound ($IC_{50}$ value) was calculated.

In the present test system, the compounds obtained in Examples 2 to 4, 6, 8 to 10, 16 to 19, 21, 22, 25, 26, 28 to 31, 34, 40, 43, 44, 46 to 48, 50, 59 to 62, 64, 65, 70, 73 to 78, 80, 83 to 93, 96 to 98, 108, 109, 112 to 117, 125, 126, 129, 132, 133, 136 to 139, 145 to 150, 154, 164, 167, 169, 171 to 176, 178 to 180, 182 to 185, 187 to 195, 197 to 199 and 201 exhibited $IC_{50}$ values of not more than 1 μM.

Experimental Example 3

Inhibition of DNA Synthesis by Cancer Cells

The cells of human colon cancer cell strain LS 174T (ATCC number: CL-188) were inoculated to a 96-well plate to a concentration of 20,000 cells per well, and then incubated in an EMEM medium (Nikken Biology and Medical Research Center) containing 0.05% bovine serum albumin not containing fatty acids (Sigma Chemical Co.) for 24 hours. After the 15-minute preincubation of these cells with the test compound, the cells were incubated in the presence of 10 nM of a TGR23 ligand [a human TGR23-2 ligand (1-20) represented by SEQ ID NO: 23 in WO 03/25179 was used] for 18 hours. Next, the cells were incubated in the presence of 0.25 μCi of [methyl-$^3$H]-thymidine (Amersham Biosciences KK) per well for 6 hours. The [methyl-$^3$H]-thymidine incorporated into the cancer cell DNA was measured in the following manner. After discarding the culture supernatant, 100 μL of ice-cold 10% trichloroacetic acid per well was added to the cells having taken up [methyl-$^3$H]-thymidine, and the cells were maintained on ice for 15 minutes. After discarding the trichloroacetic acid solution, 300 μL of a 0.2 N sodium hydroxide solution per well was added to the immobilized cells, and then the cells were kept warm overnight at 37° C. The amount of [methyl-$^3$H]-thymidine in the cell lysate was measured with a liquid scintillation counter.

The rate of DNA synthesis inhibition by the test compound was defined as the relative value obtained by subtracting the amount of [methyl-$^3$H]-thymidine uptake determined without stimulation from the uptake amount determined in the presence of the test compound and 10 nM of the TGR23 ligand, when the value obtained by subtracting the amount of [methyl-$^3$H]-thymidine uptake determined without stimulation from the uptake amount determined in the presence of the stimulation by 10 nM of the TGR23 ligand was taken as 100%. The $IC_{50}$ value of the test compound in DNA synthesis was defined as the concentration of the test compound required to achieve 50% of the DNA synthesis inhibition rate.

In the present test system, the compounds obtained in Examples 17, 25, 28, 85, 96 to 97, 138, 147 and 201 exhibited $IC_{50}$ values of not more than 1 μM.

Experimental Example 4

Cell Growth Inhibition

The cells of human colon cancer cell strain LS 174T (ATCC number: CL-188) were inoculated in a 96-well plate to a concentration of 40,000 cells per well, and then the cells were incubated for 24 hours in an EMEM medium containing 0.05% bovine serum albumin not containing fatty acids. After a 15-minute pretreatment of these cells with the test compound, LS 174T cells were incubated for 24 hours in the presence of 10 nM of a TGR23 ligand [a human TGR23-2 ligand (1-20) represented by SEQ ID NO: 23 in WO 03/25179 was used]. Cell growth was evaluated by the MTT method. Cells were lysed by keeping them warm in an MTT solution (3-(4,5-dimethylthiazol-2-yl)-2,5-diphenyl tetrazolium bromide) at a final concentration of 0.5 mg/mL at 37° C. for 4 hours, and then in a 5% SDS solution at 37° C. for 24 hours. The absorbance of the cell lysate was measured using a 96-well plate reader. The value of absorbance change of the cell lysate obtained by subtracting the absorbance at 640 nm from the absorbance at 540 nm, was used as an index reflecting the number of cells.

The cell growth inhibitory rate of the test compound was defined as the relative value obtained by subtracting the absorbance change determined without stimulation from the absorbance change determined in the presence of the test compound and 10 nM of the TGR23 ligand, when the value obtained by subtracting the absorbance change determined without stimulation from the absorbance change determined in the presence of stimulation by 10 nM of the TGR23 ligand was taken as 100%. The $IC_{50}$ value of the test compound for cell growth was defined as the concentration of the test compound required to achieve 50% of the cell growth inhibitory rate. The $IC_{50}$ value of the test compound for cell growth was defined as the concentration of the test compound required to achieve 50% of the cell growth inhibitory rate.

In the present test system, the compounds obtained in Examples 17 and 25 exhibited $IC_{50}$ values of not more than 1 μM.

Preparation Example 1

| | |
|---|---|
| (1) Compound of Example 1 | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Calcium carboxymethylcellulose | 20 mg |
| total | 120 mg |

The above-mentioned (1) to (6) were mixed according to a conventional method and were tableted by a tablet machine to obtain tablets.

Preparation Example 2

| | |
|---|---|
| (1) Compound of Example 2 | 10.0 mg |
| (2) Lactose | 60.0 mg |
| (3) Corn starch | 35.0 mg |
| (4) Gelatin | 3.0 mg |
| (5) Magnesium stearate | 2.0 mg | a mixture of 10.0 mg of Compound obtained in Example 2, 60.0 mg of lactose and 35.0 mg of Corn starch was granulated using 0.03 ml of a 10% aqueous solution of gelatin (3.0 mg in terms of gelatin) through a 1 mm mesh sieve, and then dried at 40° C. and sieved.

The obtained granules were mixed with 2 mg of magnesium stearate and compressed. The obtained uncoated tablets were sugar-coated with an aqueous suspension of sucrose, titanium dioxide, talc and gum Arabic. The thus-coated tablets were glazed with bees wax to obtain finally-coated tablets.

Preparation Example 3

| | | |
|---|---|---|
| (1) Compound of Example 3 | 10.0 mg | |
| (2) Lactose | 70.0 mg | |
| (3) Corn starch | 50.0 mg | |
| (4) Soluble starch | 7.0 mg | |
| (5) Magnesium stearate | 3.0 mg | |

10.0 mg of the compound obtained in Example 3 and 3.0 mg of magnesium stearate were granulated with 0.07 ml (7.0 mg in terms of soluble starch) of an aqueous soluble starch solution, dried, and mixed with 70.0 mg of lactose and 50.0 mg of corn starch. The mixture was compressed to obtain tablets.

INDUSTRIAL APPLICABILITY

Compound (I) of the present invention has an excellent TGR23 antagonist activity based on the specific chemical structure of the compound, and thus is useful as a safe prophylactic and/or therapeutic medicine against cancer.

The present invention claims priority of JP-A NO. 2003-306054 and JP-A No. 2004-93606, the entire contents of which are incorporated in the present specification. Further, the documents including patent documents and patent applications cited in the present specification are incorporated into the present specification to the same extent as disclosed in the cited documents.

The invention claimed is:

1. A compound represented by the formula:

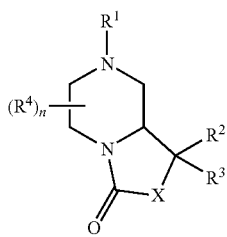

(I)

wherein $R^1$ is a group represented by the formula: $—(C=O)—OR^6$ or $—(C=O)—NR^7R^8$, wherein $R^6$ is a hydrocarbon group which may have substituent(s) selected from the following Group A, or a heterocyclic group which may have substituent(s) selected from the following Group A and an oxo group;

$R^7$ is a hydrogen atom, a hydrocarbon group which may have substituent(s) selected from the following Group A, a heterocyclic group which may have substituent(s) selected from the following Group A and an oxo group, a $C_{6-12}$ aryl-carbonyl group, a $C_{1-6}$ alkoxy-carbonyl group, or a 5- or 6-membered aromatic heterocyclic carbonyl group; and $R^8$ is a hydrogen atom, a $C_{1-6}$ alkyl group, or an amino group which may have 1 or 2 substituents selected from the following Group A; or $R^7$ and $R^8$ may form, together with the adjacent nitrogen atom, a ring which may have substituent(s) selected from the following Group A;

$R^2$ is (i) a hydrogen atom,
(ii) a $C_{1-6}$ alkyl group,
(iii) a $C_{3-6}$ cycloalkyl group,
(iv) a phenyl group which may have substituent(s) selected from a halogen atom and a $C_{1-6}$ alkyl group, or
(v) a benzyl group, $R^3$ is (i) a $C_{1-6}$ alkyl group,
(ii) a $C_{3-6}$ cycloalkyl group,
(iii) a phenyl group which may have substituent(s) selected from a halogen atom and a $C_{1-6}$ alkyl group, or
(iv) a benzyl group, $R^4$ is a $C_{1-6}$ alkyl group;

n is an integer from 0 to 4 (when n is an integer from 2 to 4, $R^4$ may be identical or different); and X is an oxygen atom, Group A:

a halogen atom,
a $C_{1-3}$ alkylenedioxy group,
a nitro group,
a cyano group,
a $C_{1-6}$ alkyl group which may have substitutent(s) selected from the following Group B,
a $C_{2-6}$ alkenyl group which may be halogenated,
a carboxy-$C_{2-6}$ alkenyl group,
a $C_{2-6}$ alkynyl group which may be halogenated,
a $C_{3-8}$ cycloalkyl group which may be halogenated and may be condensed with one or two benzene rings,
a $C_{6-14}$ aryl group which may be halogenated,
a $C_{1-8}$ alkoxy group which may be halogenated,
a $C_{1-6}$ alkoxy-carbonyl-$C_{1-6}$ alkoxy group,
a hydroxy group,
a $C_{6-14}$ aryloxy group,
a $C_{7-16}$ aralkyloxy group,
a mercapto group,
a $C_{1-6}$ alkylthio group which may be halogenated,
a $C_{6-14}$ arylthio group,
a $C_{7-16}$ aralkylthio group,
an amino group,
a mono-$C_{1-6}$ alkylamino group,
a di-$C_{1-6}$ alkylamino group,
a mono- or di-$C_{6-14}$ arylamino group which may be halogenated, a sulfonyl-amino group which may be substituted with a benzene ring which may be substituted with a nitro group,
a $C_{3-7}$ cycloalkylamino group,
a $C_{1-6}$ alkylsulfonyl-amino group,
a $C_{3-8}$ cycloalkyl-$C_{1-6}$ alkyl-amino group,
a $C_{1-6}$ alkyl-carbonyl-amino group,
a $C_{2-8}$ alkenyl-amino group,
$C_{1-6}$ alkoxy-$C_{1-6}$ alkylamino group,
an azidocarbonyl-amino group,
an aminocarbonylamino group,
a $C_{7-13}$ aralkyl-amino group,
a formyl group,
a carboxy group,
a $C_{1-6}$ alkyl-carbonyl group,
a $C_{3-6}$ cycloalkyl-carbonyl group,
a $C_{1-6}$ alkoxy-carbonyl group,
a 5- to 7-membered cyclic amino-carbonyl group,
a $C_{6-14}$ aryl-carbonyl group,
a $C_{7-16}$ aralkyl-carbonyl group,
a $C_{6-14}$ aryloxy-carbonyl group,
a $C_{7-16}$ aralkyloxy-carbonyl group,
a 5- to 6-membered heterocyclic carbonyl group,
a carbamoyl group,
a mono-$C_{1-6}$ alkyl-carbamoyl group,
a di-$C_{1-6}$ alkyl-carbamoyl group,
a $C_{6-14}$ aryl-carbamoyl group,
a 5- to 6-membered heterocyclic carbamoyl group,
a $C_{1-6}$ alkylsulfonyl group,
a $C_{6-14}$ arylsulfonyl group,
a formylamino group,
a $C_{1-6}$ alkyl-carbonylamino group,
a $C_{6-14}$ aryl-carbonylamino group,
a $C_{1-6}$ alkoxy-carbonylamino group,
a $C_{1-6}$ alkylsulfonylamino group,
a $C_{6-14}$ arylsulfonylamino group,
a $C_{1-6}$ alkyl-carbonyloxy group,
a $C_{6-14}$ aryl-carbonyloxy group,
a $C_{1-6}$ alkoxy-carbonyloxy group,
a mono-$C_{1-6}$ alkyl-carbamoyloxy group,
a di-$C_{1-6}$ alkyl-carbamoyloxy group,
a $C_{6-14}$ aryl-carbamoyloxy group,
a 5- to 6-membered heterocyclic carbonyloxy group,
a 5- to 10-membered cyclic amino group which may have substitutent(s) selected from the following Group C and may be condensed with a benzene ring,
a 5- or 7-membered non-aromatic heterocyclic group which may have substitutent(s) selected from the following Group D,
a 5- to 10-membered aromatic heterocyclic group which may have substitutent(s) selected from the following Group D,
a sulfo group, and
an oxo group;
Group B:
(i) a halogen atom,
(ii) an amino group which may have one or two substituents selected from a halogen atom, a $C_{1-6}$ alkoxy-carbonyl group, a $C_{1-6}$ alkyl group, a $C_{1-6}$ alkoxy-$C_{1-6}$ alkyl group, an azidocarbonyl group, an aminocarbonyl group and a $C_{7-13}$ aralkyl group,
(iii) a 5- to 10-membered aromatic heterocyclic group which may be oxidized and may have a cyano group,
(iv) a 5- to 7-membered cyclic amino group which may be have one to five $C_{1-6}$ alkyl groups and may be condensed with one or two benzene rings,
(v) a $C_{1-6}$ alkoxy-carbonyl group,
(vi) a carboxy group,
(vii) a 5- to 7-membered saturated cyclic amino-carbonyl group,
(viii) a $C_{6-12}$ aryl group,
(ix) a $C_{6-12}$ aryl-carbonyl group,
(x) a hydroxy group,
(xi) a $C_{3-8}$ cycloalkyl group,
(xii) a $C_{2-8}$ alkenyl group, and
(xiii) a carbamoyl group;
Group C:
a $C_{1-6}$ alkyl group,
a hydroxy group,
a $C_{1-6}$ alkoxy-carbonyl group,
a $C_{6-14}$ aryl group,
a $C_{1-6}$ alkyl-carbonyl group,
a 5- to 10-membered aromatic heterocyclic group, and
an oxo group;
Group D:
a $C_{1-6}$ alkyl group,
a hydroxy group,
a cyano group,
a $C_{6-14}$ aryl group,
a $C_{1-6}$ alkyl-carbonyl group,
a 5- to 10-membered aromatic heterocyclic group, and
an oxo group;
or a pharmaceutically acceptable salt thereof.

2. The compound according to claim 1, wherein $R^6$ is
an aromatic group which may have substituent(s) selected from the Group A as defined in claim 1,
a heterocyclic group which may have substituent(s) selected from the Group A as defined in claim 1 and an oxo group, or
a chain hydrocarbon group which may have substituent(s) selected from the Group A as defined in claim 1.

3. The compound according to claim 2, wherein $R^6$ is
a $C_{6-12}$ aryl group which may have substituent(s) selected from the Group A as defined in claim 1, or
a $C_{1-6}$ alkyl group having a 5- to 7-membered cyclic amino group which may have substituent(s) selected from the Group C as defined in claim 1.

4. The compound according to claim 1, wherein $R^7$ is a hydrogen atom, a hydrocarbon group which may have substituent(s) selected from the Group A as defined in claim 1, a heterocyclic group which may have substituent(s) selected from the Group A as defined in claim 1 and an oxo group, a $C_{6-12}$ aryl-carbonyl group, or a $C_{1-6}$ alkoxy-carbonyl group.

5. The compound according to claim 4, wherein $R^7$ is:
(a) a $C_{1-6}$ alkyl group which may have (i) a 5- to 7-membered cyclic amino group which may have substituent(s) selected from the Group C as defined in claim 1, and/or (ii) a 5- to 10-membered aromatic heterocyclic group which may have substituent(s) selected from the Group D as defined in claim 1,
(b) a $C_{6-12}$ aryl group which may have substituent(s) selected from the Group A as defined in claim 1, or
(c) a $C_{7-13}$ aralkyl group which may have substituent(s) selected from the Group A as defined in claim 1.

6. The compound according to claim 1, wherein $R^7$ is a group having an aromatic group which may have substituent(s) selected from the Group A as defined in claim 1.

7. The compound according to claim 1, wherein $R^7$ and $R^8$ form, together with the adjacent nitrogen atom, a 5- to 10-membered heterocyclic ring which may have substituent(s) selected from the Group A as defined in claim 1.

8. The compound according to claim 1, wherein $R^8$ is a hydrogen atom, or an amino group which may have 1 or 2 substituents selected from the Group A as defined in claim 1.

9. The compound according to claim 1, wherein $R^1$ is a group represented by the formula: —(C=O)—NR$^7$R$^8$.

10. The compound according to claim 1, wherein $R^2$ is a phenyl group which may have substituent(s) selected from a halogen atom and a $C_{1-6}$ alkyl group.

11. The compound according to claim 1, wherein $R^3$ is a phenyl group which may have substituent(s) selected from a halogen atom and a $C_{1-6}$ alkyl group.

12. The compound according to claim 1, wherein n is 0.

13. The compound according to claim 1, wherein
$R^1$ is a group represented by the formula: —(C=O)—NR$^7$R$^8$, wherein
$R^7$ is
(a) a hydrogen atom,
(b) a $C_{6-12}$ aryl group which may have a halogen atom,
(c) a $C_{7-13}$ aralkyl group which may have a halogen atom,
(d) a 5- or 6-membered aromatic heterocyclic group,
(e) a $C_{1-6}$ alkyl group which may have a 5- to 7-membered cyclic amino group, or
(f) a 5- or 6-membered non-aromatic heterocyclic group which may have a $C_{1-6}$ alkyl group; and
$R^8$ is a hydrogen atom or a $C_{6-12}$ arylamino group; or
$R^7$ and $R^8$ may form, together with the adjacent nitrogen atom, a 5- to 10-membered heterocyclic ring which may have a 5- to 7-membered cyclic amino group);
$R^2$ and $R^3$ are respectively a phenyl group;
n is 0; and
X is an oxygen atom.

14. The compound according to claim 1, wherein
$R^1$ is a group represented by the formula: —(C=O)—OR$^6$ or —(C=O)—NR$^7$R$^8$, wherein
$R^6$ is
(a) a $C_{7-13}$ aralkyl group,
(b) a $C_{2-6}$ alkenyl group which may have a $C_{6-12}$ aryl group which may be halogenated,
(c) a $C_{6-12}$ aryl group which may have a substituent selected from a halogen atom, a $C_{1-6}$ alkoxy group, a nitro group, and a $C_{1-6}$ alkyl group which may be halogenated,
(d) a 5- or 6-membered aromatic heterocyclic group, or
(e) a $C_{1-6}$ alkyl group which may have a substituent selected from a $C_{6-12}$ aryl group, a $C_{6-12}$ aryloxy group, and a $C_{3-8}$ cycloalkyl group which may be condensed with one or two benzene rings;
$R^7$ is
(a) a hydrogen atom,
(b) a $C_{6-12}$ aryl group which may have a substituent selected from a $C_{1-6}$ alkoxy-carbonyl group, a halogen atom and a $C_{1-6}$ alkoxy group,
(c) a $C_{7-13}$ aralkyl group which may have a substituent selected from a halogen atom, a $C_{1-6}$ alkyl group which may be halogenated, a $C_{1-6}$ alkylsulfonyl group and a mono- or di-$C_{1-6}$ alkylamino group,
(d) a $C_{1-6}$ alkyl group which may have a 5- or 6-membered aromatic heterocyclic group, or
(e) a $C_{3-8}$ cycloalkyl group which may be condensed with one or two benzene rings; and
$R^8$ is a hydrogen atom, a $C_{1-6}$ alkyl group or a $C_{6-12}$ arylamino group; or
$R^7$ and $R^8$ may form, together with the adjacent nitrogen atom, a 5- to 10-membered non-aromatic heterocyclic ring;
$R^2$ and $R^3$ are respectively a $C_{1-6}$ alkyl group, a $C_{3-6}$ cycloalkyl group or a phenyl group;
n is 0; and
X is an oxygen atom.

15. The compound according to claim 1, wherein
$R^1$ is a group represented by the formula: —(C=O)—OR$^6$ or —(C=O)—NR$^7$R$^8$,
wherein
$R^6$ is
(a) a $C_{7-13}$ aralkyl group,
(b) a $C_{2-6}$ alkenyl group which may have a $C_{6-12}$ aryl group which may be halogenated,
(c) a $C_{6-12}$ aryl group which may have a substituent selected from
 (i) a halogen atom,
 (ii) a $C_{1-6}$ alkoxy group,
 (iii) a nitro group, and
 (iv) a $C_{1-6}$ alkyl group which may have a substituent selected from (1) a halogen atom, and (2) an amino group which may have one or two substituents selected from a $C_{1-6}$ alkoxy-carbonyl group and a $C_{1-6}$ alkyl group,
(d) a 5- or 6-membered aromatic heterocyclic group,
(e) a $C_{1-6}$ alkyl group which may have a substituent selected from
 (i) a $C_{6-12}$ aryloxy group,
 (ii) a $C_{3-8}$ cycloalkyl group which may be condensed with one or two benzene rings,
 (iii) a $C_{6-12}$ arylamino group which may be halogenated,
 (iv) a carboxy group,
 (v) a 5- to 7-membered cyclic amino group,
 (vi) a $C_{6-12}$ aryl group, and
 (vii) a halogen atom,
(f) a 6-membered non-aromatic heterocyclic group which may have a $C_{1-6}$ alkoxy-carbonyl group, or
(g) a 5- to 10-membered aromatic heterocyclic group which may have an oxo group;
$R^7$ is
(a) a hydrogen atom,
(b) a $C_{6-12}$ aryl group which may have a substituent selected from a $C_{1-6}$ alkoxy-carbonyl group, a halogen atom and a $C_{1-6}$ alkoxy group,
(c) a $C_{7-13}$ aralkyl group which may have a substituent selected from
 (i) a halogen atom
  (ii) a $C_{1-6}$ alkyl group which may have a substituent selected from an amino group which may be substituted with a $C_{1-6}$ alkoxy-carbonyl group, and a halogen atom,
 (iii) a $C_{1-6}$ alkylsulfonyl group, and
 (iv) a mono- or di-$C_{1-6}$ alkylamino group,
(d) a $C_{1-6}$ alkyl group which may have a substituent selected from
 (i) a 5- or 6-membered aromatic heterocyclic group which may be oxidized and may have a cyano group,
 (ii) a 5- to 7-membered cyclic amino group which may have a $C_{1-6}$ alkyl group and may be condensed with a benzene ring,
 (iii) a $C_{1-6}$ alkoxy-carbonyl group,
 (iv) a carboxy group,
 (v) a 5- to 7-membered saturated cyclic aminocarbonyl group,
 (vi) a $C_{6-12}$ aryl group,
 (vii) a $C_{6-12}$ aryl-carbonyl group,
 (viii) a hydroxy group, and
 (ix) an amino group which may have one or two substituents selected from a $C_{1-6}$ alkyl group, a $C_{1-6}$ alkoxy-$C_{1-6}$ alkyl group, an azidocarbonyl group, an aminocarbonyl group and a $C_{7-13}$ aralkyl group, (e) a $C_{3-8}$ cycloalkyl group which may be condensed with one or two benzene rings, (f) a 5- or 10-membered aromatic heterocyclic group which may have a substituent selected from an oxo group and a $C_{1-6}$ alkoxy-carbonyl group, (g) a $C_{6-12}$ aryl-carbonyl group, (h) a $C_{1-6}$ alkoxy-carbonyl group, or (i) a 5- to 7-membered non-aromatic heterocyclic group which may have a substituent selected from a $C_{1-6}$ alkyl group, a $C_{1-6}$ alkoxy-carbonyl group and an oxo group, and may be condensed with a benzene ring; and $R^8$ is a hydrogen atom, a $C_{1-6}$ alkyl group or a $C_{6-12}$ aryl amino group; or $R^7$ and $R^8$ may form, together with the adjacent nitrogen atom, a 5- to 10-membered non-aromatic heterocyclic ring which may have a 5- to 7-membered saturated cyclic amino group;

$R^2$ is a hydrogen atom, a $C_{1-6}$ alkyl group, a $C_{3-6}$ cycloalkyl group, a phenyl group which may be halogenated, or a benzyl group;

$R^3$ is a $C_{1-6}$ alkyl group, a $C_{3-6}$ cycloalkyl group, a phenyl group which may be halogenated, or a benzyl group;

n is 0; and

X is an oxygen atom.

16. The compound according to claim 1, wherein $R^1$ is a group represented by the formula: —(C=O)—OR$^6$ or —(C=O)—NR$^7$R$^8$, wherein $R^6$ is (a) a $C_{7-13}$ aralkyl group, (b) a $C_{2-6}$ alkenyl group which may have a $C_{6-12}$ aryl group which may be halogenated, (c) a $C_{6-12}$ aryl group which may have a substituent selected from:
  (i) a halogen atom,
  (ii) a $C_{1-6}$ alkoxy group,
  (iii) a nitro group,
  (iv) a formyl group, and
  (v) a $C_{1-6}$ alkyl group which may have a substituent selected from (1) a halogen atom, (2) an amino group which may have one or two substituents selected from a $C_{1-6}$ alkoxy-carbonyl group and a $C_{1-6}$ alkyl group, and (3) a 5- to 7-membered cyclic amino group which may be substituted, (d) a 5- or 6-membered aromatic heterocyclic group, (e) a $C_{1-6}$ alkyl group which may have a substituent selected from:
  (i) a $C_{6-12}$ aryloxy group,
  (ii) a $C_{3-8}$ cycloalkyl group which may be condensed with one or two benzene rings,
  (iii) a $C_{6-12}$ arylamino group which may be halogenated,
  (iv) a carboxy group,
  (v) a 5- to 7-membered cyclic amino group,
  (vi) a 5- to 7-membered non-aromatic heterocyclic group,
  (vii) a $C_{6-12}$ aryl group, and
  (viii) a halogen atom, (f) a 5- to 7-membered non-aromatic heterocyclic group which may have a $C_{1-6}$ alkoxy-cabronyl group, a formyl group, or a $C_{1-6}$ alkyl group which may have a substituent selected from:
  (i) a $C_{1-6}$ alkoxy-carbonyl group,
  (ii) a carbamoyl group,
  (iii) a hydroxy group,
  (iv) a 5- to 7-membered cyclic amino-carbonyl group,
  (v) a $C_{3-8}$ cycloalkyl group, and
  (vi) a $C_{2-8}$ alkenyl group, (g) a 5- to 10-membered aromatic heterocyclic group which may have an oxo group, or (h) a 5- to 10-membered cyclic amino group which may have an oxo group and may be condensed with a benzene ring;

$R^7$ is (a) a hydrogen atom, (b) a $C_{6-12}$ aryl group which may have a substituent selected from:
  (i) a $C_{1-6}$ alkoxy-carbonyl group,
  (ii) a halogen atom, and
  (iii) a $C_{1-6}$ alkoxy group, (c) a $C_{7-13}$ aralkyl group which may have a substituent selected from:
  (i) a halogen atom,
  (ii) a $C_{1-6}$ alkyl group which may have a substituent selected from an amino group which may be substituted with a $C_{1-6}$ alkoxy-carbonyl group, and a halogen atom,
  (iii) a $C_{1-6}$ alkylsulfonyl group, and
  (iv) a mono- or di-$C_{1-6}$ alkylamino group, (d) a $C_{1-6}$ alkyl group which may have one or two substituents selected from:
  (i) a 5- or 6-membered aromatic heterocyclic group which may be oxidized and may be substituted with a cyano group, a hydroxy group or a $C_{1-6}$ alkyl group,
  (ii) a 5- to 7-membered cyclic amino group which may have a $C_{1-6}$ alkyl group, a hydroxy group, an oxo group or a $C_{1-6}$ alkoxy-carbonyl group, and may be condensed with a benzene ring,
  (iii) a $C_{1-6}$ alkoxy-carbonyl group,
  (iv) a carboxy group,
  (v) a 5- to 7-membered cyclic aminocarbonyl group,
  (vi) a $C_{6-12}$ aryl group which may be halogenated,
  (vii) a $C_{6-12}$ aryl-carbonyl group,
  (viii) a hydroxy group,
  (ix) an amino group which may have one or two substituents selected from (1) a $C_{1-6}$ alkyl group which may be substituted with a $C_{3-8}$ cycloalkyl group, (2) a $C_{1-6}$ alkoxy-$C_{1-6}$ alkyl group, (3) an azidocarbonyl group, (4) an aminocarbonyl group, (5) a $C_{7-13}$ aralkyl group, (6) a $C_{3-8}$ cycloalkyl group, (7) a sulfonyl group which may be substituted with a benzene ring which may be substituted with a nitro group, (8) a $C_{2-8}$ alkenyl group, (9) a $C_{1-6}$ alkylsulfonyl group, and (10) a $C_{1-6}$ alkyl-carbonyl group,
  (x) a $C_{3-8}$ cycloalkyl group, and
  (xi) a 5- to 7-membered non-aromatic heterocyclic group, (e) a $C_{3-8}$ cycloalkyl group which may be condensed with one or two benzene rings, (f) a 5- to 10-membered aromatic heterocyclic group which may have a substituent selected from an oxo group, a $C_{1-6}$ alkoxy-carbonyl group and a $C_{1-6}$ alkyl group, (g) a $C_{6-12}$ aryl-carbonyl group, (h) a $C_{1-6}$ alkoxy-carbonyl group, (i) a 5- to 7-membered non-aromatic heterocyclic group which may have a substituent selected from a $C_{1-6}$ alkyl group, a $C_{1-6}$ alkoxy-carbonyl group and an oxo group, and may be condensed with a benzene ring, (j) a 5- to 7-membered cyclic amino-$C_{1-6}$ alkyl-carbonyl group, (k) a $C_{3-8}$ cycloalkyl group which may be substituted with a $C_{1-6}$ alkyl group which may have a 5- to 7-membered cyclic amino group, or (l) a $C_{6-12}$ arylamino group; and $R^8$ is a hydrogen atom or a $C_{1-6}$ alkyl group; or R⁷ and R⁸ may form, together with the adjacent nitrogen atom, a 5- to 10-membered non-aromatic heterocyclic ring which may have a substituent selected from a 5- to 7-membered saturated cyclic amino group and a $C_{1-6}$ alkyl group);

$R^2$ is
(i) a hydrogen atom
(ii) a $C_{1-6}$ alkyl group,
(iii) a $C_{3-6}$ cycloalkyl group,
(iv) a phenyl group which may have a substituent selected from a halogen atom and a $C_{1-6}$ alkyl group, or
(v) a benzyl group;

$R^3$ is
(i) a $C_{1-6}$ alkyl group,
(ii) a $C_{3-6}$ cycloalkyl group,
(iii) a phenyl group which may have a substituent selected from a halogen atom and a $C_{1-6}$ alkyl group, or
(iv) a benzyl group;

n is 0; and

X is an oxygen atom.

17. A compound according to claim 1, wherein the compound is:

phenyl tetrahydro-3-oxo-1,1-diphenyl-3H-oxazolo[3,4-a]pyrazine-7(1H)-carboxylate or a pharmaceutically acceptable salt thereof, (+)-N-[(4-fluorophenyl)methyl]-tetrahydro-3-oxo-1,1-diphenyl-3H-oxazolo[3,4-a]pyrazine-7(1H)-carboxamide or a pharmaceutically acceptable salt thereof, (−)-N-[(4-fluorophenyl)methyl]-tetrahydro-3-oxo-1,1-diphenyl-3H-oxazolo[3,4-a]pyrazine-7(1H)-carboxamide or a pharmaceutically acceptable salt thereof, (+)-N-[2-(3,6-dihydropyridin-1(2H)-yl)ethyl]-tetrahydro-3-oxo-1,1-diphenyl-3H-oxazolo[3,4-a]pyrazine-7(1H)-carboxamide or a pharmaceutically acceptable salt thereof, (−)-N-[2-(3,6-dihydropyridin-1(2H)-yl)ethyl]-tetrahydro-3-oxo-1,1-diphenyl-3H-oxazolo[3,4-a]pyrazine-7(1H)-carboxamide or a pharmaceutically acceptable salt thereof, 1,1-bis(3-fluorophenyl)-N-[2-(3,6-dihydropyridin-1(2H)-yl)ethyl]tetrahydro-3-oxo-3H-oxazolo[3,4-a]pyrazine-7(1H)-carboxamide or a pharmaceutically acceptable salt thereof, N-[2-(3,6-dihydropyridin-1(2H)-yl)ethyl]-tetrahydro-3-oxo-1,1-diphenyl-3H-oxazolo[3,4-a]pyrazine-7(1H)-carboxamide or a pharmaceutically acceptable salt thereof, 1,1-bis(3-fluorophenyl)-N-[2-(cyclopropylamino)ethyl]-tetrahydro-3-oxo-3H-oxazolo[3,4-a]pyrazine-7(1H)-carboxamide hydrochloride, tetrahydro-3-oxo-1,1-diphenyl-N-[(3-thienyl)methyl]-3H-oxazolo[3,4-a]pyrazine-7(1H)-carboxamide or a pharmaceutically acceptable salt thereof, N-[2-[(cyclopropylmethyl)amino]ethyl]-tetrahydro-3-oxo-1,1-diphenyl-3H-oxazolo[3,4-a]pyrazine-7(1H)-carboxamide hydrochloride, N-[(4-fluorophenyl)methyl]-tetrahydro-3-oxo-1,1-diphenyl-3H-oxazolo[3,4-a]pyrazine-7(1H)-carboxamide or a pharmaceutically acceptable salt thereof, or 1,1-bis(3-fluorophenyl)-tetrahydro-3-oxo-N-[2-(1-piperidinyl)ethyl]-3H-oxazolo[3,4-a]pyrazine-7(1H)-carboxamide or a pharmaceutically acceptable salt thereof.

18. A medicine comprising the compound according to claim 1 or a pharmaceutically acceptable salt thereof, and a pharmaceutically acceptable carrier.

\* \* \* \* \*

UNITED STATES PATENT AND TRADEMARK OFFICE
CERTIFICATE OF CORRECTION

PATENT NO. : 7,795,267 B2
APPLICATION NO. : 10/570270
DATED : September 14, 2010
INVENTOR(S) : Kohji Fukatsu et al.

It is certified that error appears in the above-identified patent and that said Letters Patent is hereby corrected as shown below:

Column 227, line 28 claim 13, after "group", delete ")";

Column 228, line 44 claim 15, before "(ii)", delete the indentation;

Column 231, line 5 claim 16, after "group", delete ")".

Signed and Sealed this
Twenty-fifth Day of January, 2011

David J. Kappos
*Director of the United States Patent and Trademark Office*

SEQUENCE LISTING

<160> NUMBER OF SEQ ID NOS: 2

<210> SEQ ID NO 1
<211> LENGTH: 371
<212> TYPE: PRT
<213> ORGANISM: Human

<400> SEQUENCE: 1

```
Met Pro Ala Asn Phe Thr Glu Gly Ser Phe Asp Ser Ser Gly Thr Gly
                  5                   10                  15

Gln Thr Leu Asp Ser Ser Pro Val Ala Cys Thr Glu Thr Val Thr Phe
              20                  25                  30

Thr Glu Val Val Glu Gly Lys Glu Trp Gly Ser Phe Tyr Tyr Ser Phe
          35                  40                  45

Lys Thr Glu Gln Leu Ile Thr Leu Trp Val Leu Phe Val Phe Thr Ile
      50                  55                  60

Val Gly Asn Ser Val Val Leu Phe Ser Thr Trp Arg Arg Lys Lys Lys
 65                  70                  75                  80

Ser Arg Met Thr Phe Phe Val Thr Gln Leu Ala Ile Thr Asp Ser Phe
                  85                  90                  95

Thr Gly Leu Val Asn Ile Leu Thr Asp Ile Asn Trp Arg Phe Thr Gly
             100                 105                 110

Asp Phe Thr Ala Pro Asp Leu Val Cys Arg Val Val Arg Tyr Leu Gln
         115                 120                 125

Val Val Leu Leu Tyr Ala Ser Thr Tyr Val Leu Val Ser Leu Ser Ile
     130                 135                 140

Asp Arg Tyr His Ala Ile Val Tyr Pro Met Lys Phe Leu Gln Gly Glu
145                 150                 155                 160

Lys Gln Ala Arg Val Leu Ile Val Ile Ala Trp Ser Leu Ser Phe Leu
                 165                 170                 175

Phe Ser Ile Pro Thr Leu Ile Ile Phe Gly Lys Arg Thr Leu Ser Asn
             180                 185                 190

Gly Glu Val Gln Cys Trp Ala Leu Trp Pro Asp Asp Ser Tyr Trp Thr
         195                 200                 205

Pro Tyr Met Thr Ile Val Ala Phe Leu Val Tyr Phe Ile Pro Leu Thr
     210                 215                 220

Ile Ile Ser Ile Met Tyr Gly Ile Val Ile Arg Thr Ile Trp Ile Lys
225                 230                 235                 240
```

```
Ser Lys Thr Tyr Glu Thr Val Ile Ser Asn Cys Ser Asp Gly Lys Leu
            245                 250                 255

Cys Ser Ser Tyr Asn Arg Gly Leu Ile Ser Lys Ala Lys Ile Lys Ala
            260                 265                 270

Ile Lys Tyr Ser Ile Ile Ile Leu Ala Phe Ile Cys Cys Trp Ser
            275                 280                 285

Pro Tyr Phe Leu Phe Asp Ile Leu Asp Asn Phe Asn Leu Leu Pro Asp
            290                 295                 300

Thr Gln Glu Arg Phe Tyr Ala Ser Val Ile Ile Gln Asn Leu Pro Ala
305                 310                 315                 320

Leu Asn Ser Ala Ile Asn Pro Leu Ile Tyr Cys Val Phe Ser Ser Ser
                325                 330                 335

Ile Ser Phe Pro Cys Arg Glu Gln Arg Ser Gln Asp Ser Arg Met Thr
            340                 345                 350

Phe Arg Glu Arg Thr Glu Arg His Glu Met Gln Ile Leu Ser Lys Pro
            355                 360                 365

Glu Phe Ile
        370

<210> SEQ ID NO 2
<211> LENGTH: 371
<212> TYPE: PRT
<213> ORGANISM: Human

<400> SEQUENCE: 2

Met Pro Ala Asn Phe Thr Glu Gly Ser Phe Asp Ser Ser Gly Thr Gly
                5                   10                  15

Gln Thr Leu Asp Ser Ser Pro Val Ala Cys Thr Glu Thr Val Thr Phe
            20                  25                  30

Thr Glu Val Val Glu Gly Lys Glu Trp Gly Ser Phe Tyr Tyr Ser Phe
            35                  40                  45

Lys Thr Glu Gln Leu Ile Thr Leu Trp Val Leu Phe Val Phe Thr Ile
        50                  55                  60

Val Gly Asn Ser Val Val Leu Phe Ser Thr Trp Arg Arg Lys Lys Lys
65                  70                  75                  80

Ser Arg Met Thr Phe Phe Val Thr Gln Leu Ala Ile Thr Asp Ser Phe
                85                  90                  95

Thr Gly Leu Val Asn Ile Leu Thr Asp Ile Ile Trp Arg Phe Thr Gly
            100                 105                 110

Asp Phe Thr Ala Pro Asp Leu Val Cys Arg Val Val Arg Tyr Leu Gln
            115                 120                 125

Val Val Leu Leu Tyr Ala Ser Thr Tyr Val Leu Val Ser Leu Ser Ile
        130                 135                 140

Asp Arg Tyr His Ala Ile Val Tyr Pro Met Lys Phe Leu Gln Gly Glu
145                 150                 155                 160

Lys Gln Ala Arg Val Leu Ile Val Ile Ala Trp Ser Leu Ser Phe Leu
                165                 170                 175

Phe Ser Ile Pro Thr Leu Ile Ile Phe Gly Lys Arg Thr Leu Ser Asn
            180                 185                 190

Gly Glu Val Gln Cys Trp Ala Leu Trp Pro Asp Asp Ser Tyr Trp Thr
            195                 200                 205

Pro Tyr Met Thr Ile Val Ala Phe Leu Val Tyr Phe Ile Pro Leu Thr
        210                 215                 220

Ile Ile Ser Ile Met Tyr Gly Ile Val Ile Arg Thr Ile Trp Ile Lys
225                 230                 235                 240
```

```
Ser Lys Thr Tyr Glu Thr Val Ile Ser Asn Cys Ser Asp Gly Lys Leu
            245             250             255

Cys Ser Ser Tyr Asn Arg Gly Leu Ile Ser Lys Ala Lys Ile Lys Ala
            260             265             270

Ile Lys Tyr Ser Ile Ile Ile Leu Ala Phe Ile Cys Cys Trp Ser
        275             280             285

Pro Tyr Phe Leu Phe Asp Ile Leu Asp Asn Phe Asn Leu Leu Pro Asp
        290             295             300

Thr Gln Glu Arg Phe Tyr Ala Ser Val Ile Ile Gln Asn Leu Pro Ala
305             310             315             320

Leu Asn Ser Ala Ile Asn Pro Leu Ile Tyr Cys Val Phe Ser Ser Ser
                325             330             335

Ile Ser Phe Pro Cys Arg Glu Arg Arg Ser Gln Asp Ser Arg Met Thr
                340             345             350

Phe Arg Glu Arg Thr Glu Arg His Glu Met Gln Ile Leu Ser Lys Pro
            355             360             365

Glu Phe Ile
    370
```